(12) United States Patent
Meo et al.

(10) Patent No.: US 11,345,694 B2
(45) Date of Patent: May 31, 2022

(54) ANTIBACTERIAL COMPOUNDS

(71) Applicant: DISCUVA LTD., Abingdon (GB)

(72) Inventors: Paul Meo, Cambridgeshire (GB); Mohammed Nawaz Khan, Cambridgeshire (GB); Cedric Charrier, Cambridgeshire (GB)

(73) Assignee: Discuva Ltd., Cambridgeshire (GB)

( * ) Notice: Subject to any disclaimer, the term of this patent is extended or adjusted under 35 U.S.C. 154(b) by 0 days.

(21) Appl. No.: 16/761,016

(22) PCT Filed: Nov. 2, 2018

(86) PCT No.: PCT/GB2018/053183
§ 371 (c)(1),
(2) Date: May 1, 2020

(87) PCT Pub. No.: WO2019/086890
PCT Pub. Date: May 9, 2019

(65) Prior Publication Data
US 2021/0163460 A1    Jun. 3, 2021

(30) Foreign Application Priority Data

Nov. 3, 2017 (GB) .................................... 1718285

(51) Int. Cl.
| C07D 413/14 | (2006.01) |
| A61P 31/04 | (2006.01) |
| C07D 401/04 | (2006.01) |
| C07D 401/14 | (2006.01) |
| C07D 405/14 | (2006.01) |

(52) U.S. Cl.
CPC ............ *C07D 413/14* (2013.01); *A61P 31/04* (2018.01); *C07D 401/04* (2013.01); *C07D 401/14* (2013.01); *C07D 405/14* (2013.01)

(58) Field of Classification Search
CPC combination set(s) only.
See application file for complete search history.

(56) References Cited

U.S. PATENT DOCUMENTS

| 2013/0177621 A1 | 7/2013 | Melander et al. |
| 2013/0210818 A1 | 8/2013 | Huang et al. |
| 2016/0194288 A1 | 7/2016 | Melander et al. |

FOREIGN PATENT DOCUMENTS

| EP | 1 721 905 A1 | 11/2006 |
| JP | 62-153274 A | 7/1987 |
| JP | H 09-124640 A | 5/1997 |
| JP | 2004-196678 A | 7/2004 |
| WO | WO 00/06563 A1 | 2/2000 |
| WO | WO 2001/62756 A1 | 8/2001 |
| WO | WO 2004/005264 A2 | 1/2004 |
| WO | WO 2005/047266 A | 5/2005 |
| WO | WO 2011/080132 A2 | 7/2011 |
| WO | WO 2012/041934 A1 | 4/2012 |
| WO | WO 2013/009140 A2 | 1/2013 |
| WO | WO 2015/173788 A1 | 11/2015 |
| WO | WO 2016/140884 A1 | 9/2016 |
| WO | WO 2016/141381 A2 | 9/2016 |
| WO | WO 2017/011920 A1 | 1/2017 |

OTHER PUBLICATIONS

Akutsu, F. et al Polymer 1998 vol. 39, pp. 6093-6098.*
Akutsu, F. Polymer 1998, pp. 6093-6098.*
CAPLUS 2007:1207167.*
Brown et al., "Trends and Exceptions of Physical Properties on Antibacterial Activity for Gram Positive and Gram Negative Pathogens," J. Med. Chem., DOI: 10.1021/jm501552x, Nov. 17, 2014, pp. 1-57 (total 58 pages).
Lorenz et al.. "Transcriptional Responses of *Escherichia coli* to a Small-Molecule Inhibitor of LoICDE, an Essential Component of the Lipoprotein Transport Pathway," Journal of Bacteriology, vol. 198, No. 23, Dec. 2016 (posted online Sep. 19, 2016), pp. 3162-3175.
Mcleod et al., "Small-Molecule Inhibitors of Gram-Negative Lipoprotein Trafficking Discovered by Phenotypic Screening." Journal of Bacteriology, vol. 197, No. 6, Mar. 2015 (posted online Jan. 12, 2015), pp. 1075-1082.
Nayar et al., "Novel Antibacterial Targets and Compounds Revealed by a High-Throughput Cell Wall Reporter Assay." Journal of Bacteriology, vol. 197, No. 10, May 2015 (posted online Mar. 2, 2015), pp. 1726-1734.
Richter et al., "Predictive Compound Accumulation Rules Yield a Broad-Spectrum Antibiotic," Nature, vol. 545, 2017 (published online May 10, 2017), pp. 299-304 (total 18 pages).
Amada el al., "Design, synthesis, and evaluation of novel 4-thiazolylimidazoles as inhibitors of transforming growth factorβ type I receptor kinase", Bioorganic & Medicinal Chemistry Letters, 2012, vol. 22, pp. 2024-2029.
Bonafoux et al., "2-Aminoimidazoies inhibitors of TGF-β receptor 1", Bioorganic & Medicinal Chemistry Letters, 2009, vol. 19, pp. 912-916.
Chaudhary et al., "Novel Combretastatin-2-aminoimidazole Analogues as Potent Tubulin Assembly Inhibitors: Exploration of Unique Pharmacophoric Impact of Bridging Skeleton and Aryl Moiety", J. Med. Chem., 2016, vol. 59, pp. 3439-3451.

(Continued)

*Primary Examiner* — Heidi Reese
(74) *Attorney, Agent, or Firm* — Cooley LLP

(57) ABSTRACT

The present invention relates to compounds of general formula (II), to compositions comprising these compounds and to methods of treating Enterobacteriaceae bacterial diseases and infections using the compounds. The compounds find application in the treatment of infection with, and diseases caused by, Enterobacteriaceae.

(Formula II)

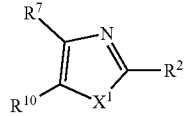

10 Claims, No Drawings

(56) References Cited

OTHER PUBLICATIONS

Database Registry [Online] Chemical Abstracts Service, Columbus, Ohio, US; Dec. 6, 2011, XP002787232, Database accession No. 1349863-71-3.
Hwang et al., "Synthesis of $P^{38}$ Map Kinase Inhibitor Analogues Compounds and Quinoxalinone Derivatives", Int J Pharm Bio Sci, Oct. 2014, vol. 5, No. 4, pp. 212-224.
International Search Report, issued in PCT/GB2018/053183, dated Feb. 28, 2019.
Kim et al., "Synthesis and Biological Evaluation of 4(5)-(6-Alkylpyridin-2-yl)imidazoles as Transforming Growth Factor-β Type 1 Receptor Kinase Inhibitors", J. Med. Chem., 2007, vol. 50, pp. 3143-3147.
Kreutzberger, "Condensations with 1,2-Hydrazinedicarboxamidine. II. 2,2'-Azoimidazoles", Journal of Organic Chemistry, Mar. 1962, vol. 27, pp. 886-891.
Mahalakshmi et al., "Synthesis, spectral characterization and antimicrobial studies of novel imidazole derivatives", Der Pharma Chemica, 2015, vol. 7, No. 1, pp. 14-19.
Singh et al., "Design and Synthesis of some Novel oxazole derivatives and their biomedicinal efficacy", Chemistry & Biology Interface, 2016, vol. 6, No. 4, pp. 263-269.
Srinivas et al., "Synthesis of nitrogen-rich imidazole, 1,2,4-triazole and tetrazole-based compounds", RSC Adv., 2014. vol. 4. pp. 7041-7051.
Steenackers et al., "Structure-Activity Relationship of 4(5)-Aryl-2-amino-1H-imidazoles, N1-Substituted 2-Aminoimidazoles and Imidazo[1,2-α]pyrimidinium Salts as Inhibitors of Biofilm Formation by *Salmonella typhimurium* and Pseudomonas aeruginosa", J. Med. Chem., 2011, vol. 54. pp. 472 484.
Storey et al., "The $pK_a$ Values of Some 2-Aminomidazolium Ions", Journal of Organic Chemistry, Oct. 1964, vol. 29, pp. 3118-3120.
Tanitame et al., "Synthesis and antibacterial activity of novel and potent DNA gyrase inhibitors with azole ring", Bioorganic & Medicinal Chemistry, 2004, vol. 12, pp. 5515-5524.
Thangavel et al., "A Novel Microwave Assisted Solvent-Free General Route to 2-Amino Imidazoles", Asian Journal of Chemistry, 2005, vol. 17, No. 4, pp. 2769-2772.
Written Opinion of the International Searching Authority, issued in PCT/GB2018/053183, dated Feb. 28, 2019.
Antolini et al., "Analogues of 4,5-bis(3,5-Dichlorophenyl)-2-Trifluoromethyl-1H-Imidazole as Potential Antibacterial Agents," Bioorganic & Medicinial Chemistry Letters, vol. 9, 1999, pp. 1023-1028.
Su et al., "A nitroenolate approach to the synthesis of 4.5-disubstituted-2-aminoimidazoles. Pilot library assembly and screening for antibiotic and antibiofilm activity," Organic & Biomolecular Chemistry, vol. 8, 2010 (published online Apr. 29, 2010), pp. 2814-2822.
Database STN, Registry No. RN 214480-41-8, "Benzenamine, 3,3'-(2-methyl-1H-imidazole-4,5-diyl)bis-(9CI)" [CA Index Name]. Chemical Abstracts Service, American Chemical Society; entered Nov. 19, 1998; 7 pages.
Database STN, Registry No. RN 309912-98-9, "Benzenamine, 4,4'-(2-methyl-1H-imidazole-4,5-diyl)bis-(9CI)" [CA Index Name], Chemical Abstracts Service, American Chemical Society; entered Dec. 19, 2000; 2 pages.
Database STN, Registry No. RN 374710-15-3, "1,3-Benzenediol, 4-[4-(2,3-dihydro-1,4-benzodioxin-6-yl)-2-methyl-1H-imidazol-5-yl]-6-propyl-" [CA Index Name]. Chemical Abstracts Service, American Chemical Society; entered Dec. 11, 2001; 3 pages.
Database STN, Registry No. RN 98145-17-6, "1H-Imidazol-2-amine, 5-(4-aminophenyl)-4-(4-methylphenyl)-" [CA Index Name], Chemical Abstracts Service, American Chemical Society; entered Sep. 22, 1985; 5 pages.
Elshaarawy, R.F.M. and C. Janiak (Mar. 21, 2014) "Toward new classes of potent antibiotics: synthesis and antimicrobial activity of novel metallosaldach-imidazolium salts" Eur J Med Chem, 75:31-42; doi: 10.1016/j.ejmech2013.09.029. Epub Sep. 19, 2013.
Pyl, T. et al. (Dec. 1, 1961) "Über 2-Phenylhydrazino-imidazole und deren benzidinartige Umlagerung" Chemische Berichte, 94(12):3217-3223.

\* cited by examiner

ANTIBACTERIAL COMPOUNDS

FIELD OF THE INVENTION

The present invention relates to a new series of antibacterial compounds as defined herein, to compositions containing these compounds and to methods of treating Enterobacteriaceae bacterial diseases and infections using the compounds. The compounds find application in the treatment of infection with, and disease caused by Gram-negative bacteria Enterobacteriaceae species that have developed resistance to existing antibiotics.

BACKGROUND TO THE INVENTION

There is an urgent need for novel antibacterial compounds to counter the emergence of new bacterial pathogens with resistance to existing antibacterial compounds. The increasing occurrence of bacterial resistance to existing antibiotics threatens to greatly enhance the burden that common infections place on society, with multidrug resistance becoming common amongst a number of bacterial pathogens. For example, antibiotic-resistant strains of the ESKAPE pathogens (*Enterococcus faecium, Staphylococcus aureus, Klebsiella pneumoniae, Acinetobacter baumannii, Pseudomonas aeruginosa* and *Enterobacter* species), such as carbapenem-resistant Enterobacteriaceae (CRE), multi-drug resistant (MDR) *Acinetobacter*, MDR *Pseudomonas aeruginosa*, methicillin-resistant *Staphylococcus aureus* (MRSA) and vancomycin-resistant *Enterococcus* (VRE) have been included in a list of antibiotic-resistant microorganisms identified as posing an urgent or serious threat to human health. Other prominent antibiotic-resistant pathogens include the Gram-positive anaerobe *Clostridium difficile*, drug-resistant *Neisseria gonorrhoeae* and drug-resistant tuberculosis.

Antibiotic-resistant Gram-negative strains, such as carbapenemases-producing Enterobacteriaceae e.g. *Escherichia coli* NDM-1 (New Delhi metallo-β-lactamase) and *Klebsiella pneumoniae* are difficult to treat and are becoming increasingly virulent. Moreover, new emerging hypervirulent, multidrug resistant and highly transmissible strains of carbapenem-resistant *Klebsiella pneumoniae* associated with fatal outbreaks have been identified, for example, ST11 carbapenem-resistant hypervirulent *Klebsiella pneumoniae* strains. Such strains are resistant to previously and currently recommended antibiotics and are now a global major public health concern.

There is therefore a need for novel antibacterial compounds that can provide effective treatment in a reliable manner, particularly for Enterobacteriaceae infections involving multidrug-resistance infection agents. There is additionally a need for the provision of antibiotic drugs which can avoid or reduce the side-effects associated with known antibacterial compounds.

It is an object of the aspects of the present invention to provide a solution to the above mentioned or other problems.

SUMMARY OF THE INVENTION

According to a first aspect of the present invention, there is provided a compound of general formula (II), or a pharmaceutically acceptable salt, hydrate, solvate or ester thereof:

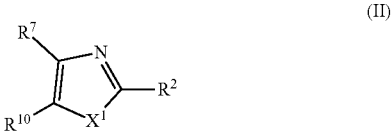

wherein $X^1$ is selected from $NR^1$ or S;

$R^1$ is selected from hydrogen or $C_{1-2}$alkyl;

$R^2$ is selected from the group consisting of S (sulfinyl), O (oxo), $NR^3R^4$, cyano, $-CH_2NR^5R^6$, methyl ($-CH_3$), halogen, hydroxyl, $-CONR^3R^4$, COOH and monocyclic 4- to 7-membered heterocyclyl, wherein the 4- to 7-membered heterocyclyl is optionally substituted with one or more $C_{1-4}$alkyl groups;

$R^3$ and $R^4$ are independently selected from the group consisting of hydrogen, $C_{1-3}$alkyl, $COR^5$, $CONR^5R^6$, $CO_2R^5$, $C_{1-2}$alkyl-$NR^5R^6$;

or $R^3$ and $R^4$ together with the nitrogen atom to which they are attached form a monocyclic 4- to 7-membered cyclic amine group, which group is optionally substituted with one or more substituents selected from the group consisting of $NR^5R^6$, $C_{1-2}$alkoxy and oxo;

$R^5$ and $R^6$ are independently selected from the group consisting of hydrogen and $C_{1-4}$alkyl;

$R^7$ is selected from the group consisting of phenyl, monocyclic 5- to 7-membered heterocyclyl and monocyclic 5- or 6-membered heteroaryl, wherein the phenyl, 5- to 7-membered heterocyclyl and 5- or 6-membered heteroaryl rings are optionally substituted with one or more substituents selected from the group consisting of halogen, $C_{1-2}$alkyl, $C_{1-2}$alkoxy, $NR^3R^4$, $CONR^3R^4$, $OR^8$, $OCF_3$, $C_{1-2}$alkoxy-CN and hydroxyl;

or $R^7$ is a fused bicyclic system selected from the group consisting of any one of (Ia) to (Ik):

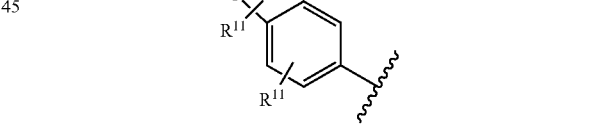

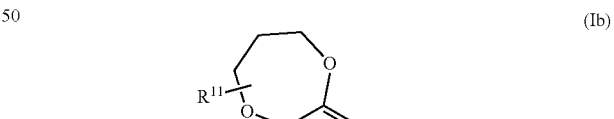

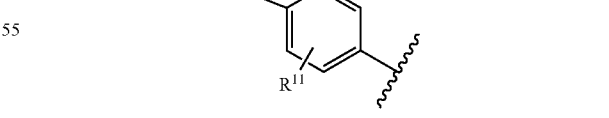

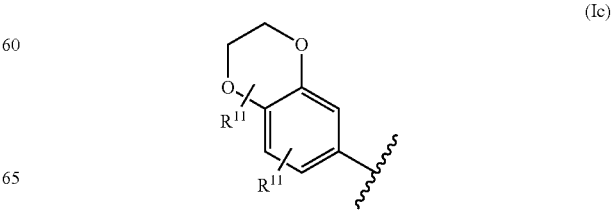

-continued (Id)
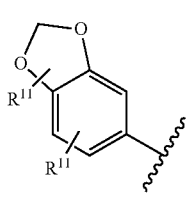

(Ie)
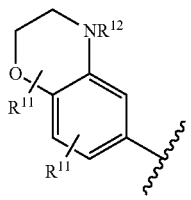

(If)
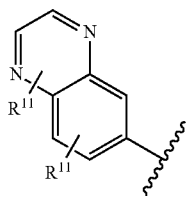

(Ig)
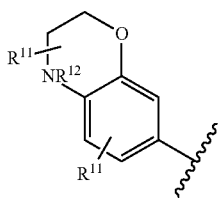

(Ih)
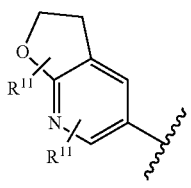

(Ii)
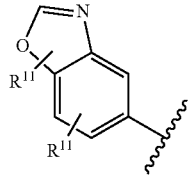

(Ij)
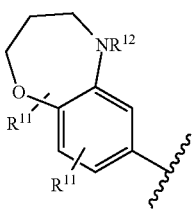

(Ik)
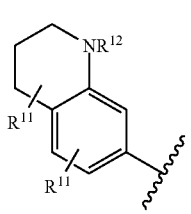

wherein each $R^{11}$ is independently selected from hydrogen, halogen, O (oxo), and $C_{1-4}$alkyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$;

$R^8$ is selected from the group consisting of 3- to 5-membered cycloalkyl and $CH_2R^9$;

$R^9$ is selected from the group consisting of phenyl, monocyclic 5- or 6-membered heteroaryl and monocyclic $C_{3-7}$cycloalkyl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{10}$ is selected from the group consisting of phenyl and monocyclic 5- or 6-membered heteroaryl ring, wherein the phenyl and 5- or 6-membered heteroaryl rings are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$);

or $R^{10}$ is a fused bicyclic system selected from the group consisting of any one of (Ia) to (Ii):

(Ia)
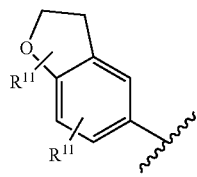

(Ib)
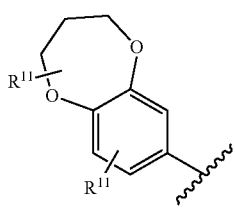

-continued
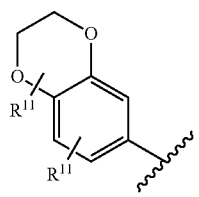 (Ic)
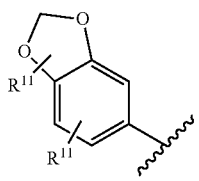 (Id)
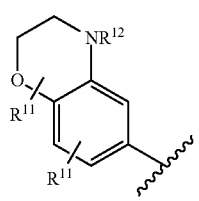 (Ie)
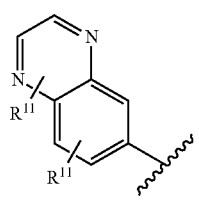 (If)
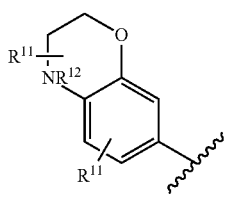 (Ig)
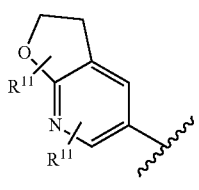 (Ih)
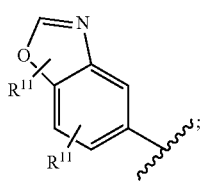 (Ii)
wherein each $R^{11}$ is independently selected from hydrogen, halogen, and $C_{1-4}$alkyl and $R^{12}$ is selected from hydrogen, and $C_{1-4}$alkyl;
provided that the compound of formula (II) is other than:
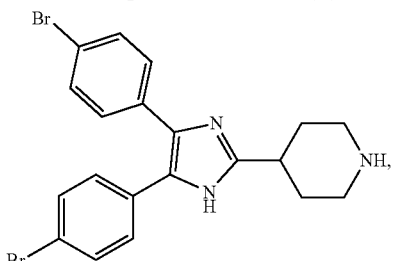
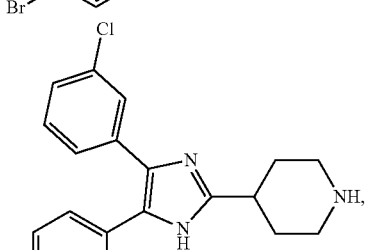
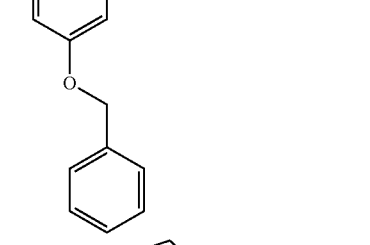
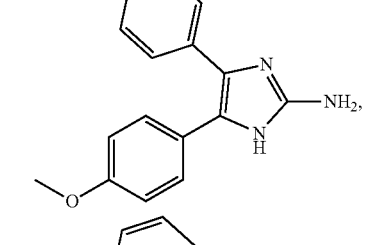
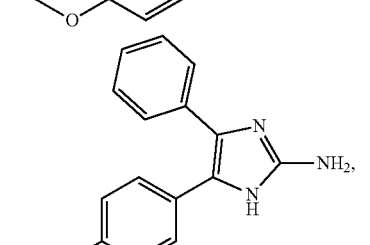
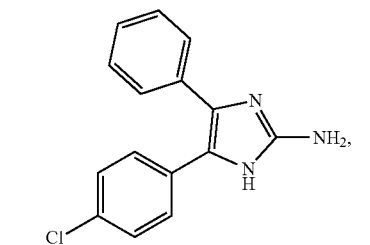
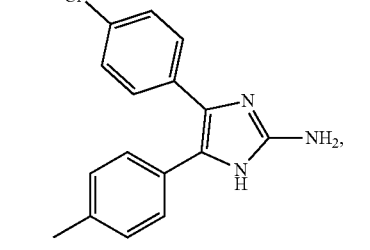

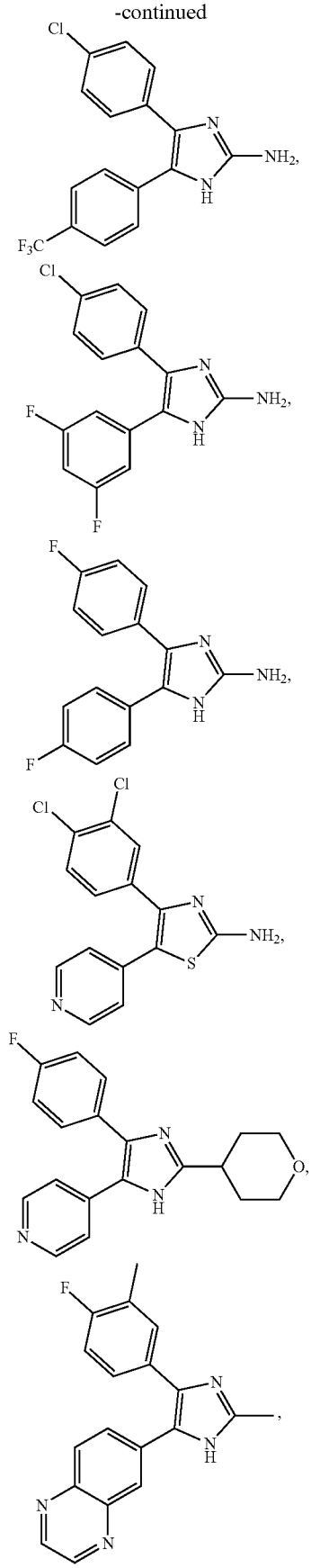
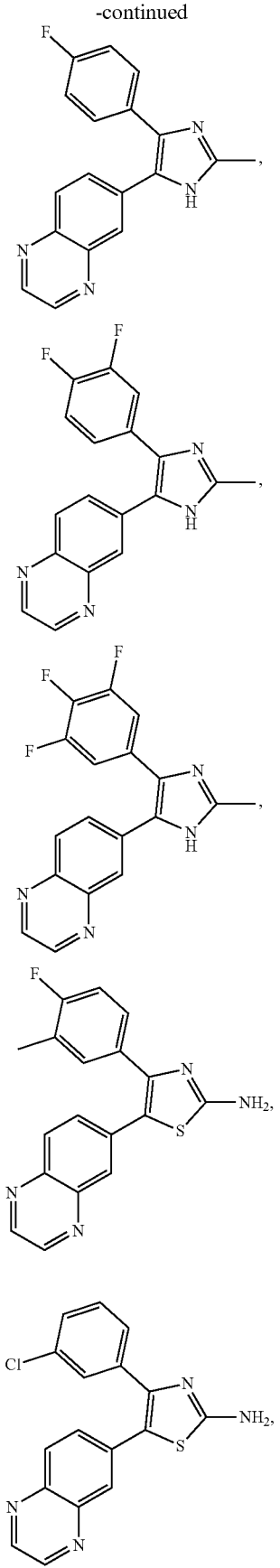

-continued

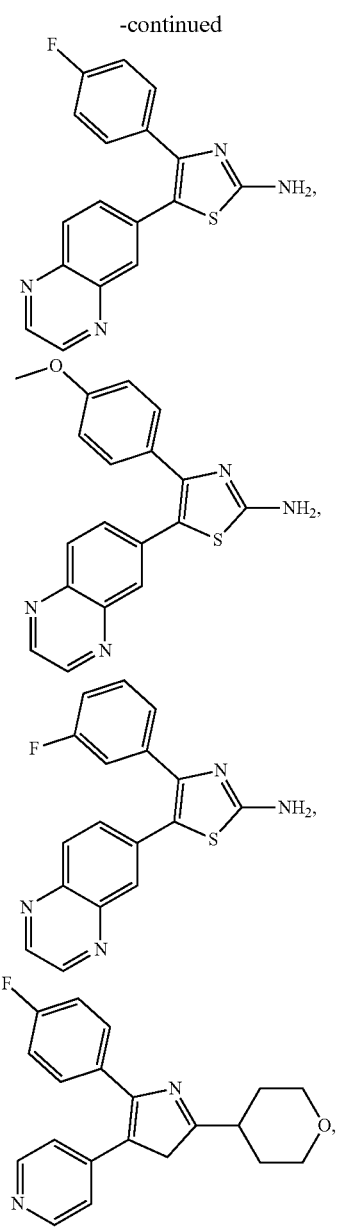

According to a second aspect of the present invention, there is provided a compound of general formula (II), or a pharmaceutically acceptable salt, hydrate, solvate or ester thereof:

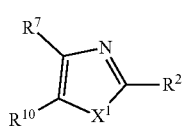
(II)

wherein

X$^1$ is selected from NR$^1$ or S;

R$^1$ is selected from hydrogen or C$_{1-2}$alkyl;

R$^2$ is selected from the group consisting of S (sulfinyl), O (oxo), NR$^3$R$^4$, cyano, —CH$_2$NR$^5$R$^6$, methyl (—CH$_3$), halogen, hydroxyl, —CONR$^3$R$^4$, and COOH;

R$^3$ and R$^4$ are independently selected from the group consisting of hydrogen, C$_{1-3}$alkyl, COR$^5$, CONR$^5$R$^6$, CO$_2$R$^5$, C$_{1-2}$alkyl-NR$^5$R$^6$;

or R$^3$ and R$^4$ together with the nitrogen atom to which they are attached form a monocyclic 4- to 7-membered cyclic amine group, which group is optionally substituted with one or more substituents selected from the group consisting of NR$^5$R$^6$, C$_{1-2}$alkoxy and oxo;

R$^5$ and R$^6$ are independently selected from the group consisting of hydrogen and C$_{1-4}$alkyl;

R$^7$ is selected from the group consisting of phenyl, monocyclic 5- to 7-membered heterocyclyl and monocyclic 5- or 6-membered heteroaryl, wherein the phenyl is substituted with one or more substituents selected from the group consisting of NR$^3$R$^4$, CONR$^3$R$^4$, OR$^8$, OCF$_3$, OCH$_2$CN and hydroxyl, and the monocyclic 5- to 7-membered heterocyclyl and monocyclic 5- or 6-membered heteroaryl are optionally substituted with one or more substituents selected from the group consisting of halogen, C$_{1-2}$alkyl, C$_{1-2}$alkoxy, NR$^3$R$^4$, CONR$^3$R$^4$, OR$^8$, OCF$_3$, C$_{1-2}$alkoxy-CN and hydroxyl;

or R$^7$ is a fused bicyclic system selected from the group consisting of any one of (Ia) to (Ik):

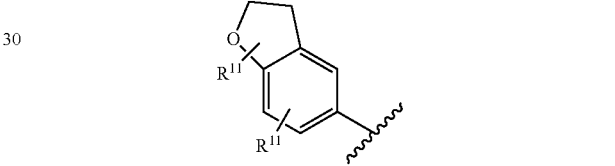
(Ia)

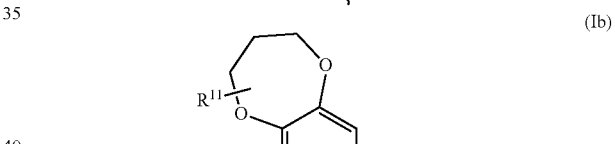
(Ib)

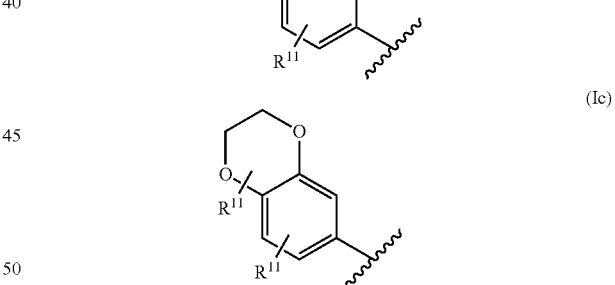
(Ic)

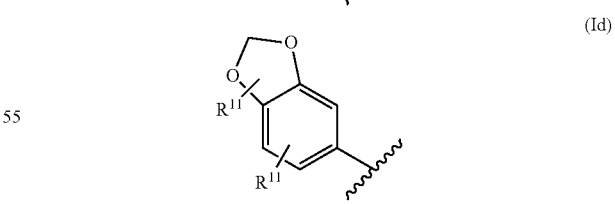
(Id)

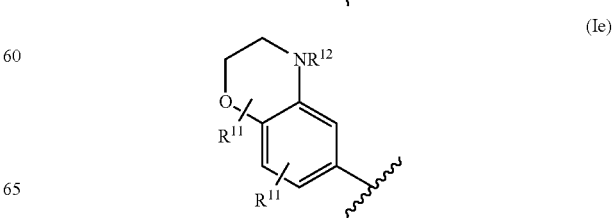
(Ie)

-continued (If)
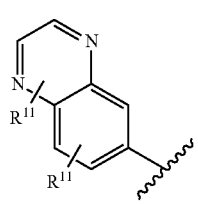

(Ig)
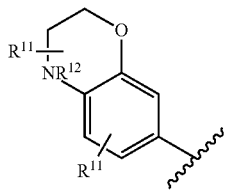

(Ih)
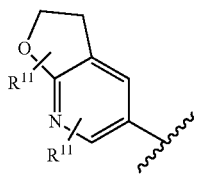

(Ii)
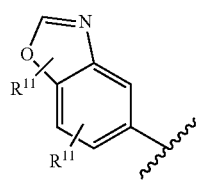

(Ij)
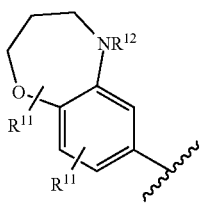

(Ik)
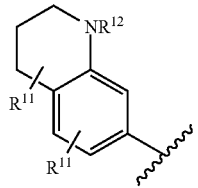

wherein each $R^{11}$ is independently selected from hydrogen, halogen, O (oxo), and $C_{1-4}$alkyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$—$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$, and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$, and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$, and $SR^3$;

$R^8$ is selected from the group consisting of 3- to 5-membered cycloalkyl and $CH_2R^9$;

$R^9$ is selected from the group consisting of phenyl, monocyclic 5- or 6-membered heteroaryl and monocyclic $C_{3-7}$cycloalkyl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{10}$ is selected from the group consisting of phenyl and monocyclic 5- or 6-membered heteroaryl ring, wherein the phenyl is optionally substituted with one or more substituents selected from the group consisting of $C_{1-4}$alkyl, O (oxo), S (sulfinyl), $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$), and the 5- or 6-membered heteroaryl rings are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$);

or $R^{10}$ is a fused bicyclic system selected from the group consisting of any one of (Ia) to (Ii):

(Ia)
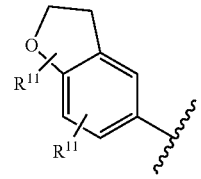

(Ib)
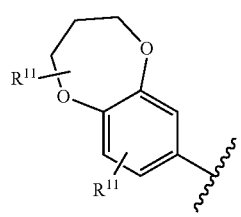

(Ic)
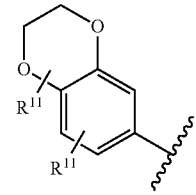

(Id) 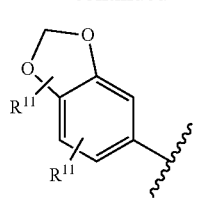

(Ie) 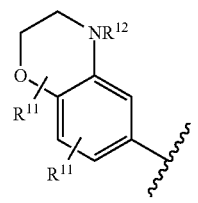

(If) 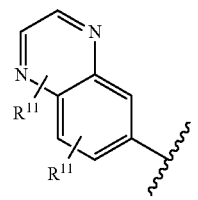

(Ig) 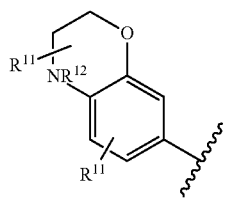

(Ih) 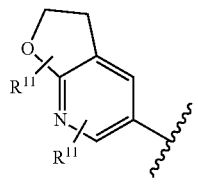

(Ii) 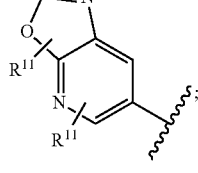

wherein each $R^{11}$ is independently selected from hydrogen, halogen, and $C_{1-4}$alkyl and $R^{12}$ is selected from hydrogen, and $C_{1-4}$alkyl.

According to a third aspect of the present invention, there is provided a compound of the invention as defined above for the first and second aspects, or a pharmaceutically acceptable salt, derivative, hydrate, solvate, complex, isomer, tautomer, bioisostere, N-oxide, ester, prodrug, isotope or protected form thereof.

According to a fourth aspect of the present invention, there is provided a compound of the invention as defined above for the first and second aspects, or a pharmaceutically acceptable salt, derivative, hydrate, solvate, complex, isomer, tautomer, bioisostere, N-oxide, ester, prodrug, isotope or protected form thereof, for use in therapy or prophylaxis of an infection with, or disease caused by, Enterobacteriaceae.

In a further aspect of the present invention, there is provided a compound of the invention as defined above for the first and second aspects, or a pharmaceutically acceptable salt, derivative, hydrate, solvate, complex, isomer, tautomer, bioisostere, N-oxide, ester, prodrug, isotope or protected form thereof, for use in a method of treatment of an infection with, or a disease caused by, Enterobacteriaceae.

In a further aspect of the present invention, there is provided a compound of the invention as defined above for the first and second aspects, or a pharmaceutically acceptable salt, derivative, hydrate, solvate, complex, isomer, tautomer, bioisostere, N-oxide, ester, prodrug, isotope or protected form thereof, together with a pharmaceutically acceptable excipient or carrier.

In a further aspect of the present invention, there is provided the use of a compound of the invention as defined above for the first and second aspects, or a pharmaceutically acceptable salt, derivative, hydrate, solvate, complex, isomer, tautomer, bioisostere, N-oxide, ester, prodrug, isotope or protected form thereof, for the manufacture of a medicament for use in the treatment of an infection with, or a disease caused by, Enterobacteriaceae.

In a further aspect of the present invention, there is provided a method of treating an infection with, or disease caused by, Enterobacteriaceae in a subject in need thereof, comprising administering to said subject an effective amount of a compound of the invention as defined above for the first and second aspects, or a pharmaceutically acceptable salt, derivative, hydrate, solvate, complex, isomer, tautomer, bioisostere, N-oxide, ester, prodrug, isotope or protected form thereof.

In a further aspect of the present invention, there is provided an Enterobacteriaceae bactericidal or bacteriostatic composition comprising a compound or composition of the invention as defined above for the first and second aspects.

In a further aspect of the present invention, there is provided a pharmaceutical formulation comprising a compound of the invention as defined above for the first and second aspects and a pharmaceutically acceptable excipient.

The compounds of the invention as defined above for the first and second aspects have bactericidal and/or bacteriostatic activity against Enterobacteriaceae and may be used in the treatment or prophylaxis of an infection with, or a disease caused by, Enterobacteriaceae.

In a further aspect of the present invention, there is provided a compound of general formula (II), or a pharmaceutically acceptable salt, hydrate, solvate or ester thereof for use in the treatment of infection with, or disease caused by the bacterium Enterobacteriaceae:

(II) 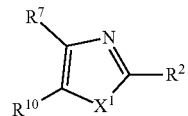

wherein
$X^1$ is selected from $NR^1$ or S;
$R^1$ is selected from hydrogen or $C_{1-2}$alkyl;
$R^2$ is selected from the group consisting of S (sulfinyl), O (oxo), $NR^3R^4$, cyano, —$CH_2NR^5R^6$, methyl (—$CH_3$), halogen, hydroxyl, —$CONR^3R^4$, COOH and monocyclic 4- to 7-membered heterocyclyl, wherein the 4- to 7-membered heterocyclyl is optionally substituted with one or more $C_{1-4}$alkyl groups;

$R^3$ and $R^4$ are independently selected from the group consisting of hydrogen, $C_{1-3}$alkyl, $COR^5$, $CONR^5R^6$, $CO_2R^5$, $C_{1-2}$alkyl-$NR^5R^6$;

or $R^3$ and $R^4$ together with the nitrogen atom to which they are attached form a monocyclic 4- to 7-membered cyclic amine group, which group is optionally substituted with one or more substituents selected from the group consisting of $NR^5R^6$, $C_{1-2}$alkoxy and oxo;

$R^5$ and $R^6$ are independently selected from the group consisting of hydrogen and $C_{1-4}$alkyl;

$R^7$ is selected from the group consisting of phenyl, monocyclic 5- to 7-membered heterocyclyl and monocyclic 5- or 6-membered heteroaryl, wherein the phenyl, 5- to 7-membered heterocyclyl and 5- or 6-membered heteroaryl are optionally substituted with one or more substituents selected from the group consisting of halogen, $C_{1-2}$alkyl, $C_{1-2}$alkoxy, $NR^3R^4$, $CONR^3R^4$, $OR^8$, $OCF_3$, $C_{1-2}$alkoxy-CN and hydroxyl;

or $R^7$ is a fused bicyclic system selected from the group consisting of any one of (Ia) to (Ik):

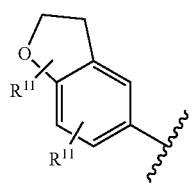
(Ia)

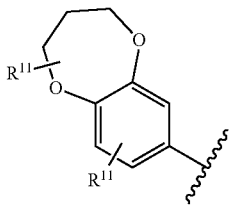
(Ib)

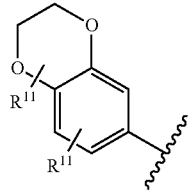
(Ic)

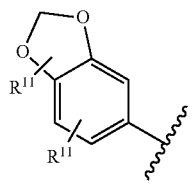
(Id)

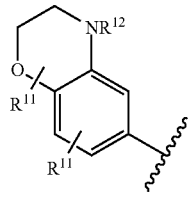
(Ie)

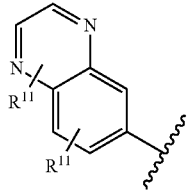
(If)

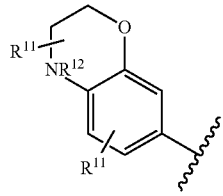
(Ig)

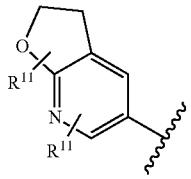
(Ih)

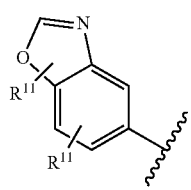
(Ii)

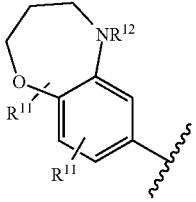
(Ij)

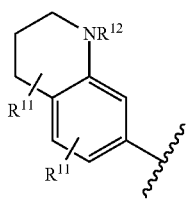
(Ik)

wherein each $R^{11}$ is independently selected from hydrogen, halogen, O (oxo), and $C_{1-4}$alkyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$—$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$, and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$, and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$, and $SR^3$;

$R^8$ is selected from the group consisting of 3- to 5-membered cycloalkyl and $CH_2R^9$;

$R^9$ is selected from the group consisting of phenyl, monocyclic 5- or 6-membered heteroaryl and monocyclic $C_{3-7}$cycloalkyl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{10}$ is selected from the group consisting of phenyl and monocyclic 5- or 6-membered heteroaryl ring, wherein the phenyl and 5- or 6-membered heteroaryl rings are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, $-CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}{}_4{}^+$);

or $R^{10}$ is a fused bicyclic system selected from the group consisting of any one of (Ia) to (Ii):

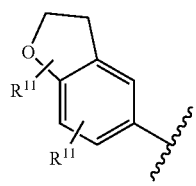
(Ia)

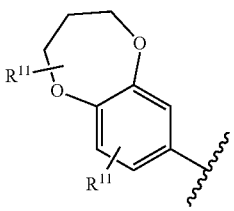
(Ib)

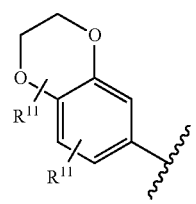
(Ic)

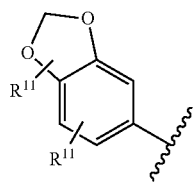
(Id)

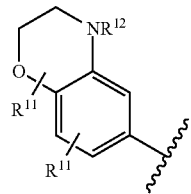
(Ie)

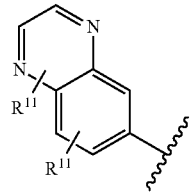
(If)

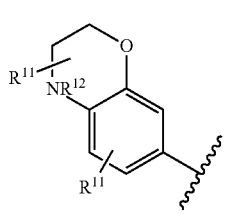
(Ig)

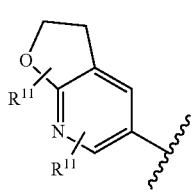
(Ih)

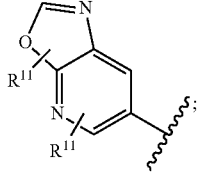
(Ii)

wherein each $R^{11}$ is independently selected from hydrogen, halogen, and $C_{1-4}$alkyl and $R^{12}$ is selected from hydrogen, and $C_{1-4}$alkyl.

Other aspects and embodiments of the invention are as defined in the claims attached hereto.

DEFINITIONS

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from trauma, injury, surgery, radiological ablation, poisoning or nutritional deficiencies.

As used herein, the term "bacterial disease" refers to any disease that involves (e.g. is caused, exacerbated, associated with or characterized by the presence of) a bacterium residing and/or replicating in the body and/or cells of a subject. The term therefore includes diseases caused or exacerbated by bacterial toxins (which may also be referred to herein as "bacterial intoxication").

As used herein, the term "bacterial infection" is used to define a condition in which a subject is infected with a bacterium. The infection may be symptomatic or asymptomatic. In the former case, the subject may be identified as infected on the basis of established diagnostic criteria. In the latter case, the subject may be identified as infected on the basis of various tests, including for example biochemical tests, serological tests, microbiological culture and/or microscopy.

Thus, the invention finds application in the treatment of subjects in which bacterial infection has been diagnosed or detected.

As used herein, the term "treatment" or "treating" refers to an intervention (e.g. the administration of an agent to a subject) which cures, ameliorates or lessens the symptoms of a disease or removes (or lessens the impact of) its cause(s) (for example, the causative bacterium). In this case, the term is used synonymously with the term "therapy". Thus, the treatment of infection according to the invention may be characterized by the (direct or indirect) bacteriostatic and/or bactericidal action of the compounds of the invention. Thus, the compounds of the invention find application in methods of killing, or preventing the growth of, bacterial cells.

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

The term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In preferred embodiments, the subject is a human, for example an infant human or a geriatric human.

The terms "Gram-negative bacterium" and "Gram-positive bacterium" are terms of art defining two distinct classes of bacteria on the basis of certain cell wall staining characteristics.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound/agent to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. Each of the two or more compounds/agents in a combination therapy may also be administered via a different route and/or according to a different dosing regimen/duration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. The combinations of the invention may produce a therapeutically efficacious effect relative to the therapeutic effect of the individual compounds/agents when administered separately.

As used herein, an "effective amount" or a "therapeutically effective amount" of a compound defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The term "adjunctive agent" as used herein is intended to define any compound or composition which yields an efficacious combination (as herein defined) when combined with a compound of the invention. The adjunctive agent or treatment may therefore contribute to efficacy (for example, by producing a synergistic or additive effect or by potentiating the activity of the compound of the invention).

The term "efficacious" includes advantageous effects such as additivity, synergism, reduced side effects, reduced toxicity or improved performance or activity. Advantageously, an efficacious effect may allow for lower doses of each or either component to be administered to a patient, thereby decreasing the toxicity, whilst producing and/or maintaining the same therapeutic effect. A synergistic effect in the present context refers to a therapeutic effect produced by the combination which is larger than the sum of the therapeutic effects of the components of the combination when presented individually. An additive effect in the present context refers to a therapeutic effect produced by the combination which is larger than the therapeutic effect of any of the components of the combination when presented individually.

The term "adjunctive" as applied to the use of the compounds and compositions of the invention in therapy or prophylaxis defines uses in which the materials are administered together with one or more other drugs, interventions, regimens or treatments (such as surgery and/or irradiation). Such adjunctive therapies may comprise the concurrent, separate or sequential administration/application of the materials of the invention and the other treatment(s). Thus, in some embodiments, adjunctive use of the materials of the invention is reflected in the formulation of the pharmaceutical compositions of the invention. For example, adjunctive use may be reflected in a specific unit dosage, or in formulations in which the compound of the invention is present in admixture with the other drug(s) with which it is to be used adjunctively (or else physically associated with the other drug(s) within a single unit dose). In other embodiments, adjunctive use of the compounds or compositions of the invention may be reflected in the composition of the pharmaceutical kits of the invention, wherein the compound of the invention is co-packaged (e.g. as part of an array of unit doses) with the other drug(s) with which it is to be used adjunctively. In yet other embodiments, adjunctive use of the compounds of the invention may be reflected in the content of the information and/or instructions co-packaged with the compound relating to formulation and/or posology.

The term "pharmaceutically acceptable salt" as applied to the compounds of the invention defines any non-toxic organic or inorganic acid addition salt of the free base which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid).

The term "pharmaceutically acceptable derivative" as applied to the compounds of the invention define compounds which are obtained (or obtainable) by chemical derivatization of the parent compounds of the invention. The pharmaceutically acceptable derivatives are therefore suitable for administration to or use in contact with mammalian tissues without undue toxicity, irritation or allergic response (i.e. commensurate with a reasonable benefit/risk ratio). Preferred derivatives are those obtained (or obtainable) by alkylation, esterification or acylation of the parent compounds of the invention. The derivatives may be active per se, or may be inactive until processed in vivo. In the latter case, the derivatives of the invention act as prodrugs. Particularly preferred prodrugs are ester derivatives which are esterified at one or more of the free hydroxyls and which are activated by hydrolysis in vivo. Other preferred prodrugs are covalently bonded compounds which release the active parent drug according to general formula (I) after cleavage of the covalent bond(s) in vivo.

In its broadest aspect, the present invention contemplates all optical isomers, racemic forms and diastereoisomers of the compounds described herein. Those skilled in the art will appreciate that, owing to the asymmetrically substituted carbon atoms present in the compounds of the invention, the compounds may be produced in optically active and racemic forms. If a chiral centre or another form of isomeric centre is present in a compound of the present invention, all forms of such isomer or isomers, including enantiomers and diastereoisomers, are intended to be covered herein. Compounds of the invention containing a chiral centre (or multiple chiral centres) may be used as a racemic mixture, an enantiomerically enriched mixture, or the racemic mixture may be separated using well-known techniques and an individual enantiomer may be used alone. Thus, references to particular compounds of the present invention encompass the products as a mixture of diastereoisomers, as individual diastereoisomers, as a mixture of enantiomers as well as in the form of individual enantiomers.

Therefore, the present invention contemplates all optical isomers and racemic forms thereof of the compounds of the invention, and unless indicated otherwise (e.g. by use of dash-wedge structural formulae) the compounds shown herein are intended to encompass all possible optical isomers of the compounds so depicted. In cases where the stereochemical form of the compound is important for pharmaceutical utility, the invention contemplates use of an isolated eutomer.

The term "bioisostere" (or simply "isostere") is a term of art used to define drug analogues in which one or more atoms (or groups of atoms) have been substituted with replacement atoms (or groups of atoms) having similar steric and/or electronic features to those atoms which they replace. The substitution of a hydrogen atom or a hydroxyl group with a fluorine atom is a commonly employed bioisosteric replacement. Sila-substitution (C/Si-exchange) is a relatively recent technique for producing isosteres. This approach involves the replacement of one or more specific carbon atoms in a compound with silicon (for a review, see Tacke and Zilch (1986) Endeavour, New Series 10: 191-197). The sila-substituted isosteres (silicon isosteres) may exhibit improved pharmacological properties, and may for example be better tolerated, have a longer half-life or exhibit increased potency (see for example Englebienne (2005) Med. Chem., 1(3): 215-226). Similarly, replacement of an atom by one of its isotopes, for example hydrogen by deuterium, may also lead to improved pharmacological properties, for example leading to longer half-life (see for example Kushner et al (1999) Can J Physiol Pharmacol. 77(2):79-88). In its broadest aspect, the present invention contemplates all bioisosteres (and specifically, all silicon Bioisosteres, and all deuterium Bioisosteres) of the compounds of the invention.

The term "approved drug" as used herein, refers to a drug which has been approved by the US Food and Drug Administration (US FDA) or the European Medicines Agency (EMA) prior to the 1 Oct. 2016.

The term "resistant strains" as used herein, refers to strains of bacteria that have shown resistance or non-susceptibility to one or more known antibacterial drug. A "non-susceptible strain" is one in which the MIC (minimum inhibitory concentration) of a given compound or class of compounds for that strain has shifted to a higher number than for corresponding susceptible strains. For example, it may refer to strains that are non-susceptible to β-lactam antibiotics, strains that are non-susceptible to one or more fluoroquinolones and/or strains that are non-susceptible to one or more other antibiotics (i.e. antibiotics other than β-lactams and fluoroquinolones). In certain embodiments, the term "resistant" may refer to one in which the MIC of a given compound or class of compounds for that strain has shifted to a significantly higher number than for corresponding susceptible strains. A bacterial strain might be said to be resistant to a given antibiotic when it is inhibited in vitro by a concentration of this drug that is associated with a high likelihood of therapeutic failure.

The term "multidrug-resistant" as used herein, refers to organisms, such as highly-resistant Gram-negative bacteria (e.g. carbapenemase-producing *Klebsiella pneumoniae*), showing in vitro resistance to more than one antimicrobial agent. Such organisms may be resistant to all of the currently available antimicrobial agents or remain susceptible only to older, potentially more toxic, antimicrobial agents.

The term "hypervirulent" as used herein, refers to organisms that are exceptionally virulent, generally as a result of the acquisition of a virulence plasmid. Such organisms are capable of producing severe illness. For completeness, "virulent" refers to organisms capable of producing extremely severe or harmful effects and illness.

The term "mycobacterial disease" defines any disease, disorder, pathology, symptom, clinical condition or syndrome in which bacteria of the genus *Mycobacterium* (i.e. mycobacteria) act as aetiological agents or in which infection with mycobacteria is implicated, detected or involved. Any mycobacterial infection may be treated, including those in which bacteria of the *Mycobacterium avium* complex (MAC) is involved. This term defines a class of genetically-related bacteria belonging to the genus *Mycobacterium* and includes *Mycobacterium avium* subspecies *avium* (MAA), *Mycobacterium avium* subspecies *hominis* (MAH), and *Mycobacterium avium* subspecies *paratuberculosis* (MAP) together with the genetically distinct *Mycobacterium avium intracellulare* (MAI). It may also be that the mycobacterial infection is caused by a mycobacterium selected from: *Mycobacterium tuberculosis, M. abscessus, M. leprae, M. bovis, M. kansasii, M. chelonae, M. africanum, M. canetti* and *M. microti*. The term therefore includes the various forms of TB, leprosy, pediatric lymphadenitis and mycobacterial skin ulcers. The term therefore covers mycobacterial conditions arising from or associated with infection by nontuberculous mycobacteria as well as tuberculous mycobacteria.

All references to particular chemical compounds herein are to be interpreted as covering the compounds per se, and also, where appropriate, pharmaceutically acceptable salts, derivatives, hydrates, solvates, complexes, isomers, tautomers, bioisosteres, N-oxides, esters, prodrugs, isotopes or protected forms thereof.

The term "$C_{1-4}$alkyl" denotes a straight or branched alkyl group having from 1 to 4 carbon atoms. For parts of the range $C_{1-4}$alkyl all subgroups thereof are contemplated such as $C_{1-3}$alkyl, $C_{1-2}$alkyl, $C_{2-4}$alkyl, $C_{2-3}$alkyl and $C_{3-4}$alkyl. Examples of said $C_{1-4}$alkyl include methyl, ethyl, n-propyl, isopropyl, n-butyl, isobutyl, sec-butyl and tert-butyl.

The term "$C_{1-3}$alkylene" denotes a straight or branched divalent saturated hydrocarbon chain having from 1 to 3 carbon atoms. The $C_{1-3}$alkylene chain may be attached to the rest of the molecule and to the radical group through one carbon within the chain or through any two carbons within the chain. Examples of $C_{1-3}$alkylene radicals include methylene [—$CH_2$—], 1,2-ethylene [—$CH_2$—$CH_2$—], 1,1-ethylene [—$CH(CH_3)$—], 1,2-propylene [—$CH_2$—$CH(CH_3)$—] and 1,3-propylene [—$CH_2$—$CH_2$—$CH_2$—]. When referring to a "$C_{1-3}$alkylene" radical, all subgroups thereof are contemplated, such as $C_{1-2}$alkylene, $C_{1-3}$alkylene or $C_{2-3}$alkylene.

The term "$C_{1-4}$alkoxy" refers to a straight or branched $C_{1-4}$alkyl group which is attached to the remainder of the molecule through an oxygen atom. For parts of the range $C_{1-4}$alkoxy, all subgroups thereof are contemplated such as $C_{1-3}$-alkoxy, $C_{1-2}$alkoxy, $C_{2-4}$alkoxy, $C_{2-3}$alkoxy and $C_{3-4}$alkoxy. Examples of said $C_{1-4}$alkoxy include methoxy, ethoxy, n-propoxy, isopropoxy, n-butoxy, isobutoxy, sec-butoxy and tert-butoxy.

The term "$C_{1-4}$alkyl-X", wherein X is a substituent means that a single X substituent is connected to any carbon atom of $C_{1-4}$alkyl. Said $C_{1-4}$alkyl-X may be attached to the rest of the molecule through a carbon atom of the $C_{1-4}$alkyl. The substituent X can be any substituent, such as $C_{1-4}$alkoxy, and $C_{3-7}$cycloalkyl. Examples of "$C_{1-4}$alkyl-X" groups include —$CH_2CH_2OCH_3$, and —$C(H)(OCH_3)CH_3$.

The term "—$SC_{1-4}$alkyl", means that the $C_{1-4}$alkyl is attached to the rest of the molecule through a S (sulphur) atom. Examples of "—$SC_{1-4}$alkyl" groups include —$SCH_2CH_3$.

"Halogen" refers to fluorine, chlorine, bromine or iodine, preferably fluorine and chlorine, most preferably fluorine.

"Hydroxy" and "Hydroxyl" refer to the —OH radical.

"Cyano" refers to the —CN radical.

"Oxo" refers to the carbonyl group =O. It will be appreciated that when an oxo is a substituent on an aromatic group, such as a phenyl group, the oxo will form part of the conjugated system of the aromatic group.

"Sulfinyl" refers to the sulfinyl group =S. It will be appreciated that when a sulfinyl is a substituent on an aromatic group, such as a phenyl group, the sulfinyl will form part of the conjugated system of the aromatic group.

"Boc" refers to a tert-butyloxycarbonyl protecting group.

"An amino acid" refers to an organic compound composed of predominately carbon, hydrogen, oxygen and nitrogen atoms, comprising both an amine (—$NH_2$) and carboxyl (—COOH) functional group, in addition to a side chain specific to each amino acid.

"A quaternary ammonium cation" refers to a positively charged ion having the structure $NR_4^+$, R being an alkyl or aryl group, not hydrogen.

"Optional" or "optionally" means that the subsequently described event or circumstance may but need not occur, and that the description includes instances where the event or circumstance occurs and instances in which it does not.

The term "$C_{3-7}$-cycloalkyl" refers to a monocyclic saturated or partially unsaturated hydrocarbon ring system having from 3 to 7 carbon atoms. Examples of said $C_{3-7}$-cycloalkyl include cyclopropyl, cyclobutyl, cyclopentyl, cyclohexyl, cyclohexenyl, cycloheptyl, and cycloheptenyl. For parts of the range "$C_{3-7}$-cycloalkyl" all subgroups thereof are contemplated such as $C_{3-7}$-cycloalkyl, $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-5}$-cycloalkyl, $C_{5-7}$-cycloalkyl, $C_{5-6}$-cycloalkyl, and $C_{6-7}$-cycloalkyl.

The terms "heterocyclyl", "$C_{4-7}$heterocyclyl" and "heterocyclic ring" denote a non-aromatic, fully saturated or partially unsaturated, preferably fully saturated, monocyclic ring system having from 4 to 7 ring atoms, especially 5 or 6 ring atoms, in which one or more of the ring atoms are other than carbon, such as nitrogen, sulphur or oxygen. The said ring system may be attached to the rest of the molecule through either a heteroatom or a carbon atom of the ring system. Examples of heterocyclic groups include but are not limited to piperidinyl, morpholinyl, homomorpholinyl, azepanyl, piperazinyl, oxo-piperazinyl, diazepinyl, tertahydropyridinyl, tetrahydropyranyl, pyrrolidinyl, tertrahydrofuranyl, and dihydropyrrolyl.

The terms "heteroaryl" and "heteroaromatic ring" denote a monocyclic heteroaromatic ring comprising 5 to 6 ring atoms in which one or more of the ring atoms are other than carbon, such as nitrogen, sulphur or oxygen. Typically, the heteroaryl ring will contain up to 4 heteroatoms, more typically up to 3 heteroatoms, more usually up to 2, for example a single heteroatom. The said heteroaromatic ring may be attached to the rest of the molecule through either a heteroatom or a carbon atom of the ring system. Examples of heteroaryl groups include but are not limited to furyl, pyrrolyl, thienyl, oxazolyl, isoxazolyl, oxadiazolyl, imidazolyl, oxatriazolyl, thiazolyl, isothiazolyl, tetrazolyl, pyrazolyl, pyridinyl, pyrimidinyl, pyridazinyl, pyrazinyl, triazinyl and thiadiazolyl. In some embodiments, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkene groups as defined below.

Examples of monocyclic non-aromatic heterocyclic groups include 5-, 6-, and 7-membered monocyclic heterocyclic groups. The monocyclic non-aromatic heterocyclic groups may be attached to the rest of the molecule through either a heteroatom or a carbon atom of the heterocyclic group. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

The term "cyclic amino group" refers to a non-aromatic, fully saturated or partially unsaturated, preferably fully saturated, monocyclic ring system having from 4 to 7 ring atoms, especially 5 or 6 ring atoms, in which one of the ring atoms is nitrogen and the group is attached to the rest of the molecule via this nitrogen atom. In such cyclic amino groups, one or more of the remaining ring atoms may be other than carbon, such as nitrogen, sulphur or oxygen. Examples of such cyclic amino groups include piperidine (1-piperidinyl), pyrrolidine (1-pyrrolidinyl), pyrrolidone, morpholine or piperazine.

The term "fused bicyclic" as used herein, refers to bicyclic compounds in which two rings share two adjacent carbon atoms.

It will be appreciated that a chemical group(s) is attached to the rest of the molecule by the atom or group listed first. In some instances, the feature "-" also denotes the attachment of chemical groups to each other, or to the rest of the molecule.

The term "one or more substituents", preferably refers to one or two substituents, more preferably to one substituent.

DETAILED DESCRIPTION

According to a first preferred embodiment of the compound of general formula (II), or a pharmaceutically acceptable salt, hydrate, solvate or ester thereof according to the first aspect of the present invention, there is provided a compound of general formula (III), or a pharmaceutically acceptable salt, hydrate, solvate or ester thereof:

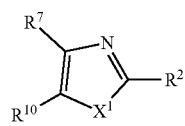

(III)

wherein
$X^1$ is selected from NH or S;
$R^2$ is selected from the group consisting of $NHR^3$, Cl, hydroxyl, —$CH_2NR^5R^6$, COOH and —$CONR^3R^4$;
$R^3$ and $R^4$ are independently selected from the group consisting of hydrogen, and $C_{1-3}$alkyl;
$R^5$ and $R^6$ are independently selected from the group consisting of hydrogen and $C_{1-2}$alkyl;
$R^7$ is selected from the group consisting of phenyl, monocyclic 6-membered nitrogen containing heterocyclyl and monocyclic 6-membered nitrogen containing heteroaryl, wherein the phenyl, 6-membered heterocyclyl and 6-membered heteroaryl groups are optionally substituted with one or more substituents selected from the group consisting of Cl, F, $NH_2$, NHMe, $C_{1-2}$alkyl, $C_{1-2}$alkoxy, $CONR^3R^4$, $OCH_2R^9$, $OCF_3$, $OCH_2CN$, and hydroxyl;
or $R^7$ is a fused bicyclic system selected from the group consisting of any one of:

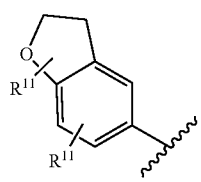

(Ia)

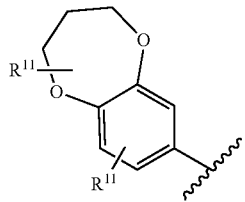

(Ib)

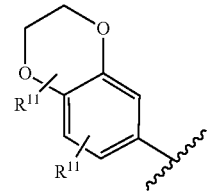

(Ic)

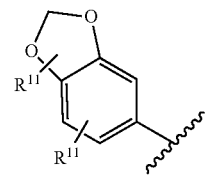

(Id)

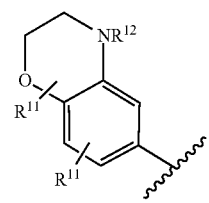

(Ie)

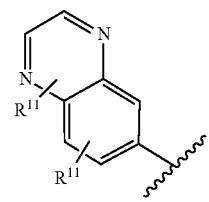

(If)

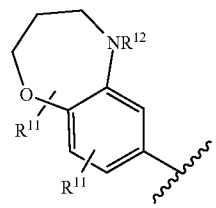

(Ij)

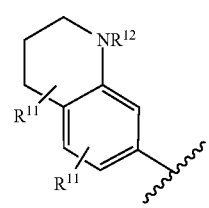

(Ik)

wherein each $R^{11}$ is independently selected from hydrogen, halogen, O (oxo), and $C_{1-4}$alkyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$;

$R^9$ is selected from the group consisting of phenyl optionally substituted with one or more substituents selected from the group consisting of Cl, F, methyl, $NH_2$, NHMe, and OH;

$R^{10}$ is selected from the group consisting of phenyl and monocyclic 6-membered nitrogen containing heteroaryl, and monocyclic 6-membered nitrogen containing heterocyclyl, wherein the phenyl, 6-membered heteroaryl and 6-membered heterocyclyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}{}_4{}^+$);

or $R^{10}$ is a fused bicyclic system selected from the group consisting of:

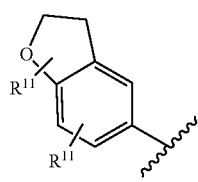

(Ia)

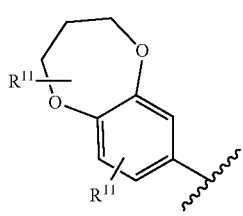

(Ib)

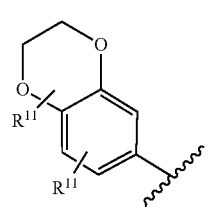

(Ic)

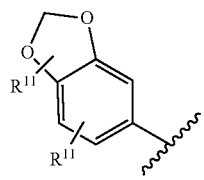

(Id)

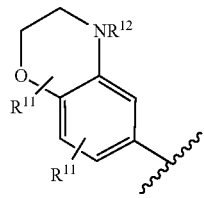

(Ie)

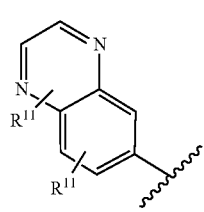

(If)

wherein each $R^{11}$ is independently selected from hydrogen, halogen, and $C_{1-4}$alkyl and $R^{12}$ is selected from hydrogen, and $C_{1-4}$alkyl.

It will be appreciated by a skilled person that for all aspects of the present invention, the group $R^{11}$ is a substituent that may be positioned at one or more positions on the ring to which it relates. Accordingly, each ring to which an $R^{11}$ group relates may have one or more $R^{11}$ groups substituted at different positions on the ring. For example, there may be a single $R^{11}$ group substituted on the ring, or there may be two $R^{11}$ groups substituted on the ring.

According to a further preferred embodiment of the first aspect of the present invention, there is provided a compound of general formula (IV), or a pharmaceutically acceptable salt, hydrate, solvate or ester thereof:

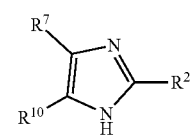

(IV)

wherein $R^2$ is selected from the group consisting of $NHR^3$ or —$CH_2NR^5R^6$;

$R^3$ and $R^4$ are independently selected from the group consisting of hydrogen and $C_{1-3}$alkyl;

$R^5$ and $R^6$ are independently selected from the group consisting of hydrogen and $C_{1-2}$alkyl;

$R^7$ is selected from the group consisting of phenyl, pyridyl, and pyrimidine, wherein the phenyl and pyridyl groups are optionally substituted with one or more substituents selected from the group consisting of Cl, F, $NH_2$, Me, NHMe, methoxy, ethoxy, $CONH_2$, CONHMe, $OCH_2R^9$, $OCF_3$, $OCH_2CN$ and hydroxyl;

or R[7] is a fused bicyclic system selected from the group consisting of:

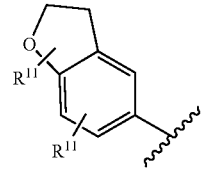 (Ia)

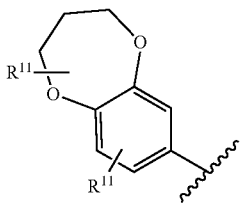 (Ib)

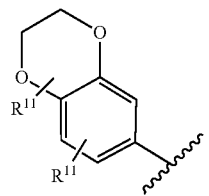 (Ic)

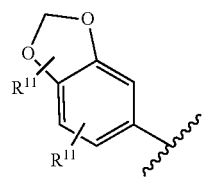 (Id)

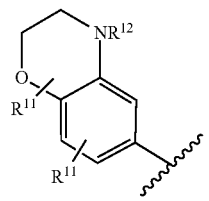 (Ie)

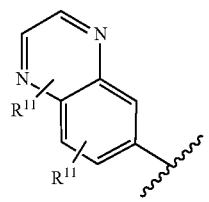 (If)

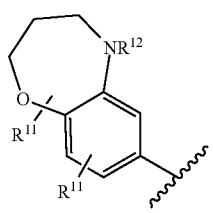 (Ij)

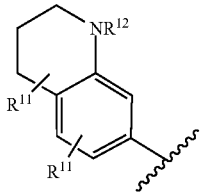 (Ik)

wherein each $R^{11}$ is independently selected from hydrogen, F, O (oxo), methyl and ethyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$;

$R^9$ is selected from the group consisting of phenyl, optionally substituted with F, methyl, $NH_2$ and OH; and $R^{10}$ is selected from the group consisting of phenyl, pyridyl and pyridinone, wherein the phenyl and pyridyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$).

Preferably, $R^2$ is $NH_2$ in any of the preceding embodiments of the first aspect of the present invention.

According to a further preferred embodiment of the first aspect of the present invention, there is provided a compound of general formula (V), or a pharmaceutically acceptable salt, hydrate, solvate or ester thereof:

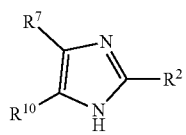 (V)

wherein
$R^2$ is $NH_2$;
$R^7$ is selected from the group consisting of phenyl and pyridyl, wherein the phenyl and pyridyl groups are optionally substituted with one or more substituents selected from the group consisting of Cl, F, $NH_2$, Me, NHMe, methoxy, $CONH_2$, $OCH_2$fluorophenyl and hydroxyl;

or $R^7$ is a fused bicyclic system selected from the group consisting of:

(Ia)
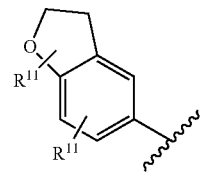

(Ib)
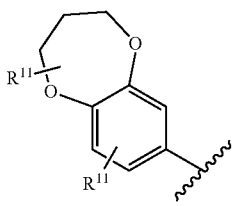

(Ic)
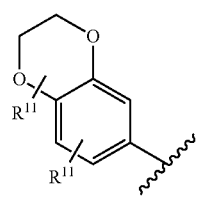

(Id)
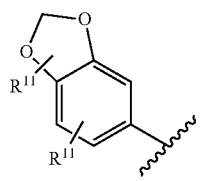

(Ie)
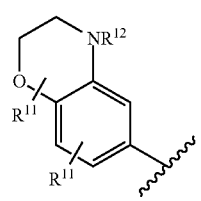

(If)
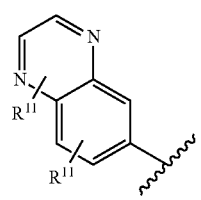

(Ij)
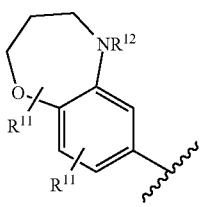

(Ik)
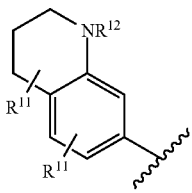

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is selected from the group consisting of phenyl and pyridyl wherein the phenyl and pyridyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$).

According to a further preferred embodiment of the first aspect of the present invention, there is provided a compound of general formula (V), or a pharmaceutically acceptable salt, hydrate, solvate or ester thereof:

(V)
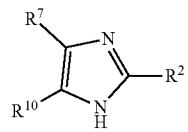

wherein $R^2$ is $NH_2$;
$R^7$ is a fused bicyclic system selected from the group consisting of:

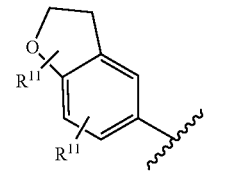
(Ia)

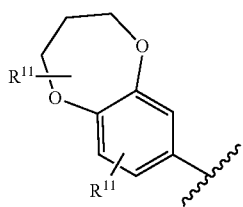
(Ib)

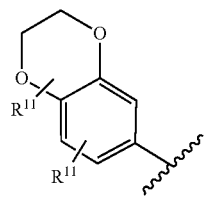
(Ic)

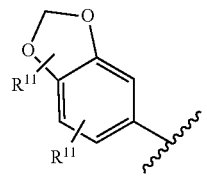
(Id)

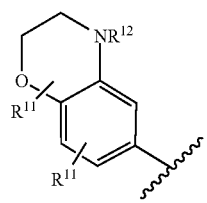
(Ie)

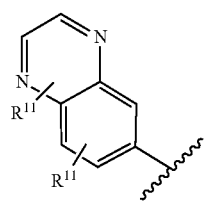
(If)

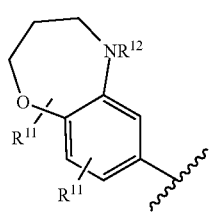
(Ij)

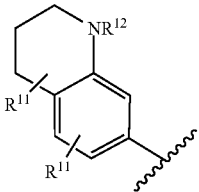
(Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is selected from the group consisting of phenyl and pyridyl, wherein the phenyl and pyridyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$).

Preferably, $R^{10}$ is selected from the group consisting of phenyl and pyridyl, wherein the phenyl and pyridyl groups are optionally substituted with one or more substituents selected from Cl, F, $NH_2$, NHMe, $C_{1-2}$alkyl, $C_{1-2}$alkoxy, $CONH_2$, CONHMe, $CONMe_2$, $OCH_2C_3$cycloalkyl, $OC_3$cycloalkyl, $OCF_3$ and hydroxyl. More preferably, the phenyl and pyridyl groups are optionally substituted with one or more substituents selected from Cl, F, $NH_2$, NHMe and $C_{1-2}$alkyl.

Preferably, $R^7$ is a fused bicyclic system selected from the group consisting of:

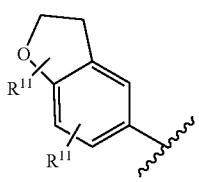
(Ia)

-continued

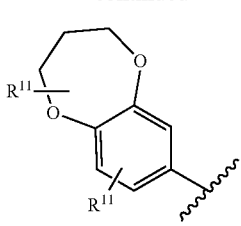 (Ib)

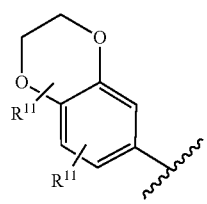 (Ic)

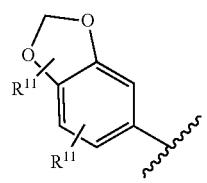 (Id)

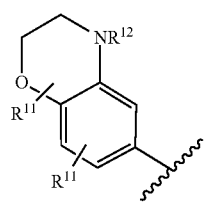 (Ie)

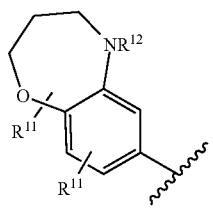 (Ij)

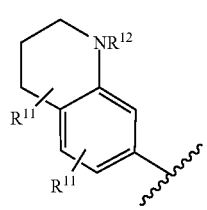 (Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$.

Preferably, $R^{10}$ is a pyridyl group, wherein the pyridyl group is optionally substituted with one or more substituents selected from Cl, F, $NH_2$, NHMe, $C_{1-2}$alkyl, $C_{1-2}$alkoxy, $CONH_2$, CONHMe, $CONMe_2$, $OCH_2C_3$cycloalkyl, $OC_3$cycloalkyl, $OCF_3$ and hydroxyl. More preferably, one or more substituents selected from Cl, F, $NH_2$, NHMe and $C_{1-2}$alkyl.

According to a further preferred embodiment of the first aspect of the present invention, there is provided a compound of general formula (V), or a pharmaceutically acceptable salt, hydrate, solvate or ester thereof:

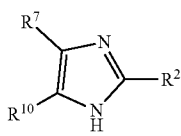 (V)

wherein $R^2$ is $NH_2$;

$R^7$ is

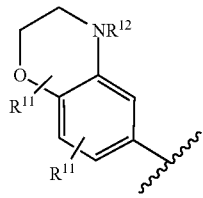 (Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;

$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is a pyridyl group, wherein the pyridyl group is optionally substituted with one or more substituents selected from the group consisting of Cl, F, $NH_2$, and methyl.

According to a further preferred embodiment of the first aspect of the present invention, there is provided a compound of general formula (V), or a pharmaceutically acceptable salt, hydrate, solvate or ester thereof:

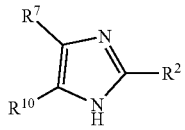
(V)

wherein $R^2$ is $NH_2$;
$R^7$ is

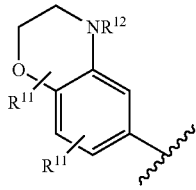
(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;
$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;
$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and
$R^{10}$ is a pyridyl group, wherein the pyridyl group is optionally substituted with methyl.

According to a further preferred embodiment of the first aspect of the present invention, there is provided a compound of general formula (V), or a pharmaceutically acceptable salt, hydrate, solvate or ester thereof:

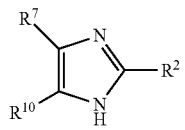
(V)

wherein $R^2$ is $NH_2$;
$R^7$ is

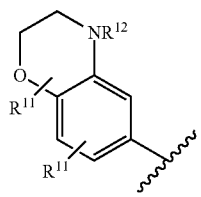
(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;
$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;
$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and
$R^{10}$ is a pyridyl group substituted with methyl, preferably $R^{10}$ is

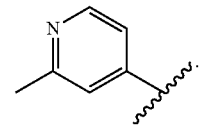

According to a first preferred aspect of the compound of general formula (II), or a pharmaceutically acceptable salt, hydrate, solvate or ester thereof according to the second aspect of the present invention, there is provided a compound, or a pharmaceutically acceptable salt, hydrate, solvate or ester thereof, having the general formula (III):

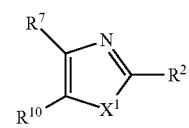
(III)

wherein
$X^1$ is selected from NH or S;
$R^2$ is selected from the group consisting of $NHR^3$, Cl, hydroxyl, —$CH_2NR^5R^6$, COOH and —$CONR^3R^4$;
$R^3$ and $R^4$ are independently selected from the group consisting of hydrogen, and $C_{1-3}$alkyl;
$R^5$ and $R^6$ are independently selected from the group consisting of hydrogen and $C_{1-2}$alkyl;
$R^7$ is selected from the group consisting of phenyl, monocyclic 6-membered nitrogen containing heterocyclyl and monocyclic 6-membered nitrogen containing heteroaryl, wherein the phenyl ring is substituted with one or more substituents selected from the group consisting of NH₂, NHMe, CONR³R⁴, OR⁸, OCF₃, OCH₂CN and hydroxyl, and the 6-membered nitrogen containing heterocyclyl and 6-membered nitrogen containing heteroaryl groups are optionally substituted with one or more substituents selected from the group consisting of Cl, F, NH₂, NHMe, C$_{1-2}$alkyl, C$_{1-2}$alkoxy, CONR³R⁴, OR⁸, OCF₃, OCH₂CN and hydroxyl;

or R⁷ is a fused bicyclic system selected from the group consisting of:

(Ia) 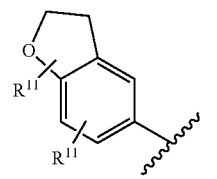

(Ib) 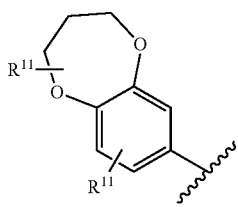

(Ic) 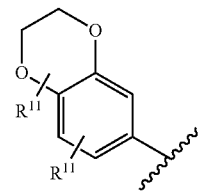

(Id) 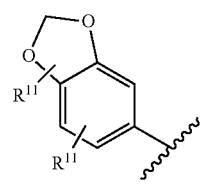

(Ie) 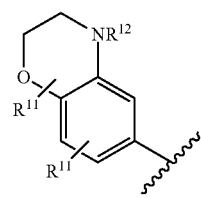

(If) 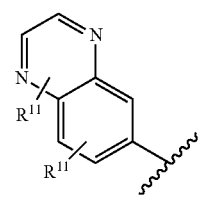

(Ij) 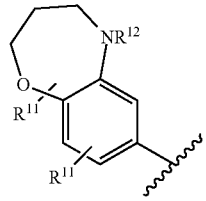

(Ik) 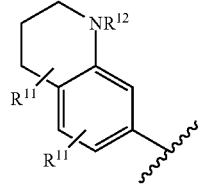

wherein each R¹¹ is independently selected from hydrogen, halogen, O (oxo), and C$_{1-4}$alkyl; and R¹² is selected from hydrogen, C$_{1-4}$alkyl, C$_{3-7}$cycloalkyl, C$_{4-7}$heterocyclyl, COR¹³, SO₂R¹³, C$_{1-4}$alkyl-CO₂R¹⁴, C$_{1-4}$alkyl-OR¹⁴, C$_{1-4}$alkyl-NR¹⁴R¹⁵, C$_{1-4}$alkyl-C$_{3-7}$cycloalkyl, COC$_{1-4}$alkyl-NR¹⁴R¹⁵, an amino acid, and a quaternary ammonium cation (NR¹⁶₄⁺);

R¹³ is selected from C$_{1-4}$alkyl, C$_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, C$_{1-2}$alkyl, O (oxo), S (sulfinyl), NR³R⁴, OR³ and SR³;

R¹⁴ and R¹⁵ are independently selected from hydrogen, C$_{1-4}$alkyl, C$_{1-4}$alkyl-hydroxyl, C$_{3-7}$cycloalkyl, phenyl, monocyclic 5- or 6-membered heteroaryl, and SO₂R¹³, the phenyl or 5- or 6-membered heteroaryl being optionally substituted with one or more substituents selected from the group consisting of halogen, C$_{1-2}$alkyl, O (oxo), S (sulfinyl), NR³R⁴, OR³ and SR³;

R¹⁶ groups are independently selected from C$_{1-4}$alkyl and phenyl, the phenyl being optionally substituted with one or more substituents selected from the group consisting of halogen, C$_{1-2}$alkyl, O (oxo), S (sulfinyl), NR³R⁴, OR³ and SR³;

R⁹ is selected from the group consisting of phenyl optionally substituted with one or more substituents selected from the group consisting of Cl, F, methyl, NH₂, NHMe, and OH;

R¹⁰ is selected from the group consisting of phenyl and monocyclic 6-membered, nitrogen containing heteroaryl, monocyclic 6-membered nitrogen containing heterocyclyl, wherein the phenyl is optionally substituted with one or more substituents selected from the group consisting of C$_{1-4}$alkyl, O (oxo), S (sulfinyl), CONR³R⁴, NR³R⁴, OR⁸, hydroxyl, OCF₃, —CF₃, R⁸, C$_{3-7}$cycloalkyl, C$_{4-7}$heterocyclyl, COR¹³, SO₂R¹³, C$_{1-4}$alkyl-CO₂R¹⁴, C$_{1-4}$alkyl-OR¹⁴, C$_{1-4}$alkyl-NR¹⁴R¹⁵, C$_{1-4}$alkyl-C$_{3-7}$cycloalkyl, COC$_{1-4}$alkyl-NR¹⁴R¹⁵, an amino acid, and a quaternary ammonium cation (NH¹⁶₄⁺), and the 6-membered heteroaryl and 6-membered heterocyclyl groups are optionally substituted with one or more substituents selected from the group consisting of halogen, C$_{1-4}$alkyl, O (oxo), S (sulfinyl), C$_{1-4}$alkoxy, CONR³R⁴, NR³R⁴, OR⁸, hydroxyl, OCF₃, —CF₃, R⁸, C$_{3-7}$cycloalkyl, C$_{4-7}$heterocyclyl, COR¹³, SO₂R¹³, C$_{1-4}$alkyl-CO₂R¹⁴, C$_{1-4}$alkyl-OR¹⁴, C$_{1-4}$alkyl-NR¹⁴R¹⁵, C$_{1-4}$alkyl-C$_{3-7}$cycloalkyl, COC$_{1-4}$alkyl-NR¹⁴R¹⁵, an amino acid, and a quaternary ammonium cation (NH¹⁶₄⁺);

or $R^{10}$ is a fused bicyclic system selected from the group consisting of:

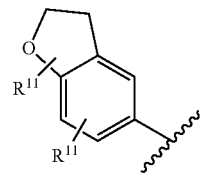
(Ia)

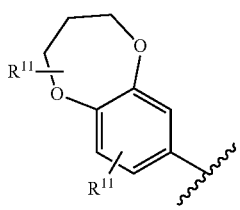
(Ib)

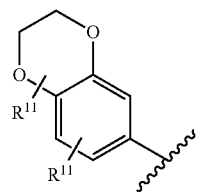
(Ic)

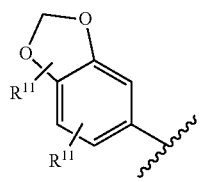
(Id)

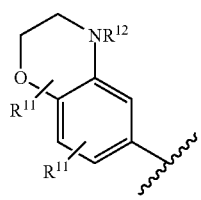
(Ie)

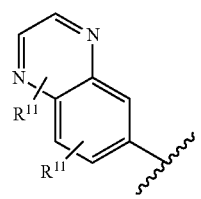
(If)

wherein each $R^{11}$ is independently selected from hydrogen, halogen, and $C_{1-4}$alkyl and $R^{12}$ is selected from hydrogen, and $C_{1-4}$alkyl.

According to a further preferred embodiment of the second aspect of the present invention, there is provided a compound, or a pharmaceutically acceptable salt, hydrate, solvate or ester thereof, having the general formula (IV):

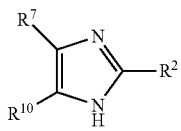
(IV)

wherein $R^2$ is selected from the group consisting of $NHR^3$ or $-CH_2NR^5R^6$;

$R^3$ and $R^4$ are independently selected from the group consisting of hydrogen, and $C_{1-3}$alkyl;

$R^5$ and $R^6$ are independently selected from the group consisting of hydrogen and $C_{1-2}$alkyl;

$R^7$ is selected from the group consisting of phenyl, pyridyl, and pyrimidine, wherein the phenyl group is substituted with one or more substituents selected from the group consisting of $NH_2$, NHMe, $CONH_2$, CONHMe, $OCH_2R^9$, $OCF_3$, $OCH_2CN$, and hydroxyl, and the pyridyl group is optionally substituted with one or more substituents selected from the group consisting of Cl, F, $NH_2$, Me, NHMe, methoxy, ethoxy, $CONH_2$, CONHMe, $OCH_2R^9$, $OCF_3$, $OCH_2CN$;

or $R^7$ is a fused bicyclic system selected from the group consisting of:

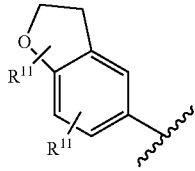
(Ia)

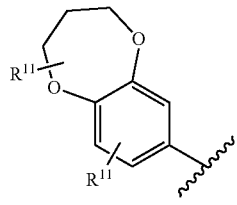
(Ib)

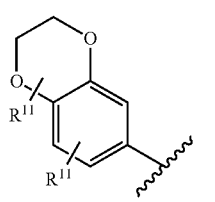
(Ic)

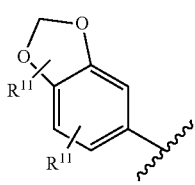
(Id)

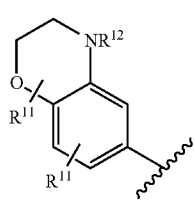
(Ie)

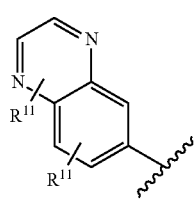 (If)

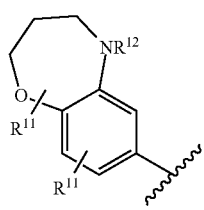 (Ij)

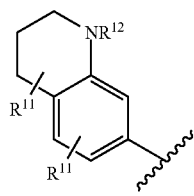 (Ik)

wherein each $R^{11}$ is independently selected from hydrogen, F, O (oxo), methyl and ethyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-4}$alkyl, O (oxo), S (sulfinyl), $NR^3R^4$, $OR^3$ and $SR^3$;

$R^9$ is selected from the group consisting of phenyl optionally substituted with F, methyl, $NH_2$ and OH; and $R^{10}$ is selected from the group consisting of phenyl, pyridyl and pyridinone, wherein the phenyl is optionally substituted with one or more substituents selected from the group consisting of $C_{1-4}$alkyl, O (oxo), S (sulfinyl), $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$), and the pyridyl is optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$).

Preferably, $R^2$ is $NH_2$ in the above preferred embodiments of the second aspect of the present invention.

According to a further preferred embodiment of the second aspect of the present invention, there is provided a compound, or a pharmaceutically acceptable salt, hydrate, solvate or ester thereof, having the general formula (V):

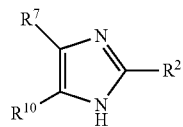 (V)

wherein $R^2$ is $NH_2$;

$R^7$ is selected from the group consisting of phenyl and pyridyl, wherein the phenyl group is substituted with one or more substituents selected from the group consisting of $NH_2$, NHMe, $CONH_2$, $OCH_2$fluorophenyl and hydroxyl, and the pyridyl group is optionally substituted with one or more substituents selected from the group consisting of Cl, F, $NH_2$, Me, NHMe, methoxy, $CONH_2$, $OCH_2$fluorophenyl and hydroxyl;

or $R^7$ is a fused bicyclic system selected from the group consisting of:

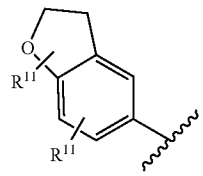 (Ia)

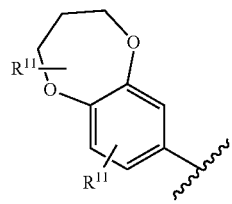 (Ib)

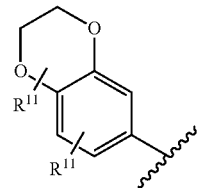 (Ic)

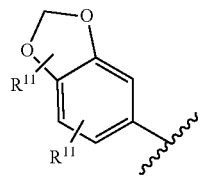 (Id)

-continued

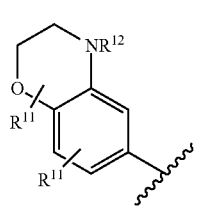
(Ie)

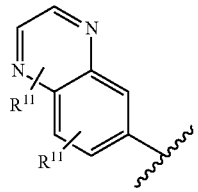
(If)

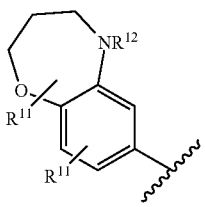
(Ij)

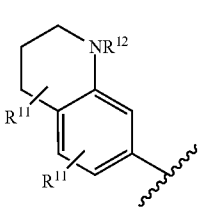
(Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$hydroxyl, $COC_{1-4}$alkyl-$NR^{14}R^{15}$, an amino acid, and a quaternary ammonium cation ($NH^{16}{}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is selected from the group consisting of phenyl and pyridyl, wherein the phenyl is optionally substituted with one or more substituents selected from the group consisting of $C_{1-4}$alkyl, O (oxo), S (sulfinyl), $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}{}_4{}^+$), and the pyridyl is are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}{}_4{}^+$).

According to a further preferred embodiment of the second aspect of the present invention, there is provided a compound or a pharmaceutically acceptable salt, hydrate, solvate or ester thereof, having the general formula (V):

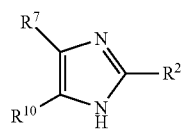
(V)

wherein $R^2$ is $NH_2$;

$R^7$ is a fused bicyclic system selected from the group consisting of:

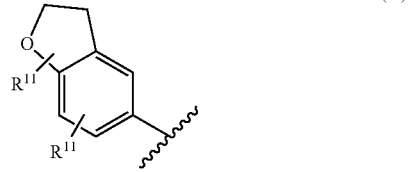
(Ia)

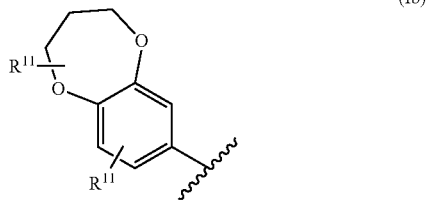
(Ib)

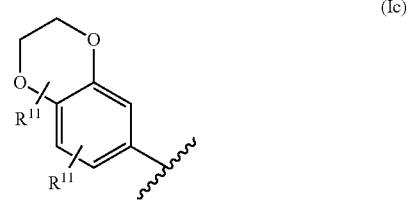
(Ic)

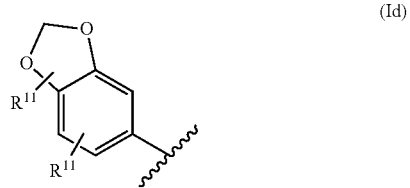
(Id)

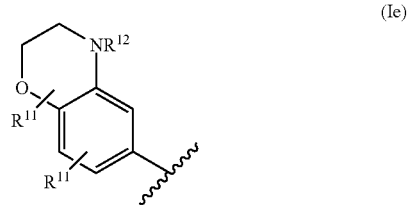
(Ie)

-continued

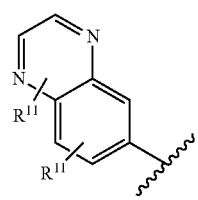
(If)

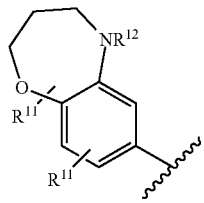
(Ij)

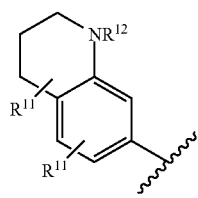
(Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation $(NR^{16}_4{}^+)$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is selected from the group consisting of phenyl and pyridyl, wherein the phenyl is optionally substituted with one or more substituents selected from the group consisting of $C_{1-4}$alkyl, O (oxo), S (sulfinyl), $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation $(NH^{16}_4{}^+)$, and the pyridyl is are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_3$_cycloalkyl, $COC_{1-4}$alkyl-$NR^{14}R^{15}$, an amino acid, and a quaternary ammonium cation $(NH^{16}_4{}^+)$.

Preferably, $R^{10}$ is selected from the group consisting of phenyl and pyridyl, wherein the phenyl is optionally substituted with one or more substituents selected from $NH_2$, NHMe, $C_{1-2}$alkyl, $CONH_2$, CONHMe, $CONMe_2$, $OCH_2C_3$cycloalkyl, $OC_3$cycloalkyl, $OCF_3$ and hydroxyl, and the pyridyl is optionally substituted with one or more substituents selected from Cl, F, $NH_2$, NHMe, $C_{1-2}$alkyl, $C_{1-2}$alkoxy, $CONH_2$, CONHMe, $CONMe_2$, $OCH_2C_3$cycloalkyl, $OC_3$cycloalkyl, $OCF_3$ and hydroxyl. More preferably, the phenyl is optionally substituted with one or more substituents selected from $NH_2$, Me and $C_{1-2}$alkyl, and the pyridyl is optionally substituted with one or more substituents selected from Cl, F, $NH_2$, NHMe and $C_{1-2}$alkyl.

Preferably, $R^7$ is a fused bicyclic system selected from the group consisting of:

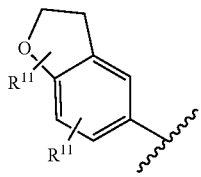
(Ia)

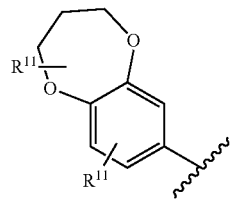
(Ib)

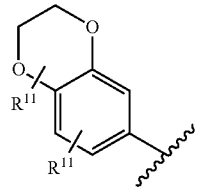
(Ic)

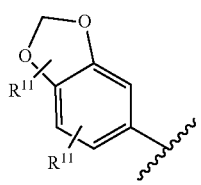
(Id)

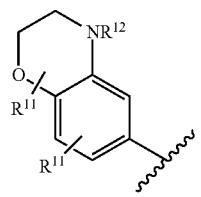
(Ie)

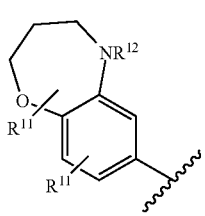
(Ij)

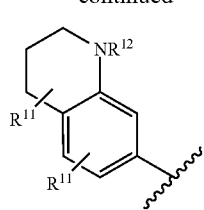
(Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$.

Preferably, $R^{10}$ is pyridyl optionally substituted with one or more substituents selected from Cl, F, $NH_2$, NHMe, $C_{1-2}$alkyl, $C_{1-2}$alkoxy, $CONH_2$, CONHMe, $CONMe_2$, $OCH_2C_3$cycloalkyl, $OC_3$cycloalkyl, $OCF_3$ and hydroxyl. More preferably, the pyridyl is optionally substituted with one or more substituents selected from Cl, F, $NH_2$, NHMe and $C_{1-2}$alkyl.

According to a further preferred embodiment of the second aspect of the present invention, there is provided a compound or a pharmaceutically acceptable salt, hydrate, solvate or ester thereof, having the general formula (V):

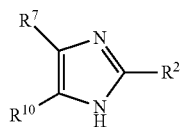
(V)

wherein $R^2$ is $NH_2$;
$R^7$ is

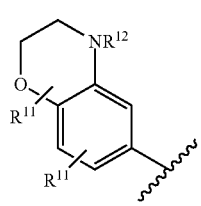
(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;

$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is a pyridyl group, wherein the pyridyl group is optionally substituted with one or more substituents selected from the group consisting of Cl, F, $NH_2$, and methyl.

According to a further preferred embodiment of the second aspect of the present invention, there is provided a compound, or a pharmaceutically acceptable salt, hydrate, solvate or ester thereof, having the general formula (V):

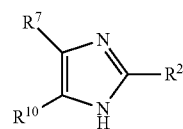
(V)

wherein $R^2$ is $NH_2$;
$R^7$ is

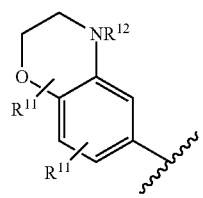
(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;

$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is a pyridyl group, wherein the pyridyl group is optionally substituted with methyl.

According to a further preferred embodiment of the second aspect of the present invention, there is provided a compound of general formula (V), or a pharmaceutically acceptable salt, hydrate, solvate or ester thereof:

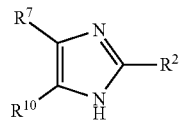
(V)

wherein $R^2$ is $NH_2$;
$R^7$ is

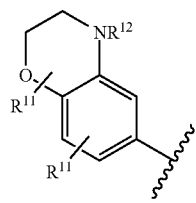
(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;
$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;
$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and
$R^{10}$ is a pyridyl group substituted with methyl, preferably $R^{10}$ is

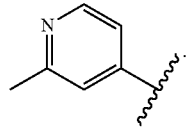

According to a first embodiment of the compound of general formula (II), or a pharmaceutically acceptable salt, hydrate, solvate or ester thereof for use in the treatment of infection with, or disease caused by the bacterium Enterobacteriaceae according to a further aspect of the present invention, there is provided a compound, or a pharmaceutically acceptable salt, hydrate, solvate or ester thereof, having the general formula (III):

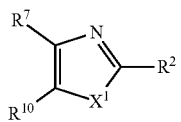
(III)

wherein
$X^1$ is selected from NH or S;
$R^2$ is selected from the group consisting of $NHR^3$, Cl, hydroxyl, —$CH_2NR^5R^6$, COOH and —$CONR^3R^4$;
$R^3$ and $R^4$ are independently selected from the group consisting of hydrogen, and $C_{1-3}$alkyl;
$R^5$ and $R^6$ are independently selected from the group consisting of hydrogen and $C_{1-2}$alkyl;
$R^7$ is selected from the group consisting of phenyl, monocyclic 6-membered nitrogen containing heterocyclyl and monocyclic 6-membered nitrogen containing heteroaryl, wherein the phenyl, 6-membered heterocyclyl and 6-membered heteroaryl groups are optionally substituted with one or more substituents selected from the group consisting of Cl, F, $NH_2$, NHMe, $C_{1-2}$alkyl, $C_{1-2}$alkoxy, $CONR^3R^4$, $OCH_2R^9$, $OCF_3$, $OCH_2CN$, and hydroxyl;
or $R^7$ is a fused bicyclic system selected from the group consisting of:

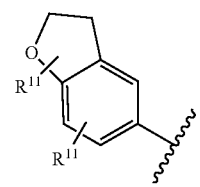
(Ia)

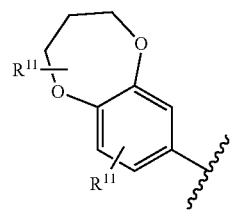
(Ib)

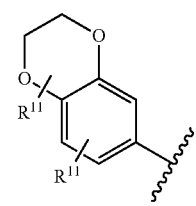
(Ic)

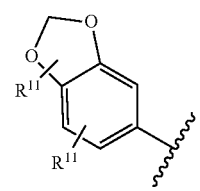
(Id)

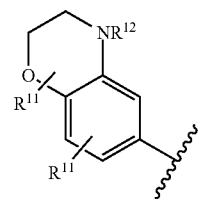
(Ie)

-continued

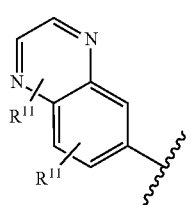
(If)

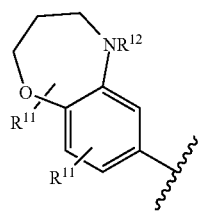
(Ij)

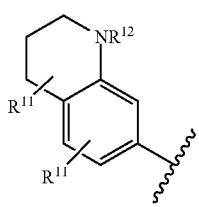
(Ik)

wherein each $R^{11}$ is independently selected from hydrogen, halogen, O (oxo), and $C_{1-4}$alkyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$;

$R^9$ is selected from the group consisting of phenyl optionally substituted with one or more substituents selected from the group consisting of Cl, F, methyl, $NH_2$, NHMe, and OH;

$R^{10}$ is selected from the group consisting of phenyl and monocyclic 6-membered, nitrogen containing heteroaryl and monocyclic 6-membered nitrogen containing heterocyclyl, wherein the phenyl, 6-membered heteroaryl and 6-membered heterocyclyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$);

or $R^{10}$ is a fused bicyclic system selected from the group consisting of:

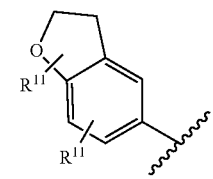
(Ia)

(Ib)

(Ic)

(Id)

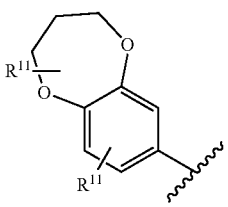

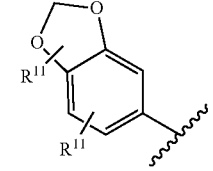
(Ie)

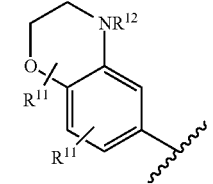
(If)

wherein each $R^{11}$ is independently selected from hydrogen, halogen, and $C_{1-4}$alkyl and $R^{12}$ is selected from hydrogen, and $C_{1-4}$alkyl.

According to a further preferred embodiment of the further aspect of the present invention, there is provided a compound, or a pharmaceutically acceptable salt, hydrate, solvate or ester thereof, having the general formula (IV):

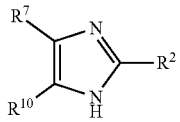
(IV)

wherein $R^2$ is selected from the group consisting of $NHR^3$ or $—CH_2NR^5R^6$;

$R^3$ and $R^4$ are independently selected from the group consisting of hydrogen, and $C_{1-3}$alkyl;

$R^5$ and $R^6$ are independently selected from the group consisting of hydrogen and $C_{1-2}$alkyl;

$R^7$ is selected from the group consisting of phenyl, pyridyl, and pyrimidine, wherein the phenyl and pyridyl groups are optionally substituted with one or more substituents selected from the group consisting of Cl, F, $NH_2$, Me, NHMe, methoxy, ethoxy, $CONH_2$, CONHMe, $OCH_2R^9$, $OCF_3$, $OCH_2CN$, and hydroxyl;

or $R^7$ is a fused bicyclic system selected from the group consisting of:

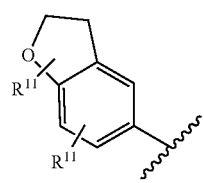
(Ia)

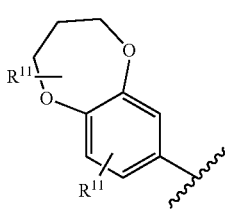
(Ib)

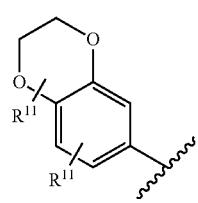
(Ic)

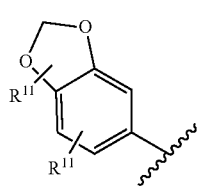
(Id)

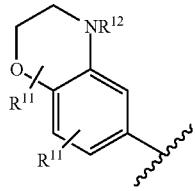
(Ie)

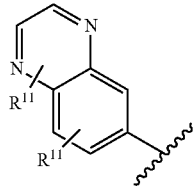
(If)

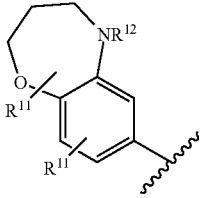
(Ij)

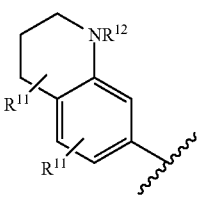
(Ik)

wherein each $R^{11}$ is independently selected from hydrogen, F, O (oxo), methyl and ethyl; and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$ $R^9$ is selected from the group consisting of phenyl, optionally substituted with F, methyl, $NH_2$ and OH; and $R^{10}$ is selected from the group consisting of phenyl, pyridyl and pyridinone, wherein the phenyl and pyridyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, OCF$_3$, —CF$_3$, R$^8$, C$_{3-7}$cycloalkyl, C$_{4-7}$heterocyclyl, COR$^{13}$, SO$_2$R$^{13}$, C$_{1-4}$alkyl-CO$_2$R$^{14}$, C$_{1-4}$alkyl-OR$^{14}$, C$_{1-4}$alkyl-NR$^{14}$R$^{15}$, C$_{1-4}$alkyl-C$_{3-7}$cycloalkyl, COC$_{1-4}$alkyl-NR$^{14}$R$^{15}$, an amino acid, and a quaternary ammonium cation (NH$^{16}_4{}^+$).

Preferably, R$^2$ is NH$_2$ in the above preferred embodiments of the further aspect of the present invention.

According to a further preferred embodiment of the further aspect of the present invention, there is provided a compound, or a pharmaceutically acceptable salt, hydrate, solvate or ester thereof, having the general formula (V):

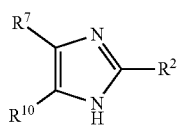

(V)

wherein

R$^2$ is NH$_2$;

R$^7$ is selected from the group consisting of phenyl and pyridyl, wherein the phenyl and pyridyl groups are optionally substituted with one or more substituents selected from the group consisting of Cl, F, NH$_2$, Me, NHMe, methoxy, CONH$_2$, OCH$_2$fluorophenyl and hydroxyl;

or R$^7$ is a fused bicyclic system selected from the group consisting of:

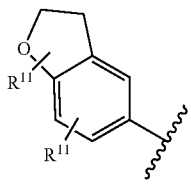
(Ia)

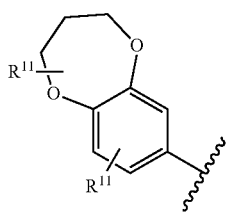
(Ib)

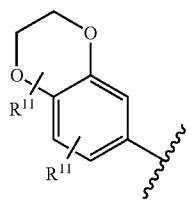
(Ic)

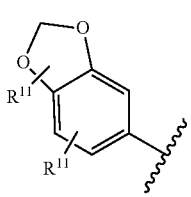
(Id)

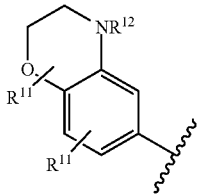
(Ie)

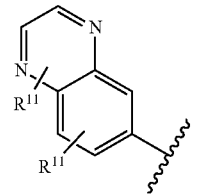
(If)

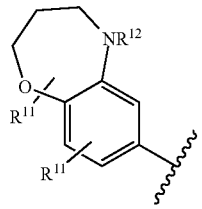
(Ij)

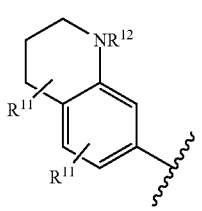
(Ik)

wherein each R$^{11}$ is hydrogen and R$^{12}$ is selected from hydrogen, C$_{1-4}$alkyl, C$_{3-7}$cycloalkyl, C$_{4-7}$heterocyclyl, COR$^{13}$, SO$_2$R$^{13}$, C$_{1-4}$alkyl-CO$_2$R$^{14}$, C$_{1-4}$alkyl-OR$^{14}$, C$_{1-4}$alky-NR$^{14}$R$^{15}$, C$_{1-4}$alkyl-C$_{3-7}$cycloalkyl, COC$_{1-4}$alkyl-NR$^{14}$R$^{15}$, an amino acid, and a quaternary ammonium cation (NR$^{16}_4{}^+$);

R$^{13}$ is selected from C$_{1-4}$alkyl, C$_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;

R$^{14}$ and R$^{15}$ are independently selected from hydrogen, C$_{1-4}$alkyl, C$_{1-4}$alkyl-hydroxyl, C$_{3-7}$cycloalkyl, phenyl, monocyclic 5- or 6-membered heteroaryl, and SO$_2$R$^{13}$, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;

R$^{16}$ groups are independently selected from C$_{1-4}$alkyl and phenyl, the phenyl being optionally substituted with one or more substituents selected from the group consisting of halogen, C$_{1-2}$alkyl, O (oxo), S (sulfinyl), NR$^3$R$^4$, OR$^3$ and SR$^3$; and R$^{10}$ is selected from the group consisting of phenyl and pyridyl, wherein the phenyl and pyridyl groups are optionally substituted with one or more substituents selected from the group consisting of halogen, C$_{1-4}$alkyl, O (oxo), S (sulfinyl), C$_{1-4}$alkoxy, CONR$^3$R$^4$, NR$^3$R$^4$, OR$^8$, hydroxyl, OCF$_3$, —CF$_3$, R$^8$, C$_{3-7}$cycloalkyl, C$_{4-7}$heterocyclyl, COR$^{13}$, SO$_2$R$^{13}$, C$_{1-4}$alkyl-CO$_2$R$^{14}$, C$_{1-4}$alkyl-OR$^{14}$, C$_{1-4}$alkyl- $NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$).

According to a further preferred embodiment of the further aspect of the present invention, there is provided a compound, or a pharmaceutically acceptable salt, hydrate, solvate or ester thereof, having the general formula (V):

(V)

wherein $R^2$ is $NH_2$;

$R^7$ is a fused bicyclic system selected from the group consisting of:

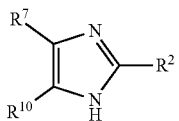
(Ia)

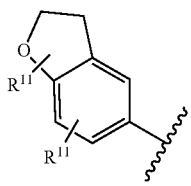
(Ib)

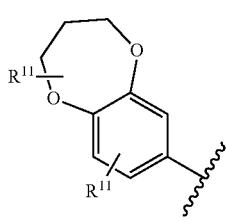
(Ic)

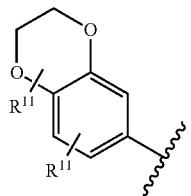
(Id)

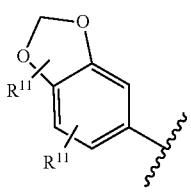
(Ie)

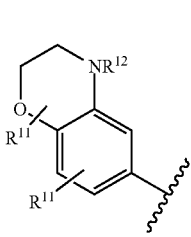

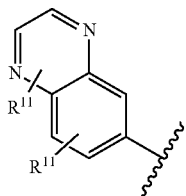
(If)

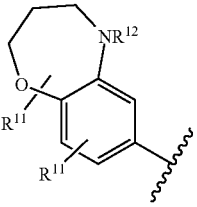
(Ij)

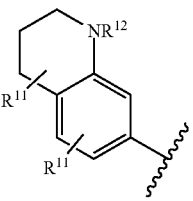
(Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is selected from the group consisting of phenyl and pyridyl, wherein the phenyl and pyridyl groups are optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NH^{16}_4{}^+$).

Preferably, $R^{10}$ is selected from the group consisting of phenyl and pyridyl, wherein the phenyl and pyridyl groups are optionally substituted with one or more substituents selected from Cl, F, $NH_2$, NHMe, $C_{1-2}$alkyl, $C_{1-2}$alkoxy, $CONH_2$, CONHMe, $CONMe_2$, $OCH_2C_3$cycloalkyl, OC₃cycloalkyl, OCF₃ and hydroxyl. More preferably, the phenyl and pyridyl groups are optionally substituted with one or more substituents selected from Cl, F, NH$_2$, NHMe and C$_{1-2}$alkyl.

Preferably, R$^7$ is a fused bicyclic system selected from the group consisting of:

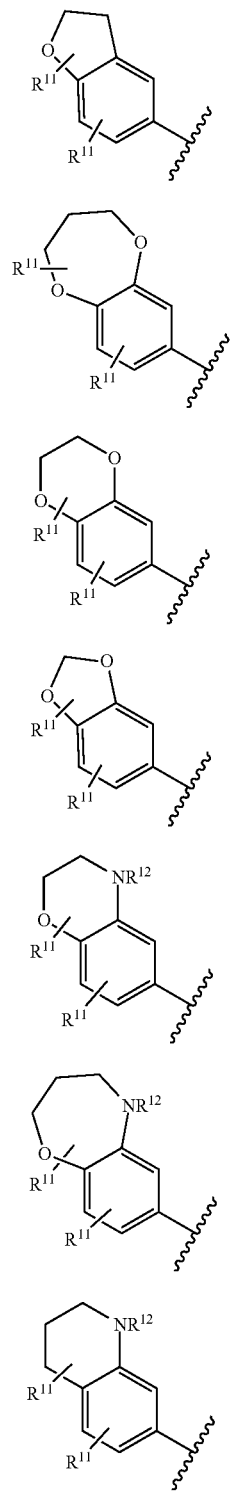

wherein each R$^{11}$ is hydrogen and R$^{12}$ is selected from hydrogen, C$_{1-4}$alkyl, C$_{3-7}$cycloalkyl, C$_{4-7}$heterocyclyl, COR$^{13}$, SO$_2$R$^{13}$, C$_{1-4}$alkyl-CO$_2$R$^{14}$, C$_{1-4}$alkyl-OR$^{14}$, C$_{1-4}$alky-NR$^{14}$R$^{15}$, C$_{1-4}$alkyl-C$_{3-7}$cycloalkyl, COC$_{1-4}$alkyl-NR$^{14}$R$^{15}$, an amino acid, and a quaternary ammonium cation (NR$^{16}{}_4{}^+$);

R$^{13}$ is selected from C$_{1-4}$alkyl, C$_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;

R$^{14}$ and R$^{15}$ are independently selected from hydrogen, C$_{1-4}$alkyl, C$_{1-4}$alkyl-hydroxyl, C$_{3-7}$cycloalkyl, phenyl, monocyclic 5- or 6-membered heteroaryl, and SO$_2$R$^{13}$, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;

R$^{16}$ groups are independently selected from C$_{1-4}$alkyl and phenyl, the phenyl being optionally substituted with one or more substituents selected from the group consisting of halogen, C$_{1-2}$alkyl, O (oxo), S (sulfinyl), NR$^3$R$^4$, OR$^3$ and SR$^3$.

Preferably, R$^{10}$ is pyridyl optionally substituted with one or more substituents selected from Cl, F, NH$_2$, NHMe, C$_{1-2}$alkyl, C$_{1-2}$alkoxy, CONH$_2$, CONHMe, CONMe$_2$, OCH$_2$C$_3$cycloalkyl, OC$_3$cycloalkyl, OCF$_3$ and hydroxyl. More preferably, the pyridyl is optionally substituted with one or more substituents selected from Cl, F, NH$_2$, NHMe and C$_{1-2}$alkyl.

According to a further preferred embodiment of the further aspect of the present invention, there is provided a compound, or a pharmaceutically acceptable salt, hydrate, solvate or ester thereof, having the general formula (V):

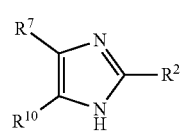

wherein R$^2$ is NH$_2$;
R$^7$ is

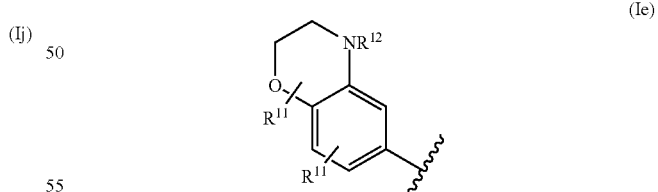

and each R$^{11}$ is hydrogen and R$^{12}$ is selected from hydrogen, C$_{1-4}$alkyl, C$_{3-7}$cycloalkyl, C$_{1-4}$alkyl-CO$_2$R$^{14}$, C$_{1-4}$alkyl-OR$^{14}$ and C$_{1-4}$alky-NR$^{14}$R$^{15}$;

R$^{14}$ and R$^{15}$ are independently selected from hydrogen, C$_{1-4}$alkyl, C$_{3-7}$cycloalkyl, phenyl, monocyclic 5- or 6-membered heteroaryl, and SO$_2$R$^{13}$, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is a pyridyl group, wherein the pyridyl group is optionally substituted with one or more substituents selected from the group consisting of Cl, F, $NH_2$, and methyl.

According to a further preferred embodiment of the further aspect of the present invention, there is provided a compound, or a pharmaceutically acceptable salt, hydrate, solvate or ester thereof, having the general formula (V):

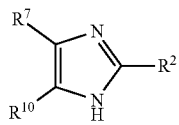

(V)

wherein $R^2$ is $NH_2$;
$R^7$ is

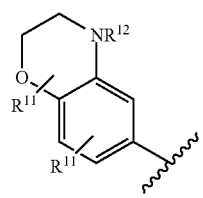

(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;

$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is a pyridyl group, wherein the pyridyl group is optionally substituted with methyl.

According to a further preferred embodiment of the further aspect of the present invention, there is provided a compound of general formula (V), or a pharmaceutically acceptable salt, hydrate, solvate or ester thereof:

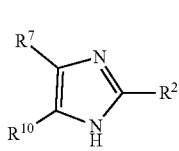

(V)

wherein $R^2$ is $NH_2$;
$R^7$ is

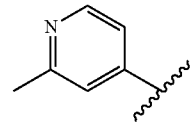

(Ie)

and each $R^{11}$ is hydrogen and $R^{12}$ is selected from hydrogen, $C_{1-4}$alkyl, $C_{3-7}$cycloalkyl, $C_{1-4}$alkyl-$CO_2R^{14}$, $C_{1-4}$alkyl-$OR^{14}$ and $C_{1-4}$alky-$NR^{14}R^{15}$;

$R^{14}$ and $R^{15}$ are independently selected from hydrogen, $C_{1-4}$alkyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is a pyridyl group substituted with methyl, preferably $R^{10}$ is Medical Uses, Methods of Treatment and Pharmaceutical Formulations The compounds of general formula (I), (II), (III), (IV) and (V), or pharmaceutically acceptable salts, hydrates, solvates or esters thereof, may be used in the treatment of bacterial infections and diseases caused by Enterobacteriaceae. Thus, the invention contemplates the compounds as described herein for use in medicine (e.g. for use in treatment or prophylaxis), methods of medical treatment or prophylaxis involving the administration of the compounds as described herein as well as pharmaceutical compositions comprising the compounds as described herein The compounds of general formula (I), (II), (III), (IV) and (V), or pharmaceutically acceptable salts, hydrates, solvates or esters thereof, may have bacteriostatic or bactericidal activity against Enterobacteriaceae.

The compounds of general formula (I), (II), (III), (IV) and (V), or a pharmaceutically acceptable salts, hydrates, solvates or esters thereof may target one or more bacteria of the following Enterobacteriaceae genera: *Arsenophonus, Brenneria, Buchnera, Budvicia, Buttiauxella, Cedecea, Citrobacter, Cosenzaea, Cronobacter, Dickeya, Edwardsiella, Enterobacillus, Enterobacter, Erwinia, Escherichia, Ewingella, Franconibacter, Gibbsiella, Hafnia, Izhakiella, Kosakonia, Klebsiella, Kluyvera, Leclercia, Lelliottia, Leminorella, Levinea, Lonsdalea, Mangrovibacter, Moellerella, Morganella, Obesumbacterium, Pantoea, Pectobacterium,*

*Phaseolibacter, Photorhabdus, Plesiomonas, Pluralibacter, Pragia, Proteus, Providencia, Pseudocitrobacter, Rahnella, Raoultella, Rosenbergiella, Rouxiella, Saccharobacter, Salmonella, Samsonia, Serratia, Shigella, Shimwellia, Siccibacter, Sodalis, Tatumella, Thorsellia, Trabulsiella, Wigglesworthia, Xenorhabdus, Yersinia* and *Yokenella*.

The compounds of general formula (I), (II), (III), (IV) and (V), or pharmaceutically acceptable salts, hydrates, solvates or esters thereof, are particularly effective at treating infections caused by Enterobacteriaceae.

Preferably, the compounds of general formula (I), (II), (III), (IV) and (V), or a pharmaceutically acceptable salts, hydrates, solvates or esters thereof, may be used to treat infections caused by Enterobacteriaceae which are in the form of a biofilm.

Preferably, the compounds of general formula (I), (II), (III), (IV) and (V), or a pharmaceutically acceptable salts, hydrates, solvates or esters thereof, may also be used in treating other conditions treatable by eliminating or reducing a Enterobacteriaceae infection. In this case they will act in a secondary manner alongside for example a chemotherapeutic agent used in the treatment of cancer.

Preferably, the compounds of general formula (I), (II), (III), (IV) and (V), or a pharmaceutically acceptable salts, hydrates, solvates or esters thereof, can be used in the treatment of the human body. They may be used in the treatment of the animal body. In particular, the compounds of general formula (I), (II), (III), (IV) and (V), or pharmaceutically acceptable salts, hydrates, solvates or esters thereof, can be used to treat commercial animals such as livestock. Alternatively, the compounds of general formula (I), (II), (III), (IV) and (V), or pharmaceutically acceptable salts, hydrates, solvates or esters thereof, can be used to treat companion animals such as cats, dogs, etc.

The Enterobactericeae disease or infection may involve intoxication with one or more bacterial toxins, including for example endotoxins, exotoxins and/or toxic enzymes. Thus, the compounds of general formula (I), (II), (III), (IV) and (V), or pharmaceutically acceptable salts, hydrates, solvates or esters thereof, find application in the treatment of Enterobacteriaceae intoxication. In such embodiments, preferred is the treatment of intoxication with bacterial endotoxins, exotoxins and/or toxic enzymes, for example with endotoxins, exotoxins and/or toxic enzymes produced by Enterobacteriaceae.

Preferably, for the compounds of general formula (I), (II), (III), (IV) and (V), or a pharmaceutically acceptable salts, hydrates, solvates or esters thereof, the dosage administered will, of course, vary with the compound employed, the mode of administration, the treatment desired and the disorder indicated. For example, if the compound of general formula (I), (II), (III), (IV) and (V), or pharmaceutically acceptable salts, hydrates, solvates or esters thereof, is administered orally, then the daily dosage of the compound of the invention may be in the range from 0.01 micrograms per kilogram body weight (μg/kg) to 100 milligrams per kilogram body weight (mg/kg).

The size of the dose for therapeutic purposes of compounds of general formula (I), (II), (III), (IV) and (V), or pharmaceutically acceptable salts, hydrates, solvates or esters thereof will naturally vary according to the nature and severity of the conditions, the age and sex of the animal or patient and the route of administration, according to well-known principles of medicine.

Dosage levels, dose frequency, and treatment durations of compounds of general formula (I), (II), (III), (IV) and (V), or pharmaceutically acceptable salts, hydrates, solvates or esters thereof are expected to differ depending on the formulation and clinical indication, age, and co-morbid medical conditions of the patient. The standard duration of treatment with compounds of general formula (I), (II), (III), (IV) and (V), or pharmaceutically acceptable salts, hydrates, solvates or esters thereof is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

Preferably, the compounds of general formula (I), (II), (III), (IV) and (V), or a pharmaceutically acceptable salts, hydrates, solvates or esters thereof, may take any form. It may be synthetic, purified or isolated from natural sources using techniques described in the art.

The compounds of general formula (I), (II), (III), (IV) and (V) may be obtained, stored and/or administered in the form of a pharmaceutically acceptable salt. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically-acceptable base addition salts include metallic ion salts and organic ion salts. Metallic ion salts include, but are not limited to, appropriate alkali metal (group Ia) salts, alkaline earth metal (group IIa) salts and other physiologically acceptable metal ions. Such salts can be made from the ions of aluminium, calcium, lithium, magnesium, potassium, sodium and zinc. Organic salts can be made from tertiary amines and quaternary ammonium salts, including in part, trimethylamine, diethylamine, N, N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound. Conventional procedures for the selection and preparation of suitable pharmaceutical formulations are described in, for example, "Pharmaceuticals—The Science of Dosage Form Designs", M. E. Aulton, Churchill Livingstone, 1988.

Preferably, the compounds of general formula (I), (II), (III), (IV) and (V), or a pharmaceutically acceptable salts, hydrates, solvates or esters thereof, are formulated as a pharmaceutical composition, comprising a pharmaceutically acceptable carrier.

Pharmaceutical compositions can include stabilizers, antioxidants, colorants and diluents. Pharmaceutically acceptable carriers and additives are chosen such that side effects from the pharmaceutical compound are minimized and the performance of the compound is not compromised to such an extent that treatment is ineffective.

The pharmaceutical compositions may be administered enterally and/or parenterally. Oral (intra-gastric) is a typical route of administration. Pharmaceutically acceptable carriers can be in solid dosage forms, including tablets, capsules, pills and granules, which can be prepared with coatings and shells, such as enteric coatings and others well known in the art. Liquid dosage forms for oral administration include pharmaceutically acceptable emulsions, solutions, suspensions, syrups and elixirs. Parenteral administration includes subcutaneous, intramuscular, intradermal, intravenous, and other routes known in the art. Enteral administration includes solution, tablets, sustained release capsules, enteric coated capsules, and syrups. When administered, the pharmaceutical composition can be at or near body temperature.

Compositions intended for oral use can be prepared according to any method known in the art for the manufacture of pharmaceutical compositions and such compositions can contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc. Tablets can be uncoated or they can be coated by known techniques, for example to delay disintegration and absorption in the gastrointestinal tract and thereby provide sustained action over a longer period. For example, a time delay material such as glyceryl monostearate or glyceryl distearate can be employed. Formulations for oral use can also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin or olive oil.

Aqueous suspensions can be produced that contain the active materials in a mixture with excipients suitable for the manufacture of aqueous suspensions. Such excipients include suspending agents, for example, sodium carboxymethylcellulose, methylcellulose, hydroxypropylmethylcellulose, sodium alginate, polyvinylpyrrolidone, gum tragacanth and gum acacia; dispersing or wetting agents can be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. Aqueous suspensions can also contain one or more preservatives, for example, ethyl or N-propyl p-hydroxybenzoate, one or more colouring agents, one or more flavouring-agents, or one or more sweetening agents, such as sucrose or saccharin. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and N-propyl p-hydroxybenzoate.

Oily suspensions may be formulated by suspending the active ingredients in an omega-3 fatty acid, a vegetable oil, for example, *arachis* oil, olive oil, sesame oil or coconut oil, or in a mineral oil such as liquid paraffin. The oily suspensions can contain a thickening agent, for example beeswax, hard paraffin or cetyl alcohol.

Sweetening agents, such as those set forth above, and flavouring agents can be added to provide a palatable oral preparation. These compositions can be preserved by addition of an antioxidant such as ascorbic acid.

Dispersible powders and granules suitable for preparation of an aqueous suspension by addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, can also be present.

Syrups and elixirs containing the compound of the invention can be formulated with sweetening agents, for example glycerol, sorbitol, or sucrose. Such formulations can also contain a demulcent, a preservative and flavouring and colouring agents.

Preferably, the compounds of general formula (I), (II), (III), (IV) and (V), or a pharmaceutically acceptable salts, hydrates, solvates or esters thereof, can be administered parenterally, for example subcutaneously, intravenously, or intramuscularly, or by infusion techniques, in the form of sterile injectable aqueous or oleaginous suspensions. Such suspensions can be formulated according to known art using suitable dispersing or wetting agents and suspending agents such as those mentioned above or other acceptable agents. A sterile injectable preparation can be a sterile injectable solution or suspension in a non-toxic parenterally acceptable diluent or solvent, for example a solution in 1,3-butanediol. Among acceptable vehicles and solvents that can be employed are water, Ringer's solution and isotonic sodium chloride solution. In addition, sterile fixed oils are conventionally employed as a solvent or suspending medium. For this purpose, any bland fixed oil may be employed, including synthetic mono- or diglycerides. In addition, omega-3 polyunsaturated fatty acids can find use in preparation of injectables. Administration can also be by inhalation, in the form of aerosols or solutions for nebulizers, or rectally, in the form of suppositories prepared by mixing the drug with a suitable non-irritating excipient which is solid at ordinary temperature, but liquid at rectal" temperature and will therefore, melt in the rectum to release the drug. Such materials are cocoa butter and polyethylene glycols. Also encompassed by the present invention is buccal and sub-lingual administration, including administration in the form of lozenges, pastilles or a chewable gum comprising the compounds set forth herein. The compounds can be deposited in a flavoured base, usually sucrose, and acacia or tragacanth.

Other methods for administration of the compounds of general formula (I), (II), (III), (IV) and (V), or pharmaceutically acceptable salts, hydrates, solvates or esters thereof, include dermal patches that release the medicaments directly into and/or through a subject's skin.

Topical delivery systems are also encompassed by the present invention and include ointments, powders, sprays, creams, jellies, collyriums, solutions or suspensions.

Compositions of the present invention can optionally be supplemented with additional agents such as, for example, viscosity enhancers, preservatives, surfactants and penetration enhancers. Viscosity-building agents include, for example, polyvinyl alcohol, polyvinyl pyrrolidone, methylcellulose, hydroxypropylmethylcellulose, hydroxyethylcellulose, carboxymethylcellulose, hydroxypropylcellulose or other agents known to those skilled in the art. Such agents are typically employed at a level of about 0.01% to about 2% by weight of a pharmaceutical composition.

Preservatives are optionally employed to prevent microbial growth prior to or during use. Suitable preservatives include polyquaternium-1, benzalkonium chloride, thimerosal, chlorobutanol, methylparaben, propylparaben, phenylethyl alcohol, edetate disodium, sorbic acid, or other agents known to those skilled in the art. Typically, such preservatives are employed at a level of about 0.001% to about 1.0% by weight of a pharmaceutical composition.

Solubility of components of the present compositions can be enhanced by a surfactant or other appropriate cosolvent in the composition. Such cosolvents include polysorbates 20, 60 and 80, polyoxyethylene/polyoxypropylene surfactants (e. g., Pluronic F-68, F-84 and P-103), cyclodextrin, or other agents known to those skilled in the art. Typically, such cosolvents are employed at a level of about 0.01% to about 2% by weight of a pharmaceutical composition.

Pharmaceutically acceptable excipients and carriers encompass all the foregoing and the like. The above considerations concerning effective formulations and administration procedures are well known in the art and are described in standard textbooks. See for example Remington: The Science and Practice of Pharmacy, 20th Edition (Lippincott, Williams and Wilkins), 2000; Lieberman et al., ed., Pharmaceutical Dosage Forms, Marcel Decker, New York, N.Y. (1980) and Kibbe et al., ed., Handbook of Pharmaceutical Excipients (3rd Edition), American Pharmaceutical Association, Washington (1999). Thus, in embodiments where the compound of the invention is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. The pharmaceutical compositions may take any suitable form, and include for example tablets, elixirs, capsules, solutions, suspensions, powders, granules, nail lacquers, varnishes and veneers, skin patches and aerosols.

The pharmaceutical composition may take the form of a kit of parts, which kit may comprise the composition of the invention together with instructions for use and/or a plurality of different components in unit dosage form.

For oral administration the compound of the invention can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch. Tablets for oral use may include the compound of the invention, either alone or together with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound of the invention is mixed with a solid diluent, and soft gelatin capsules wherein the active ingredient is mixed with water or an oil such as peanut oil, liquid paraffin or olive oil. Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds of the invention will generally be provided in sterile aqueous solutions or suspensions, buffered to an appropriate pH and isotonicity.

The compounds of general formula (I), (II), (III), (IV) and (V), or pharmaceutically acceptable salts, hydrates, solvates or esters thereof, may also be presented as liposome formulations.

In another embodiment, the compounds of general formula (I), (II), (III), (IV) and (V), or pharmaceutically acceptable salts, hydrates, solvates or esters thereof, are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of general formula (I), (II), (III), (IV) and (V), or pharmaceutically acceptable salts, hydrates, solvates or esters thereof, may also be administered parenterally, that is, subcutaneously, intravenously, intramuscularly, or interperitoneally. In such embodiments, the compound is provided as injectable doses in a physiologically acceptable diluent together with a pharmaceutical carrier (which can be a sterile liquid or mixture of liquids). Suitable liquids include water, saline, aqueous dextrose and related compound solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethyleneglycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carbomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil.

Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound of the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of general formula (I), (II), (III), (IV) and (V), or pharmaceutically acceptable salts, hydrates, solvates or esters thereof, may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

When used adjunctively, the compounds of general formula (I), (II), (III), (IV) and (V), or pharmaceutically acceptable salts, hydrates, solvates or esters thereof, may be formulated for use with one or more other drug(s). In particular, the compounds of general formula (I), (II), (III), (IV) and (V), or pharmaceutically acceptable salts, hydrates, solvates or esters thereof, may be used in combination with analgesics, anti-inflammatories (e.g. steroids), immunomodulatory agents and anti-spasmodics.

Thus, adjunctive use may be reflected in a specific unit dosage designed to be compatible (or to synergize) with the other drug(s), or in formulations in which the compound is admixed with one or more anti-inflammatories, cytokines or immunosuppressive agents (or else physically associated with the other drug(s) within a single unit dose). Adjunctive uses may also be reflected in the composition of the pharmaceutical kits of the invention, in which the compound of the invention is co-packaged (e.g. as part of an array of unit doses) with the antimicrobial agents and/or anti-inflammatories. Adjunctive use may also be reflected in information and/or instructions relating to the co-administration of the compound with antimicrobial agents and/or anti-inflammatories.

The compounds of general formula (I), (II), (III), (IV) and (V), or pharmaceutically acceptable salts, hydrates, solvates or esters thereof, may be administered in combination with other active compounds (e.g. antifungal compounds, antiviral compounds) and, in particular, with other antibacterial compounds. The compound of general formula (I), (II), (III), (IV) and (V), or pharmaceutically acceptable salts, hydrates, solvates or esters thereof, and the other active (e.g. the other antibacterial compound) may be administered in different pharmaceutical formulations either simultaneously or sequentially with the other active. Alternatively, the compound of general formula (I), (II), (III), (IV) and (V), or pharmaceutically acceptable salts, hydrates, solvates or esters thereof, and the other active (e.g. the other antibacterial compound) may form part of the same pharmaceutical formulation.

All publications, patents, patent applications and other references mentioned herein are hereby incorporated by reference in their entireties for all purposes as if each individual publication, patent or patent application were specifically and individually indicated to be incorporated by reference and the content thereof recited in full.

Features, integers, characteristics, compounds, chemical moieties or groups described in conjunction with a particular aspect, embodiment or example of the invention are to be understood to be applicable to any other aspect, embodiment or example described herein unless incompatible therewith.

EXAMPLES

The invention will now be described with reference to specific examples. These are merely exemplary and for illustrative purposes only; they are not intended to be limiting in any way to the scope of the monopoly claimed or to the invention described. These examples constitute the best mode currently contemplated for practicing the invention.

The following abbreviations have been used:
Ac acetyl
$Ac_2O$ acetic anhydride
AcOH acetic acid
aq aqueous
Ar aryl
Boc tert-butoxycarbonyl
nBuLi N-butyllithium
calcd calculated
CDI carbonyldiimidazole
conc concentrated
d day
DCE dichloroethane
DCM dichloromethane
DIBALH diisobutylaluminium hydride
DIPEA diisopropylethylamine
DMAP 4-dimethylaminopyridine
DMF dimethylformamide
EDC 1-ethyl-3-(3-dimethylaminopropyl)carbodiimide hydrochloride
ES+ electrospray ionization
EtOAc ethyl acetate
EtOH ethanol
Ex Example
h hour(s)
HBTU O-benzotriazole-N,N,N',N'-tetramethyl-uronium-hexafluoro-phosphate
HOBt 1-hydroxybenzotriazole hydrate
HPLC High Performance Liquid Chromatography
HRMS High-Resolution Mass Spectrometry Int Intermediate
LCMS Liquid Chromatography Mass Spectrometry
LDA lithium diisopropylamide
M molar
Me methyl
mCPBA meta-chloroperbenzoic acid
MeCN acetonitrile
MeOH methanol
min minute(s)
Ms methanesulfonate
MS Mass Spectrometry
NaBH(OAc)$_3$ sodium triacetoxyborohydride
NIS N-iodosuccinimide
NMP N-methylpyrrolidone
Rf Retention time
RT (or rt) room temperature
sat saturated
SCX Strong Cation Exchange
SM starting material
TFA trifluoroacetic acid
THF Tetrahydrofuran
Experimental Method Reactions were conducted at room temperature unless otherwise specified. Microwave reactions were performed with a CEM Discover microwave reactor using process vials fitted with aluminium caps and septa. Preparative flash chromatography was performed using silica gel (100-200 mesh).

Prep HPLC was performed using one of the following methods: Instrument—Agilent-1260 infinity; Column: Sunfire C8 (19×250) mm, 5μ or Sunfire C18 (19×250) mm, 5μ; Solvents: solvent A=5 mM Ammonium acetate in water; solvent B=acetonitrile/solvent A=0.1% TFA; solvent B=acetonitrile; Detection wavelength 214 nm. Instrument—Waters 2767 autoprep with 2998 detector; Column: X TERRA C18 (19×250) mm, 10μ or Sunfire C18 (19×250) mm, 10μ; Solvents: solvent A=5 mM Ammonium acetate in water; solvent B=acetonitrile/solvent A=acetonitrile; solvent B=0.1% TFA in Water; Detection wavelength 214 nm. The purest fractions were collected, concentrated and dried under vacuum. Compounds were typically dried in a vacuum oven at 40° C. prior to purity analysis. Compound analysis was performed by Waters Acquity UPLC, Waters 3100 PDA Detector, SQD; Column: Acquity BEH C-18, 1.7 micron, 2.1×100 mm; Gradient [time (min)/solvent B in A (%)]: 0.00/10, 1.00/10, 2.00/15, 4.50/55, 6.00/90, 8.00/90, 9.00/10, 10.00/10; Solvents: solvent A=5 mM ammonium acetate in water; solvent B=acetonitrile; Injection volume 1 μL; Detection wavelength 214 nm; Column temperature 30° C.; Flow rate 0.3 mL/min or Waters Acquity UPLC, Waters 3100 PDA Detector, SQD; Column: Acquity HSS-T3, 1.8 micron, 2.1×100 mm; Gradient [time (min)/solvent B in A (%)]: 0.00/10, 1.00/10, 2.00/15, 4.50/55, 6.00/90, 8.00/90, 9.00/10, 10.00/10; Solvents: solvent A=0.1% trifluoroacetic acid in water; solvent B=acetonitrile; Injection volume 1 μL; Detection wavelength 214 nm; Column temperature 30° C.; Flow rate 0.3 mL/min.

400 MHz 1H nuclear magnetic resonance spectra (NMR) were recorded on an Avance Bruker AV400 spectrometer. In the NMR spectra the chemical shifts (b) are expressed in ppm relative to the residual solvent peak. Abbreviations have the following significances: b=broad signal, s=singlet, d=doublet, t=triplet, dd=doublet of doublets, ddd=doublet of double doublets. Abbreviations may be compounded and other patterns are unabbreviated.

The compounds prepared were named using ChemBio-Draw Ultra 13.0 by CambridgeSoft.

In the absence of intermediate synthesis, the compounds are commercially available.

Examples and Intermediate Compounds

Synthetic Route 1

5-(3,4-Dimethoxyphenyl)-4-(2-methylpyridin-4-yl)-1H-imidazol-2-amine (Example 1)

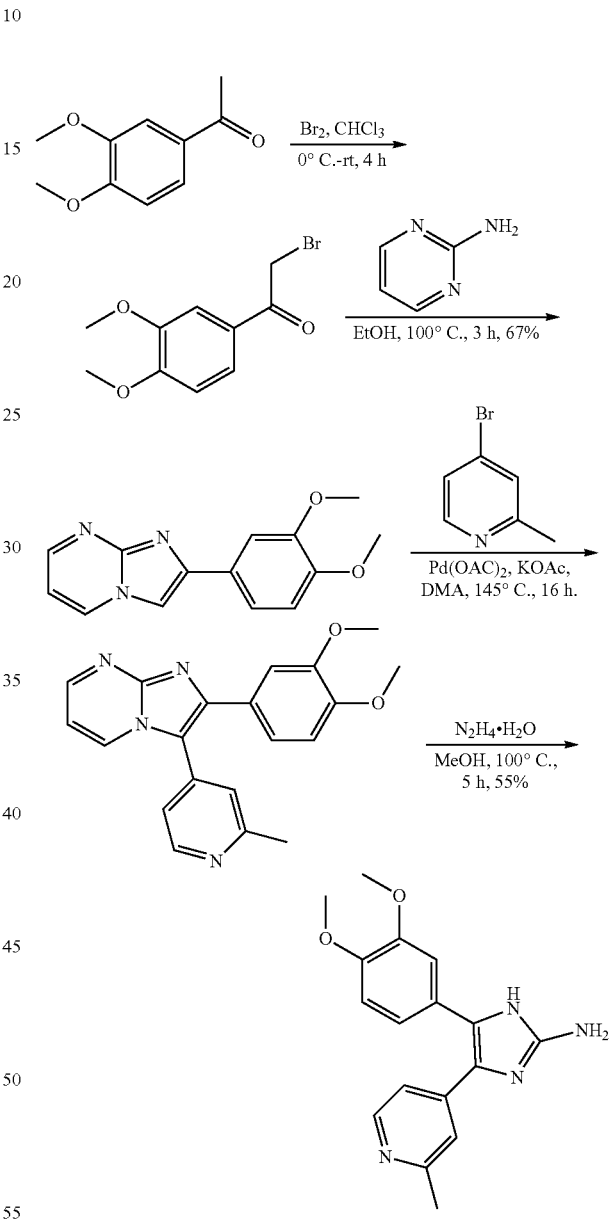

2-Bromo-1-(3,4-di methoxyphenyl)ethan-1-one

To a solution of 1-(3,4-dimethoxyphenyl)ethan-1-one (5.0 g, 27.7 mmol) in CHCl$_3$ (100 mL) was added a solution of bromine (1.4 mL, 27.7 mmol) in CHCl$_3$ (25 mL) at 0° C. drop wise over a period of 1 h. The reaction mixture was stirred at 0° C. for 3 h and allowed to warm to rt. The TLC showed the reaction to be complete. The reaction mixture was quenched with saturated bicarbonate solution (100 mL) and extracted with DCM (2×100 mL). The organic layer was washed with brine (100 mL), dried (Na₂SO₄), filtered and concentrated under reduced pressure to give 2-bromo-1-(3,4-dimethoxyphenyl)ethan-1-one as a brown solid. Yield: 3.1 g (crude). The crude product was used without further purification.

2-(3,4-Dimethoxyphenyl)imidazo[1,2-a]pyrimidine

To a solution of 2-bromo-1-(3,4-dimethoxyphenyl)ethan-1-one (3.0 g, 11.6 mmol) in EtOH (30 mL) was added pyrimidin-2-amine (1.1 g, 11.6 mmol) at rt. The reaction mixture was stirred at 100° C. for 3 h. The TLC showed the reaction to be complete. The reaction mixture was cooled to rt. The solid precipitated was filtered, washed with Et₂O (50 mL) and dried under reduced pressure to afford 2-(3,4-dimethoxyphenyl)imidazo[1,2-a]pyrimidine as a yellow solid. Yield: 2.01 g (67%); MS (ESI+) for CHNOS m/z 256.17 [M+H]⁻. ¹H NMR (400 MHz, DMSO-d₆): δ 9.20 (d, J=6.6 Hz, 1H), 8.90 (d, J=2.3 Hz, 1H), 8.65 (s, 1H), 7.50-7.68 (m, 3H), 7.16 (d, J=8.9 Hz, 1H), 3.88 (s, 3H), 3.84 (s, 3H).

2-(3,4-Dimethoxyphenyl)-3-(2-methylpyridin-4-yl)imidazo[1,2-a]pyrimidine

A mixture of 2-(3,4-dimethoxyphenyl)imidazo[1,2-a]pyrimidine (1.0 g, 3.92 mmol), 4-bromo-2-methylpyridine (539 mg, 3.13 mmol) and potassium acetate (768 mg, 7.84 mmol) in dimethylacetamide (10.0 mL) was purged with N₂ gas for 10 min and Pd(OAC)₂ (43 mg, 0.19 mmol) was added under an atmosphere of nitrogen. The reaction mixture was purged with N₂ gas for 5 min and stirred further at 145° C. for 16 h. The TLC showed the reaction to be complete. The reaction was diluted with H₂O (50 mL) and extracted with EtOAc (3×50 mL), the combined organic layers were washed with brine (100 mL), dried (Na₂SO₄), filtered and concentrated under reduced pressure. The crude LCMS showed the formation of two regioisomers with desired mass 60% and 33% respectively. The crude material was used in the next step without further purification. Yield: 620 mg (crude). MS (ESI+) for CHNOS m/z 347.17 [M+H]⁺

5-(3,4-Di methoxyphenyl)-4-(2-methylpyridin-4-yl)-1H-imidazol-2-amine

To a solution of 2-(3,4-di methoxyphenyl)-3-(2-methylpyridin-4-yl)imidazo[1,2-a]pyrimidine (400 mg, 1.15 mmol) was added hydrazine hydrate (0.3 mL, 5.8 mmol) at rt. The reaction mixture was stirred at 100° C. for 5 h. The TLC showed the reaction to be complete. The reaction mixture was allowed to cool to rt and concentrated under reduced pressure. The residue was diluted with water (20 mL) and the precipitated solid was collected by filtration, washed with water (25 mL) and dried under reduced pressure. The solid was further triturated with Et₂O (10 mL) and dried under presser to afford 5-(3,4-dimethoxyphenyl)-4-(2-methylpyridin-4-yl)-1H-imidazol-2-amine as a yellow solid. Yield: 200 mg (55%); MS (ESI+) for CHNOS m/z 311.21 [M+H]+; LC purity 99.7% (Ret. Time—4.42 min); 1H NMR (400 MHz, DMSO-d6): δ 10.93 (bs, 1H), 8.19 (d, J=4.8 Hz, 1H), 6.93-7.45 (m, 5H), 5.37 (bs, 2H), 3.77 (s, 3H), 3.68 (s, 3H), 2.35 (s, 3H).

Intermediate 1

1-(6-Methoxypyridin-3-yl)ethan-1-one

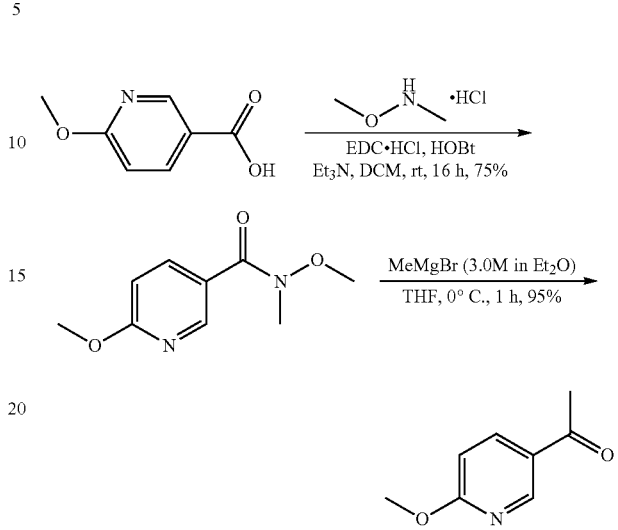

N,6-Dimethoxy-N-methylnicotinamide

To a solution of 6-methoxynicotinic acid (5 g, 32.6 mmol) in DCM (50 mL) were added EDCl.HCl (12.5 g, 65.3 mmol), HOBT (4.99 g, 32.6 mmol) and triethylamine (13.7 mL, 98.0 mmol) at rt. The reaction mixture was stirred at rt for 15 min and N,O-dimethylhydroxylamine hydrochloride (3.8 g, 39.2 mmol) was added. The reaction mixture was further stirred at rt for 16 h. The TLC showed the reaction to be complete. The reaction mixture was diluted with water (100 mL) and extracted with DCM (2×50 mL) and the organic layer was washed with brine (100 mL), dried (Na₂SO₄), filtered and concentrated under reduced pressure. The residue was purified by column chromatography using silica gel (100-200 mesh), eluting with 10% EtOAc in hexane to afford N,6-dimethoxy-N-methylnicotinamide as a yellow liquid. Yield: 4.8 g (75%); MS (ESI+) for CHNOS m/z 197.17 [M+H]⁺. ¹H NMR (400 MHz, DMSO-d₆): δ 8.49 (s, 1H), 7.96 (d, J=8.6 Hz, 1H), 6.88 (d, J=8.6 Hz, 1H), 3.90 (s, 3H), 3.57 (s, 3H), 3.26 (s, 3H).

1-(6-Methoxypyridin-3-yl)ethan-1-one

To a solution of N,6-dimethoxy-N-methylnicotinamide (4.8 g, 24.4 mmol) in THF (50 mL) was added methyl magnesium bromide (3M in Et₂O, 24.4 mL, 73.3 mmol) at 0° C. The reaction mixture was stirred at 0° C. for 1 h. The TLC showed the reaction to be complete. The reaction mixture was quenched with saturated aqueous ammonium chloride solution (25 mL) and extracted with EtOAc (3×25 mL) and the organic layer was washed with brine (50 mL), dried (Na₂SO₄), filtered and concentrated under reduced pressure to afford 1-(6-methoxypyridin-3-yl)ethan-1-one as a yellow solid. Yield: 3.51 g (95%); MS (ESI+) for CHNOS m/z 152.13 [M+H]⁺. ¹H NMR (400 MHz, DMSO-d₆): δ 8.82 (d, J=2.3 Hz, 1H), (dd, J=2.3, 8.7 Hz, 1H), 6.92 (d, J=8.7 Hz, 1H), 3.94 (s, 3H), 2.55 (s, 3H).

Intermediate 2

1-(4-((4-Fluorobenzyl)oxy)phenyl)ethan-1-one

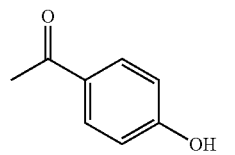

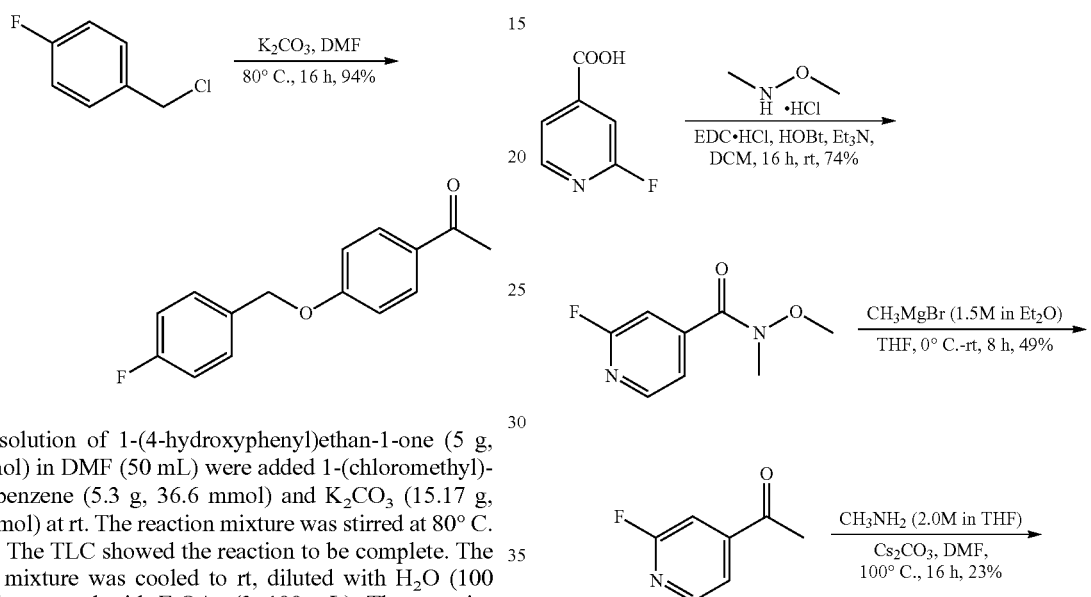

To a solution of 1-(4-hydroxyphenyl)ethan-1-one (5 g, 36.6 mmol) in DMF (50 mL) were added 1-(chloromethyl)-4-fluorobenzene (5.3 g, 36.6 mmol) and $K_2CO_3$ (15.17 g, 109.9 mmol) at rt. The reaction mixture was stirred at 80° C. for 16 h. The TLC showed the reaction to be complete. The reaction mixture was cooled to rt, diluted with $H_2O$ (100 mL) and extracted with EtOAc (3×100 mL). The organics were dried ($Na_2SO_4$), filtered and concentrated under reduced pressure. The crude residue was triturated with $Et_2O$ (50 mL), filtered and dried under reduced pressure to afford 1-(4-((4-fluorobenzyl)oxy)phenyl)ethan-1-one as an off white solid. Yield: 8.5 g (94%); MS (ESI+) for CHNOS m/z 245.08 [M+H]$^+$; $^1$H NMR (400 MHz, DMSO-d$_6$) δ 7.92 (d, J=8.0 Hz, 2H), 7.47-7.57 (m, 2H), 7.18-7.27 (m, 2H), 7.11 (d, J=8.0 Hz, 2H), 5.18 (s, 2H), 2.52 (s, 3H).

Intermediate 3

1-(2,3-Dihydrobenzofuran-5-yl)ethan-1-one

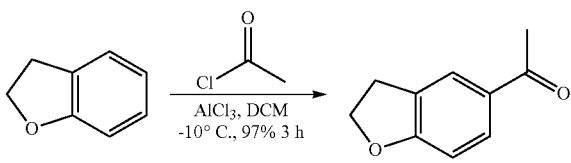

To a solution of 2,3-dihydrobenzofuran (1 g, 8.3 mmol) in DCM (10 mL) was added acetyl chloride (1.3 g, 16.6 mmol) and $AlCl_3$ (3.3 g, 24.6 mmol) slowly at −10° C. The reaction mixture was stirred at −10° C. for 3 h. The TLC showed the reaction to be complete. The reaction mixture was diluted with 5% aqueous HCl (10 mL) and extracted with DCM (3×10 mL). The combined organic layers were washed with saturated aqueous bicarbonate solution (100 mL), brine (100 mL), dried ($Na_2SO_4$), filtered and concentrated under reduced pressure to afford 1-(2,3-dihydrobenzofuran-5-yl)ethan-1-one as a brown liquid. Yield: 1.34 g (97%); MS (ESI+) for CHNOS m/z 163.0[M+H]$^+$; $^1$H NMR (400 MHz, CDCl$_3$): δ 7.86 (s, 1H), 7.79 (d, J=8.4 Hz, 1H), 6.80 (d, J=8.4 Hz, 1H), 4.66 (t, J=8.8 Hz, 2H), 3.25 (t, J=8.8 Hz, 2H), 2.52 (s, 3H).

Intermediate 4

1-(2-(Methylamino)pyridin-4-yl)ethan-1-one

2-Fluoro-N-methoxy-N-methylisonicotinamide

To a solution of 2-fluoroisonicotinic acid (5.0 g, 36.5 mmol) in DCM (100 mL) were added N-methoxymethanamine hydrochloride (5.3 g, 54.7 mmol), HOBT (5.17 g, 38.32 mmol), EDC.HCl (14.1 g, 91.2 mmol) and Et$_3$N (20.4 mL, 146 mmol) at rt. The reaction mixture was stirred at rt for 16 h. The TLC showed reaction to be complete. The reaction mixture was diluted with water (100 mL) and extracted with DCM (3×100 mL). The organic layer was dried ($Na_2SO_4$), filtered and concentrated under reduced pressure. The residue was purified by combiflash chromatography using 40 g silica column, eluting with 20% EtOAc in hexane to afford 2-fluoro-N-methoxy-N-methylisonicotinamide as a light brown solid. Yield: 5.0 g (74%); MS (ESI+) for CHNOS m/z 185.20[M+H]$^+$; $^1$H NMR (400 MHz, CDCl$_3$): δ 8.27-8.31 (m, 1H), 7.38-7.43 (m, 1H), 7.17 (s, 1H), 3.37 (s, 3H), 3.55 (s, 3H).

1-(2-Fluoropyridin-4-yl)ethan-1-one

To a solution of 2-fluoro-N-methoxy-N-methylisonicotinamide (5.0 g, 27.0 mmol) in dry THF (120 mL) was added MeMgBr (1.5M sol in Et$_2$O, 27 mL, 40.5 mmol) slowly at rt. The reaction mixture was stirred at rt for 8 h. The TLC showed reaction to be complete. The reaction mixture was quenched with ice-water (50 mL) and extracted with the EtOAc (3×50 mL). The organic layer was dried (Na$_2$SO$_4$), filtered and concentrated under reduced pressure to afford 1-(2-fluoropyridin-4-yl)ethan-1-one as a pale yellow liquid which was used for next reaction without further purification. Yield: 2.2 g (49.6%); MS (ESI+) for CHNOS m/z 140.15 [M+H]$^+$; $^1$H NMR (400 MHz, CDCl$_3$): δ 8.39 (d, J=5.1 Hz, 1H), 7.63 (d, J=5.1 Hz, 1H), 7.37 (bs, 1H), 2.63 (s, 3H).

1-(2-(Methylamino)pyridin-4-yl)ethan-1-one

To a mixture of 1-(2-fluoropyridin-4-yl)ethan-1-one (6.0 g, 42.9 mmol) and Cs$_2$CO$_3$ (41.9 g, 128.6 mmol) in dry DMF (60 mL) was added methylamine (2.0M in THF, 42.7 mL, 85.7 mmol) at rt. The reaction vessel was sealed and the reaction mixture was stirred at 120° C. for 16 h. The TLC showed reaction to be complete. The reaction mixture was diluted with cold water (50 mL) and extracted with EtOAc (3×50 mL). The organic layer was dried (Na$_2$SO$_4$), filtered and concentrated under reduced pressure. The residue was purified by combiflash chromatography using 40 g silica column, eluting with 10% EtOAc in hexane to afford 1-(2-(methylamino)pyridin-4-yl)ethan-1-one as a yellow solid. Yield: 1.5 g (23.4%); (MS (ESI+) for CHNOS m/z 151.10 [M+H]$^+$; $^1$H NMR (400 MHz, DMSO-d$_6$): δ 8.13 (d, J=5.84 Hz, 1H), 6.85-6.87 (m, 2H), 6.79 (bs, 1H), 2.80 (bs, 3H), 2.49 (s, 3H).

The following intermediates were prepared in a similar manner to 2-bromo-1-(3,4-dimethoxyphenyl) ethan-1-one.

Intermediate 8

1-(Benzo[d][1,3]dioxol-5-yl)-2-bromoethan-1-one

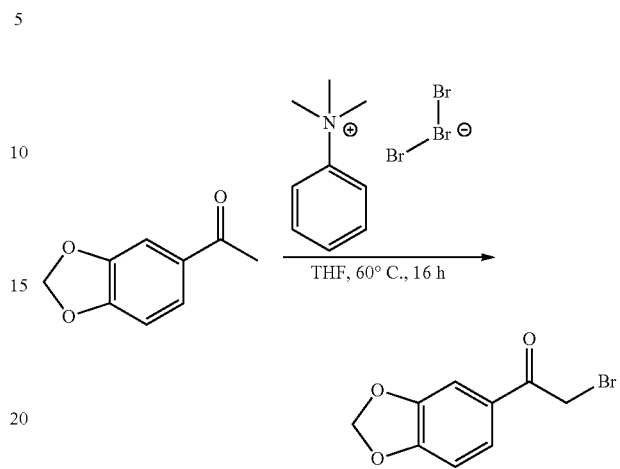

To a solution of 1-(benzo[d][1,3]dioxol-5-yl)ethan-1-one (1 g, 6.09 mmol) in THF (20 mL) was added trimethylphenylammonium tribromide (2.75 g, 7.01 mmol) at rt. The reaction mixture was stirred at 60° C. for 16 h. The TLC showed the reaction to be complete. The reaction mixture was diluted with water (20 mL) and extracted with ethyl acetate (2×30 mL). The combined organic layers were washed with brine (100 mL), dried (Na$_2$SO$_4$), filtered and concentrated under reduced pressure to afford 1-(benzo[d][1,3]dioxol-5-yl)-2-bromoethan-1-one as a brown solid. Yield: 1.4 g (crude); MS (ESI+) for CHNOS m/z 243.19 [M+H]$^+$. The crude product was used in the next step without further purification.

| Name | Int | Structure | Yield | Spectral Data 1H NMR & LCMS |
|---|---|---|---|---|
| 2-Bromo-1-(2,3-dihydrobenzofuran-5-yl)ethan-1-one | 5 | 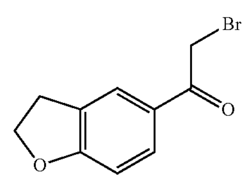 [SMILES: O=C(CBr)c1ccc2c(c1)CCO2] | 50% | MS (ESI+) for CHNOS m/z 241.09 [M + H]$^+$; $^1$H NMR (400 MHz, DMSO-d$_6$): δ 7.81-7.96 (m, 2H), 6.89 (d, J = 8.3 Hz, 1H), 4.75 (s, 2H), 4.65 (t, J = 8.8 Hz, 2H), 3.24 (t, J = 8.8 Hz, 2H) |
| 2-Bromo-1-(3-fluoro-4-methoxyphenyl)ethan-1-one | 6 | 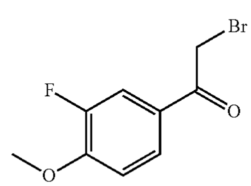 | 70% | $^1$H NMR (400 MHz, DMSO-d$_6$): δ 7.76-7.89 (m, 2H), 7.24-7.41 (m, 1H), 4.87 (s, 2H), 3.94 (s, 3H). |
| 2-Bromo-1-(3-chloro-4-methoxyphenyl)ethan-1-one | 7 | 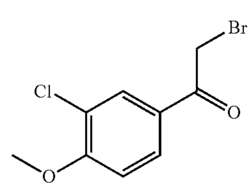 | 56% | MS (ESI−) for CHNOS m/z 261.23 [M − H]$^-$ |

The following intermediates were prepared in a similar manner to 1-(benzo[d][1,3]dioxol-5-yl)-2-bromoethan-1-one.

| Name | Int | Structure | Yield | Spectral Data 1H NMR & LCMS |
|---|---|---|---|---|
| 2-Bromo-1-(4-((4-fluorobenzyl)oxy)phenyl)ethan-1-one | 9 | | 76% | MS (ESI−) for CHNOS m/z 321.02 [M − H]− |
| 2-Bromo-1-(3-fluoro-4-hydroxyphenyl)ethan-1-one | 10 | 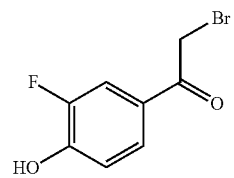 [SMILES: O=C(CBr)c1ccc(O)c(F)c1] | 40% | MS (ESI−) for CHNOS m/z 231.04 [M − H]−; 1H NMR (400 MHz, DMSO-$d_6$): δ 11.05 (bs, 1H), 7.55-7.94 (m, 2H), 6.95-7.18 (m, 1H), 4.82 (s, 2H) |
| 2-Bromo-1-(4-((4-fluorobenzyl)oxy)phenyl)ethan-1-one | 11 | | 94% | MS (ESI−) for CHNOS m/z 320.92M − H]−; 1H NMR (400 MHz, DMSO-$d_6$): δ 7.93-8.02 (m, 2H), 7.44-7.58 (m, 2H), 7.12-7.21 (m, 4H), 5.21 (s, 2H), 4.84 (s, 2H) |
| 2-Bromo-1-(4-hydroxypehnyl)ethan-1-one | 12 | 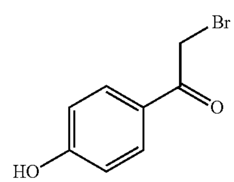 [SMILES: O=C(CBr)c1ccc(O)cc1] | 50% | MS (ESI−) for CHNOS m/z 212.94 [M − H]+; 1H NMR (400 MHz, DMSO-$d_6$) δ 10.52 (bs, 1H), 7.65-8.01 (m, 2H), 6.65-7.01 (m, 2H), 4.78 (s, 2 H) |

Intermediate 13

2-Bromo-1-(2-methylpyridin-4-yl)ethan-1-one. hydrogen bromide

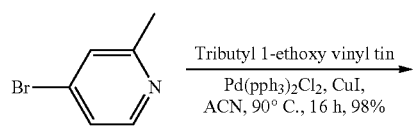

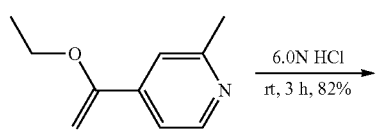

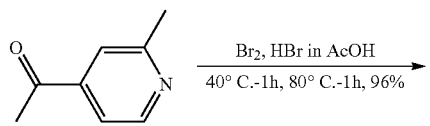

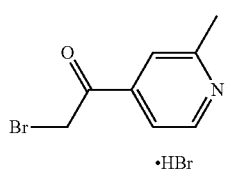

4-(1-Ethoxyvinyl)-2-methylpyridine

To a mixture of 4-bromo-2-methylpyridine (2.5 g, 14.5 mmol) and tributyl 1-ethoxy vinyl tin (10.5 g, 29.1 mmol) in toluene (15 mL) was purged $N_2$ gas at rt for 10 min and Pd(PPh$_3$)$_4$ (1.7 g, 1.45 mmol) was added to it under $N_2$ atmosphere. The reaction mixture was purged with $N_2$ gas for 5 min at rt and stirred further at 110° C. for 16 h. The TLC showed the reaction to be complete. The reaction mixture was allowed to cool to rt before the solvent was removed under reduced pressure. The residue was stirred with hexane (25 mL) and filtered through celite bed. The celite bed was washed with hexane (50 mL). The combined filtrate was concentrated under reduced pressure. The crude residue was purified by column chromatography using silica gel, eluting with 0-5% EtOAc in hexane to afford 4-(1-ethoxyvinyl)-2-methylpyridine as a colourless oil. Yield:

2.35 g (98%); (MS (ESI+) for CHNOS m/z 164.10 [M+H]⁺.
¹H NMR (400 MHz, DMSO-d₆): δ 8.41 (d, J=5.2 Hz, 1H), 7.35 (s, 1H), 8.41 (d, J=4.7 Hz, 1H), 5.01 (s, 1H), 4.46 (s, 1H), 3.91 (q, J=6.9 Hz, 2H), 2.47 (s, 3H), 1.35 (t, J=6.9 Hz, 3H).

1-(2-Methyl pyridin-4-yl)ethan-1-one

A suspension of 4-(1-ethoxyvinyl)-2-methylpyridine (2.6 g, 15.9 mmol) in 6N HCl (10 mL) was stirred at rt for 3 h. The TLC showed the reaction to be complete. The reaction mixture was diluted with water (20 mL), basified to pH 11 with 5N NaOH and extracted with EtOAC (3×20 mL). The organic layer was dried (Na₂SO₄), filtered and concentrated under reduced pressure to afford 1-(2-methylpyridin-4-yl)ethan-1-one as a colourless oil. Yield: 1.8 g (82%); (MS (ESI+) for CHNOS m/z 136.05 [M+H]⁺; ¹H NMR (400 MHz, DMSO-d₆): δ 8.65 (d, J=5.0 Hz, 1H), 7.69 (s, 1H), 7.60 (d, J=4.2 Hz, 1H), 2.49 (s, 3H), 2.57 (s, 3H).

2-Bromo-1-(2-methylpyridin-4-yl)ethan-1-one

To a solution of 1-(2-methylpyridin-4-yl)ethan-1-one (1.85 g, 13.6 mmol) in HBr (33% in AcOH, 15 mL) was added a solution of bromine (0.7 mL, 13.6 mmol) in HBr (33% in AcOH, 3.5 mL) at 0° C. slowly. The reaction mixture was stirred at 40° C. for 1 h and then further stirred at 80° C. for 1 h. The TLC showed the reaction to be complete. The reaction mixture was cooled to rt, poured in Et₂O (100 mL) and stirred at rt for 30 min. The precipitate was filtered, washed with Et₂O (20 mL) and dried under reduced pressure to afford 2-bromo-1-(2-methylpyridin-4-yl)ethan-1-one (HBr salt) as a yellow solid. Yield: 2.8 g (96%); ¹H NMR (400 MHz, DMSO-d₆): δ 8.89 (d, J=5.5 Hz, 1H), 8.12 (s, 1H), 8.00 (d, J=5.2 Hz, 1H), 5.03 (s, 2H), 2.70 (s, 3H).

The following intermediates were prepared in a similar manner to 1-(2-methylpyridin-4-yl) ethan-1-one.

| Name | Int | Structure | Yield | Spectral Data 1H NMR & LCMS |
|---|---|---|---|---|
| 1-(2,6-Dimethylpyridin-4-yl)ethan-1-one | 14 | 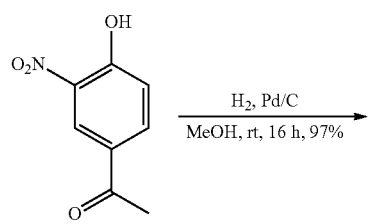 | 45% | MS (ESI+) for CHNOS m/z 150.08 [M + H]⁺ |

Intermediate 15

1-(3,4-dihydro-2H-benzo[b][1,4]oxazin-6-yl)ethan-1-one

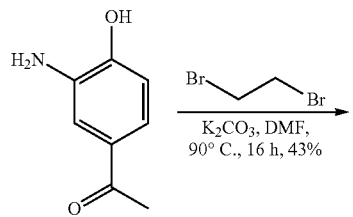

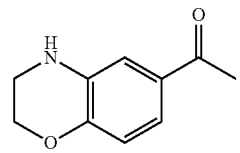

1-(3-Amino-4-hydroxyphenyl)ethan-1-one

To a stirred solution of 1-(4-Hydroxy-3-nitrophenyl)ethan-1-one (10 g, 55 mmol) in MeOH (100 mL) was added 10% Pd/C (1.0 g) at rt. The reaction mixture was stirred at rt for under H₂ atmosphere (1 atm) for 16 h. The TLC showed reaction to be complete. The reaction mixture was filtered through a celite bed. The celite bed was washed with MeOH (30 m). The filtrate was concentrated under reduced pressure. The residue was purified by combiflash chromatography using 40 g silica column, eluting with 10% EtOAc in hexane to afford 1-(3-Amino-4-hydroxyphenyl)ethan-1-one as a brown solid. Yield: 8.1 g (97%); MS (ESI−) for CHNOS m/z 150.02[M+H]⁺. ¹H NMR (400 MHz, DMSO-d₆): δ 10.1 (bs, 1H), 7.21 (s, 1H), 7.11-7.14 (m, 1H), 6.60 (d, J=8.1 Hz, 1H), 4.76 (bs, 2H), 2.40 (s, 3H).

1-(3,4-Dihydro-2H-benzo[b][1,4]oxazin-6-yl)ethan-1-one

To a solution of 1-(3-Amino-4-hydroxyphenyl)ethan-1-one (8.0 g, 52.6 mmol) in DMF (100 mL) were added K₂CO₃ (29 g, 210 mmol) and 1,2-dibromoethane (39.5 g, 210 mmol) at rt. The reaction mixture was further stirred at 90° C. for 16 h. The TLC showed reaction to be complete. The reaction mixture was diluted with cold water (200 mL) and extracted with EtOAc (3×100 mL). The organic layer was dried (Na₂SO₄), filtered and concentrated under reduced pressure. The residue was purified by combiflash chromatography using 40 g silica column, eluting with 50% EtOAc in hexane to afford 1-(3,4-dihydro-2H-benzo[b][1,4]oxazin-6-yl)ethan-1-one as a brown solid. Yield: 4.03 g (43%); MS (ESI+) for CHNOS m/z 219.19 [M+H]⁺. ¹H NMR (400 MHz, DMSO-d₆): δ 7.15-7.21 (m, 2H), 6.68-6.72 (d, J=8.12 Hz, 1H), 6.01 (bs, 1H), 4.15-4.21 (m, 2H), 3.25-3.31 (m, 2H), 2.51 (s, 3H).

The following intermediates were prepared in a similar manner to 2-bromo-1-(2-methylpyridin-4-yl)ethan-1-one.hydrogen bromide.

| Name | Int | Structure | Yield | Spectral Data 1H NMR & LCMS |
|---|---|---|---|---|
| 2-Bromo-1-(2,6-dimethylpyridin-4-yl)ethan-1-one hydrobromide | 16 | 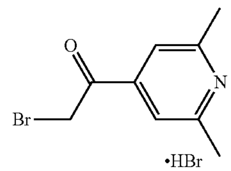 | 52% | MS (ESI+) for CHNOS m/z 327.98 [M + H]+ |
| 2-Bromo-1-(2-(methylamino)pyridin-4-yl)ethan-1-one hydrobromide | 17 | 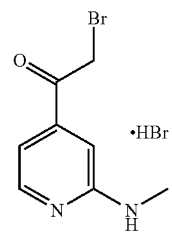 | 84% | MS (ESI+) for CHNOS m/z 229.01 [M + H]+; 1H NMR (400 MHz, DMSO-d6): δ 8.78 (bs, 1H), 8.09 (d, J = 6.4 Hz, 1H), 7.37 (s, 1H), 7.11 (dd, J = 5.24 Hz, 1H), 4.94 (s, 2H), 2.96 (s, 3H) |
| 2-Bromo-1-(3,4-dihydro-2H-benzo[b][1,4]oxazin-6-yl)ethan-1-one. hydrobromide | 18 | 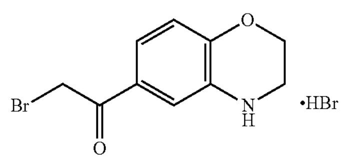 [SMILES: O=C(CBr)c1ccc2c(c1)NCCO2 ; Br] | 62% | MS (ESI+) for CHNOS m/z 256.03 [M + H]+; 1H NMR (400 MHz, DMSO-d6): δ 7.15-7.28 (m, 2H), 7.65 (d, J = 8.0 Hz, 1H), 4.73 (s, 2H), 4.31 (bs, 2H), 3.34 (bs, 2H) |

Intermediate 19

1-(6-Bromo-2-methyl-2,3-dihydro-4H-benzo[b][1,4]oxazin-4-yl)ethan-1-one

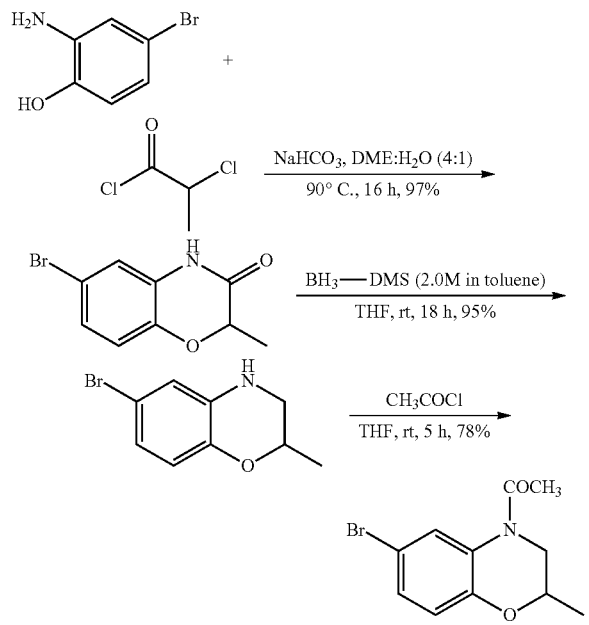

6-Bromo-2-methyl-2H-benzo[b][1,4]oxazin-3(4H)-one

To a mixture of 2-amino-4-bromophenol (2.0 g, 10.7 mmol), NaHCO3 (2.7 g, 32.1 mmol) in DME:H2O (4:1, 20 mL) was added 2-chloropropanoyl chloride (1.3 mL, 12.8 mmol) at rt. The reaction mixture was stirred at 90° C. for 16 h. The TLC showed reaction to be complete. The reaction mixture was diluted with water (50 mL) and extracted with EtOAc (3×50 mL). The organics were dried (Na2SO4), filtered and concentrated under reduced pressure to give 6-bromo-2-methyl-2H-benzo[b][1,4]oxazin-3(4H)-one as a brown solid. Yield: 2.5 g (97%). 1H NMR (400 MHz, DMSO-d6): δ 10.74 (bs, 1H), 6.88-7.12 (m, 3H), 4.68 (q, J=6.7 Hz, 1H), 1.41 (d, J=6.7 Hz, 3H). MS (ESI−) for CHNOS m/z 239.93 [M−H]−.

6-Bromo-2-methyl-3,4-dihydro-2H-benzo[b][1,4]oxazine

To a solution of 6-bromo-2-methyl-2H-benzo[b][1,4]oxazin-3(4H)-one (1.0 g, 4.14 mmol) in dry THF (30 mL) was added BH3-DMS (2.0M in toluene, 6.3 mL, 12.5 mmol) at rt slowly. The reaction mixture was stirred at rt for 18 h. The TLC showed reaction to be complete. The reaction mixture was quenched with cold methanol (10 mL) and resulted mixture was evaporated under reduced pressure. The residue was diluted with saturated aq NaHCO3 (20 mL) and extracted with EtOAc (3×20 mL). The organics were dried (Na2SO4), filtered and concentrated under reduced pressure to 6-bromo-2-methyl-3,4-dihydro-2H-benzo[b][1,4]oxazine as a brown solid. Yield: 900 mg (95%). 1H NMR (400 MHz, DMSO-d6): δ 6.50-6.77 (m, 3H), 6.06 (bs, 1H), 4.03-4.06 (m, 1H), 3.31 (bs, 1H), 2.86-2.93 (m, 1H), 1.25 (d, J=6.4 Hz, 3H). MS (ESI+) for CHNOS m/z 227.88 [M+H]+.

1-(6-Bromo-2-methyl-2,3-dihydro-4H-benzo[b][1,4]oxazin-4-yl)ethan-1-one

To a solution of 6-bromo-2-methyl-3,4-dihydro-2H-benzo[b][1,4]oxazine (800 mg, 3.52 mmol) in dry THF (20 mL) was added acetyl chloride (0.5 mL, 7.01 mmol) at rt. The reaction mixture was stirred at rt for 5 h. The TLC showed reaction to be complete. The reaction mixture was diluted with cold H₂O (20 mL) and extracted with EtOAc (3×25 mL). The combined organic layer was dried (Na₂SO₄), filtered and concentrated under reduced pressure to give 1-(6-bromo-2-methyl-2,3-dihydro-4H-benzo[b][1,4]oxazin-4-yl)ethan-1-one as a brown solid. Yield: 830 mg (78%). ¹H NMR (400 MHz, DMSO-d₆): δ 8.20 (bs, 1H), 7.10-7.23 (m, 1H), 6.84 (d, J=8.7 Hz, 1H), 4.29-4.40 (m, 1H), 4.10 (bs, 1H), 3.32 (bs, 1H), 2.25 (s, 3H), 1.29 (d, J=6.1 Hz, 3H). MS (ESI+) for CHNOS m/z 269.90 [M+H]⁺.

Intermediate 20

6-Bromo-3,4-dihydro-2H-benzo[b][1,4]oxazin-2-one

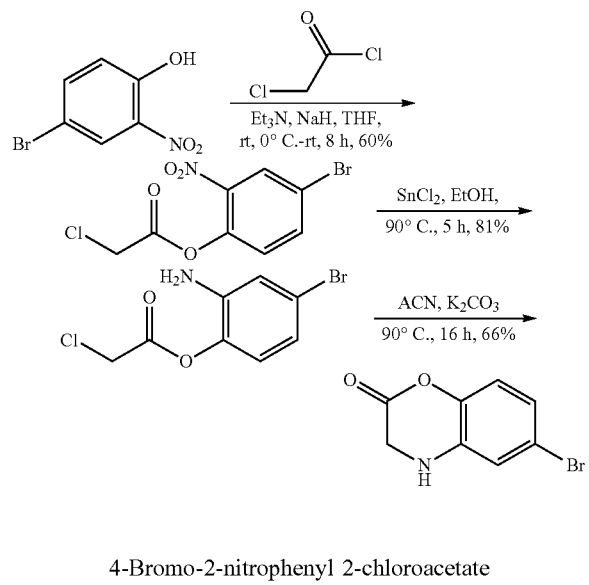

4-Bromo-2-nitrophenyl 2-chloroacetate

To a suspension of NaH (60% dispersion in mineral oil, 1.44 g, 36.7 mmol) in dry THF (30 mL) was added a solution of 4-bromo-2-nitrophenol (4.0 g, 18.3 mmol) in THF (20 mL) dropwise at 0° C. The resulted mixture was stirred at 0° C. for 1 h and 2-chloroacetyl chloride (2.0 mL, 25.6 mmol) was added to it slowly. The resulted reaction mixture was allowed to warm to rt and stirred further for 7 h. The TLC showed reaction to be complete. The reaction mixture was diluted with cold H₂O (50 mL) and extracted with EtOAc (3×50 mL). The combined organic layer was dried (Na₂SO₄), filtered and concentrated under reduced pressure. The crude residue was purified by column chromatography using silica gel (100-200 mesh), eluting with 0-10% EtOAc in hexane to afford 4-bromo-2-nitrophenyl 2-chloroacetate as a yellow solid. Yield: 3.2 g (60%). ¹H NMR (400 MHz, DMSO-d₆): δ 8.38 (d, J=2.3 Hz, 1H), 8.07 (dd, J=2.3, 8.7 Hz, 1H), 7.52 (d, J=8.7 Hz, 1H), 4.81 (s, 2H).

2-Amino-4-bromophenyl 2-chloroacetate

To a solution of 4-bromo-2-nitrophenyl 2-chloroacetate (3.0 g, 10.3 mmol) in EtOH (40 mL) were added conc. HCl (2.5 mL) and SnCl₂ (9.8 g, 51.7 mmol) at rt. The resulted mixture was stirred at 90° C. for 5 h. The TLC showed reaction to be complete. The solvent was evaporated under reduced pressure. The residue was neutralized to pH 7 using saturated aq Na₂CO₃ solution and extracted with EtOAc (3×50 mL). The organics were dried (Na₂SO₄), filtered and concentrated under reduced pressure. The crude residue was purified by column chromatography using silica gel (100-200 mesh), eluting with 0-20% EtOAc in hexane to afford 2-amino-4-bromophenyl 2-chloroacetate as a brown solid. Yield: 2.2 g (81%). MS (ESI+) for CHNOS m/z 264.01 [M+H]⁺.

6-Bromo-3,4-dihydro-2H-benzo[b][1,4]oxazin-2-one

To a solution of 2-amino-4-bromophenyl 2-chloroacetate (1.2 g, 4.58 mmol) in CH₃CN (15 mL) was added K₂CO₃ (3.2 g, 22.9 mmol) at rt. The resulted mixture was stirred at 90° C. for 16 h. THE TLC showed reaction to be complete. The solvent was evaporated under vacuum. The residue was diluted with H₂O (25 mL) and extracted with EtOAc (3×25 mL). The organics were dried (Na₂SO₄), filtered and concentrated under reduced pressure. The crude residue was purified by column chromatography using silica gel (100-200 mesh), eluting with 0-20% EtOAc in hexane to afford 6-bromo-3,4-dihydro-2H-benzo[b][1,4]oxazin-2-one as a brown solid. Yield: 680 mg (66%). ¹H NMR (400 MHz, DMSO-d₆): δ 7.08 (dd, J=2.1, 8.5 Hz, 1H), 7.02 (d, J=2.1 Hz, 1H), 6.91 (d, J=8.5 Hz, 1H), 4.59 (s, 2H). MS (ESI-) for CHNOS m/z 226.01 [M-H]⁺.

Intermediate 21

6-Bromo-8-fluoro-2H-benzo[b][1,4]oxazin-3(4H)-one

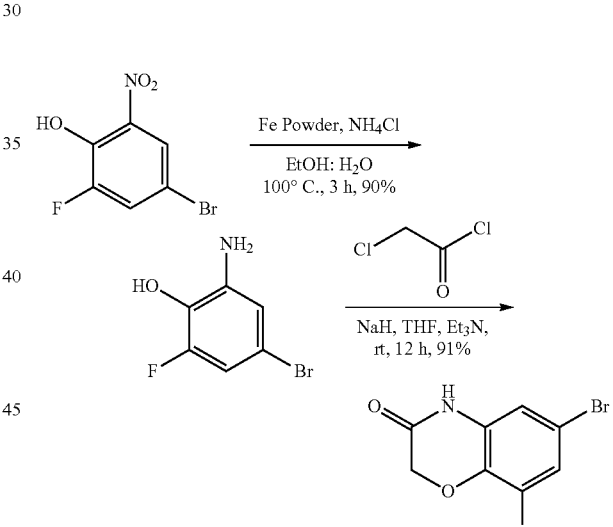

2-Amino-4-bromo-6-fluorophenol

To a solution of 4-bromo-2-fluoro-6-nitrophenol (8.0 g, 33.9 mmol) in EtOH:H₂O (4:1, 100 mL) were added Fe powder (9.1 g, 169.4 mmol) and AlCl₃ (22.5 g, 169.4 mmol) at rt. The reaction mixture was stirred and refluxed for 3 h. The TLC showed reaction to be complete. The reaction mixture was filtered through a celite bed. The celite bed was further washed with EtOH (50 mL). The solvent was evaporated under reduced pressure. The residue was diluted with H₂O (50 mL) and extracted with EtOAc (3×50 mL). The combined organic layer was dried (Na₂SO₄), filtered and concentrated under reduced pressure. The crude residue was purified by column chromatography using silica gel (100-200 mesh), eluting with 0-5% EtOAc in hexane to afford 2-amino-4-bromo-6-fluorophenol as a brown solid. Yield: 6.2 g (90%). MS (ESI−) for CHNOS m/z 203.89 [M−H]⁺.

6-Bromo-8-fluoro-3,4-dihydro-2H-benzo[b][1,4]oxazine

To a solution of 2-amino-4-bromo-6-fluorophenol (5.0 g, 24.4 mmol) in dry THF (50 mL) were added Et$_3$N (5.1 mL, 36.6 mmol) and 2-chloroacetyl chloride (2.1 mL, 26.4 mmol) at 0° C. The reaction mixture was allowed to warm to rt and stirred for 2 h. After 2 h reaction mixture was again cooled to 0° C. and NaH (60% dispersion in mineral oil, 2.43 g, 6.10 mmol) was added portion wise. The reaction mixture was further stirred at rt for 12 h. The TLC showed reaction to be complete. The reaction mixture was diluted with cold H$_2$O (50 mL) and extracted with EtOAc (3×50 mL). The combined organic layer was dried (Na$_2$SO$_4$), filtered and concentrated under reduced pressure. The residue was triturated with Et$_2$O (50 mL) to afford 6-bromo-8-fluoro-3,4-dihydro-2H-benzo[b][1,4]oxazine as a brown solid. Yield: 5.3 g (91%). $^1$H NMR (400 MHz, DMSO-d$_6$): δ 11.01 (bs, 1H), 7.18-7.29 (m, 1H), 6.88 (s, 1H), 4.68 (s, 2H) MS (ESI−) for CHNOS m/z 243.98 [M−H]⁺.

The following intermediate was prepared in a similar manner to 1-(6-bromo-2-methyl-2,3-dihydro-4H-benzo[b][1,4]oxazin-4-yl) ethan-1-one.

| Name | Int | Structure | Yield | Spectral Data 1H NMR & LCMS |
|---|---|---|---|---|
| 6-Bromo-8-fluoro-3,4-dihydro-2H-benzo[b][1,4]oxazine | 22 | 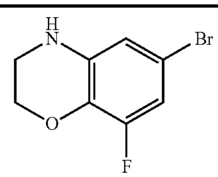 | 26% | MS (ESI−) for CHNOS m/z 230.10 [M − H]⁺; $^1$H NMR (400 MHz, DMSO-d$_6$): δ 6.49-6.63 (m, 2H), 6.38 (bs, 1H), 4.13 (t, J = 4.4 Hz, 2H), 3.30 (bs, 2H) |

Intermediate 23

1-(6-Bromo-2,3-dihydro-4H-benzo[b][1,4]oxazin-4-yl)ethan-1-one

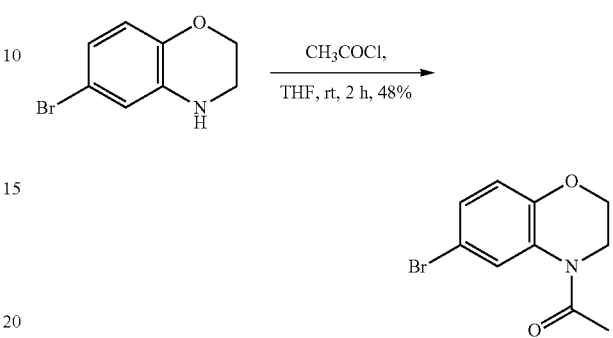

To a solution of 6-bromo-3,4-dihydro-2H-benzo[b][1,4]oxazine (600 mg, 2.8 mmol) in THF (10 mL) was added acetyl chloride (330 mg, 4.2 mmol) slowly at rt. The reaction mixture was stirred at rt for 2 h. The TLC showed the reaction to be complete. The reaction mixture was quenched with saturated aq solution of NaHCO$_3$ (10 mL) and extracted with EtOAc (3×10 mL). The organic layer was dried (Na$_2$SO$_4$), filtered and concentrated under reduced pressure to afford 1-(6-bromo-2,3-dihydro-4H-benzo[b][1,4]oxazin-4-yl)ethan-1-one as a yellow solid. Yield: 350 mg (48%); $^1$H NMR (400 MHz, DMSO-d$_6$): δ 8.21 (bs, 1H), 7.18 (d, J=8.5 Hz, 1H), 6.85 (d, J=8.5 Hz, 1H), 4.25-4.27 (m, 2H), 3.82-3.85 (m, 2H), 2.25 (s, 3H).

The following intermediates were prepared in a similar manner to 1-(6-bromo-2-methyl-2,3-dihydro-4H-benzo[b][1,4]oxazin-4-yl) ethan-1-one.

| Name | Int | Structure | Yield | Spectral Data 1H NMR & LCMS |
|---|---|---|---|---|
| 1-(4-Acetyl-3,4-dihydro-2H-benzo[b][1,4]oxazin-6-yl)-2-bromoethan-1-one | 24 | 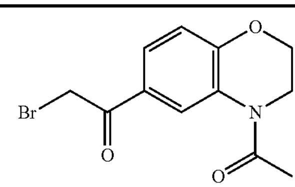 | 63% | MS (ESI+) for CHNOS m/z 298.04 [M + H]⁺ |
| 1-(6-Bromo-8-fluoro-2,3-dihydro-4H-benzo[b][1,4]oxazin-4-yl)ethan-1-one | 25 | 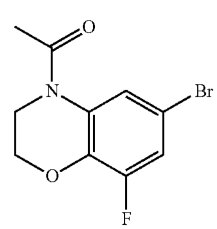 | 68% | $^1$H NMR (400 MHz, DMSO-d$_6$): δ 8.01 (bs, 1H), 7.29-7.34 (m, 1H), 4.34 (t, J = 4.5 Hz, 2H), 3.66 (t, J = 4.5 Hz, 2H), 2.26 (s, 3H) |
| 1-(6-Bromo-7-fluoro-2,3-dihydro-4H-benzo[b][1,4]oxazin-4-yl)ethan-1-one | 26 | 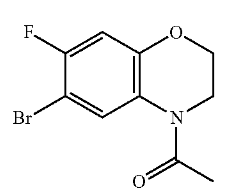 | 65% | MS (ESI+) for CHNOS m/z 273.98 [M + H]⁺ |

| Name | Int | Structure | Yield | Spectral Data 1H NMR & LCMS |
|------|-----|-----------|-------|------------------------------|
| 1-(7-Bromo-3,4-dihydroquinolin-1(2H)-yl)ethan-1-one | 27 | COCH₃ structure with Br | 69% | MS (ESI+) for CHNOS m/z 254.16 M + H]⁺ |

Intermediate 28

5-Bromo-2-((4-fluorobenzyl)oxy)pyridine

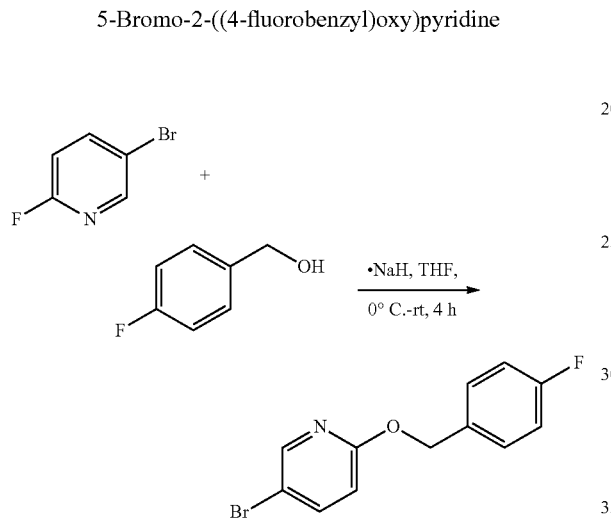

To a solution of (4-fluorophenyl)methanol (1 g, 5.08 mmol) in THF (10 mL) was added NaH (60% in mineral oil, 455 mg, 11.36 mmol) at 0° C. slowly. The reaction mixture was stirred at 0° C. for 30 min and 5-bromo-2-fluoropyridine (1.1 g, 8.52 mmol) was added slowly at 0° C. The reaction mixture was further stirred at 80° C. for 3 h. The TLC showed the reaction to be complete. The reaction mixture was quenched with saturated aq NH₄Cl (25 mL) and extracted with EtOAc (3×25 mL). The organics were dried (Na₂SO₄), filtered and concentrated under reduced pressure to afford 5-bromo-2-((4-fluorobenzyl)oxy)pyridine as a yellow solid. Yield: 1.5 g (crude). MS (ESI+) for CHNOS m/z 281.90 [M+H]⁺.

Intermediate 29 tert-Butyl 7-bromo-3,4-dihydrobenzo[b][1,4]oxazepine-5(2H)-carboxylate

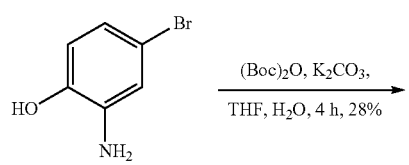

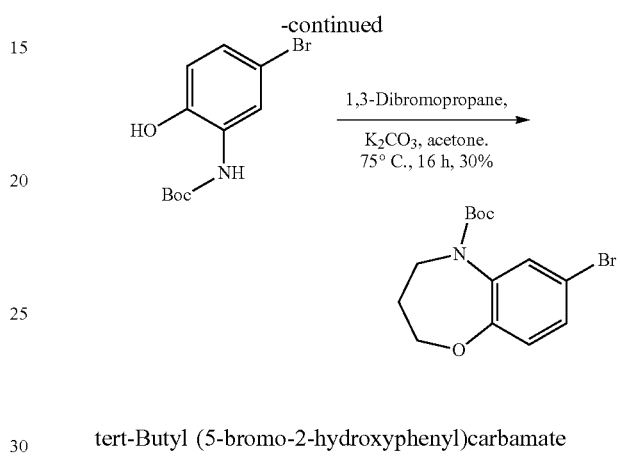

tert-Butyl (5-bromo-2-hydroxyphenyl)carbamate

To a stirred solution of 2-amino-4-bromophenol (5.0 g, 26.6 mmol) in THF:H20 (1:1, 100 mL) were added K₂CO₃ (18.3 g, 133 mmol) followed by di-tert-butyl dicarbonate (15.1 g, 69.14 mmol). The reaction mixture was stirred at rt for 4 h. The TLC showed reaction to be complete. The reaction mixture was extracted with EtOAc (3×50 mL). The organics were dried (Na2SO4), filtered and concentrated under reduced pressure. The crude was diluted with methanol (10 mL) and 1.0 M aq. NaOH (20 mL) and H₂O (20 mL) The resulted reaction mixture was stirred for 30 min at rt and MeOH was removed under reduced pressure. The residue was neutralized to pH 7 by using 1.0 N HCl and extracted with DCM (3×50 mL). The organics were dried (Na₂SO₄), filtered and concentrated under reduced pressure. The crude residue was purified by column chromatography using silica gel (100-200 mesh), eluting with 0-5% EtOAc in hexane to afford tert-butyl (5-bromo-2-hydroxyphenyl)carbamate as a brown solid. Yield: 2.1 g (28%). MS (ESI+) for CHNO m/z 187.92 [M−100+H]⁺.

tert-Butyl 7-bromo-3,4-dihydrobenzo[b][1,4]oxazepine-5(2H)-carboxylate

To a stirred solution of tert-butyl (5-bromo-2-hydroxyphenyl)carbamate (1.85 g, 6.42 mmol) in acetone (50 mL) were added K₂CO₃ (7.0 g, 51.36 mmol) and 1,3-dibromopropane (3.9 g, 19.26 mmol) at rt. The reaction mixture was stirred at 75° C. for 16 h. The TLC showed reaction to be complete. The reaction mixture was filtered through celite bed. The celite bed was washed with acetone (20 mL). The filtrate was concentrated under reduced pressure. The residue was diluted with H₂O (20 mL) and extracted with EtOAc (3×20 mL). The organics were dried (Na₂SO₄), filtered and concentrated under reduced pressure. The crude residue was purified by column chromatography using silica gel (100-200 mesh), eluting with 0-5% EtOAc in hexane to afford tert-butyl 7-bromo-3,4-dihydrobenzo[b][1,4] oxazepine-5(2H)-carboxylate as a white solid. Yield: 620 mg (30%). MS (ESI+) for CHNO m/z 328.17 [M+H]⁺.

The following intermediates were prepared in a similar manner to 2-(3,4-dimethoxyphenyl)imidazo[1,2-a]pyrimidine.

| Name | Int | Structure | Yield | Spectral Data 1H NMR & LCMS |
|---|---|---|---|---|
| 2-(2,3-Dihydrobenzofuran-5-yl)imidazo[1,2-a]pyrimidine | 30 | 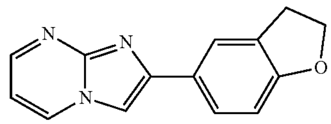 [SMILES: c1cnc2nc(-c3ccc4c(c3)CCO4)cn2c1] | 72% | MS (ESI+) for CHNOS m/z 238.08 [M + H]⁺; ¹H NMR (400 MHz, DMSO-d₆): δ 9.24 (d, J = 6.0 Hz, 1H), 8.92 (s, 1H), 8.57 (s, 1H), 7.98 (s, 1H), 7.76 (d, J = 8.5 Hz, 1H), 7.55-7.60 (m, 1H), 6.90-7.01 (m, 1H), 4.64 (t, J = 8.8 Hz, 2H), 3.27 (t, J = 8.8 Hz, 2H) |
| 2-(4-Chlorophenyl)imidazo[1,2-a]pyrimidine | 31 | 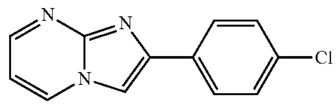 [SMILES: Clc1ccc(-c2cn3cccnc3n2)cc1] | 29% | MS (ESI+) for CHNOS m/z 230.11 [M + H]⁺; LC purity 99.7% (Ret. Time—4.27 min); ¹H NMR (400 MHz, DMSO-d₆): δ 8.97 (dd, J = 1.9, 6.7 Hz, 1H), 8.56 (dd, J = 1.9, 4.0 Hz, 1H), 8.43 (s, 1H), 8.03 (d, J = 8.6 Hz, 2H), 7.52 (d, J = 8.6 Hz, 2H), 7.08 (dd, J = 4.0, 6.7 Hz, 1H) |
| 2-(3,4-Dihydro-2H-benzo[b][1,4]dioxepin-7-yl)imidazo[1,2-a]pyrimidine | 32 | 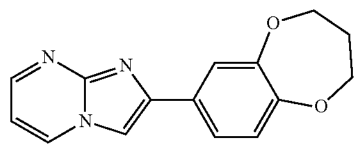 [SMILES: c1cnc2nc(-c3ccc4c(c3)OCCCO4)cn2c1] | 46% | MS (ESI+) for CHNOS m/z 268.16 [M + H]⁺ |
| 2-(4-Fluoro-3-methoxyphenyl)imidazo[1,2-a]pyrimidine | 33 | 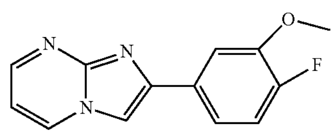 [SMILES: COc1cc(-c2cn3cccnc3n2)ccc1F] | 57% | MS (ESI+) for CHNOS m/z 244.11 [M + H]⁺; 1H NMR (400 MHz, DMSO-d₆): δ 9.11 (d, J = 5.9 Hz, 1H), 8.74 (s, 1H), 8.57 (s, 1H), 7.79 (d, J = 7.1 Hz, 1H), 7.55-7.65 (m, 1H), 7.25-7.41 (m, 2H), 3.96 (s, 3H). |
| 2-(4-((4-Fluorobenzyl)oxy)phenyl)imidazo[1,2-a]pyrimidine | 34 | 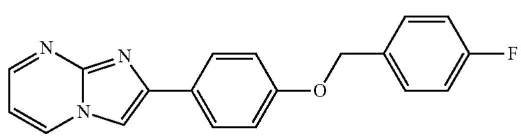 [SMILES: Fc1ccc(COc2ccc(-c3cn4cccnc4n3)cc2)cc1] | 33% | MS (ESI+) for CHNOS m/z 320.22 [M + H]⁺; 1H NMR (400 MHz, DMSO-d₆): δ 9.21 (d, J = 6.4 Hz, 1H), 8.91 (d, J = 2.8 Hz, 1H) 8.58 (s, 1H), 7.95 (d, J = 8.5 Hz, 2H), 7.50-7.61 (m, 3H), 7.15-7.30 (m, 4H), 5.19 (s, 2H) |
| 2-(3-Fluoro-4-methoxyphenyl)imidazo[1,2-a]pyrimidine | 35 | 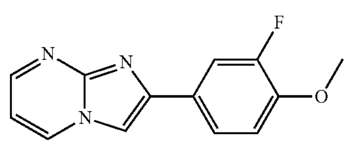 [SMILES: COc1ccc(-c2cn3cccnc3n2)cc1F] | 29% | MS (ESI+) for CHNOS m/z 244.15 [M + H]⁺; ¹H NMR (400 MHz, DMSO-d₆): δ 8.94 (d, J = 4.8 Hz, 1H), 8.51 (d, J = 2.0 Hz, 1H), 8.34 (s, 1H), 7.73-7.87 (m, 2H), 7.19-7.31 (m, 1H), 7.02-7.07 (m, 1H), 3.89 (m, 3H) |
| 2-(3-chloro-4-methoxyphenyl)imidazo[1,2-a]pyrimidine | 36 | 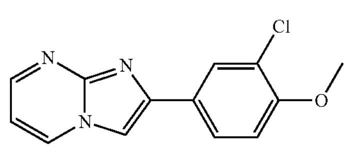 [SMILES: COc1ccc(-c2cn3cccnc3n2)cc1Cl] | 80% | MS (ESI+) for CHNOS m/z 260.05 [M + H]⁺ |
| 2-Fluoro-4-(imidazo[1,2-a]pyrimidin-2-yl)phenol | 37 | 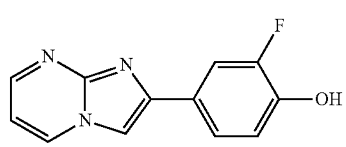 [SMILES: Oc1ccc(-c2cn3cccnc3n2)cc1F] | 54% | MS (ESI+) for CHNOS m/z 230.05 [M + H]⁺; ¹H NMR (400 MHz, DMSO-d₆): δ 10.33 (bs, 1H), 9.09 (d, J = 6.2 Hz, 1H), 8.72 (s, 1H), 8.43 (s, 1H), 7.50-7.90 (m, 2H), 7.20 (bs, 1H), 6.92-7.20 (m, 1H) |

-continued

| Name | Int | Structure | Yield | Spectral Data 1H NMR & LCMS |
|---|---|---|---|---|
| 2-(4-((4-Fluorobenzyl)oxy)phenyl)imidazo[1,2-a]pyrimidine | 38 | 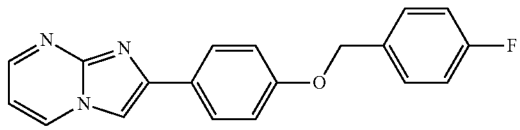 [SMILES: Fc1ccc(COc2ccc(-c3cn4cccnc4n3)cc2)cc1] | 52% | MS (ESI+) for CHNOS m/z 320.07 [M + H]+; 1H NMR (400 MHz, DMSO-d6): δ 8.98 (d, J = 5.3 Hz, 1H), 8.55 (d, J = 2.1 Hz, 1H), 8.32 (s, 1H), 7.94 (d, J = 8.6 Hz, 2H), 7.50-7.60 (m, 2H), 7.07-7.29 (m, 5H), 5.15 (s, 2H) |
| 2-(4-(Trifluoromethoxy)phenyl)imidazo[1,2-a]pyrimidine | 39 | 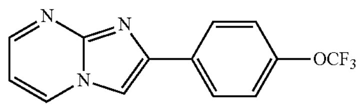 [SMILES: FC(F)(F)Oc1ccc(-c2cn3cccnc3n2)cc1] | 78% | MS (ESI+) for CHNOS m/z 280.15 [M + H]+ |
| 2-(4-Methoxyphenyl)imidazo[1,2-a]pyrimidine | 40 | 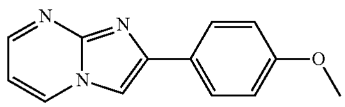 [SMILES: COc1ccc(-c2cn3cccnc3n2)cc1] | 96% | MS (ESI+) for CHNOS m/z 226.12 [M + H]+; 1H NMR (400 MHz, DMSO-d6): δ 9.28 (d, J = 6.5 Hz, 1H), 8.97 (bs, 1H), 8.66 (s, 1H), 7.96 (d, J = 8.5 Hz, 2H), 7.58-7.63 (m, 1H), 6.93 (d, J = 8.5 Hz, 2H), 3.85 (s, 3H) |
| 2-(3-Methoxyphenyl)imidazo[1,2-a]pyrimidine | 41 | 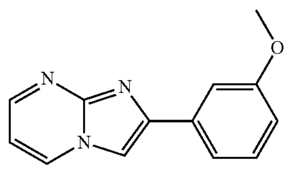 [SMILES: COc1cccc(-c2cn3cccnc3n2)c1] | 51% | MS (ESI+) for CHNOS m/z 226.06 [M + H]+; LC purity 98.3% (Ret. Time—4.3 min) 1H NMR (400 MHz, DMSO-d6), 9.20 (d, J = 6.8 Hz, 1H), 8.88 (d, J = 2.9 Hz, 1H), 8.69 (s, 1H), 7.56-7.62 (m, 2H), 7.45-7.50 (m, 2H), 7.07 (d, J = 7.5 Hz, 1H), 3.86 (s, 3H) |
| 2-(Benzo[d][1,3]dioxol-5-yl)imidazo[1,2-a]pyrimidine | 42 | 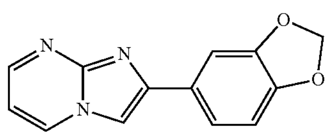 [SMILES: c1cnc2nc(-c3ccc4c(c3)OCO4)cn2c1] | 48% | MS (ESI+) for CHNOS m/z 240.06 [M + H]+ |
| 2-(2-Methylpyridin-4-yl)imidazo[1,2-a]pyrimidine | 43 | 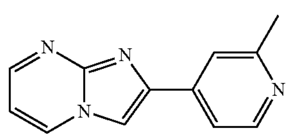 [SMILES: Cc1cc(-c2cn3cccnc3n2)ccn1] | 58% | (MS (ESI+) for CHNOS m/z 211.17 [M + H]+ |
| 2-(6-Methoxypyridin-3-yl)imidazo[1,2-a]pyrimidine | 44 | 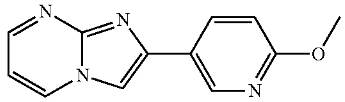 [SMILES: COc1ccc(-c2cn3cccnc3n2)cn1] | 4% | MS (ESI+) for CHNOS m/z 227.06 [M + H]+; 1H NMR (400 MHz, DMSO-d6): δ 8.97 (d, J = 6.5 Hz, 1H), 8.81 (s, 1H), 8.53 (bs, 1H), 8.36 (s, 1H), 8.27 (d, J = 8.7 Hz, 1H), 7.01-7.08 (m, 1H), 6.87-6.96 (s, 1H), 3.85 (s, 3H) |
| 2-(2,3-Dihydrobenzo[b][1,4]dioxin-6-yl)imidazo[1,2-a]pyrimidine | 45 | 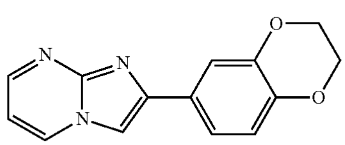 [SMILES: c1cnc2nc(-c3ccc4c(c3)OCCO4)cn2c1] | 6% | MS (ESI+) for CHNOS m/z 254.12 M + H]+; 1H NMR (400 MHz, DMSO-d6): δ 8.91 (d, J = 6.2 Hz, 1H), 8.49 (s, 1H), 8.26 (s, 1H), 7.37-7.58 (m, 2H), 6.83-7.09 (m, 2H), 4.29 (s, 4H) |
| 4-(Imidazo[1,2-a]pyrimidin-2-yl)phenol | 46 | 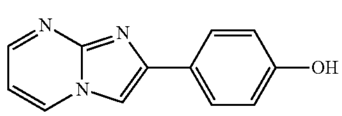 [SMILES: Oc1ccc(-c2cn3cccnc3n2)cc1] | 88% | MS (ESI+) for CHNOS m/z 212.00 [M + H]+ |
| 2-(2,6-Dimethylpyridin-4-yl)imidazo[1,2-a]pyrimidine | 47 | 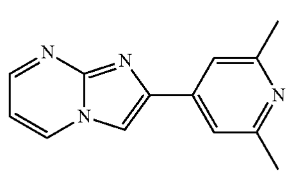 [SMILES: Cc1cc(-c2cn3cccnc3n2)cc(C)n1] | 30% | MS (ESI+) for CHNO m/z 225.12 [M + H]+ |

| Name | Int | Structure | Yield | Spectral Data 1H NMR & LCMS |
|---|---|---|---|---|
| 2-(Pyridin-4-yl)imidazo[1,2-a]pyrimidine | 48 | 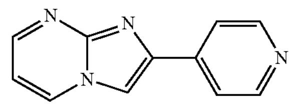 [SMILES: c1cnc2nc(-c3ccncc3)cn2c1] | 43% | MS (ESI+) for CHNO m/z 197.13 [M + H]+ |
| 4-(Imidazo[1,2-a]pyrimidin-2-yl)-N-methylpyridin-2-amine | 49 | 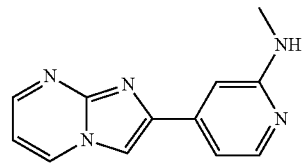 [SMILES: CNc1cc(-c2cn3cccnc3n2)ccn1] | 36% | MS (ESI+) for CHNO m/z 226.08 [M + H]+ |
| 1-(6-(Imidazo[1,2-a]pyrimidin-2-yl)-2,3-dihydro-4H-benzo[b][1,4]oxazin-4-yl)ethan-1-one | 50 | 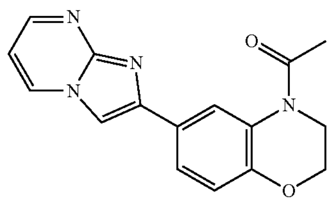 [SMILES: CC(=O)N1CCOc2ccc(-c3cn4cccnc4n3)cc21] | crude | MS (ESI+) for CHNOS m/z 295.11 [M + H]+ |

Intermediate 51

4-(Imidazo[1,2-a]pyrimidin-3-yl)pyridin-2-amine

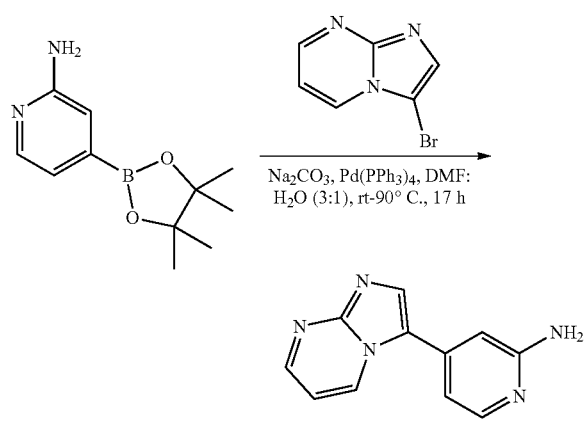

A mixture of 4-(4,4,5,5-tetramethyl-1,3,2-dioxaborolan-2-yl)pyridin-2-amine (1.0 g, 4.54 mmol), 3-bromoimidazo[1,2-a]pyrimidine (899 mg, 4.54 mmol) and Na₂CO₃ (963 mg, 9.09 mmol) in DMF:H₂O (3:1, 20 mL) was degassed with N₂ for 15 min at rt. Pd(PPh₃)₄ (525 mg, 0.45 mmol) was added to this degassed mixture at rt. The reaction mixture was again purged with N₂ for 5 min. The reaction vessel was sealed and stirred at 90° C. for 16 h. The TLC showed reaction to be complete. The reaction mixture was allowed to cool to rt and concentrated under reduced pressure. The crude residue was triturated with MeOH (25 mL) and the precipitated solid was filtered through the sintered funnel. The filtrate was concentrated under reduced pressure. The residue was purified by combiflash chromatography using 12 g silica column, eluting with 10% MeOH in DCM to afford 4-(imidazo[1,2-a]pyrimidin-3-yl)pyridin-2-amine as a brown solid. Yield: 500 mg (51%); MS (ESI+) for CHNOS m/z 212.0[M+H]+; $^{1}$H NMR (400 MHz, DMSO-$d_6$): δ 8.96-9.05 (m, 1H), 8.55-8.61 (m, 1H), 8.40 (s, 1H), 7.94-8.01 (m, 1H), 6.98-7.15 (m, 3H), 6.05-6.15 (bs, 2H).

The following intermediates were prepared in a similar manner to 2-(3,4-dimethoxyphenyl)-3-(2-methylpyridin-4-yl)imidazo[1,2-a]pyrimidine.

| Name | Int | Structure | Yield | Spectral Data 1H NMR & LCMS |
|---|---|---|---|---|
| 2-(3,4-Dimethoxy-phenyl)-3-(2-methylpyridin-4-yl)imidazo[1,2-a]pyrimidine | 52 | | 45% | MS (ESI+) for CHNOS m/z 347.17 [M + H]+ |

-continued

| Name | Int | Structure | Yield | Spectral Data 1H NMR & LCMS |
|---|---|---|---|---|
| 2-(6-Methoxypyridin-3-yl)-3-(2-methylpyridin-4-yl)imidazo[1,2-a]pyrimidine | 53 | 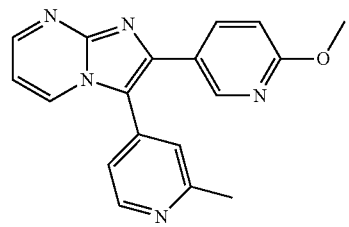 [SMILES: COc1ccc(-c2nc3ncccn3c2-c2ccnc(C)c2)cn1] | 34% | MS (ESI+) for CHNOS m/z 318.08 [M + H]+ |
| 2-(2,3-Dihydro-benzofuran-5-yl)-3-(2-methylpyridin-4-yl)imidazo[1,2-a]pyrimidine | 54 | 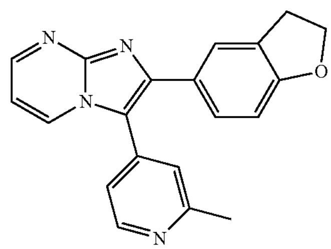 [SMILES: Cc1cc(-c2c(-c3ccc4c(c3)CCO4)nc3ncccn23)ccn1] | 53% | MS (ESI+) for CHNOS m/z 329.10 [M + H]+ |
| 2-(4-Chlorophenyl)-3-(2-methylpyridin-4-yl)imidazo[1,2-a]pyrimidine | 55 | 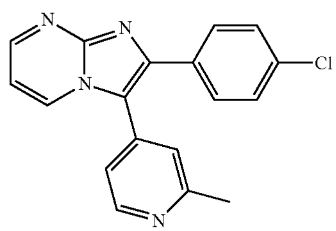 [SMILES: Cc1cc(-c2c(-c3ccc(Cl)cc3)nc3ncccn23)ccn1] | 92% | MS (ESI+) for CHNOS m/z 321.03 [M + H]+ |
| 2-(3,4-Dihydro-2H-benzo[b][1,4]dioxepin-7-yl)-3-(2-methylpyridin-4-yl)imidazo[1,2-a]pyrimidine | 56 | 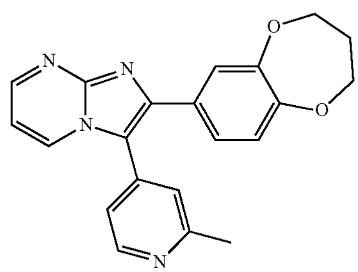 [SMILES: Cc1cc(-c2c(-c3ccc4c(c3)OCCCO4)nc3ncccn23)ccn1] | 51% | MS (ESI+) for CHNOS m/z 359.17 [M + H]+ |
| 2-(4-Fluoro-3-methoxyphenyl)-3-(2-methylpyridin-4-yl)imidazo[1,2-a]pyrimidine | 57 | 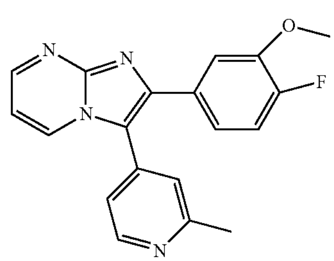 [SMILES: COc1cc(-c2nc3ncccn3c2-c2ccnc(C)c2)ccc1F] | 43% | MS (ESI+) for CHNOS m/z 335.23 [M + H]+ |
| 4-(2-(4-((4-Fluorobenzyl)oxy)phenyl)imidazo[1,2-a]pyrimidin-3-yl)pyridin-2-amine | 58 | 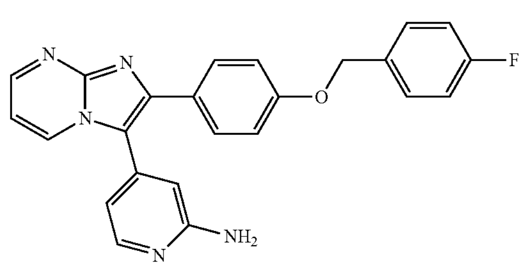 [SMILES: Nc1cc(-c2c(-c3ccc(OCc4ccc(F)cc4)cc3)nc3ncccn23)ccn1] | 61% | MS (ESI+) for CHNOS m/z 412.08 [M + H]+ |

-continued

| Name | Int | Structure | Yield | Spectral Data 1H NMR & LCMS |
|---|---|---|---|---|
| 4-(2-(2,3-Dihydro-benzofuran-5-yl)imidazo[1,2-a]pyrimidin-3-yl)pyridin-2-amine | 59 | 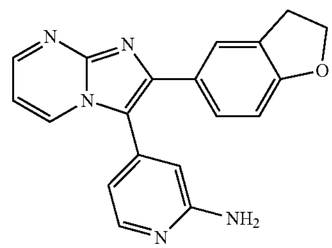 [SMILES: Nc1cc(-c2c(-c3ccc4c(c3)CCO4)nc3ncccn23)ccn1] | 20% | MS (ESI+) for CHNOS m/z 330.10 [M + H]+ |
| 4-(2-(2,3-Dihydro-benzofuran-5-yl)imidazo[1,2-a]pyrimidin-3-yl)-N-methylpyridin-2-amine | 60 | 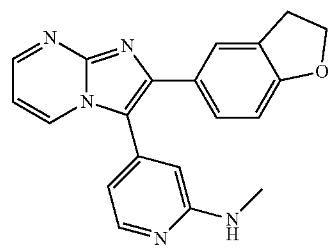 [SMILES: CNc1cc(-c2c(-c3ccc4c(c3)CCO4)nc3ncccn23)ccn1] | 39% | MS (ESI+) for CHNOS m/z 344.12 [M + H]+ |
| N,N-Dimethyl-3-(2-(2-methylpyridin-4-yl)imidazo[1,2-a]pyrimidin-3-yl)benzamide | 61 | 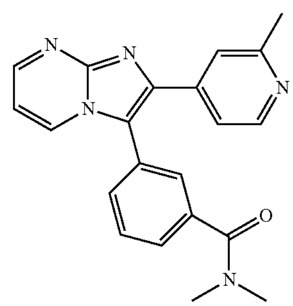 [SMILES: Cc1cc(-c2nc3ncccn3c2-c2cccc(C(=O)N(C)C)c2)ccn1] | 24% | MS (ESI+) for CHNOS m/z 358.09 [M + H]+ |
| 2-(3-Fluoro-4-methoxyphenyl)-3-(2-methylpyridin-4-yl)imidazo[1,2-a]pyrimidine | 62 | 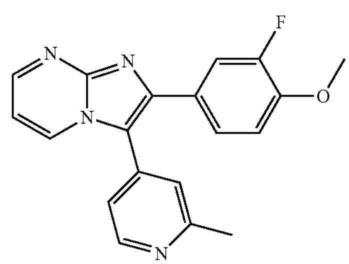 [SMILES: COc1ccc(-c2nc3ncccn3c2-c2ccnc(C)c2)cc1F] | 53% | MS (ESI+) for CHNOS m/z 335.11 [M + H]+ |
| 2-(3-Chloro-4-methoxyphenyl)-3-(2-methylpyridin-4-yl)imidazo[1,2-a]pyrimidine | 63 | 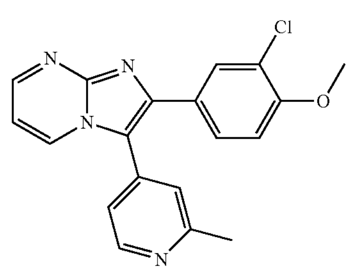 [SMILES: COc1ccc(-c2nc3ncccn3c2-c2ccnc(C)c2)cc1Cl] | 62% | MS (ESI+) for CHNOS m/z 351.25 [M + H]+ |

-continued

| Name | Int | Structure | Yield | Spectral Data 1H NMR & LCMS |
|---|---|---|---|---|
| 2-Fluoro-4-(3-(2-methylpyridin-4-yl)imidazo[1,2-a]pyrimidin-2-yl)phenol | 64 | 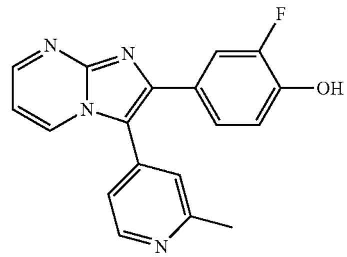 [SMILES: Cc1cc(-c2c(-c3ccc(O)c(F)c3)nc3ncccn23)ccn1] | 42% | MS (ESI+) for CHNOS m/z 321.04 [M + H]+ |
| 4-(2-(2,3-Dihydrobenzo[b][1,4]dioxin-6-yl)imidazo[1,2-a]pyrimidin-3-yl)pyridin-2(1H)-one | 65 | 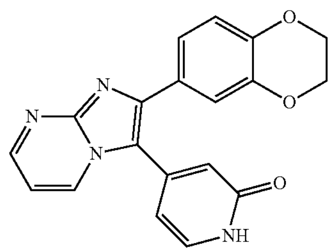 [SMILES: O=c1cc(-c2c(-c3ccc4c(c3)OCCO4)nc3ncccn23)cc[nH]1] | 44% | MS (ESI+) for CHNOS m/z 347.26 [M + H]+ |
| 2-(4-((4-Fluorobenzyl)oxy)phenyl)-3-(2-methylpyridin-4-yl)imidazo[1,2-a]pyrimidine | 66 | 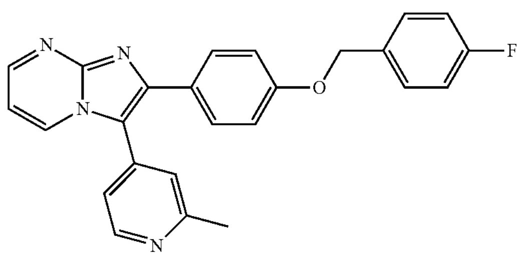 [SMILES: Cc1cc(-c2c(-c3ccc(OCc4ccc(F)cc4)cc3)nc3ncccn23)ccn1] | 31% | MS (ESI+) for CHNOS m/z 411.26 [M + H]+ |
| 3-(2-Methylpyridin-4-yl)-2-(4-(trifluoromethoxy)phenyl)imidazo[1,2-a]pyrimidine | 67 | 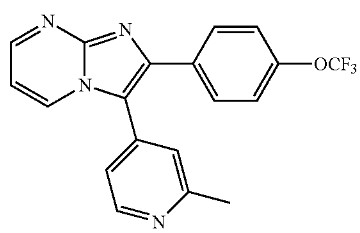 [SMILES: Cc1cc(-c2c(-c3ccc(OC(F)(F)F)cc3)nc3ncccn23)ccn1] | 31% | MS (ESI+) for CHNOS m/z 371.23 [M + H]+ |
| 2-(4-Methoxyphenyl)-3-(2-methylpyridin-4-yl)imidazo[1,2-a]pyrimidine | 68 | 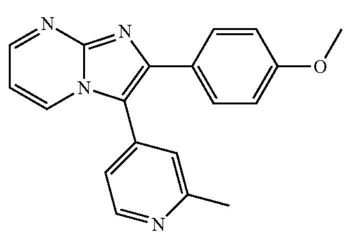 [SMILES: COc1ccc(-c2nc3ncccn3c2-c2ccnc(C)c2)cc1] | Crude | MS (ESI+) for CHNOS m/z 317.27 [M + H]+ |
| 2-(2,3-Dihydrobenzo[b][1,4]dioxin-6-yl)-3-(pyridin-3-yl)imidazo[1,2-a]pyrimidine | 69 | 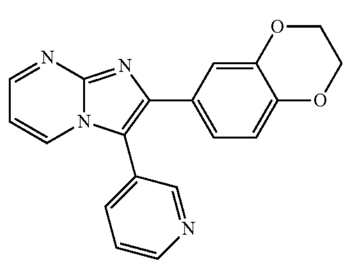 [SMILES: c1cncc(-c2c(-c3ccc4c(c3)OCCO4)nc3ncccn23)c1] | Crude | MS (ESI+) for CHNOS m/z 331.21 [M + H]+ |

-continued

| Name | Int | Structure | Yield | Spectral Data 1H NMR & LCMS |
|---|---|---|---|---|
| 2-(2,3-Dihydrobenzo[b][1,4]dioxin-6-yl)-3-(2-methylpyridin-4-yl)imidazo[1,2-a]pyrimidine | 70 | 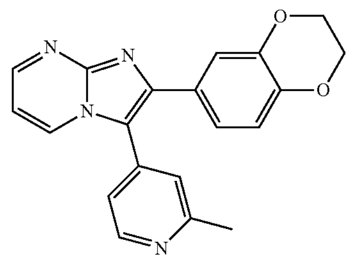 [SMILES: Cc1cc(-c2c(-c3ccc4c(c3)OCCO4)nc3ncccn23)ccn1] | Crude | MS (ESI+) for CHNOS m/z 345.12 [M + H]+ |
| 4-(2-(2,3-Dihydrobenzo[b][1,4]dioxin-6-yl)imidazo[1,2-a]pyrimidin-3-yl)pyridin-2-amine | 71 | 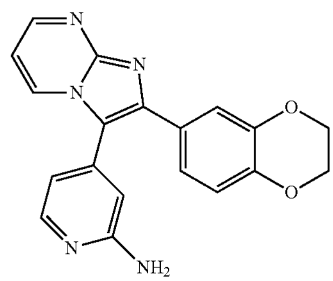 [SMILES: Nc1cc(-c2c(-c3ccc4c(c3)OCCO4)nc3ncccn23)ccn1] | Crude | (MS (ESI+) for CHNOS m/z 346.11 [M + H]+ |
| 2-(3-Methoxyphenyl)-3-(2-methylpyridin-4-yl)imidazo[1,2-a]pyrimidine | 72 | 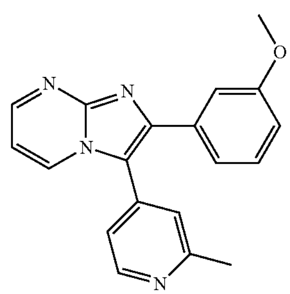 [SMILES: COc1cccc(-c2nc3ncccn3c2-c2ccnc(C)c2)c1] | 71% | Peak 1, MS (ESI+) for CHNOS m/z 317.10 [M + H]+ |
| 2-(Benzo[d][1,3]dioxol-5-yl)-3-(2-methylpyridin-4-yl)imidazo[1,2-a]pyrimidine | 73 | 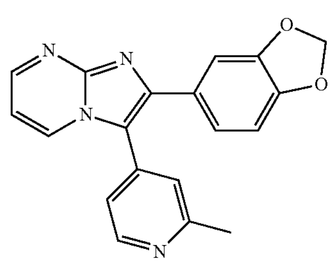 [SMILES: Cc1cc(-c2c(-c3ccc4c(c3)OCO4)nc3ncccn23)ccn1] | Crude | MS (ESI+) for CHNOS m/z 331.27 [M + H]+ |
| 1-(6-(2-(2-Methylpyridin-4-yl)imidazo[1,2-a]pyrimidin-3-yl)-2,3-dihydro-4H-benzo[b][1,4]oxazin-4-yl)ethan-1-one | 74 | 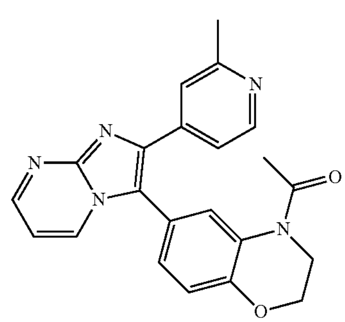 [SMILES: CC(=O)N1CCOc2ccc(-c3c(-c4ccnc(C)c4)nc4ncccn34)cc21] | 46% | MS (ESI+) for CHNOS m/z 386.47 [M + H]+ |

| Name | Int | Structure | Yield | Spectral Data 1H NMR & LCMS |
|------|-----|-----------|-------|------------------------------|
| 3-(6-((4-Fluorobenzyl)oxy)pyridin-3-yl)-2-(2-methylpyridin-4-yl)imidazo[1,2-a]pyrimidine | 75 | 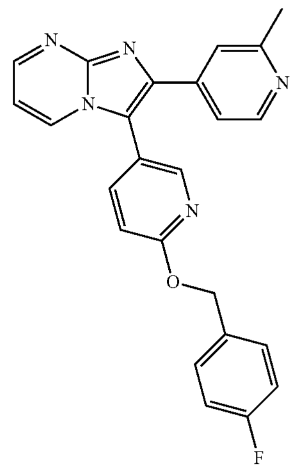 [SMILES: Cc1cc(-c2nc3ncccn3c2-c2ccc(OCc3ccc(F)cc3)nc2)ccn1] | Crude | MS (ESI+) for CHNOS m/z 412.18 [M + H]+ |
| 3-(5-Fluoro-6-methoxypyridin-3-yl)-2-(2-methylpyridin-4-yl)imidazo[1,2-a]pyrimidine | 76 | 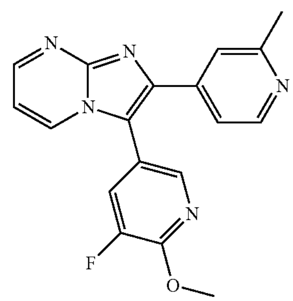 [SMILES: COc1ncc(-c2c(-c3ccnc(C)c3)nc3ncccn23)cc1F] | Crude | MS (ESI+) for CHNOS m/z 336.2 [M + H]+ |
| 6-(2-(2-Methylpyridin-4-yl)imidazo[1,2-a]pyrimidin-3-yl)quinoxaline | 77 | 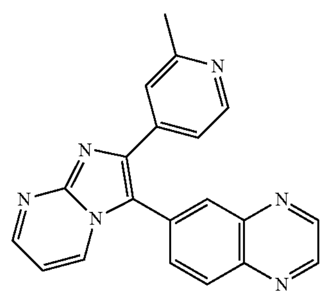 [SMILES: Cc1cc(-c2nc3ncccn3c2-c2ccc3nccnc3c2)ccn1] | Crude | MS (ESI+) for CHNOS m/z 339.09 [M + H]+ |
| 2-Methyl-6-(2-(2-methylpyridin-4-yl)imidazo[1,2-a]pyrimidin-3-yl)-2H-benzo[b][1,4]oxazin-3(4H)-one Intermediate for | 78 | 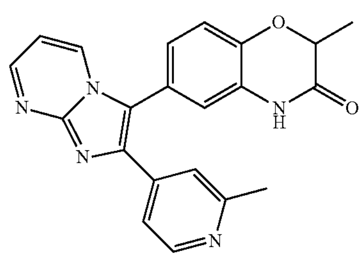 [SMILES: Cc1cc(-c2nc3ncccn3c2-c2ccc3c(c2)NC(=O)C(C)O3)ccn1] | Crude | MS (ESI+) for CHNOS m/z 372.08 [M + H]+ |
| 1-(2-Methyl-6-(2-(2-methylpyridin-4-yl)imidazo[1,2-a]pyrimidin-3-yl)-2,3-dihydro-4H-benzo[b][1,4]oxazin-4-yl)ethan-1-one | 79 | 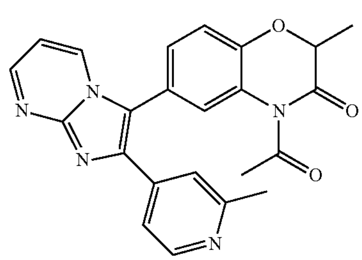 | Crude | MS (ESI+) for CHNOS m/z 400.2 [M + H]+ |

-continued

| Name | Int | Structure | Yield | Spectral Data 1H NMR & LCMS |
|---|---|---|---|---|
| 4-(3-(2-Methylpyridin-4-yl)imidazo[1,2-a]pyrimidin-2-yl)phenol | 80 | 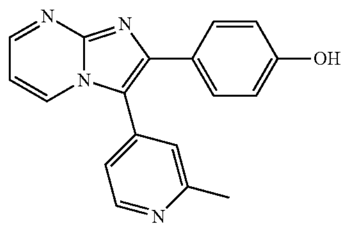 [SMILES: Cc1cc(-c2c(-c3ccc(O)cc3)nc3ncccn23)ccn1] | Crude | MS (ESI+) for CHNOS m/z 303.01 [M + H]+ |
| 1-(6-(2-(2,6-Dimethylpyridin-4-yl)imidazo[1,2-a]pyrimidin-3-yl)-2,3-dihydro-4H-benzo[b][1,4]oxazin-4-yl)ethan-1-one | 81 | 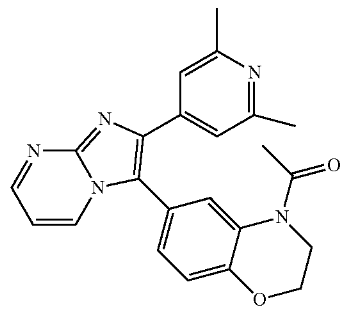 [SMILES: CC(=O)N1CCOc2ccc(-c3c(-c4cc(C)nc(C)c4)nc4ncccn34)cc21] | Crude | MS (ESI+) for CHNO m/z 400.34 [M + H]+ |
| 2-Methyl-5-(2-(2-methylpyridin-4-yl)imidazo[1,2-a]pyrimidin-3-yl)benzo[d]oxazole | 82 | 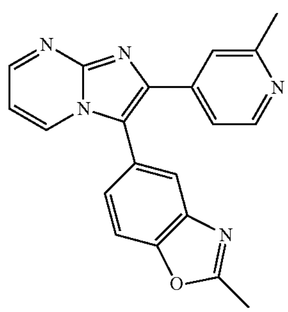 [SMILES: Cc1cc(-c2nc3ncccn3c2-c2ccc3oc(C)nc3c2)ccn1] | Crude | MS (ESI+) for CHNOS m/z 341.96 [M + H]+ |
| 2-(2,3-Dihydro-benzofuran-5-yl)-3-(pyridin-4-yl)imidazo[1,2-a]pyrimidine | 83 | 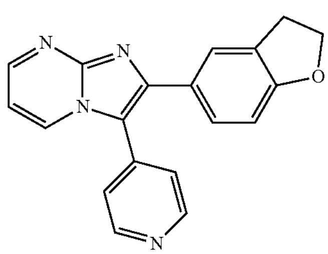 [SMILES: c1cnc2nc(-c3ccc4c(c3)CCO4)c(-c3ccncc3)n2c1] | Crude | MS (ESI+) for CHNOS m/z 314.96 [M + H]+ |
| 1-(6-(2-(Pyridin-4-yl)imidazo[1,2-a]pyrimidin-3-yl)-2,3-dihydro-4H-benzo[b][1,4]oxazin-4-yl | 84 | 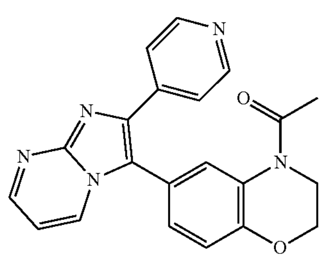 [SMILES: CC(=O)N1CCOc2ccc(-c3c(-c4ccncc4)nc4ncccn34)cc21] | Crude | MS (ESI+) for CHNO m/z 371.98 [M + H]+ |

| Name | Int | Structure | Yield | Spectral Data 1H NMR & LCMS |
|---|---|---|---|---|
| 1-(6-(2-(2-(Methylamino) pyridin-4-yl) imidazo[1,2-a]pyrimidin-3-yl)-2,3-dihydro-4H-benzo[b][1,4] oxazin-4-yl)ethan-1-one | 85 | 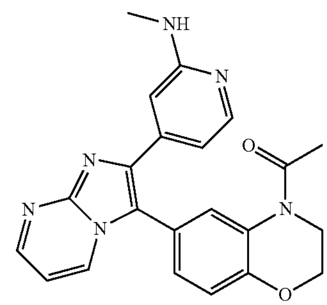 [SMILES: CNc1cc(-c2nc3ncccn3c2-c2ccc3c(c2)N(C(C)=O)CCO3)ccn1] | Crude | MS (ESI+) for CHNOS m/z 401.19 [M + H]+ |
| 3-(2-Methyl-2,3,3a,7a-tetrahydro-benzofuran-5-yl)-2-(2-methylpyridin-4-yl)imidazo[1,2-a]pyrimidine | 86 | 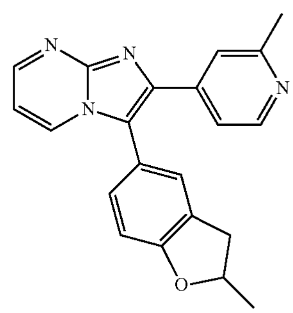 [SMILES: Cc1cc(-c2nc3ncccn3c2-c2ccc3c(c2)CC(C)O3)ccn1] | Crude | MS (ESI−) for CHNOS m/z 343.14 [M − H]+ |
| 1-(6-(2-(2-Aminopyridin-4-yl)imidazo[1,2-a]pyrimidin-3-yl)-2,3-dihydro-4H-benzo[b][1,4] oxazin-4-yl) ethan-1-one | 87 | 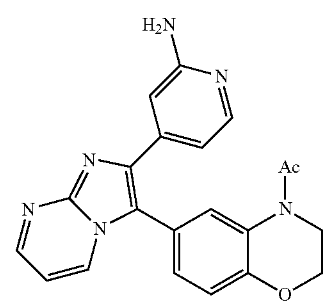 [SMILES: CC(=O)N1CCOc2ccc(-c3c(-c4ccnc(N)c4)nc4ncccn34)cc21] | Crude | MS (ESI+) for CHNOS m/z 387.22 [M + H]+ |
| 1-(6-(3-(2-Chloropyridin-4-yl)imidazo[1,2-a]pyrimidin-2-yl)-2,3-dihydro-4H-benzo[b][1,4] oxazin-4-yl)ethan-1-one | 88 | 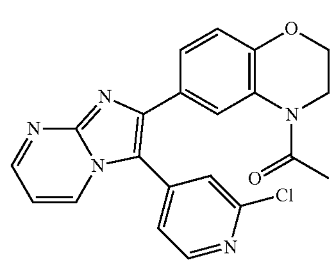 [SMILES: CC(=O)N1CCOc2ccc(-c3nc4ncccn4c3-c3ccnc(Cl)c3)cc21] | Crude | MS (ESI+) for CHNOS m/z 406.16 [M + H]+ |
| 1-(6-(3-(2-(triFluoromethyl) pyridin-4-yl)imidazo[1,2-a]pyrimidin-2-yl)-2,3-dihydro-4H-benzo[b][1,4] oxazin-4-yl)ethan-1-one | 89 | 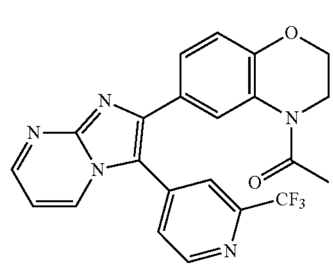 | Crude | MS (ESI+) for CHNOS m/z 440.18 [M + H]+ |

| Name | Int | Structure | Yield | Spectral Data 1H NMR & LCMS |
|---|---|---|---|---|
| 1-(6-(3-(2-Fluoropyridin-4-yl)imidazo[1,2-a]pyrimidin-2-yl)-2,3-dihydro-4H-benzo[b][1,4]oxazin-4-yl)ethan-1-one | 90 | 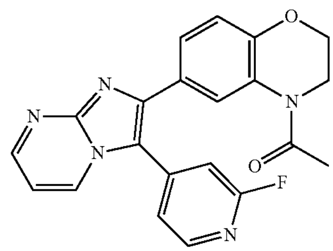 [SMILES: CC(=O)N1CCOc2ccc(-c3nc4ncccn4c3-c3ccnc(F)c3)cc21] | Crude | MS (ESI+) for CHNOS m/z 390.12 [M + H]+ |
| tert-Butyl 7-(2-(2-methylpyridin-4-yl)imidazo[1,2-a]pyrimidin-3-yl)-3,4-dihydrobenzo[b][1,4]oxazepine-5(2H)-carboxylate | 91 | 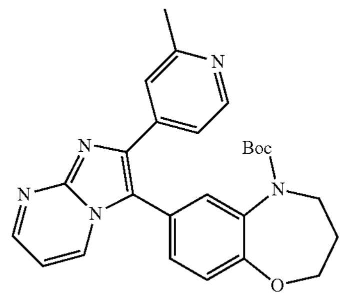 [SMILES: Cc1cc(-c2nc3ncccn3c2-c2ccc3c(c2)N(C(=O)OC(C)(C)C)CCCO3)ccn1] | Crude | MS (ESI+) for CHNO m/z 458.18 [M + H]+ |
| 1-(8-Fluoro-6-(3-(2-methylpyridin-4-yl)imidazo[1,2-a]pyrimidin-2-yl)-2,3-dihydro-4H-benzo[b][1,4]oxazin-4-yl)ethan-1-one | 92 | 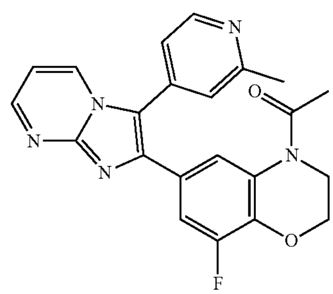 [SMILES: CC(=O)N1CCOc2c(F)cc(-c3nc4ncccn4c3-c3ccnc(C)c3)cc21] | Crude | MS (ESI+) for CHNOS m/z 404.14 [M + H]+ |
| 8-Fluoro-6-(3-(2-methylpyridin-4-yl)imidazo[1,2-a]pyrimidin-2-yl)-2H-benzo[b][1,4]oxazin-3(4H)-one | 93 | 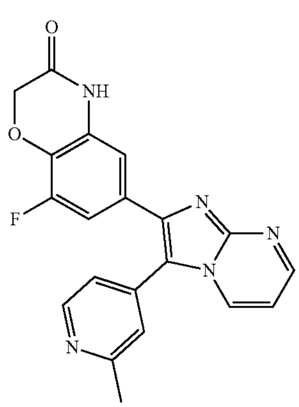 [SMILES: Cc1cc(-c2c(-c3cc(F)c4c(c3)NC(=O)CO4)nc3ncccn23)ccn1] | Crude | MS (ESI+) for CHNOS m/z 376.08 [M + H]+ |

-continued

| Name | Int | Structure | Yield | Spectral Data 1H NMR & LCMS |
|---|---|---|---|---|
| 6-(3-(2-Methylpyridin-4-yl)imidazo[1,2-a]pyrimidin-2-yl)-2H-benzo[b][1,4]oxazin-3(4H)-one | 94 | 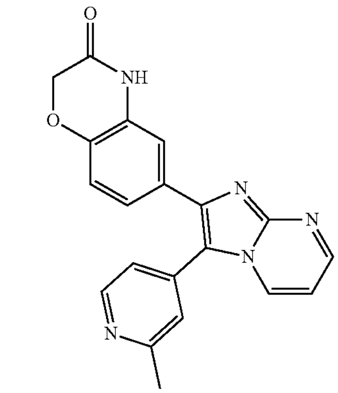 [SMILES: Cc1cc(-c2c(-c3ccc4c(c3)NC(=O)CO4)nc3ncccn23)ccn1] | Crude | MS (ESI+) for CHNOS m/z 358.12 [M + H]+ |
| 1-(7-Fluoro-6-(2-(2-methylpyridin-4-yl)imidazo[1,2-a]pyrimidin-3-yl)-2,3-dihydro-4H-benzo[b][1,4]oxazin-4-yl)ethan-1-one | 95 | 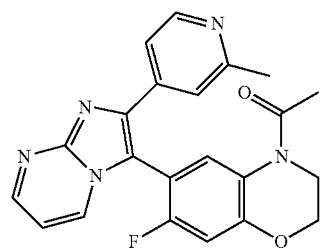 [SMILES: CC(=O)N1CCOc2cc(F)c(-c3c(-c4ccnc(C)c4)nc4ncccn34)cc21] | Crude | MS (ESI+) for CHNOS m/z 404.13 [M + H]+ |
| 6-(3-(2-Methylpyridin-4-yl)imidazo[1,2-a]pyrimidin-2-yl)-3,4-dihydro-2H-benzo[b][1,4]oxazin-2-one | 96 | 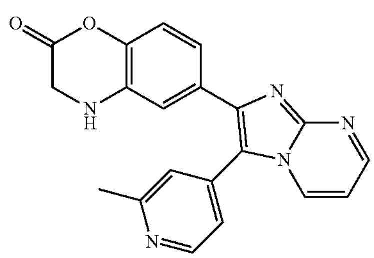 [SMILES: Cc1cc(-c2c(-c3ccc4c(c3)NCC(=O)O4)nc3ncccn23)ccn1] | Crude | MS (ESI+) for CHNOS m/z 358.20 [M + H]+ |
| 7-Fluoro-6-(2-(2-methylpyridin-4-yl)imidazo[1,2-a]pyrimidin-3-yl)-2H-benzo[b][1,4]oxazin-3(4H)-one | 97 | 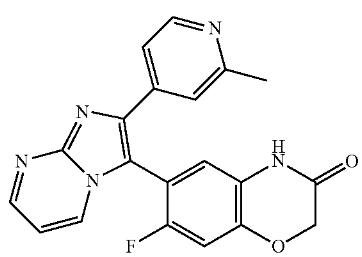 [SMILES: Cc1cc(-c2nc3ncccn3c2-c2cc3c(cc2F)OCC(=O)N3)ccn1] | Crude | MS (ESI+) for CHNOS m/z 376.13 [M + H]+ |
| 3-(8-Fluoro-2,3-dihydrobenzo[b][1,4]dioxin-6-yl)-2-(2-methylpyridin-4-yl)imidazo[1,2-a]pyrimidine | 98 | 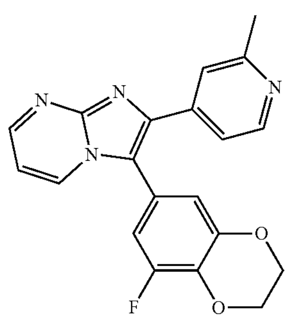 [SMILES: Cc1cc(-c2nc3ncccn3c2-c2cc(F)c3c(c2)OCCO3)ccn1] | Crude | MS (ESI+) for CHNOS m/z 363.21 [M + H]+ |

| Name | Int | Structure | Yield | Spectral Data 1H NMR & LCMS |
|---|---|---|---|---|
| 1-(7-(2-(2-Methylpyridin-4-yl)imidazo[1,2-a]pyrimidin-3-yl)-3,4-dihydroquinolin-1(2H)-yl)ethan-1-one | 99 | 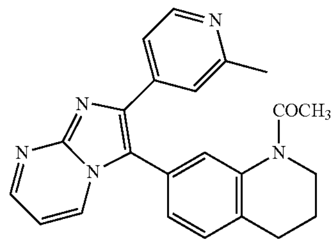 [SMILES: CC(=O)N1CCCc2ccc(-c3c(-c4ccnc(C)c4)nc4ncccn34)cc21] | Crude | MS (ESI+) for CHNOS m/z 384.27 [M + H]+ |
| 2-(7-Fluoro-2,3-dihydrobenzo[b][1,4]dioxin-6-yl)-3-(2-methylpyridin-4-yl)imidazo[1,2-a]pyrimidine | 100 | 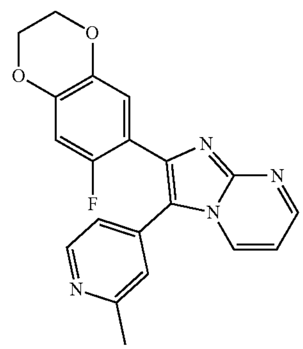 [SMILES: Cc1cc(-c2c(-c3cc4c(cc3F)OCCO4)nc3ncccn23)ccn1] | Crude | MS (ESI+) for CHNOS m/z 363.18 [M + H]+ |
| 3-(5-Fluoro-2,3-dihydrobenzo[b][1,4]dioxin-6-yl)-2-(2-methylpyridin-4-yl)imidazo[1,2-a]pyrimidine | 101 | 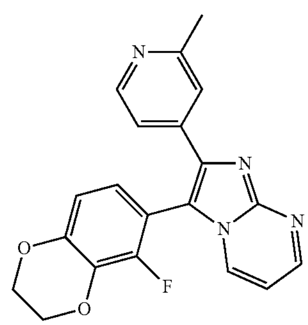 [SMILES: Cc1cc(-c2nc3ncccn3c2-c2ccc3c(c2F)OCCO3)ccn1] | Crude | MS (ESI+) for CHNOS m/z 363.15 [M + H]+ |
| 6-(2-(2-Methylpyridin-4-yl)imidazo[1,2-a]pyrimidin-3-yl)-2H-benzo[b][1,4]oxazin-3(4H)-one | 102 | 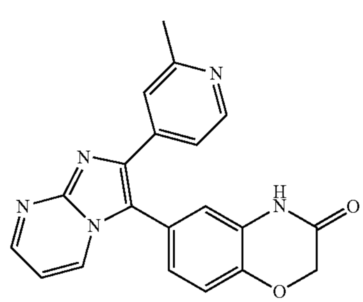 [SMILES: Cc1cc(-c2nc3ncccn3c2-c2ccc3c(c2)NC(=O)CO3)ccn1] | The crude LCMS showed 24% desired product. The crude was enriched up to 88% by combiflash using 40 g silica coloumn, eluting with 0-12% meoH in DCM followed by the trituration with Diethylether | MS (ESI+) for CHNOS m/z 358.04 [M + H]+ |

Intermediate 103

2-(4-(cyclopropylmethoxy)-3-fluorophenyl)-3-(2-methylpyridin-4-yl)imidazo[1,2-a]pyrimidine

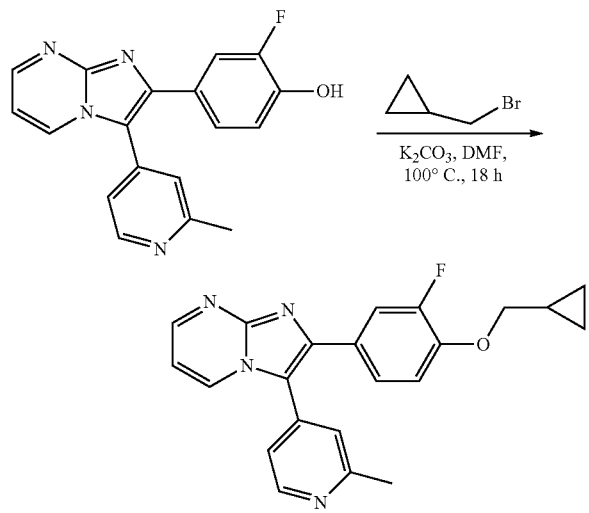

To a solution of 2-fluoro-4-(3-(2-methylpyridin-4-yl)imidazo[1,2-a]pyrimidin-2-yl)phenol (350 mg, 1.09 mmol) in DMF (5 mL) were added $K_2CO_3$ (453 mg, 3.28 mmol) and (bromomethyl)cyclopropane (295 mg, 2.19 mmol) at rt. The reaction mixture was stirred 100° C. for 18 h. The TLC showed reaction to complete. The reaction mixture was allowed to cool to rt, diluted with water (100 mL) and extracted with EtOAc (3×50 mL). The organics were washed with brine (100 mL), dried ($Na_2SO_4$), filtered and concentrated under reduced pressure to afford 2-(4-(cyclopropylmethoxy)-3-fluorophenyl)-3-(2-methylpyridin-4-yl)imidazo[1,2-a]pyrimidine as brown waxy. Yield: 380 mg (crude). The crude LCMS showed two peaks with desired mass 25% and 67% respectively. MS (ESI+) for CHNOS m/z 375.05 $[M+H]^+$.

The following intermediates were prepared in a similar manner to 2-(4-(cyclopropylmethoxy)-3-fluorophenyl)-3-(2-methylpyridin-4-yl)imidazo[1,2-a]pyrimidine.

| Name | Int | Structure | Yield | Spectral Data 1H NMR & LCMS |
|------|-----|-----------|-------|------------------------------|
| 2-(4-Cyclopropoxy-3-fluorophenyl)-3-(2-methylpyridin-4-yl)imidazo[1,2-a]pyrimidine | 104 | 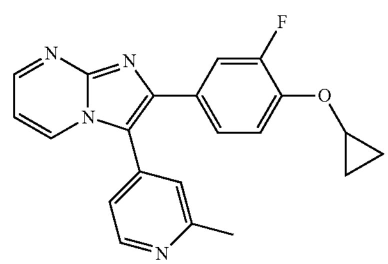 [SMILES: Cc1cc(-c2c(-c3ccc(OC4CC4)c(F)c3)nc3ncccn23)ccn1] | 69% | MS (ESI+) for CHNOS m/z 361.11 $[M + H]^+$ |
| 2-(3-fluoro-4-((4-fluorobenzyl)oxy)phenyl)-3-(2-methylpyridin-4-yl)imidazo[1,2-a]pyrimidine | 105 | 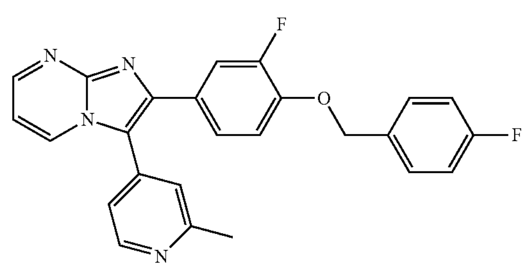 [SMILES: Cc1cc(-c2c(-c3ccc(OCc4ccc(F)cc4)c(F)c3)nc3ncccn23)ccn1] | 45% | MS (ESI+) for CHNOS m/z 429.23 $[M + H]^+$ |
| 2-(4-Ethoxy-3-fluorophenyl)-3-(2-methylpyridin-4-yl)imidazo[1,2-a]pyrimidine | 106 | 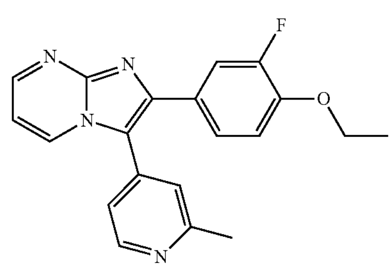 [SMILES: CCOc1ccc(-c2nc3ncccn3c2-c2ccnc(C)c2)cc1F] | 64% | MS (ESI+) for CHNOS m/z 349.09 $[M + H]^+$ |

| Name | Int | Structure | Yield | Spectral Data 1H NMR & LCMS |
|---|---|---|---|---|
| 2-(4-(2-(2-Methylpyridin-4-yl)imidazo[1,2-a]pyrimidin-3-yl)phenoxy)acetonitrile | 107 | 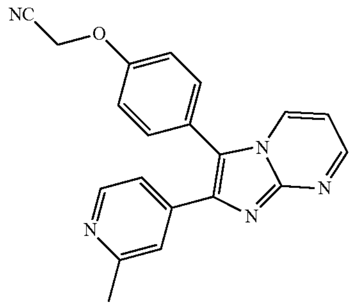 [SMILES: Cc1cc(-c2nc3ncccn3c2-c2ccc(OCC#N)cc2)ccn1] | Crude | MS (ESI+) for CHNOS m/z 342.00 [M + H]+ |

Intermediate 108

4-Methyl-6-(2-(2-methylpyridin-4-yl)imidazo[1,2-a]pyrimidin-3-yl)-3,4-dihydro-2H-benzo[b][1,4]oxazine

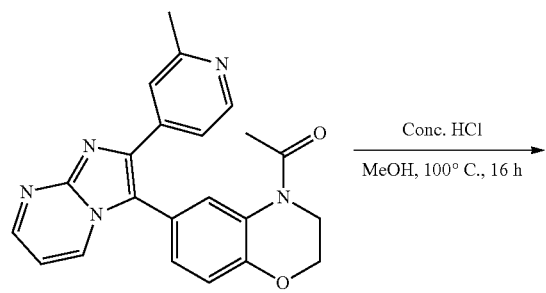

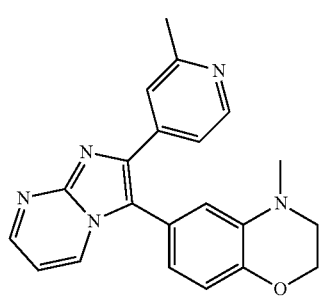

6-(2-(2-Methylpyridin-4-yl)imidazo[1,2-a]pyrimidin-3-yl)-3,4-dihydro-2H-benzo[b][1,4]oxazine To a solution of 1-(6-(2-(2-methylpyridin-4-yl)imidazo[1,2-a]pyrimidin-3-yl)-2,3-dihydro-4H-benzo[b][1,4]oxazin-4-yl)ethan-1-one (3.5 g, 6.47 mmol) in EtOH (30 mL) were added Conc. HCl (5 mL) at rt. The reaction mixture was stirred at 100° C. for 16 h. The TLC showed reaction to be complete. The reaction mixture was allowed to cool to rt, neutralized with saturated aq NaHCO$_3$ solution and extracted with 10% MeOH in DCM (3×50 mL). The organics were washed with brine (100 mL), dried (Na$_2$SO$_4$), filtered and concentrated under reduced pressure. The crude residue was enriched up to 82% by column chromatography using silica gel (100-200 mesh), eluting with 0-5% MeOH in DCM to afford 6-(2-(2-methylpyridin-4-yl)imidazo[1,2-a]pyrimidin-3-yl)-3,4-dihydro-2H-benzo[b][1,4]oxazine as a yellow solid. Yield: 1.7 g (mixture of regioisomers). The LCMS showed two peaks with desired mass 31% and 52% respectively. (ESI+) for CHNOS m/z 344.12 [M+H]+.

4-Methyl-6-(2-(2-methylpyridin-4-yl)imidazo[1,2-a]pyrimidin-3-yl)-3,4-dihydro-2H-benzo[b][1,4]oxazine To a solution of 6-(2-(2-methylpyridin-4-yl)imidazo[1,2-a]pyrimidin-3-yl)-3,4-dihydro-2H-benzo[b][1,4]oxazine (150 mg, 0.436 mmol) in CH$_3$CN (10 mL) were added formaldehyde (136 mg, 4.36 mmol), formic acid (201 mg, 4.36 mmol) and acetic acid (0.1 mL) at rt. The reaction mixture was stirred at rt for 30 min and NaBH$_4$ (166 mg, 4.36 mmol) was added to it. The reaction mixture was further stirred at rt for 16 h. The TLC showed reaction to be complete. The reaction was diluted with water (20 mL) and extracted with 10% MeOH in DCM (3×20 mL). The organics were washed with brine (20 mL), dried (Na$_2$SO$_4$), filtered and concentrated under reduced pressure to afford 4-methyl-6-(2-(2-methylpyridin-4-yl)imidazo[1,2-a]pyrimidin-3-yl)-3,4-dihydro-2H-benzo[b][1,4]oxazine as a yellow solid. Yield: 130 mg (crude); MS (ESI+) for CHNOS m/z 358.15[M+H]+.

The following intermediates were prepared in a similar manner 6-(2-(2-methylpyridin-4-yl)imidazo[1,2-a]pyrimidin-3-yl)-3,4-dihydro-2H-benzo[b][1,4]oxazine.

| Name | Int | Structure | Yield | Spectral Data 1H NMR & LCMS |
|------|-----|-----------|-------|------------------------------|
| 6-(2-(2,6-Dimethylpyridin-4-yl)imidazo[1,2-a]pyrimidin-3-yl)-3,4-dihydro-2H-benzo[b][1,4]oxazine | 109 | 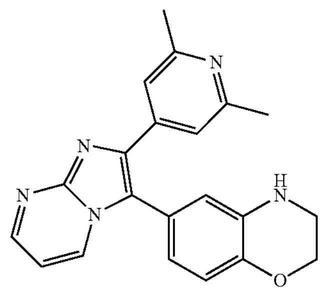 [SMILES: Cc1cc(-c2nc3ncccn3c2-c2ccc3c(c2)NCCO3)cc(C)n1] | Crude | MS (ESI+) for CHNO m/z 358.13 |
| 2-Methyl-6-(2-(2-methylpyridin-4-yl)imidazo[1,2-a]pyrimidin-3-yl)-3,4-dihydro-2H-benzo[b][1,4]oxazine | 110 | 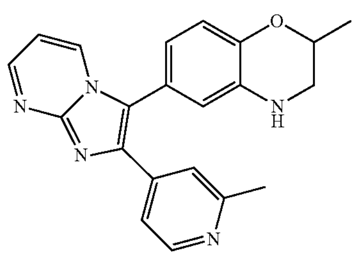 [SMILES: Cc1cc(-c2nc3ncccn3c2-c2ccc3c(c2)NCC(C)O3)ccn1] | Crude | MS (ESI+) for CHNOS m/z 358.02 [M + H] |
| 6-(2-(Pyridin-4-yl)imidazo[1,2-a]pyrimidin-3-yl)-3,4-dihydro-2H-benzo[b][1,4]oxazine | 111 | 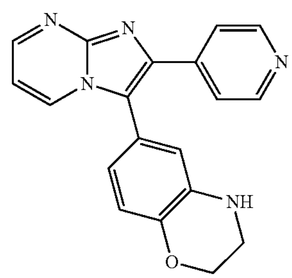 [SMILES: c1cnc2nc(-c3ccncc3)c(-c3ccc4c(c3)NCCO4)n2c1] | Crude | MS (ESI+) for CHNO m/z 329.98 [M + H]+ |
| 4-(3-(3,4-Dihydro-2H-benzo[b][1,4]oxazin-6-yl)imidazo[1,2-a]pyrimidin-2-yl)-N-methylpyridin-2-amine | 112 | 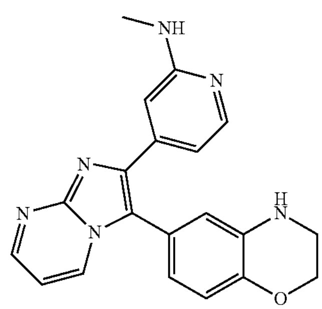 [SMILES: CNc1cc(-c2nc3ncccn3c2-c2ccc3c(c2)NCCO3)ccn1] | Crude | MS (ESI+) for CHNO m/z 359.04 [M + H]+ |
| 4-(3-(3,4-Dihydro-2H-benzo[b][1,4]oxazin-6-yl)imidazo[1,2-a]pyrimidin-2-yl)pyridin-2-amine | 113 | 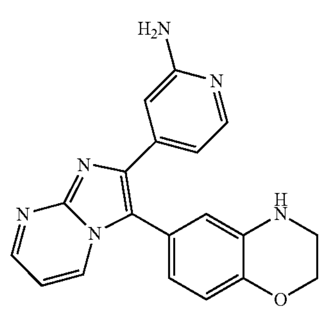 [SMILES: Nc1cc(-c2nc3ncccn3c2-c2ccc3c(c2)NCCO3)ccn1] | Crude | MS (ESI+) for CHNOS m/z 345.19 [M + H]+ |

-continued

| Name | Int | Structure | Yield | Spectral Data 1H NMR & LCMS |
|---|---|---|---|---|
| 6-(3-(2-Chloropyridin-4-yl)imidazo[1,2-a]pyrimidin-2-yl)-3,4-dihydro-2H-benzo[b][1,4]oxazine | 114 | 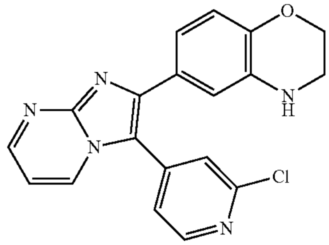 [SMILES: Clc1cc(-c2c(-c3ccc4c(c3)NCCO4)nc3ncccn23)ccn1] | Crude | MS (ESI+) for CHNOS m/z 364.01 [M + H]+ |
| 6-(3-(2-(triFluoromethyl)pyridin-4-yl)imidazo[1,2-a]pyrimidin-2-yl)-3,4-dihydro-2H-benzo[b][1,4]oxazine | 115 | 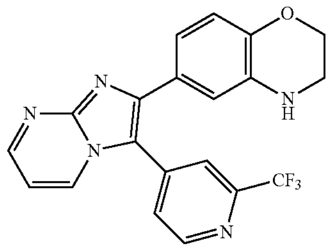 | Crude | MS (ESI+) for CHNOS m/z 398.20 [M + H]+ |
| 6-(3-(2-Fluoropyridin-4-yl)imidazo[1,2-a]pyrimidin-2-yl)-3,4-dihydro-2H-benzo[b][1,4]oxazine | 116 | 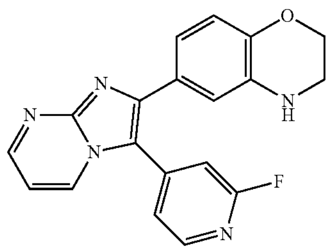 [SMILES: Fc1cc(-c2c(-c3ccc4c(c3)NCCO4)nc3ncccn23)ccn1] | Crude | MS (ESI+) for CHNOS m/z 348.14 [M + H]+ |
| 8-Fluoro-6-(3-(2-methylpyridin-4-yl)imidazo[1,2-a]pyrimidin-2-yl)-3,4-dihydro-2H-benzo[b][1,4]oxazine | 117 | 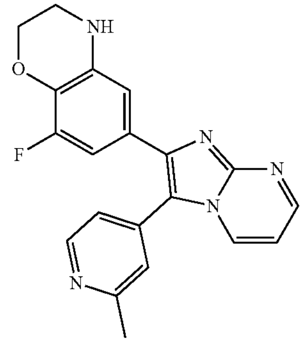 [SMILES: Cc1cc(-c2c(-c3cc(F)c4c(c3)NCCO4)nc3ncccn23)ccn1] | Crude | MS (ESI+) for CHNOS m/z 362.13 [M + H]+ |
| 7-Fluoro-6-(2-(2-methylpyridin-4-yl)imidazo[1,2-a]pyrimidin-3-yl)-3,4-dihydro-2H-benzo[b][1,4]oxazine | 118 | 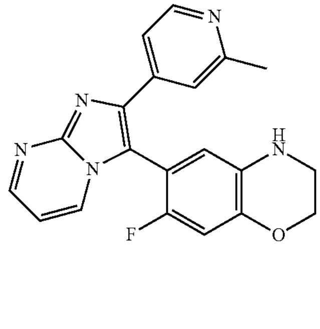 [SMILES: Cc1cc(-c2nc3ncccn3c2-c2cc3c(cc2F)OCCN3)ccn1] | Crude | MS (ESI+) for CHNOS m/z 362.13 [M + H]+ |

| Name | Int | Structure | Yield | Spectral Data 1H NMR & LCMS |
|---|---|---|---|---|
| 7-(2-(2-Methylpyridin-4-yl)imidazo[1,2-a]pyrimidin-3-yl)-1,2,3,4-tetrahydroquinoline | 119 | 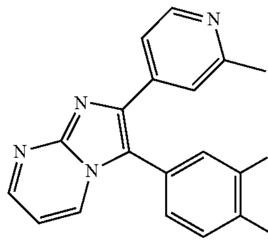 | Crude | MS (ESI+) for CHNOS m/z 342.18 [M + H]+ |

Intermediate 120

7-(2-(2-Methylpyridin-4-yl)imidazo[1,2-a]pyrimidin-3-yl)-2,3,4,5-tetrahydrobenzo[b][1,4]oxazepine

Intermediate 121

6-(2-(2-Methylpyridin-4-yl)imidazo[1,2-a]pyrimidin-3-yl)-4-(methylsulfonyl)-3,4-dihydro-2H-benzo[b][1,4]oxazine

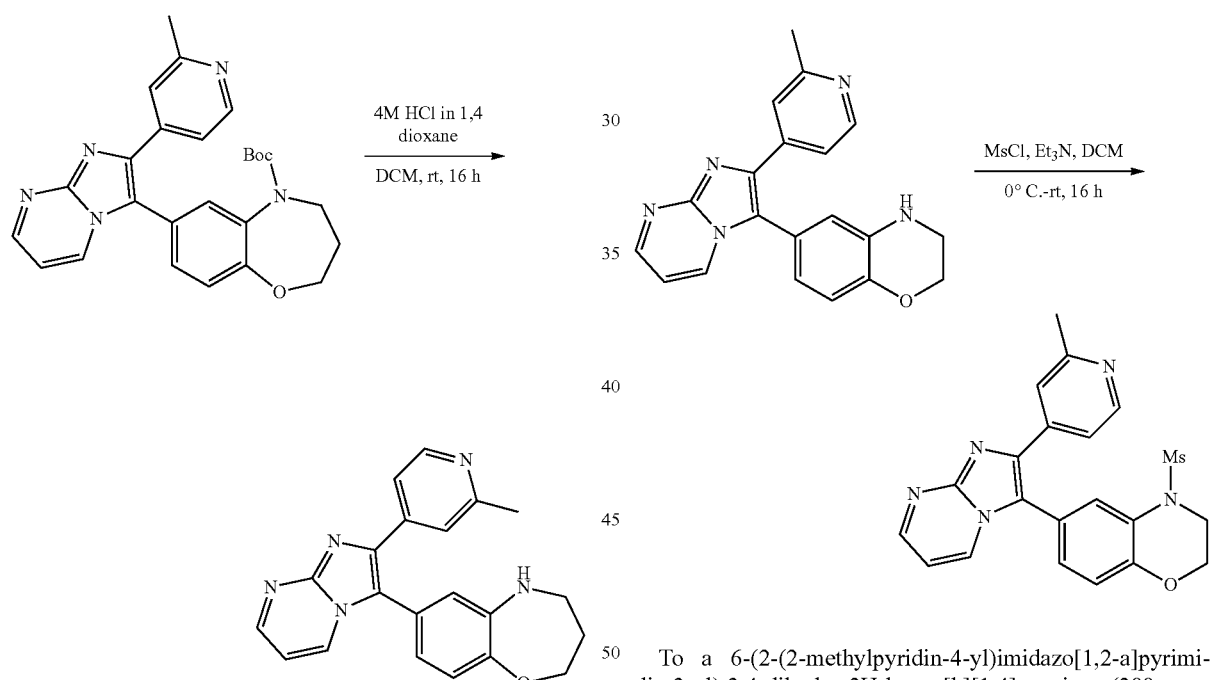

To a solution of tert-butyl 7-bromo-3,4-dihydrobenzo[b][1,4]oxazepine-5(2H)-carboxylate (5, 350 mg, 0.765 mmol) in DCM (10 mL) was added 4.0 M HCl in dioxane (2.0 mL). The reaction mixture was stirred at rt for 16 h. The reaction mixture was concentrated under reduced pressure, triturated with Et$_2$O (5.0 mL) and dried under reduced pressure to afford 7-(2-(2-methylpyridin-4-yl)imidazo[1,2-a]pyrimidin-3-yl)-2,3,4,5-tetrahydrobenzo[b][1,4]oxazepine as brown solid Yield: 410 mg (Crude). MS (ESI+) for CHNO m/z 358.12 [M+H]+.

To a 6-(2-(2-methylpyridin-4-yl)imidazo[1,2-a]pyrimidin-3-yl)-3,4-dihydro-2H-benzo[b][1,4]oxazine (200 mg, 0.58 mmol) in DCM (5 mL) was added Et$_3$N (117 mg, 1.16 mmol) at 0° C. The reaction mixture was stirred at 0° C. for 0.5 h and mesyl chloride (100 mg, 0.87 mmol) was added to it. The reaction mixture was warmed to rt and further stirred for 16 h. The TLC showed reaction to be complete. The reaction mixture was diluted with saturated aq NaHCO$_3$ solution (10 mL) and extracted with 10% MeOH in DCM (3×20 mL). The organics were washed with brine (100 mL), dried (Na$_2$SO$_4$), filtered and concentrated under reduced pressure. The residue was triturated with Et$_2$O (5.0 mL) and dried under reduced to afford 6-(2-(2-methylpyridin-4-yl)imidazo[1,2-a]pyrimidin-3-yl)-4-(methylsulfonyl)-3,4-dihydro-2H-benzo[b][1,4]oxazine as a brown waxy solid. The crude data showed product and it was used in the next step without further purification.

Intermediate 122

4-Ethyl-6-(2-(2-methylpyridin-4-yl)imidazo[1,2-a]pyrimidin-3-yl)-3,4-dihydro-2H-benzo[b][1,4]oxazine

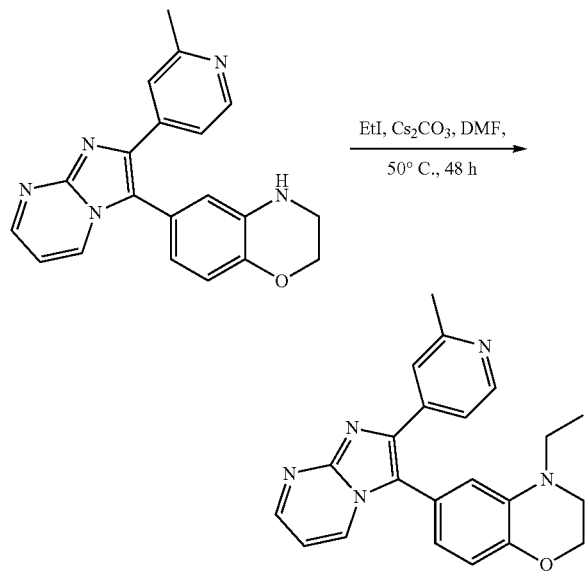

To a solution of 6-(2-(2-methylpyridin-4-yl)imidazo[1,2-a]pyrimidin-3-yl)-3,4-dihydro-2H-benzo[b][1,4]oxazine (300 mg, 0.87 mmol) in DMF (10 mL) were added $Cs_2CO_3$ (284 mg, 8.7 mmol) and ethyliodide (953 mg, 6.1 mmol) at rt. The reaction mixture was stirred at 50° C. for 48 h. The TLC showed reaction to be completed. The reaction mixture was diluted with water (10 mL) and extracted with EtOAc (3×10 mL). The organic layer was dried ($Na_2SO_4$), filtered and concentrated under reduced pressure. The residue was enriched to 74% purity by combiflash, using 12 g silica column, eluting with 5% MeOH in DCM to afford 4-ethyl-6-(2-(2-methylpyridin-4-yl)imidazo[1,2-a]pyrimidin-3-yl)-3,4-dihydro-2H-benzo[b][1,4]oxazine as a light brown solid. Yield: 71 mg (mixture of regioisomers); (MS (ESI+) for CHNOS m/z 372.21[M+H]$^+$. The LCMS showed two peaks with desired mass 36% and 38% respectively.

Intermediate 123

Methyl 3-(6-(2-(2-methylpyridin-4-yl)imidazo[1,2-a]pyrimidin-3-yl)-2,3-dihydro-4H-benzo[b][1,4]oxazin-4-yl)propanoate

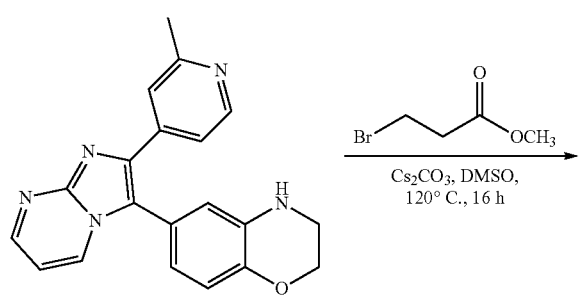

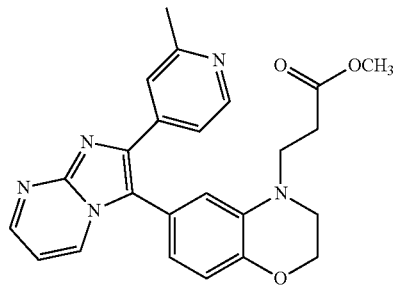

To a solution of 6-(2-(2-methylpyridin-4-yl)imidazo[1,2-a]pyrimidin-3-yl)-3,4-dihydro-2H-benzo[b][1,4]oxazine (500 mg, 1.45 mmol) in DMSO (5.0 mL) were added KI (50 mg, cat.), $Cs_2CO_3$ (1.49 g, 4.3 mmol) and methyl-3-bromopropanoate (243 mg, 1.45 mmol) at rt. The reaction mixture was stirred at 120° C. for 16 h. The TLC showed reaction to be completed. The reaction mixture was diluted with cold water (20 mL) and extracted with 5% MeOH in DCM (3×25 mL). The organic layer was dried ($Na_2SO_4$), filtered and concentrated under reduced pressure. The residue was purified by combiflash chromatography using 12 g silica column, eluting with 10% MeOH in DCM to afford methyl 3-(6-(2-(2-methylpyridin-4-yl)imidazo[1,2-a]pyrimidin-3-yl)-2,3-dihydro-4H-benzo[b][1,4]oxazin-4-yl)propanoate as a yellow waxy liquid which was enriched up to 33% by trituration with $Et_2O$. Yield: 398 mg (crude); MS (ESI+) for CHNOS m/z 430.38[M+H]$^+$; The crude LCMS showed two peaks with desired mass 25% and 8% respectively.

Intermediate Synthesis 124

2-(2-(6-(2-(2-Methylpyridin-4-yl)imidazo[1,2-a]pyrimidin-3-yl)-2,3-dihydro-4H-benzo[b][1,4]oxazin-4-yl)-2-oxoethyl)isoindoline-1,3-dione

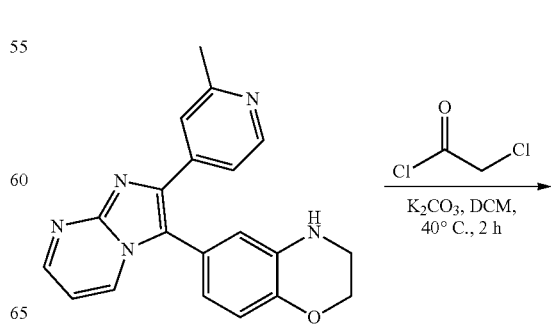

-continued

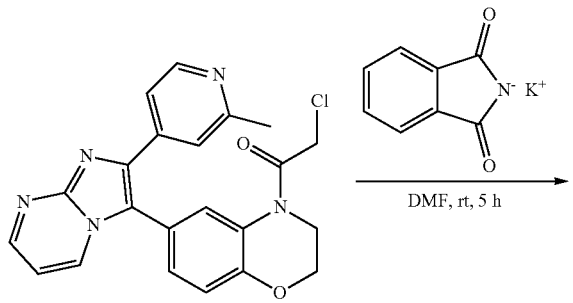

2-Chloro-1-(6-(2-(2-methylpyridin-4-yl)imidazo[1,2-a]pyrimidin-3-yl)-2,3-dihydro-4H-benzo[b][1,4]oxazin-4-yl)ethan-1-one To a solution of 6-(2-(2-methylpyridin-4-yl)imidazo[1,2-a]pyrimidin-3-yl)-3,4-dihydro-2H-benzo[b][1,4]oxazine (400 mg, 1.1 mmol) in DCM (20 mL) were added Et$_3$N (0.5 mL, 3.4 mmol), followed by chloroacetyl chloride (197 mg, 1.7 mmol) slowly at 0° C. The reaction mixture was stirred at rt for 4 h. The TLC showed reaction to be complete. The reaction mixture was diluted with water (30 mL) and extracted with 10% MeOH in DCM (3×25 mL). The organic layer was dried (Na$_2$SO$_4$), filtered and concentrated under reduced pressure. The residue was purified by combiflash chromatography using 12 g silica column, eluting with 5% MeOH in DCM to afford 2-chloro-1-(6-(2-(2-methylpyridin-4-yl)imidazo[1,2-a]pyrimidin-3-yl)-2,3-dihydro-4H-benzo[b][1,4]oxazin-4-yl)ethan-1-one as a yellow solid. Yield: 320 mg (65%, mixture of regioisomers); MS (ESI+) for CHNOS m/z 419.97[M+H]$^+$. The LCMS showed two peaks with desired mass 72% and 23% respectively.

2-(2-(6-(2-(2-Methylpyridin-4-yl)imidazo[1,2-a]pyrimidin-3-yl)-2,3-dihydro-4H-benzo[b][1,4]oxazin-4-yl)-2-oxoethyl)isoindoline-1,3-dione To a solution of 2-chloro-1-(6-(2-(2-methylpyridin-4-yl)imidazo[1,2-a]pyrimidin-3-yl)-2,3-dihydro-4H-benzo[b][1,4]oxazin-4-yl)ethan-1-one (300 mg, 0.70 mmol) in DMF (10 mL) was added potassium phthalimide (198 mg, 1.07 mmol) at rt. The reaction mixture was stirred at rt for 5 h. The TLC showed reaction to be complete. The reaction mixture was diluted with water (10 mL) and extracted with 10% MeOH in DCM (3×10 mL). The organic layer was dried (Na$_2$SO$_4$), filtered and concentrated under reduced pressure. The residue was triturated with the Et$_2$O (10 mL) to yield 2-(2-(6-(2-(2-methylpyridin-4-yl)imidazo[1,2-a]pyrimidin-3-yl)-2,3-dihydro-4H-benzo[b][1,4]oxazin-4-yl)-2-oxoethyl)isoindoline-1,3-dione as a waxy solid. Yield: 180 mg (crude, mixture of regioisomers); MS (ESI+) for CHNOS m/z 531.03 [M+H]$^+$.

Intermediate 125

2-(2,3-Dihydrobenzo[b][1,4]dioxin-6-yl)-3-(pyrimidin-4-yl)imidazo[1,2-a]pyrimidine

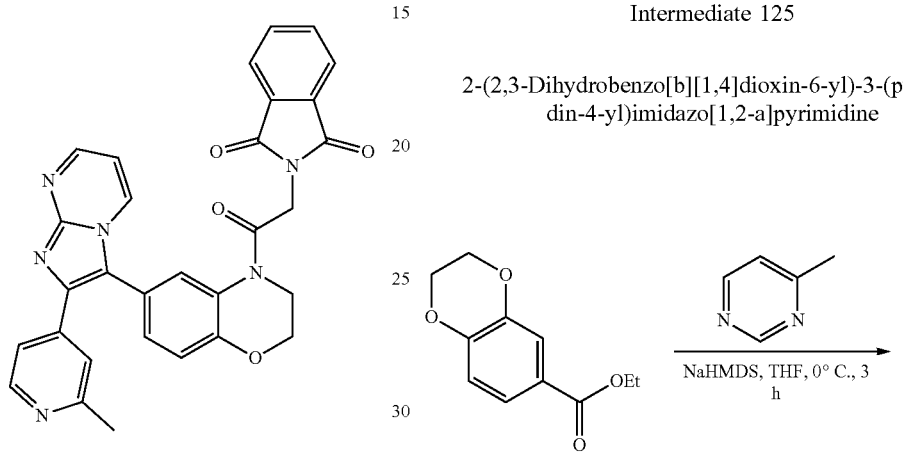

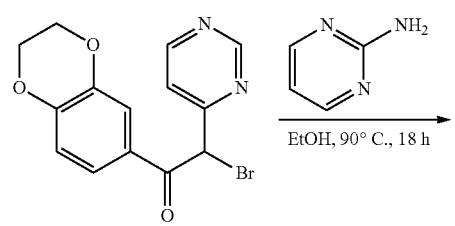

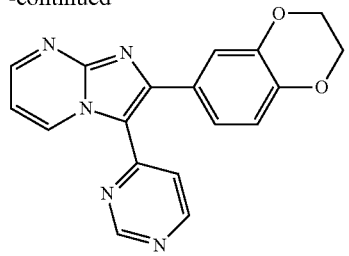

1-(2,3-Dihydrobenzo[b][1,4]dioxin-6-yl)-2-(pyrimidin-4-yl)ethan-1-one

To a solution of 4-methylpyrimidine (543 mg, 5.8 mmol) in THF (30 mL) was added NaHMDS (1M in THF, 12 mL, 12 mmol) slowly at rt. The reaction mixture was stirred at rt for 30 min and a solution of ethyl 2,3-dihydrobenzo[b][1,4]dioxine-6-carboxylate (1 g, 4.8 mmol) in THF (5 mL) was added slowly at rt. The reaction mixture was stirred at rt for 2 h. The TLC showed the reaction to be complete. The reaction mixture was poured into saturated aq NH$_4$Cl (50 mL) and extracted with EtOAc (3×50 mL). The organics were washed with brine (100 mL), dried (Na$_2$SO$_4$), filtered and concentrated under reduced pressure. The crude residue was enriched up to 80% purity by trituration with pentane (25 mL), filtered and dried under reduced pressure to afford 1-(2,3-dihydrobenzo[b][1,4]dioxin-6-yl)-2-(pyrimidin-4-yl)ethan-1-one as a yellow solid. Yield: 1 g (81%). MS (ESI+) for CHNOS m/z 257.18 [M+H]$^+$.

2-Bromo-1-(2,3-dihydrobenzo[b][1,4]dioxin-6-yl)-2-(pyrimidin-4-yl)ethan-1-one To a solution of 1-(2,3-dihydrobenzo[b][1,4]dioxin-6-yl)-2-(pyrimidin-4-yl)ethan-1-one (1 g, 3.9 mmol) in DMF (5 mL) was added NBS (0.83 g, 4.7 mmol) at rt. The reaction mixture was stirred at rt for 1 h. The TLC showed the reaction to be complete. The reaction mixture was diluted with water (25 mL) and extracted with EtOAc (3×25 mL). The organics were washed with brine (50 mL), dried (Na$_2$SO$_4$), filtered and concentrated under reduced pressure to afford 2-bromo-1-(2,3-dihydrobenzo[b][1,4]dioxin-6-yl)-2-(pyrimidin-4-yl)ethan-1-one as a brown waxy solid. Yield: 1.2 g crude (84% by LCMS). MS (ESI+) for CHNOS m/z 335.05 [M+H]$^+$. The crude product was used in the next step without further purification.

2-(2,3-Dihydrobenzo[b][1,4]dioxin-6-yl)-3-(pyrimidin-4-yl)imidazo[,2-a]pyrimidine To a solution of 2-bromo-1-(2,3-dihydrobenzo[b][1,4]dioxin-6-yl)-2-(pyrimidin-4-yl)ethan-1-one (1.2 g, 3.59 mmol) in EtOH (30 mL) was added pyrimidin-2-amine (341 mg, 35.9 mmol). The reaction mixture was stirred at 90° C. for 48 h. The TLC showed the reaction to be complete. The solvent was evaporated under reduced pressure. The crude residue was diluted with H$_2$O (25 mL) and extracted with EtOAc (3×25 mL). The organics were washed with brine, dried (Na$_2$SO$_4$), filtered and concentrated under reduced pressure to afford 2-(2,3-dihydrobenzo[b][1,4]dioxin-6-yl)-3-(pyrimidin-4-yl)imidazo[1,2-a]pyrimidine as a brown waxy oil. Yield: 600 mg (crude, 37% by LCMS); MS (ESI+) for CHNOS m/z 332.21 [M+H]$^+$. The crude was used in the next step without further purification.

Intermediate 126

4-(2-Hydroxyethyl)-6-(2-(2-methylpyridin-4-yl)imidazo[1,2-a]pyrimidin-3-yl)-2H-benzo[b][1,4]oxazin-3(4H)-one

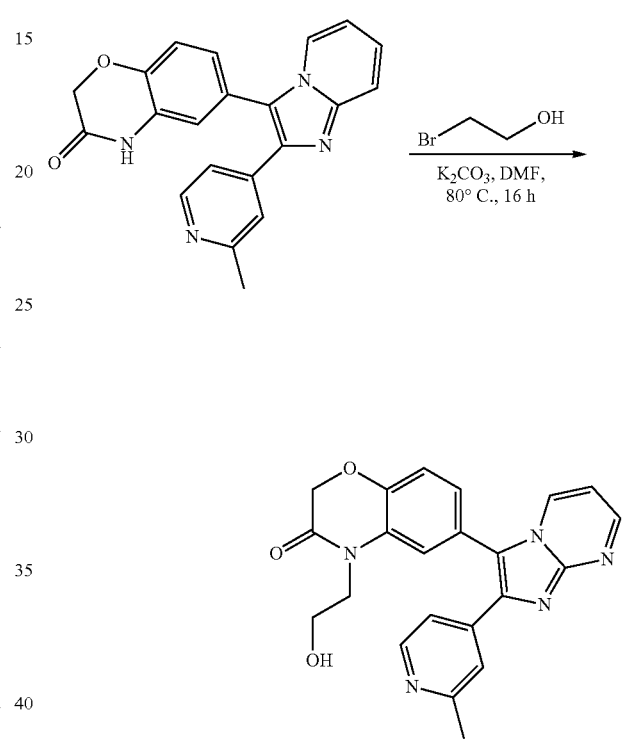

To a solution of 6-(2-(2-methylpyridin-4-yl)imidazo[1,2-a]pyrimidin-3-yl)-2H-benzo[b][1,4]oxazin-3(4H)-one (600 mg, 1.68 mmol) in DMF (5.0 mL) were added K$_2$CO$_3$ (1.16 g, 8.40 mmol) and 2-bromoethan-1-ol (421 mg, 3.36 mmol) at rt. The reaction mixture was stirred at 80° C. for 16 h. The TLC showed reaction to complete. The reaction mixture was allowed to cool to rt, diluted with water (50 mL) and extracted with 10% meOH in DCM (3×50 mL). The organics were washed with brine (100 mL), dried (Na$_2$SO$_4$), filtered and concentrated under reduced pressure to 4-(2-hydroxyethyl)-6-(2-(2-methylpyridin-4-yl)imidazo[1,2-a]pyrimidin-3-yl)-2H-benzo[b][1,4]oxazin-3(4H)-one as a yellow solid. Yield: 470 mg (crude, 74% by LCMS). The crude was enriched up to 74% by combiflash using 12 g silica column, eluting with 0-5% MeOH in DCM. MS (ESI+) for CHNOS m/z 402.17 [M+H]$^+$.

The following intermediates were prepared in a similar manner to 4-(2-Hydroxyethyl)-6-(2-(2-methylpyridin-4-yl)imidazo[1,2-a]pyrimidin-3-yl)-2H-benzo[b][1,4]oxazin-3(4H)-one.

| Name | Int | Structure | Yield | Spectral Data 1H NMR & LCMS |
|---|---|---|---|---|
| tert-Butyl (2-(6-(2-(2-methylpyridin-4-yl)imidazo[1,2-a]pyrimidin-3-yl)-3-oxo-2,3-dihydro-4H-benzo[b][1,4]oxazin-4-yl)ethyl)carbamate | 127 | 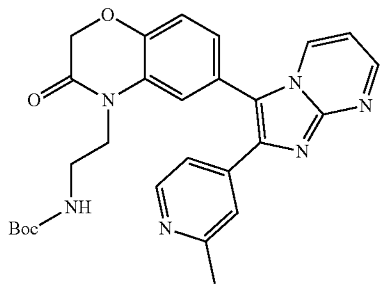 [SMILES: Cc1cc(-c2nc3ncccn3c2-c2ccc3c(c2)N(CCNC(=O)OC(C)(C)C)C(=O)CO3)ccn1] | 33% The crude LCMS shows ~46% conversion to desired product. The crude was enriched up to 83% by combiflash using 12 g silica column, eluting with 0-10% MeOH in DCM | MS (ESI+) for CHNOS m/z 501.10 [M + H]+ |
| 4-(Cyclopropylmethyl)-6-(2-(2-methylpyridin-4-yl)imidazo[1,2-a]pyrimidin-3-yl)-2H-benzo[b][1,4]oxazin-3(4H)-one | 128 | | The crude data showed 32% desired product. Enriched up to 46% by combiflash using 12 g column, eluting with 0-10% MeOH in DCM | MS (ESI+) for CHNOS m/z 412.21 [M + H]+ |
| 4-Isopropyl-6-(2-(2-methylpyridin-4-yl)imidazo[1,2-a]pyrimidin-3-yl)-2H-benzo[b][1,4]oxazin-3(4H)-one | 129 | 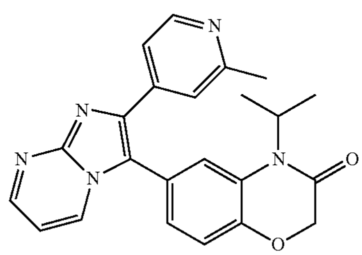 [SMILES: Cc1cc(-c2nc3ncccn3c2-c2ccc3c(c2)N(C(C)C)C(=O)CO3)ccn1] | 40% The crude LCMS showed two peaks with desired mass 11% and 20% respectively. Enrich up to 65% mixture of two peaks with same mass by combiflash using 12 g silica column, eluting with 0-10% MeOH in DCM | MS (ESI+) for CHNOS m/z 400.19 [M + H]+ |
| 4-Cyclopentyl-6-(2-(2-methylpyridin-4-yl)imidazo[1,2-a]pyrimidin-3-yl)-2H-benzo[b][1,4]oxazin-3(4H)-one For J23-453 | 130 | 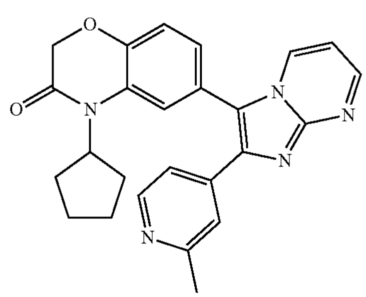 [SMILES: Cc1cc(-c2nc3ncccn3c2-c2ccc3c(c2)N(C2CCCC2)C(=O)CO3)ccn1] | 59% The crude LCMS showed two peaks with desired mass 21% and 20% respectively. Enrich up to 90% mixture of two peaks with same mass by combiflash using 12 g silica column, eluting with 0-10% MeOH in DCM | MS (ESI+) for CHNOS m/z 426.22 [M + H]+ |
| 4-(2-(2-Hydroxyethoxy)ethyl)-6-(2-(2-methylpyridin-4-yl)imidazo[1,2-a]pyrimidin-3-yl)-2H-benzo[b][1,4]oxazin-3(4H)-one | 131 | 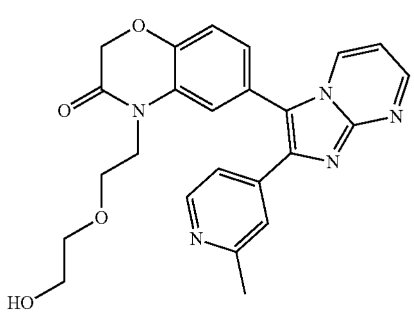 [SMILES: Cc1cc(-c2nc3ncccn3c2-c2ccc3c(c2)N(CCOCCO)C(=O)CO3)ccn1] | 38% The crude LCMS shows ~43% conversion to desired product. The crude was enriched up to 80% by combiflash using 12 g silica column, eluting with 0-10% MeOH in DCM | MS (ESI+) for CHNOS m/z 446.11 [M + H]+ |

The following compounds were prepared in a similar manner 5-(3,4-Dimethoxyphenyl)-4-(2-methylpyridin-4-yl)-1H-imidazol-2-amine.

| Name | Ex | Structure | Yield | Spectral Data 1H NMR & LCMS |
|---|---|---|---|---|
| 4-(6-Methoxypyridin-3-yl)-5-(2-methylpyridin-4-yl)-1H-imidazol-2-amine | 2 | 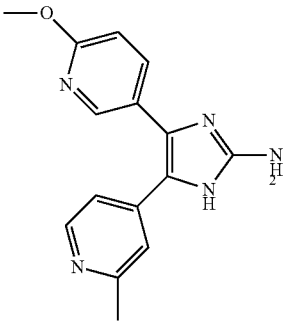 [SMILES: COc1ccc(-c2nc(N)[nH]c2-c2ccnc(C)c2)cn1] | 17% | MS (ESI+) for CHNOS m/z 282.06 [M + H]+; LC purity 97.6% (Ret. Time- 3.67 min); ¹H NMR (400 MHz, DMSO-d₆): δ 11.09 (bs, 1H), 8.18-8.23 (m, 2H), 7.68 (dd, J = 2.4, 8.6 Hz, 1H), 7.21 (bs, 1H), 7.04 (d, J = 4.6 Hz, 1H), 6.83 (d, J = 8.0 Hz, 1H), 5.51 (bs, 2H), 3.87 (s, 3H), 2.36 (s, 3H) |
| 4-(2,3-Dihydrobenzofuran-5-yl)-5-(2-methylpyridin-4-yl)-1H-imidazol-2-amine | 3 | 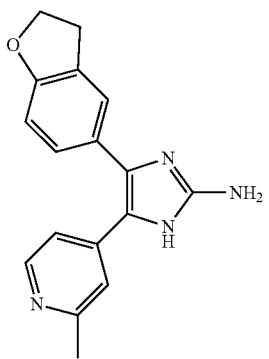 [SMILES: Cc1cc(-c2[nH]c(N)nc2-c2ccc3c(c2)CCO3)ccn1] | 18% | MS (ESI+) for CHNOS m/z 293.7 [M + H]+; LC purity 96.1% (Ret. Time- 3.96 min); 1H NMR (400 MHz DMSO-d₆ + d-TFA)): δ 8.64 (d, J = 6.5 Hz, 1H), 7.77 (s, 1H), 7.56 (d, J = 6.2 Hz, 1H), 7.42 (s, 1H), 7.27 (d, J = 8.5 Hz, 1H), 6.93 (d, J = 6.2 Hz, 1H), 4.60-4.67 (m, 2H), 3.20-3.26 (m, 2H), 2.63 (s, 3H) |
| 5-(4-Chlorophenyl)-4-(2-methylpyridin-4-yl)-1H-imidazol-2-amine | 4 | 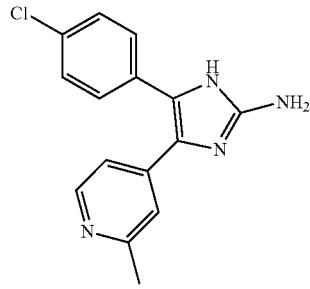 [SMILES: Cc1cc(-c2nc(N)[nH]c2-c2ccc(Cl)cc2)ccn1] | 56% | MS (ESI+) for CHNOS m/z 284.98 [M + H]+; LC purity 97.3% (Ret. Time- 4.49 min); 1H NMR (400 MHz, DMSO-d₆ + d-TFA): δ 8.55 (d, J = 6.4 Hz, 1H), 7.72 (bs, 1H), 7.20-7.50 (m, 5H), 2.57 (s, 3H) |
| 4-(3,4-dihydro-2H-benzo[b][1,4]dioxepin-7-yl)-5-(2-methylpyridin-4-yl)-1H-imidazol-2-amine | 5 | 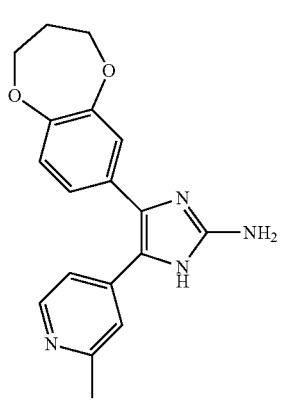 [SMILES: Cc1cc(-c2[nH]c(N)nc2-c2ccc3c(c2)OCCCO3)ccn1] | 9% | MS (ESI+) for CHNOS m/z 323.03 [M + H]+; LC purity 95.4% (Ret. Time- 4.05 min); 1H NMR (400 MHz, DMSO-d6 + d- TFA ): δ 8.63 (d, J = 6.0 Hz, 1H), 7.78 (s, 1H), 7.56 (bs, 1H), 7.04-7.20 (m, 3H), 4.16-4.21 (m, 4H), 2.61 (s, 3H), 2.14 (bs, 2H) |

| Name | Ex | Structure | Yield | Spectral Data 1H NMR & LCMS |
|---|---|---|---|---|
| 5-(4-Fluoro-3-methoxyphenyl)-4-(2-methylpyridin-4-yl)-1H-imidazol-2-amine | 6 | 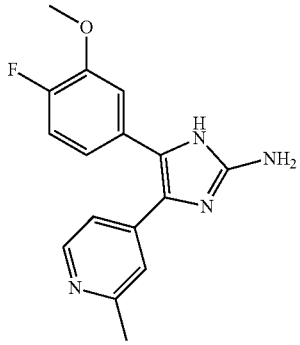 [SMILES: COc1cc(-c2[nH]c(N)nc2-c2ccnc(C)c2)ccc1F] | 30% | MS (ESI+) for CHNOS m/z 299.03 [M + H]+; LC purity 98.3% (Ret. Time- 3.75 min); $^1$H NMR (400 MHz, DMSO-$d_6$): δ 11.09 (bs, 1H), 8.23 (d, J = 5.6 Hz, 1H), 7.05-7.30 (m, 4H), 6.97 (s, 1H), 5.50 (bs, 2H), 3.76 (s, 3H), 2.36 (s, 3H) |
| 4-(2-Amino-4-(4-((4-fluorobenzyl)oxy)phenyl)-1H-imidazol-5-yl)pyridin-2-amine | 7 | 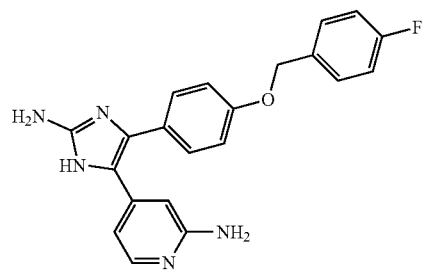 [SMILES: Nc1cc(-c2[nH]c(N)nc2-c2ccc(OCc3ccc(F)cc3)cc2)ccn1] | 58% | MS (ESI+) for CHNOS m/z 376.02 [M + H]+; LC purity 97.9% (Ret. Time- 4.86 min); $^1$H NMR (400 MHz, DMSO-$d_6$ + $D_2O$): δ 7.74 (d, J = 6.8 Hz, 1H), 7.45-7.51 (m, 2H), 7.38 (d, J = 8.6 Hz, 2H), 7.15-7.23 (m, 2H), 7.10 (d, J = 8.6 Hz, 2H), 6.83 (s, 1H), 6.58 (d, J = 6.8 Hz, 1H), 5.09 (s, 2H) |
| 4-(2-Amino-4-(2,3-dihydrobenzofuran-5-yl)-1H-imidazol-5-yl)pyridin-2-amine | 8 | 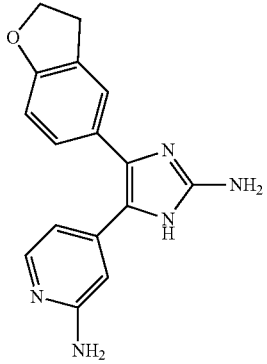 [SMILES: Nc1cc(-c2[nH]c(N)nc2-c2ccc3c(c2)CCO3)ccn1] | 6% | MS (ESI+) for CHNOS m/z 294.04 [M + H]+; LC purity 93.1% (Ret. Time- 3.58 min); $^1$H NMR (400 MHz, DMSO-$d_6$): δ 10.76 (s, 1H), 7.66 (bs, 1H), 7.00-7.40 (m, 2H), 6.55-6.90 (m, 2H), 6.10-6.55 (m, 1H), 5.60 (bs, 2H), 5.20 (bs 2H), 4.53 (bs, 2H), 3.16 (bs, 2H) |
| 4-(2-Amino-4-(2,3-dihydrobenzofuran-5-yl)-1H-imidazol-5-yl)-N-methylpyridin-2-amine | 9 | 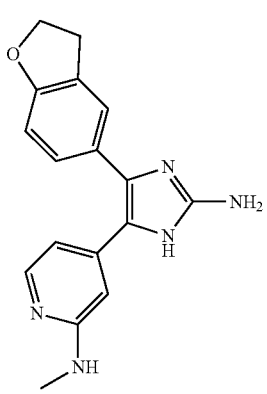 [SMILES: CNc1cc(-c2[nH]c(N)nc2-c2ccc3c(c2)CCO3)ccn1] | 6% | MS (ESI+) for CHNOS m/z 308.04 [M + H]+; LC purity 92.2% (Ret. Time- 3.82 min); $^1$H NMR (400 MHz, DMSO-$d_6$): δ 10.87 (bs, 1H), 7.75 (d, J = 5.2 Hz, 1H), 7.27 (s, 1H), 7.12 (d, J = 7.8 Hz, 1H), 6.73 (d, J = 8.1 Hz, 1H), 6.42-6.52 (m, 2H), 6.20 (d, J = 4.3 Hz, 1H), 5.26 (bs, 2H), 4.53 (t, J = 8.6 Hz, 2H), 3.15 (t, J = 8.6 Hz, 2H), 2.68 (d, J = 4.8 Hz, 3H) |

-continued

| Name | Ex | Structure | Yield | Spectral Data 1H NMR & LCMS |
|---|---|---|---|---|
| 4-(2-Amino-4-(2-methylpyridin-4-yl)-1H-imidazol-5-yl)-N,N-dimethylbenzamide | 10 | 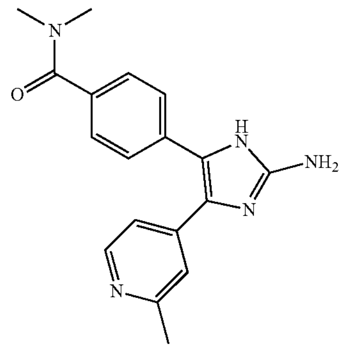 [SMILES: Cc1cc(-c2nc(N)[nH]c2-c2ccc(C(=O)N(C)C)cc2)ccn1] | 8% | MS (ESI+) for CHNOS m/z 322.02 [M + H]+; LC purity 97.9% (Ret. Time- 4.63 min); $^1$H NMR (400 MHz, DMSO-$d_6$): δ 11.22 (bs, 1H), 8.23 (d, J = 4.9 Hz, 1H), 7.43-7.52 (m, 2H), 7.34-7.42 (m, 2H), 7.24 (bs, 1H), 7.07-7.16 (m, 1H), 5.56 (bs, 2H), 2.97 (bs, 6H), 2.36 (s, 3H) |
| 5-(3-Fluoro-4-methoxyphenyl)-4-(2-methylpyridin-4-yl)-1H-imidazol-2-amine | 11 | 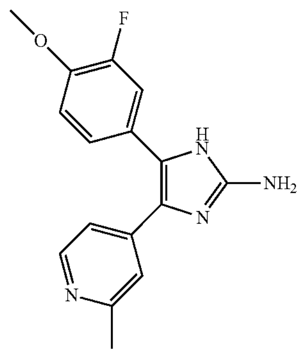 [SMILES: COc1ccc(-c2[nH]c(N)nc2-c2ccnc(C)c2)cc1F] | 21% | MS (ESI+) for CHNOS m/z 299.00 [M + H]+; LC purity 97.4% (Ret. Time- 4.02 min); $^1$H NMR (400 MHz, DMSO-$d_6$): δ 11.31 (bs, 1H), 8.23 (d, J = 5.2 Hz, 1H), 7.11-7.29 (m, 4H), 7.08 (d, J = 4.6 Hz, 1H), 5.62 (bs, 2H), 3.86 (s, 3H), 2.37 (s, 3H) |
| 4-(3-Chloro-4-methoxyphenyl)-5-(2-methylpyridin-4-yl)-1H-imidazol-2-amine | 12 | 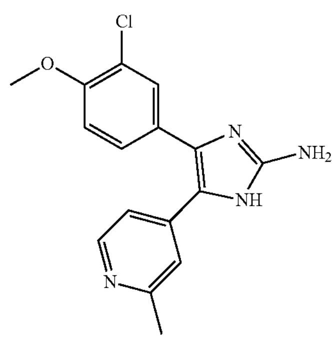 [SMILES: COc1ccc(-c2nc(N)[nH]c2-c2ccnc(C)c2)cc1Cl] | 19% | MS (ESI+) for CHNOS m/z 315.00 [M + H]+; LC purity 98.4% (Ret. Time- 4.34 min); $^1$H NMR (400 MHz, DMSO-$d_6$): δ 11.07 (bs, 1H), 8.22 (d, J = 5.2 Hz, 1H), 7.44 (d, J = 1.5 Hz, 1H), 7.05-7.40 (m, 4H), 5.48 (bs, 2H), 3.87 (s, 3H), 2.37 (s, 3H) |
| 5-(4-(Cyclopropyl-methoxy)-3-fluorophenyl)-4-(2-methylpyridin-4-yl)-1H-imidazol-2-amine | 13 | | 26% | MS (ESI+) for CHNOS m/z 339.03 [M + H]+; LC purity 96.7% (Ret. Time- 4.87 min); $^1$H NMR (400 MHz, DMSO-$d_6$): δ 11.04 (bs, 1H), 8.21 (d, J = 5.2 Hz, 1H), 7.02-7.40 (m, 5H), 5.46 (bs, 2H), 3.90 (d, J = 7.0 Hz, 2H), 2.36 (s, 3H), 1.21-1.25 (m, 1H), 0.56-0.60 (m, 2H), 0.32-0.35 (m, 2H) |

-continued

| Name | Ex | Structure | Yield | Spectral Data 1H NMR & LCMS |
|---|---|---|---|---|
| 5-(4-Cyclopropoxy-3-fluorophenyl)-4-(2-methylpyridin-4-yl)-1H-imidazol-2-amine | 14 | 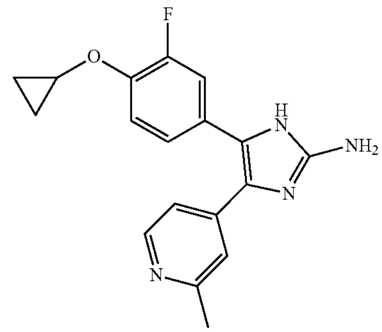 [SMILES: Cc1cc(-c2nc(N)[nH]c2-c2ccc(OC3CC3)c(F)c2)ccn1] | 22% | MS (ESI+) for CHNOS m/z 325.02 [M + H]+; LC purity 97.2% (Ret. Time- 4.54 min); $^1$H NMR (400 MHz, DMSO-$d_6$): δ 11.00 (bs, 1H), 8.22 (s, 1H), 6.91-7.51 (m, 5H), 5.36-5.60 (m, 2H), 3.96 (bs, 1H), 2.37 (s, 3H), 0.59-0.90 (m, 4H) |
| 4-(2-Amino-4-(2-methylpyridin-4-yl)-1H-imidazol-5-yl)-2-fluorophenol | 15 | 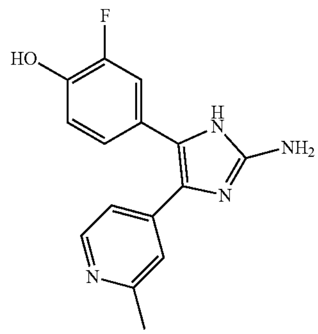 [SMILES: Cc1cc(-c2nc(N)[nH]c2-c2ccc(O)c(F)c2)ccn1] | 28% | MS (ESI+) for CHNOS m/z 285.02 [M + H]+; LC purity 98.3% (Ret. Time- 3.50 min); $^1$H NMR (400 MHz, DMSO-$d_6$ + d-TFA): δ 8.64 (d, J = 6.5 Hz, 1H), 7.77 (s, 1H), 7.56 (d, J = 5.8 Hz, 1H), 7.32-7.38 (m, 1H), 7.05-7.19 (m, 2H), 2.61 (s, 3H) |
| 5-(3-Fluoro-4-((4-fluorobenzyl)oxy)phenyl)-4-(2-methylpyridin-4-yl)-1H-imidazol-2-amine | 16 | 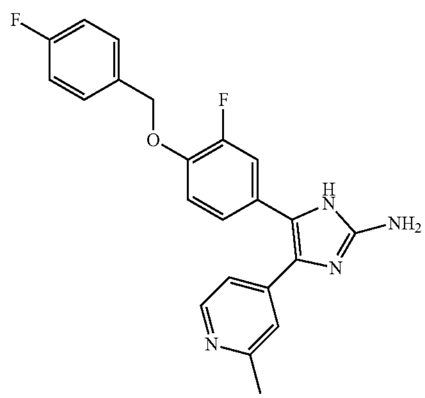 [SMILES: Cc1cc(-c2nc(N)[nH]c2-c2ccc(OCc3ccc(F)cc3)c(F)c2)ccn1] | 55% | MS (ESI+) for CHNOS m/z 393.03 [M + H]+; LC purity 90% (Ret. Time- 5.27 min); $^1$H NMR (400 MHz, DMSO-$d_6$): δ 11.01 (bs, 1H), 8.16-8.29 (m, 1H), 7.49-7.58 (m, 2H), 7.01-7.36 (m, 7H), 5.51 (bs, 1H), 5.38 (bs, 1H), 5.14-5.20 (m, 2H), 2.36 (s, 3H) |
| 5-(4-Ethoxy-3-fluorophenyl)-4-(2-methylpyridin-4-yl)-1H-imidazol-2-amine | 17 | 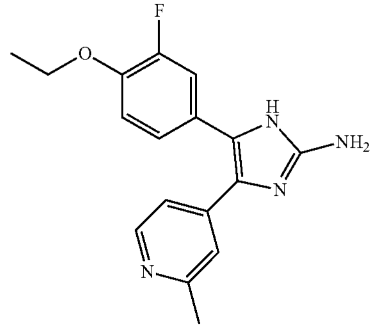 [SMILES: CCOc1ccc(-c2[nH]c(N)nc2-c2ccnc(C)c2)cc1F] | 62% | MS (ESI+) for CHNOS m/z 313.03 [M + H]+; LC purity 92.7% (Ret.Time- 4.53 min); $^1$H NMR (400 MHz, DMSO-$d_6$): δ 10.99 (bs, 1H), 9.19-8.30 (m, 1H), 7.01-7.39 (m, 5H), 5.35-550 (m, 2H), 4.11 (q, J = 6.3 Hz, 2H), 2.36 (s, 3H), 1.35 (t, J = 6.3 Hz, 3H) |

-continued

| Name | Ex | Structure | Yield | Spectral Data 1H NMR & LCMS |
|---|---|---|---|---|
| 4-(2-Amino-4-(2,3-dihydrobenzo[b][1,4]dioxin-6-yl)-1H-imidazol-5-yl)pyridin-2(1H)-one | 18 | 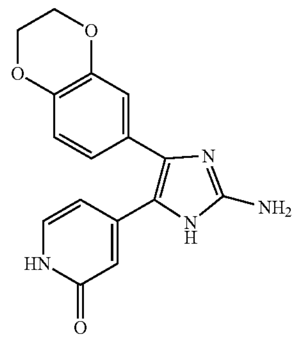 [SMILES: Nc1nc(-c2ccc3c(c2)OCCO3)c(-c2cc[nH]c(=O)c2)[nH]1] | 16% | MS (ESI+) for CHNOS m/z 310.97 [M + H]⁺; LC purity 96.0% (Ret.Time- 4.65 min); $^1$H NMR (400 MHz, DMSO-$d_6$ + d-TFA): δ 7.76 (bs, 1H), 6.78-7.08 (m, 4H), 6.71 (bs, 1H), 4.22 (s, 4H) |
| 4-(4-((4-Fluorobenzyl)oxy)phenyl)-5-(2-methylpyridin-4-yl)-1H-imidazol-2-amine | 19 | 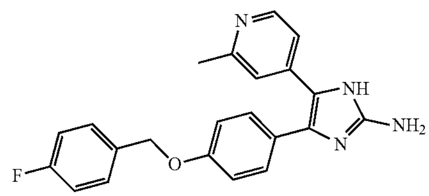 [SMILES: Cc1cc(-c2[nH]c(N)nc2-c2ccc(OCc3ccc(F)cc3)cc2)ccn1] | 82% | MS (ESI+) for CHNOS m/z 375.03 [M + H]⁺; LC purity 96.9% (Ret.Time- 5.14 min); $^1$H NMR (400 MHz, DMSO-$d_6$): δ 10.93 (bs, 1H), 8.12-8.23 (m, 1H), 7.48-7.58 (m, 2H), 7.19-7.42 (m, 5H), 6.94-7.16 (m, 3H), 5.29-5.56 (m, 2H), 5.07-5.15 (m, 2H), 2.33 (s, 3H) |
| 5-(2-Methylpyridin-4-yl)-4-(4-(trifluoromethoxy)phenyl)-1H-imidazol-2-amine | 20 | 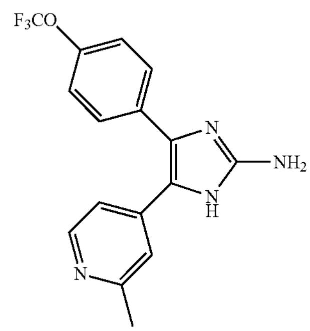 [SMILES: Cc1cc(-c2[nH]c(N)nc2-c2ccc(OC(F)(F)F)cc2)ccn1] | 37% | MS (ESI+) for CHNOS m/z 334.94 [M + H]⁺; LC purity 99.3% (Ret.Time- 4.09 min); $^1$H NMR (400 MHz, DMSO-$d_6$): δ 11.09 (bs, 1H), 8.24 (s, 1H), 7.0-7.65 (m, 6H), 5.50 (bs, 2H), 2.36 (s, 3H) |
| 5-(4-Methoxyphenyl)-4-(2-methylpyridin-4-yl)-1H-imidazol-2-amine | 21 | 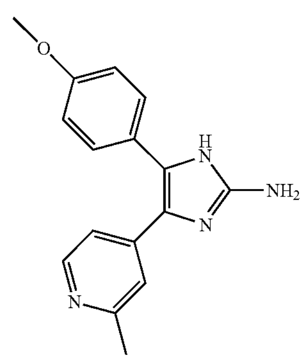 [SMILES: COc1ccc(-c2[nH]c(N)nc2-c2ccnc(C)c2)cc1] | 26% | MS (ESI+) for CHNOS m/z 281.16 [M + H]⁺; LC purity 97.4% (Ret. Time- 3.95 min); $^1$H NMR (400 MHz, DMSO-$d_6$ at 369.2K): δ 11.09 (bs, 1H), 8.19 (d, J = 5.2 Hz, 1H), 7.35 (d, J = 8.4 Hz, 2H), 7.24 (s, 1H), 7.08 (bs, 1H), 6.94 (d, J = 8.4 Hz, 2H), 5.06 (bs, 2H), 3.81 (s, 3H), 2.36 (s, 3H) |
| 4-(2,3-Dihydrobenzo[b][1,4]dioxin-6-yl)-5-(pyridin-3-yl)-1H-imidazol-2-amine | 22 | 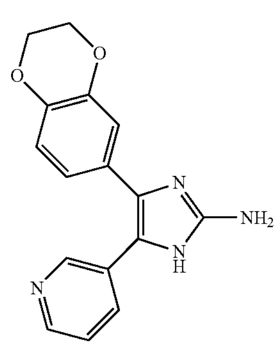 [SMILES: Nc1nc(-c2ccc3c(c2)OCCO3)c(-c2cccnc2)[nH]1] | 28% | MS (ESI+) for CHNOS m/z 295.03 [M + H]⁺; LC purity 98.4% (Ret.Time- 3.90 min); $^1$H NMR (400 MHz, DMSO-$d_6$): δ 11.37 (bs, 1H), 8.57 (s, 1H), 8.35 (d, J = 3.6 Hz, 1H), 7.74 (d, J = 7.9 Hz, 1H), 7.390 (dd, J = 4.8, 7.6 Hz, 1H), 6.80-6.90 (m, 3H), 5.69 (bs, 2H), 4.23 (s, 3H) |

-continued

| Name | Ex | Structure | Yield | Spectral Data 1H NMR & LCMS |
|---|---|---|---|---|
| 4-(2,3-Dihydrobenzo[b][1,4]dioxin-6-yl)-5-(2-methylpyridin-4-yl)-1H-imidazol-2-amine | 23 | 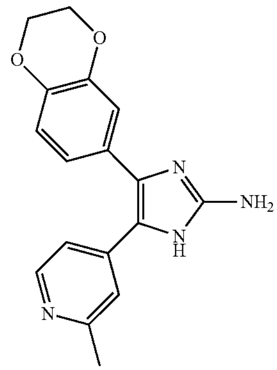 [SMILES: Cc1cc(-c2[nH]c(N)nc2-c2ccc3c(c2)OCCO3)ccn1] | 11% | MS (ESI+) for CHNOS m/z 309.16 [M + H]$^+$; LC purity 99.7% (Ret. Time- 3.57 min); $^1$H NMR (400 MHz, DMSO-d$_6$): δ 10.92 (bs, 1H), 8.19 (d, J = 5.2 Hz, 1H), 7.01-7.91 (m, 2H), 6.82-6.99 (m, 3H), 5.34 (bs, 2H), 4.26 (s, 4H), 2.36 (s, 3H) |
| 4-(2-Amino-4-(2,3-dihydrobenzo[b][1,4]dioxin-6-yl)-1H-imidazol-5-yl)pyridin-2-amine | 24 | 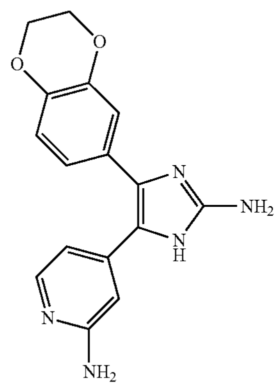 [SMILES: Nc1cc(-c2[nH]c(N)nc2-c2ccc3c(c2)OCCO3)ccn1] | 19% | MS (ESI+) for CHNOS m/z 310.03 [M + H]$^+$; LC purity 91.8% (Ret. Time- 3.53 min); $^1$H NMR (400 MHz, DMSO-d$_6$): δ 10.79 (bs, 1H), 7.70 (d, J = 4.9 Hz, 1H), 6.74-6.94 (m, 3H), 5.38-6.62 (m, 2H), 5.70 (bs, 2H), 5.26 (bs, 2H), 4.24 (s, 4H) |
| 4-(3-Methoxyphenyl)-5-(2-methylpyridin-4-yl)-1H-imidazol-2-amine | 25 | 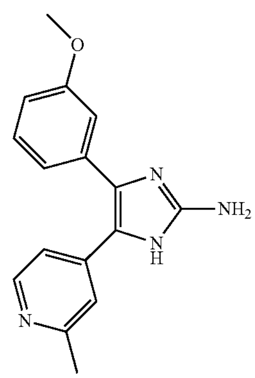 [SMILES: COc1cccc(-c2nc(N)[nH]c2-c2ccnc(C)c2)c1] | 18% | MS (ESI+) for CHNOS m/z 281.16 [M + H]$^+$; LC purity 96.4% (Ret. Time- 4.03 min); $^1$H NMR (400 MHz, DMSO-d$_6$): δ 11.07 (bs, 1H), 8.22 (d, J = 4.9 Hz, 1H), 7.20-7.31 (m, 2H), 7.12 (bs, 1H), 6.98 (bs, 2H), 6.84 (d, J = 8.6 Hz, 1H), 5.47 (s, 2H), 3.72 (s, 3H), 2.25 (s, 3H) |
| 4-(Benzo[d][1,3]dioxol-5-yl)-5-(2-methylpyridin-4-yl)-1H-imidazol-2-amine | 26 | 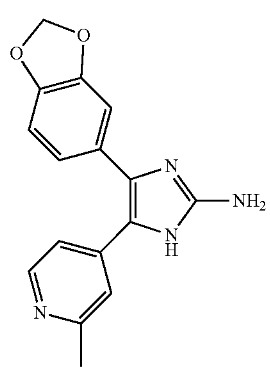 [SMILES: Cc1cc(-c2[nH]c(N)nc2-c2ccc3c(c2)OCO3)ccn1] | 56% | MS (ESI+) for CHNOS m/z 295.03 [M + H]$^+$; LC purity 95.3% (Ret. Time- 3.94 min); $^1$H NMR (400 MHz, DMSO-d$_6$): δ 11.16 (bs, 1H), 8.21 (d, J = 5.2 Hz, 1H), 7.25 (s, 1H), 7.08 (d, J = 4.9 Hz, 1H), 6.86-6.95 (m, 3H), 6.08 (s, 2H), 5.51 (bs, 2H), 2.36 (s, 3H) |

| Name | Ex | Structure | Yield | Spectral Data 1H NMR & LCMS |
|---|---|---|---|---|
| 4-(3,4-Dihydro-2H-benzo[b][1,4]oxazin-6-yl)-5-(2-methylpyridin-4-yl)-1H-imidazol-2-amine | 27 | 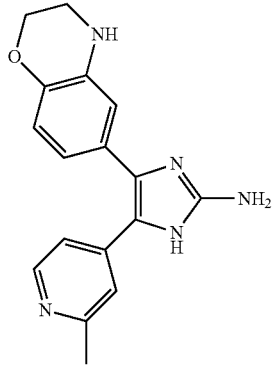 [SMILES: Cc1cc(-c2[nH]c(N)nc2-c2ccc3c(c2)NCCO3)ccn1] | 36% | MS (ESI+) for CHNOS m/z 308.05 [M + H]+; LC purity 93.8% (Ret. Time- 3.85 min); $^1$H NMR (400 MHz, DMSO-$d_6$): δ 10.81 (bs, 1H), 8.15 (d, J = 5.2 Hz, 1H), 7.29 (s, 1H), 7.12 (bs, 1H), 6.63 (bs, 2H), 6.50 (d, J = 7.7 Hz, 1H), 5.81 (bs, 1H), 5.28 (bs, 2H), 4.12-4.15 (m, 2H), 3.23-3.38 (m, 2H), 2.35 (s, 3H) |
| 4-(6-((4-Fluorobenzyl)oxy)pyridin-3-yl)-5-(2-methylpyridin-4-yl)-1H-imidazol-2-amine | 28 | 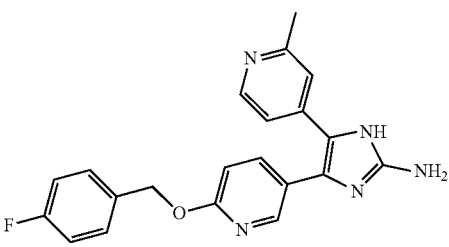 [SMILES: Cc1cc(-c2[nH]c(N)nc2-c2ccc(OCc3ccc(F)cc3)nc2)ccn1] | 22% | MS (ESI+) for CHNOS m/z 376.02 [M + H]+; LC purity 91.8% (Ret. Time- 4.94 min); $^1$H NMR (400 MHz, DMSO-$d_6$): δ 11.17 (bs, 1H), 8.19-8.29 (m, 2H), 7.71 (d, J = 8.0 Hz, 1H), 7.46-7.59 (m, 2H), 7.16-7.29 (m, 3H), 7.05 (d, J = 4.2 Hz, 1H), 6.89 (d, J = 8.4 Hz, 1H), 5.58 (bs, 2H), 5.35 (s, 2H), 2.36 (s, 3H) |
| 4-(5-Fluoro-6-methoxypyridin-3-yl)-5-(2-methylpyridin-4-yl)-1H-imidazol-2-amine | 29 | 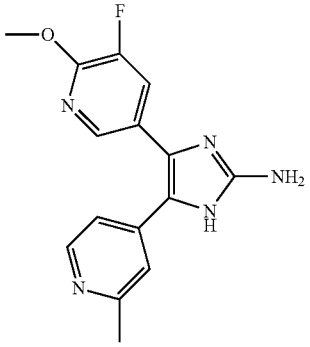 [SMILES: COc1ncc(-c2nc(N)[nH]c2-c2ccnc(C)c2)cc1F] | 21% | MS (ESI+) for CHNOS m/z 300.0 [M + H]+; LC purity 98.2% (Ret. Time- 3.97 min); $^1$H NMR (400 MHz, DMSO-$d_6$): δ 11.33 (bs, 1H), 8.26 (d, J = 5.3 Hz, 1H), 8.01 (s, 1H), 7.60-7.66 (m, 1H), 7.23 (s, 1H), 7.07 (d, J = 4.6 Hz, 1H), 5.64 (bs, 2H), 3.96 (s, 3H), 2.38 (s, 3H) |
| 2-(2,3-Dihydrobenzo[b][1,4]dioxin-6-yl)-3-(pyrimidin-4-yl)imidazo[1,2-a]pyrimidine | 30 | 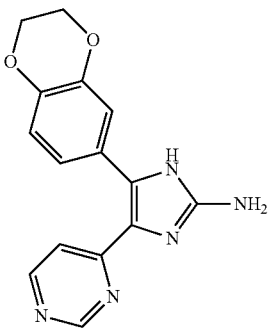 [SMILES: Nc1nc(-c2ccncn2)c(-c2ccc3c(c2)OCCO3)[nH]1] | 5% | MS (ESI+) for CHNOS m/z 295.97 [M + H]+; LC purity 92.6% (Ret. Time- 3.96 min); $^1$H NMR (400 MHz, DMSO-$d_6$): δ 11.21 (bs, 1H), 8.91 (s, 1H), 8.44 (d, J = 5.3 Hz, 1H), 7.34 (bs, 1H), 7.02-7.15 (m, 2H), 6.88 (d, J = 8.3 Hz, 1H), 5.76 (bs, 2H), 4.28 (s, 4H) |

-continued

| Name | Ex | Structure | Yield | Spectral Data<br>1H NMR & LCMS |
|---|---|---|---|---|
| 5-(2-Methylpyridin-4-yl)-4-(quinoxalin-6-yl)-1H-imidazol-2-amine | 31 | 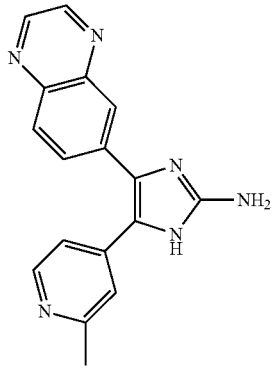 | 5% | MS (ESI+) for CHNOS m/z 300.00 [M + H]+; LC purity 98.9% (Ret. Time- 4.72 min); $^1$H NMR (400 MHz, DMSO-$d_6$): δ 11.49 (bs, 1H), 8.90 (d, J = 10 Hz, 2H), 8.30 (d, J = 5.0 Hz, 1H), 8.09 (s, 1H), 8.02 (d, J = 8.8 Hz, 1H), 7.88 (d, J = 8.6 Hz, 1H), 7.31 (s,1H), 7.17 (d, J = 4.4 Hz, 1H), 5.72 (bs, 2H), 2.40 (s, 3H) |
| 4-(2,3-Dihydrobenzo[b][1,4]dioxin-6-yl)-5-(2-methylpyridin-4-yl)-1H-imidazol-2-amine | 32 | 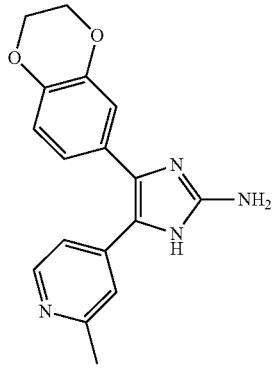 [SMILES: Cc1cc(-c2[nH]c(N)nc2-c2ccc3c(c2)OCCO3)ccn1] | 11% | Purified using 100 to 200 mesh silica gel in 5% MeOH/DCM.<br>MS (ESI+) for CHNOS m/z 309.16 [M + H]+; LC purity 99.7% (Ret.Time- 3.57 min); $^1$H NMR (400 MHz, DMSO-$d_6$): δ 10.92 (bs, 1H), 8.19 (d, J = 5.2 Hz, 1H), 7.01-7.91 (m, 2H), 6.82-6.99 (m, 3H), 5.34 (bs, 2H), 4.26 (s, 4H), 2.36 (s, 3H) |
| 6-(2-Amino-5-(2-methylpyridin-4-yl)-1H-imidazol-4-yl)-2-methyl-2H-benzo[b][1,4]oxazin-3(4H)-one | 33 | 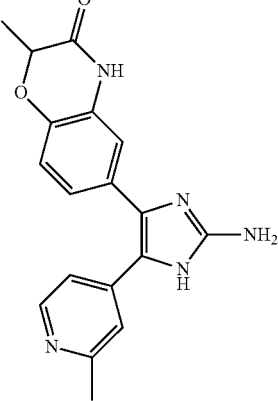 | 6% | Purified by prep HPLC.<br>MS (ESI+) for CHNOS m/z 336.04 [M + H]+; LC purity 98.7% (Ret. Time- 3.88 min); 1H NMR (400 MHz, DMSO-$d_6$): δ 11.28 (bs, 1H), 10.67 (s, 1H), 8.23 (d, J = 5.4 Hz, 1H), 7.24 (s, 1H), 7.09 (d, J = 4.8 Hz, 1H), 6.93-7.02 (m, 3H), 5.59 (bs, 2H), 4.69 (q, J = 6.6 Hz, 1H), 2.37 (s, 3H), 1.43 (d, J = 5.4 Hz, 3H) |
| 4-(2-Methyl-3,4-dihydro-2H-benzo[b][1,4]oxazin-6-yl)-5-(2-methylpyridin-4-yl)-1H-imidazol-2-amine | 34 | 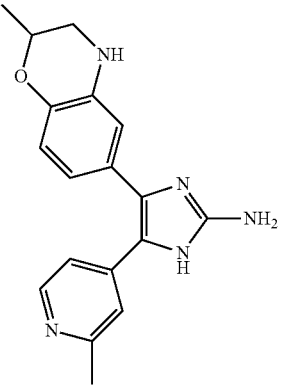 [SMILES: Cc1cc(-c2[nH]c(N)nc2-c2ccc3c(c2)NCC(C)O3)ccn1] | 45% | MS (ESI+) for CHNOS m/z 322.10 [M + H]+; LC purity 97.1% (Ret. Time- 4.04 min); $^1$H NMR (400 MHz, DMSO-$d_6$): δ 11.06 (bs, 1H), 8.17 (d, J = 5.2 Hz, 1H), 7.28 (s, 1H), 7.12 (d, J = 4.5 Hz, 1H), 6.60-6.64 (m, 2H), 6.50 (d, J = 6.9 Hz, 1H), 5.84 (bs, 1H), 5.41 (bs, 2H), 4.09-4.14 (m, 1H), 3.33 (bs, 1H), 2.89-2.96 (m, 1H), 2.35 (s, 3H), 1.28 (d, J = 6.1 Hz, 3H) |

-continued

| Name | Ex | Structure | Yield | Spectral Data 1H NMR & LCMS |
|---|---|---|---|---|
| 2-(4-(2-Amino-5-(2-methylpyridin-4-yl)-1H-imidazol-4-yl)phenoxy)acetonitrile | 35 | 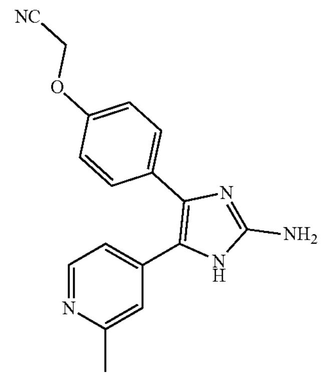 [SMILES: Cc1cc(-c2[nH]c(N)nc2-c2ccc(OCC#N)cc2)ccn1] | 29% | MS (ESI+) for CHNOS m/z 306.06 [M + H]⁺; LC purity 98.5% (Ret. Time- 3.96 min); ¹H NMR (400 MHz, DMSO-d₆): δ 11.04 (bs, 1H), 8.19 (d, J = 5.2 Hz, 1H), 7.40 (d, J = 8.3 Hz, 2H), 7.22 (bs, 1H), 6.99-7.13 (m, 3H), 5.44 (bs, 2H), 5.20 (s, 2H), 2.34 (s, 3H). |
| 4-(3,4-Dihydro-2H-benzo[b][1,4]oxazin-6-yl)-5-(2,6-dimethylpyridin-4-yl)-1H-imidazol-2-amine | 36 | 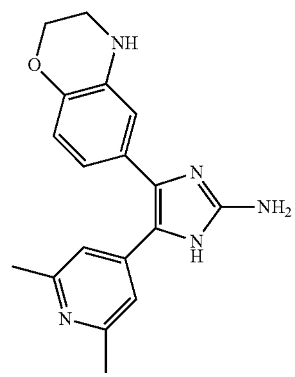 [SMILES: Cc1cc(-c2[nH]c(N)nc2-c2ccc3c(c2)NCCO3)cc(C)n1] | 14% | MS (ESI+) for CHNOS m/z 322.10 [M + 1]⁺; LC purity 99.4% (Ret. Time- 3.75 min); ¹H NMR (400 MHz, DMSO-d₆ + d-TFA): 7.53 (s, 2H), 6.70-6.82 (m, 2H), 6.65 (d, J = 7.5 Hz, 1H), 4.20 (bs, 2H), 3.34 (bs, 2H), 2.56 (s, 6H) |
| 4-(2-Methylbenzo[d]oxazol-5-yl)-5-(2-methylpyridin-4-yl)-1H-imidazol-2-amine | 37 | 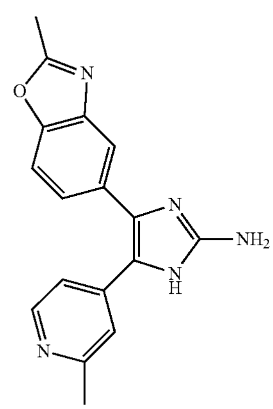 [SMILES: Cc1cc(-c2[nH]c(N)nc2-c2ccc3oc(C)nc3c2)ccn1] | 9% | MS (ESI+) for CHNOS m/z 306.06 [M + H]⁺; LC purity 90.0% (Ret. Time- 4.70 min); ¹H NMR (400 MHz, DMSO-d₆): δ 11.46 (bs, 1H), 8.20 (d, J = 5.3 Hz, 1H), 7.62-7.67 (m, 2H), 7.37 (d, J = 8.5 Hz, 1H), 7.24 (s, 1H), 7.04 (d, J = 5.3 Hz, 1H), 5.69 (bs, 2H), 2.61 (s, 3H), 2.35 (s, 3H) |
| 4-(2,3-Dihydrobenzofuran-5-yl)-5-(pyridin-4-yl)-1H-imidazol-2-amine | 38 | | 8% | MS (ESI+) for CHNOS m/z 279.04 [M + H]⁺; LC purity 99.6% (Ret. Time- 3.48 min); ¹H NMR (400 MHz, DMSO-d₆ + d-TFA): δ 8.79 (d, J = 6.8 Hz, 2H), 7.81 (d, J = 6.8 Hz, 2H), 7.42 (s, 1H), 7.28 (d, J = 7.2 Hz, 1H), 6.92 (d, J = 8.2 Hz, 1H), 4.62 (t, J = 8.8 Hz, 2H), 3,23 (t, J = 8.8 Hz, 2H) |

-continued

| Name | Ex | Structure | Yield | Spectral Data 1H NMR & LCMS |
|---|---|---|---|---|
| 4-(3,4-Dihydro-2H-benzo[b][1,4]oxazin-6-yl)-5-(pyridin-4-yl)-1H-imidazol-2-amine | 39 | 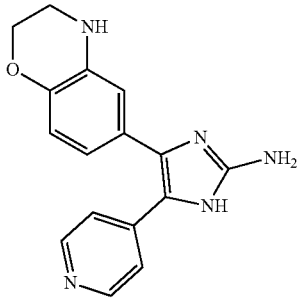 [SMILES: Nc1nc(-c2ccc3c(c2)NCCO3)c(-c2ccncc2)[nH]1] | 2% | MS (ESI+) for CHNOS m/z 294.08 [M + H]⁺; LC purity 99.7% (Ret. Time- 4.62 min); ¹H NMR (400 MHz, DMSO-d₆ + D₂O): δ 8.64 (d, J = 6.4 Hz, 2H), 7.65 (d, J = 6.4 Hz, 2H), 6.77 (d, J = 8.1 Hz, 1H), 6.65 (d, J = 1.7 Hz, 1H), 6.60 (dd, J = 1.7, 8.1 Hz, 1H), 4.16 (bs, 2H), 3.28 (bs, 2H) |
| 4-(2-Amino-4-(3,4-dihydro-2H-benzo[b][1,4]oxazin-6-yl)-1H-imidazol-5-yl)-N-methylpyridin-2-amine | 40 | 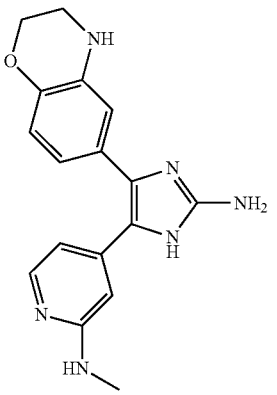 [SMILES: CNc1cc(-c2[nH]c(N)nc2-c2ccc3c(c2)NCCO3)ccn1] | 18% | MS (ESI+) for CHNOS m/z 323 [M + H]⁺; LC purity 92.5% (Ret. Time- 4.79 min); ¹H NMR (400 MHz, DMSO-d₆ + d-TFA): δ 7.80 (d, J = 6.5 Hz, 1H), 6.74-6.98 (m, 4H), 6.60 (d, J = 6.5 Hz, 1H), 4.22 (bs, 2H), 3.39 (bs, 2H), 2.87 (s, 3H) |
| 4-(2-Methyl-2,3-dihydro-benzofuran-5-yl)-5-(2-methylpyridin-4-yl)-1H-imidazol-2-amine | 41 Racemic | 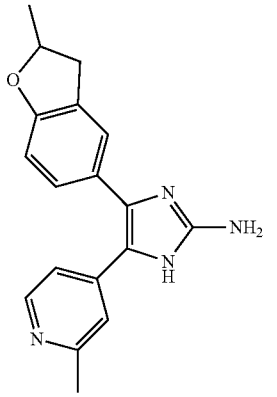 [SMILES: Cc1cc(-c2[nH]c(N)nc2-c2ccc3c(c2)CC(C)O3)ccn1] | 19% | MS (ESI+) for CHNOS m/z 307.06 [M + H]⁺; LC purity 93.6% (Ret. Time- 4.09 min); ¹H NMR (400 MHz, DMSO-d₆): δ 10.91 (bs, 1H), 8.16 (s, 1H), 6.98-7.38 (m, 4H), 6.65-6.69 (m, 1H), 5.28-5.46 (m, 2H), 4.94 (bs, 1H), 3.26-3.29 (m, 1H), 2.74-2.79 (m, 1H), 2.34 (s, 3H), 1.40 (d, J = 6.0 Hz, 3H) |
| 4-(2-Amino-4-(3,4-dihydro-2H-benzo[b][1,4]oxazin-6-yl)-1H-imidazol-5-yl)pyridin-2-amine | 42 | 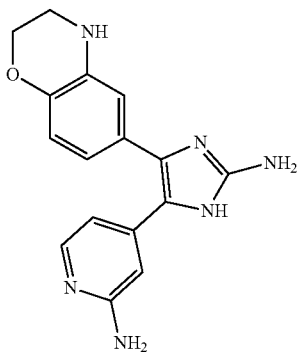 [SMILES: Nc1cc(-c2[nH]c(N)nc2-c2ccc3c(c2)NCCO3)ccn1] | 12% | MS (ESI+) for CHNOS m/z 309.2 [M + H]⁺; LC purity 98.1% (Ret. Time- 3.27 min); ¹H NMR (400 MHz, DMSO-d₆): δ 10.68 (bs, 1H), 7.66 (d, J = 4.7 Hz, 1H), 6.41-6.69 (m, 5H), 5.77 (bs, 1H), 5.64 (bs, 2H), 5.20 (bs, 2H), 41.2 (bs, 2H), 3.28 (bs, 2H) |

| Name | Ex | Structure | Yield | Spectral Data 1H NMR & LCMS |
|---|---|---|---|---|
| 4-(3,4-Dihydro-2H-benzo[b][1,4]oxazin-6-yl)-5-(2-methylpyridin-4-yl)-1H-imidazol-2-amine | 43 | 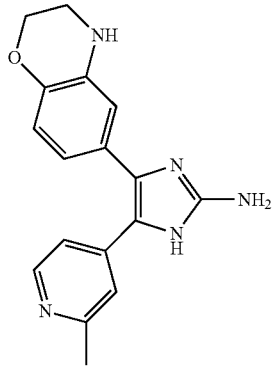 [SMILES: Cc1cc(-c2[nH]c(N)nc2-c2ccc3c(c2)NCCO3)ccn1] | 36% | CHNOS m/z 308.17 [M + H]$^+$; LC purity 99.3% (Ret. Time- 3.79 min); $^1$H NMR (400 MHz, DMSO-d$_6$): δ 11.13 (bs, 1H), 8.18 (d, J = 5.3 Hz, 1H), 7.29 (s, 1H), 7.13 (d, J = 4.7 Hz, 1H), 6.63 (bs, 2H), 6.50 (dd, J = 1.6, 8.1 Hz, 1H), 5.83 (bs, 1H), 5.47 (bs, 2H), 4.13 (bs, 2H), 3.32 (bs, 2H), 2.35 (s, 3H) |
| 4-(4-Methyl-3,4-dihydro-2H-benzo[b][1,4]oxazin-6-yl)-5-(2-methylpyridin-4-yl)-1H-imidazol-2-amine | 44 | 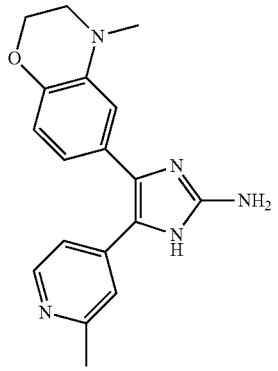 [SMILES: Cc1cc(-c2[nH]c(N)nc2-c2ccc3c(c2)N(C)CCO3)ccn1] | 6% | CHNOS m/z 322.09 [M + H]$^+$; LC purity 97.3% (Ret. Time- 4.05 min); $^1$H NMR (400 MHz, DMSO-d$_6$ + D$_2$O): δ 8.17 (d, J = 5.9 Hz, 1H), 7.28 (s, 1H), 7.14 (d, J = 4.2 Hz, 1H), 6.56-6.70 (m, 3H), 4.22 (bs, 2H), 3.21 (bs, 2H), 2.71 (s, 3H), 2.34 (s, 3H) |
| 5-(2-Chloropyridin-4-yl)-4-(3,4-dihydro-2H-benzo[b][1,4]oxazin-6-yl)-1H-imidazol-2-amine | 45 | 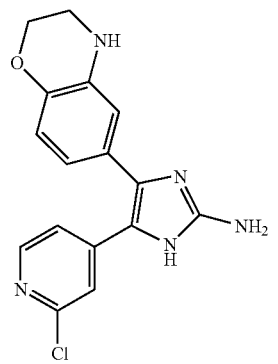 [SMILES: Nc1nc(-c2ccc3c(c2)NCCO3)c(-c2ccnc(Cl)c2)[nH]1] | 11% | MS (ESI+) for CHNOS m/z 328.10 [M + H]$^+$; LC purity 98.3% (Ret. Time- 4.41 min); 1H NMR (400 MHz, DMSO-d$_6$): δ 11.14 (bs, 1H), 8.11 (d, J = 5.3 Hz, 1H), 7.42 (s, 1H), 7.32 (bs, 1H), 6.60-6.70 (m, 2H), 6.51 (d, J = 8.0 Hz, 1H), 5.90 (bs, 1H), 5.52 (bs, 2H), 4.15 (bs, 2H), 3.29 (bs, 2H) |
| 4-(3,4-Dihydro-2H-benzo[b][1,4]oxazin-6-yl)-5-(2-(trifluoromethyl)pyridin-4-yl)-1H-imidazol-2-amine | 46 | 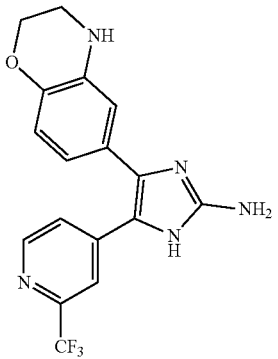 [SMILES: Nc1nc(-c2ccc3c(c2)NCCO3)c(-c2ccnc(C(F)(F)F)c2)[nH]1] | 25% | MS (ESI+) for CHNOS m/z 362.12 [M + H]$^+$; LC purity 99.1% (Ret. Time- 4.71 min); $^1$H NMR (400 MHz, DMSO-d$_6$ + d-TFA): δ 8.65 (d, J = 5.1 Hz, 1H), 7.83 (s, 1H), 7.52 (d, J = 4.6 Hz, 1H), 6.81-6.89 (m, 2H), 6.76 (d, J = 8.1 Hz, 1H), 4.22 (bs, 2H), 3.34 (bs, 2H) |

-continued

| Name | Ex | Structure | Yield | Spectral Data 1H NMR & LCMS |
|---|---|---|---|---|
| 4-(3,4-Dihydro-2H-benzo[b][1,4]oxazin-6-yl)-5-(2-fluoropyridin-4-yl)-1H-imidazol-2-amine | 47 | 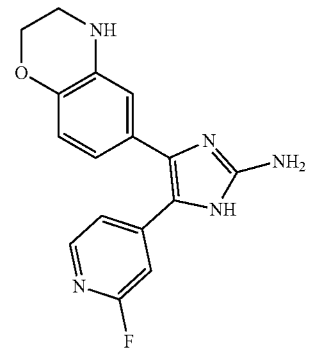 [SMILES: Nc1nc(-c2ccc3c(c2)NCCO3)c(-c2ccnc(F)c2)[nH]1] | 19% | MS (ESI+) for CHNOS m/z 312.06 [M + H]+; LC purity 99.4% (Ret. Time- 4.14 min); $^1$H NMR (400 MHz, DMSO-d$_6$ + d-TFA): δ 8.16 (d, J = 5.3 Hz, 1H), 7.22 (d, J = 5.1 Hz, 1H), 7.09 (s, 1H), 6.80-6.89 (m, 2H), 6.78 (d, J = 8.0 Hz, 1H), 4.23 (bs, 2H), 3.38 (bs, 2H) |
| 5-(2-Methylpyridin-4-yl)-4-(2,3,4,5-tetrahydrobenzo[b][1,4]oxazepin-7-yl)-1H-imidazol-2-amine | 48 | 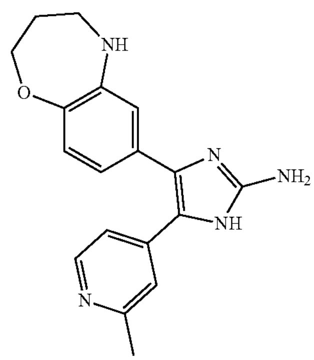 [SMILES: Cc1cc(-c2[nH]c(N)nc2-c2ccc3c(c2)NCCCO3)ccn1] | 16% | MS (ESI+) for CHNOS m/z 322.17 [M + H]+; LC purity 99.7% (Ret. Time- 3.84 min); $^1$H NMR (400 MHz, DMSO-d$_6$ + d-TFA): δ 8.68 (d, J = 6.4 Hz, 1H), 7.77 (s, 1H), 7.63 (d, J = 6.2 Hz, 1H), 7.46 (s, 1H), 7.37 (d, J = 8.3 Hz, 1H), 7.26 (d, J = 8.3 Hz, 1H), 4.17 (bs, 2H), 3.36 (bs, 2H), 2.61 (s, 3H), 2.16 (bs, 2H) |
| 4-(8-Fluoro-3,4-dihydro-2H-benzo[b][1,4]oxazin-6-yl)-5-(2-methylpyridin-4-yl)-1H-imidazol-2-amine | 49 | 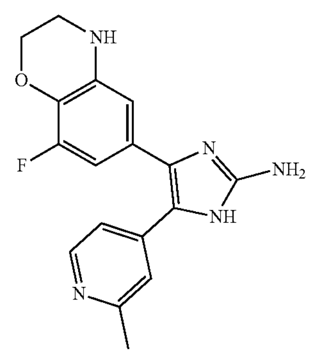 [SMILES: Cc1cc(-c2[nH]c(N)nc2-c2cc(F)c3c(c2)NCCO3)ccn1] | 15% | MS (ESI+) for CHNOS m/z 326.15 [M + H]+; LC purity 98.2% (Ret. Time- 3.92 min); $^1$H NMR (400 MHz, DMSO-d$_6$ + d-TFA): δ 8.65 (d, J = 6.4 Hz, 1H), 7.80 (s, 1H), 7.60 (d, J = 5.1 Hz, 1H), 6.52-6.58 (m, 2H), 4.22 (bs, 2H), 3.35 (bs, 2H), 2.63 (s, 3H) |
| 6-(2-Amino-5-(2-methylpyridin-4-yl)-1H-imidazol-4-yl)-8-fluoro-2H-benzo[b][1,4]oxazin-3(4H)-one | 50 | 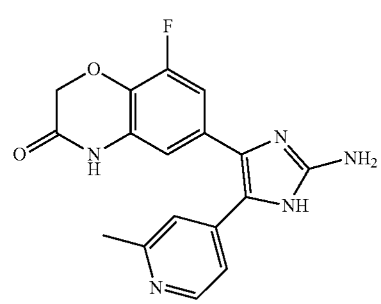 [SMILES: Cc1cc(-c2[nH]c(N)nc2-c2cc(F)c3c(c2)NC(=O)CO3)ccn1] | 12% | MS (ESI+) for CHNOS m/z 340.14 [M + H]+; LC purity 98.6% (Ret. Time- 3.83 min); $^1$H NMR (400 MHz, DMSO-d$_6$ + D$_2$O): δ 8.21 (d, J = 5.3 Hz, 1H), 7.20 (s, 1H), 7.07 (d, J = 4.6 Hz, 1H), 6.76-6.88 (m, 2H), 4.64 (s, 2H), 2.36 (s, 3H) |

-continued

| Name | Ex | Structure | Yield | Spectral Data 1H NMR & LCMS |
|---|---|---|---|---|
| 6-(2-Amino-5-(2-methylpyridin-4-yl)-1H-imidazol-4-yl)-2H-benzo[b][1,4]oxazin-3(4H)-one | 51 | 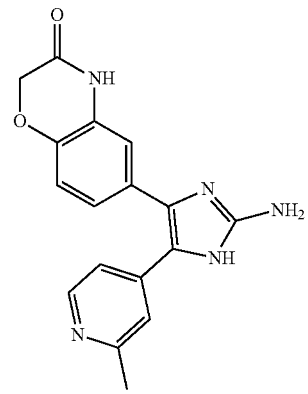 [SMILES: Cc1cc(-c2[nH]c(N)nc2-c2ccc3c(c2)NC(=O)CO3)ccn1] | 9% | MS (ESI+) for CHNOS m/z 322.24 [M + H]+; LC purity 99.8% (Ret. Time- 3.50 min); $^1$H NMR (400 MHz, DMSO-$d_6$ + d-TFA): δ 8.65 (d, J = 6.5 Hz, 1H), 7.78 (s, 1H), 7.58 (d, J = 6.2 Hz, 1H), 6.68-7.10 (m, 3H), 4.65 (s, 2H), 2.62 (s, 3H) |
| 4-(7-Fluoro-3,4-dihydro-2H-benzo[b][1,4]oxazin-6-yl)-5-(2-methylpyridin-4-yl)-1H-imidazol-2-amine | 52 | 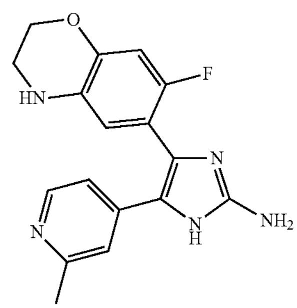 [SMILES: Cc1cc(-c2[nH]c(N)nc2-c2cc3c(cc2F)OCCN3)ccn1] | 9% | MS (ESI+) for CHNOS m/z 326.21 [M + H]+; LC purity 92.9% (Ret. Time- 3.54 min); $^1$H NMR (400 MHz, DMSO-$d_6$ + $D_2O$): δ 8.12 (d, J = 5.3 Hz, 1H), 7.15 (bs, 1H), 6.97 (bs, 1H), 6.50-6.70 (m, 2H), 4.15 (bs, 2H), 3.35 (bs, 2H), 2.31 (s, 3H) |
| 6-(2-Amino-5-(2-methylpyridin-4-yl)-1H-imidazol-4-yl)-3,4-dihydro-2H-benzo[b][1,4]oxazin-2-one | 53 | 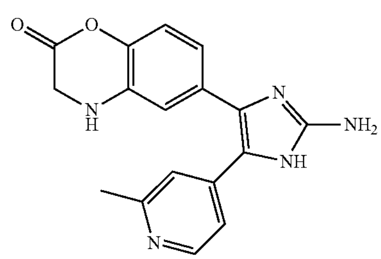 [SMILES: Cc1cc(-c2[nH]c(N)nc2-c2ccc3c(c2)NCC(=O)O3)ccn1] | 11% | MS (ESI+) for CHNOS m/z 322.14 [M + H]+; LC purity 98.6% (Ret. Time- 3.57 min); $^1$H NMR (400 MHz, DMSO-$d_6$ + d-TFA): δ 8.62 (d, J = 6.5 Hz, 1H), 7.77 (s, 1H), 7.57 (d, J = 6.4 Hz, 1H), 6.67-7.09 (m, 3H), 4.63 (s, 2H), 2.61 (s, 3H) |
| 6-(2-Amino-5-(2-methylpyridin-4-yl)-1H-imidazol-4-yl)-7-fluoro-2H-benzo[b][1,4]oxazin-3(4H)-one | 54 | 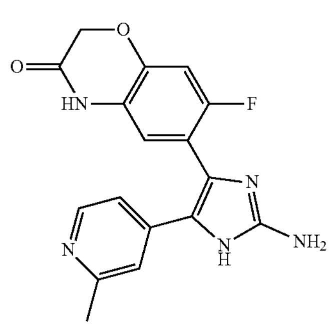 [SMILES: Cc1cc(-c2[nH]c(N)nc2-c2cc3c(cc2F)OCC(=O)N3)ccn1] | 9% | MS (ESI+) for CHNOS m/z 340.14 [M + H]+; LC purity 99.3% (Ret. Time- 3.55 min); $^1$H NMR (400 MHz, DMSO-$d_6$ + $D_2O$): δ 8.43 (d, J = 6.1 Hz, 1H), 7.51 (s, 1H), 7.32 (d, J = 5.5 Hz, 1H), 7.05-7.10 (m, 1H), 6.95 (d, J = 7.1 Hz, 1H), 4.67 (s, 2H), 2.54 (s, 3H) |

-continued

| Name | Ex | Structure | Yield | Spectral Data 1H NMR & LCMS |
|---|---|---|---|---|
| 5-(2-Methylpyridin-4-yl)-4-(4-(methylsulfonyl)-3,4-dihydro-2H-benzo[b][1,4]oxazin-6-yl)-1H-imidazol-2-amine | 55 | 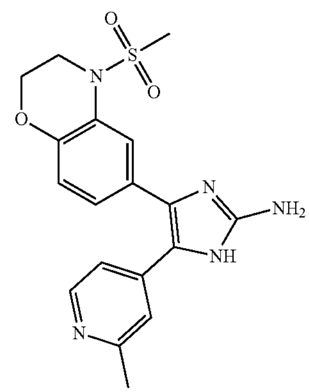 [SMILES: Cc1cc(-c2[nH]c(N)nc2-c2ccc3c(c2)N(S(C)(=O)=O)CCO3)ccn1] | 18% | MS (ESI+) for CHNOS m/z 386.17 [M + H]+; LC purity 96.3% (Ret. Time-3.71 min); ¹H NMR (400 MHz, DMSO-d₆ + D₂O): δ 8.17 (d, J = 5.2 Hz, 1H), 7.59 (s, 1H), 7.21 (s, 1H), 7.03-7.16 (m, 2H), 6.96 (d, J = 8.4 Hz, 1H), 4.27 (s, 2H), 3.78 (bs, 2H), 3.04 (s, 3H), 2.34 (s, 3H) |
| 4-(8-fluoro-2,3-dihydrobenzo[b][1,4]dioxin-6-yl)-5-(2-methylpyridin-4-yl)-1H-imidazol-2-amine | 56 | 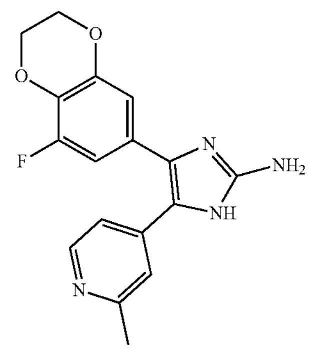 [SMILES: Cc1cc(-c2[nH]c(N)nc2-c2cc(F)c3c(c2)OCCO3)ccn1] | 13% | MS (ESI+) for CHNOS m/z 327.12 [M + H]+; LC purity 97.6% (Ret. Time- 3.68 min); ¹H NMR (400 MHz, DMSO-d₆ + D₂O): δ 8.21 (d, J = 5.2 Hz, 1H), 7.21 (s, 1H), 7.08 (d, J = 4.6 Hz, 1H), 6.70-6.79 (m, 1H), 6.69 (s, 1H), 4.26 (bs, 4H), 2.37 (s, 3H) |
| 4-(4-Ethyl-3,4-dihydro-2H-benzo[b][1,4]oxazin-6-yl)-5-(2-methylpyridin-4-yl)-1H-imidazol-2-amine | 57 | 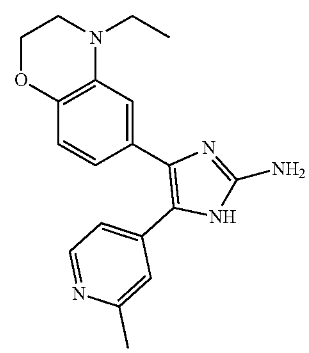 [SMILES: CCN1CCOc2ccc(-c3nc(N)[nH]c3-c3ccnc(C)c3)cc21] | 30% | MS (ESI+) for CHNOS m/z 336.24 [M + H]+; LC purity 91.8% (Ret. Time- 4.01 min); ¹H NMR (400 MHz, DMSO-d₆): 510.92 (bs, 1H), 8.17 (d, J = 5.3 Hz, 1H), 7.29 (bs, 1H), 7.15 (bs, 1H), 6.62-6.78 (m, 2H), 6.56 (d, J = 7.8 Hz, 1H), 5.32 (bs, 2H), 4.18 (bs, 2H), 3.30 (bs, 2H), 3.23 (q, J = 7.0 Hz, 2H), 2.34 (s, 3H), 0.99 (t, J = 7.0 Hz, 3H) |
| 5-(2-Methylpyridin-4-yl)-4-(1,2,3,4-tetrahydroquinolin-7-yl)-1H-imidazol-2-amine | 58 | | 22% | MS (ESI+) for CHNOS m/z 306.28 [M + H]+; LC purity 98.2% (Ret. Time- 4.55 min); ¹H NMR (400 MHz, DMSO-d₆ + d-TFA): δ 8.66 (d, J = 6.4 Hz, 1H), 7.77 (s, 1H), 7.58 (d, J = 6.1 Hz, 1H), 7.28 (d, J = 7.8 Hz, 1H), 7.02 (d, J = 7.8 Hz, 1H), 6.98 (s, 1H), 3.30-3.35 (m, 2H), 2.78-2.85 (m, 2H), 2.63 (s, 3H), 1.90-1.95 (m, 2H) |

-continued

| Name | Ex | Structure | Yield | Spectral Data 1H NMR & LCMS |
|---|---|---|---|---|
| 4-(7-Fluoro-2,3-dihydrobenzo[b][1,4]dioxin-6-yl)-5-(2-methylpyridin-4-yl)-1H-imidazol-2-amine | 59 | 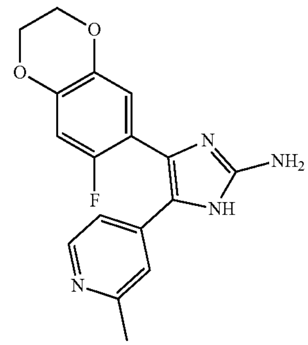 [SMILES: Cc1cc(-c2[nH]c(N)nc2-c2cc3c(cc2F)OCCO3)ccn1] | 21% | MS (ESI+) for CHNOS m/z 327.19 [M + H]+; LC purity 99.8% (Ret. Time- 3.68 min); $^1$H NMR (400 MHz, DMSO-d$_6$ + d-TFA): δ 8.63 (d, J = 6.4 Hz, 1H), 7.75 (s, 1H), 7.53 (d, J = 6.1 Hz, 1H), 6.89-7.15 (m, 2H), 4.24-4.34 (m, 4H), 2.62 (s, 3H) |
| 4-(5-Fluoro-2,3-dihydrobenzo[b][1,4]dioxin-6-yl)-5-(2-methylpyridin-4-yl)-1H-imidazol-2-amine | 60 | 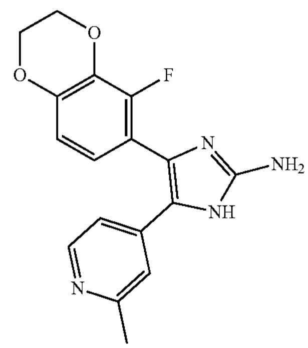 [SMILES: Cc1cc(-c2[nH]c(N)nc2-c2ccc3c(c2F)OCCO3)ccn1] | 38% | MS (ESI+) for CHNOS m/z 327.20 [M + H]+; LC purity 95.1% (Ret. Time- 4.03 min); $^1$H NMR (400 MHz, DMSO-d$_6$): δ 11.19 (bs, 1H), 8.18 (d, J = 5.3 Hz, 1H), 7.19 (s, 1H), 6.95 (d, J = 4.8 Hz, 1H), 6.73-6.88 (m, 2H), 5.57 (bs, 2H), 4.34 (s, 4H), 2.35 (s, 3H) |
| Methyl 3-(6-(2-amino-5-(2-methylpyridin-4-yl)-1H-imidazol-4-yl)-2,3-dihydro-4H-benzo[b][1,4]oxazin-4-yl)propanoate | 61 | 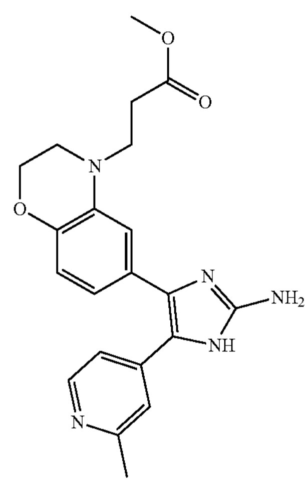 [SMILES: COC(=O)CCN1CCOc2ccc(-c3nc(N)[nH]c3-c3ccnc(C)c3)cc21] | 3% | MS (ESI+) for CHNOS m/z 394.30 [M + H]+; LC purity 99.4% (Ret. Time- 4.72 min); $^1$H NMR (400 MHz, DMSO-d$_6$ + D$_2$O): δ 8.13 (d, J = 5.3 Hz, 1H), 7.26 (s, 1H), 7.13 (d, J = 4.6 Hz, 1H), 6.60-6.74 (m, 2H), 6.53 (d, J = 7.9 Hz, 1H), 4.12 (bs, 2H), 3.82 (s, 3H), 3.40 (t, J = 6.5 Hz, 2H), 3.26 (bs, 2H), 2.33 (s, 3H), 2.23 (t, J = 6.5 Hz, 2H) |
| 2-Amino-1-(6-(2-amino-5-(2-methylpyridin-4-yl)-1H-imidazol-4-yl)-2,3-dihydro-4H-benzo[b][1,4]oxazin-4-yl)ethan-1-one | 62 | 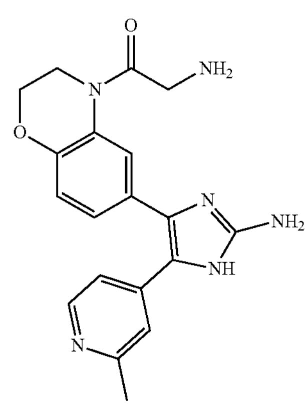 [SMILES: Cc1cc(-c2[nH]c(N)nc2-c2ccc3c(c2)N(C(=O)CN)CCO3)ccn1] | 16% | MS (ESI+) for CHNOS m/z 365.21 [M + H]+; LC purity 98.4% (Ret. Time- 2.95 min); $^1$H NMR (400 MHz, DMSO-d$_6$ + d-TFA): δ 8.67 (d, J = 6.1 Hz, 1H), 8.16 (bs, 1H), 7.81 (s, 1H), 7.65 (d, J = 4.4 Hz, 1H), 7.29 (d, J = 8.4 Hz, 1H), 7.14 (d, J = 5.3 Hz, 1H), 4.39 (s, 2H), 4.14 (s, 2H), 3.88 (bs, 2H), 2.63 (s, 3H) |

| Name | Ex | Structure | Yield | Spectral Data 1H NMR & LCMS |
|---|---|---|---|---|
| 1-(6-(2-Amino-5-(2-methylpyridin-4-yl)-1H-imidazol-4-yl)-2,3-dihydro-4H-benzo[b][1,4]oxazin-4-yl)ethan-1-one | 63 | 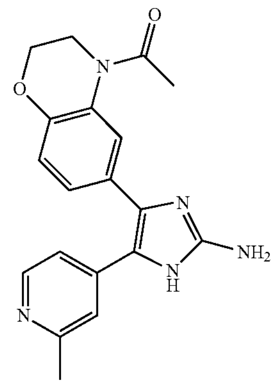 [SMILES: CC(=O)N1CCOc2ccc(-c3nc(N)[nH]c3-c3ccnc(C)c3)cc21] | 43% | MS (ESI+) for CHNOS m/z 350.16 [M + H]+; LC purity 97% (Ret. Time- 1.32 min); $^1$H NMR (400 MHz, DMSO-d$_6$): δ 11.09 (bs, 1H), 8.19 (d, J = 6.1 Hz, 1H), 7.30 (s, 1H), 7.05-7.18 (m, 3H), 6.89 (d, J = 8.0 Hz, 1H), 5.52 (bs, 2H), 4.29 (bs, 2H), 3.86 (bs, 2H), 2.35 (s, 3H), 2.18 (s, 3H) |
| 4-(4-(2-Methoxyethyl)-3,4-dihydro-2H-benzo[b][1,4]oxazin-6-yl)-5-(2-methylpyridin-4-yl)-1H-imidazol-2-amine | 64 | 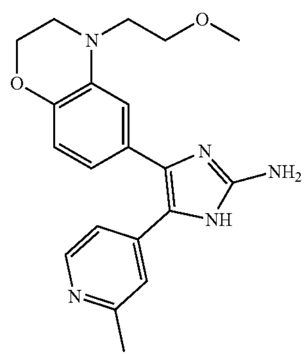 [SMILES: COCCN1CCOc2ccc(-c3nc(N)[nH]c3-c3ccnc(C)c3)cc21] | 13% | MS (ESI+) for CHNOS m/z 366.26 [M + H]+; LC purity 96.1% (Ret. Time- 4.59 min); $^1$H NMR (400 MHz, DMSO-d$_6$): δ 11.12 (bs, 1H), 8.19 (d, J = 5.3 Hz, 1H), 7.29 (s, 1H), 7.14 (d, J = 4.5 Hz, 1H), 6.64-6.74 (m, 2H), 6.56 (dd, J = 1.2, 8.0 Hz, 1H), 5.50 (bs, 2H), 4.15 (bs, 2H), 3.30-3.46 (m, 6H), 3.19 (s, 3H), 2.36 (s, 3H) |
| 4-(4-Cyclopropyl-3,4-dihydro-2H-benzo[b][1,4]oxazin-6-yl)-5-(2-methylpyridin-4-yl)-1H-imidazol-2-amine | 65 | 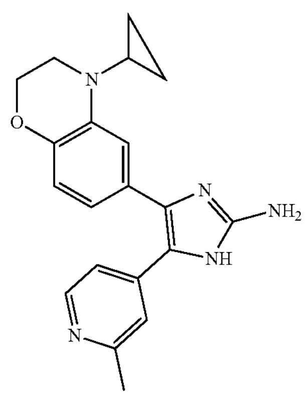 [SMILES: Cc1cc(-c2[nH]c(N)nc2-c2ccc3c(c2)N(C2CC2)CCO3)ccn1] | 15% | MS (ESI+) for CHNOS m/z 348.25 [M + H]+; LC purity 98.5% (Ret. Time- 4.16 min); $^1$H NMR (400 MHz, DMSO-d$_6$): δ 10.95 (bs, 1H), 8.20 (d, J = 5.2 Hz, 1H), 7.30 (s, 1H), 7.17 (bs, 2H), 6.62-6.78 (m, 2H), 5.39 (bs, 2H), 4.21 (bs, 2H), 3.25 (bs, 2H), 2.35 (s, 3H), 2.12 (bs, 1H), 0.35-0.60 (m, 4H) |
| 6-(2-Amino-4-(2-methylpyridin-4-yl)-1H-imidazol-5-yl)-4-(2-hydroxyethyl)-2H-benzo[b][1,4]oxazin-3(4H)-one | 66 | 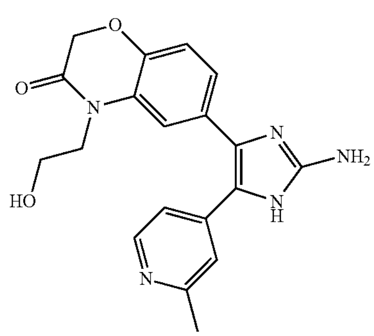 [SMILES: Cc1cc(-c2[nH]c(N)nc2-c2ccc3c(c2)N(CCO)C(=O)CO3)ccn1] | 27% | Purified by combiflash (4 g column), eluting with 0-15% MeOH in DCM followed by trituration with Et$_2$O MS (ESI+) for CHNOS m/z 366.21 [M + H]+; LC purity 98.6% (Ret. Time- 3.38 min); $^1$H NMR (400 MHz, DMSO-d$_6$ + d-TFA): δ 8.64 (d, J = 6.2 Hz, 1H), 7.78 (s, 1H), 7.60 (d, J = 6.2 Hz, 1H), 7.45 (s, 1H), 7.11-7.19 (m, 2H), 4.73 (s, 2H), 3.92 (bs, 2H), 3.52-3.56 (m, 2H), 2.62 (s, 3H) |

-continued

| Name | Ex | Structure | Yield | Spectral Data 1H NMR & LCMS |
|---|---|---|---|---|
| tert-butyl (2-(6-(2-amino-4-(2-methylpyridin-4-yl)-1H-imidazol-5-yl)-3-oxo-2,3-dihydro-4H-benzo[b][1,4]oxazin-4-yl)ethyl)carbamate | Int 132 | 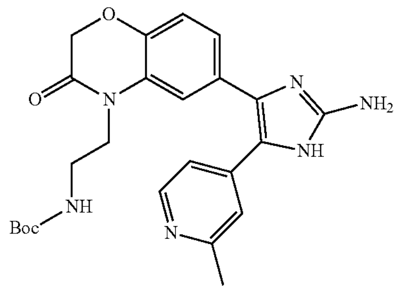 [SMILES: Cc1cc(-c2[nH]c(N)nc2-c2ccc3c(c2)N(CCNC(=O)OC(C)(C)C)C(=O)CO3)ccn1] | 23% | Purified by combiflash (4 g column), eluting with 0-10% MeOH in DCM followed by trituration with Et₂O MS (ESI+) for CHNOS m/z 465.13 [M + H]⁺ |
| 6-(2-Amino-4-(2-methylpyridin-4-yl)-1H-imidazol-5-yl)-4-(cyclopropylmethyl)-2H-benzo[b][1,4]oxazin-3(4H)-one | 67 | | 23% | Enriched up to 92% by combiflash (12 mg column), eluting with 0-10% MeOH in DCM followed by trituration with Et₂O MS (ESI+) for CHNOS m/z 376.21 [M + H]⁺; LC purity 96.9% (Ret. Time- 4.31 min); ¹H NMR (400 MHz, DMSO-d₆ + d-TFA): δ 8.64 (d, J = 6.5 Hz, 1H), 7.79 (s, 1H), 7.59 (d, J = 6.5 Hz, 1H), 7.45 (s, 1H), 7.11-7.20 (m, 2H), 4.75 (s, 2H), 3.79 (d, J = 6.8 Hz, 2H), 2.62 (s, 3H), 1.13 (bs, 1H), 0.37-0.42 (m, 2H), 0.29-0.33 (m, 2H) |
| 6-(2-Amino-4-(2-methylpyridin-4-yl)-1H-imidazol-5-yl)-4-isopropyl-2H-benzo[b][1,4]oxazin-3(4H)-one | 68 | 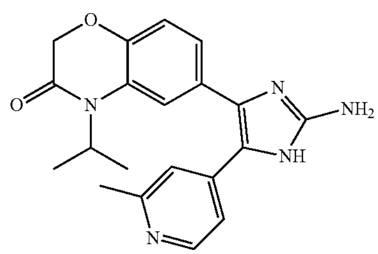 [SMILES: Cc1cc(-c2[nH]c(N)nc2-c2ccc3c(c2)N(C(C)C)C(=O)CO3)ccn1] | 22% | Enriched up to 70% by combiflash (12 g column), eluting with 0-10% MeOH in DCM followed by trituration with Et₂O MS (ESI+) for CHNOS m/z 364.20 [M + H]⁺; LC purity 98.9% (Ret. Time- 3.89 min); ¹H NMR (400 MHz, DMSO-d₆): δ 11.08 (bs, 1H), 8.24 (d, J = 5.2 Hz, 1H), 7.24 (bs, 2H), 7.05-7.18 (m, 2H), 7.01 (d, J = 8.2 Hz, 1H), 5.50 (bs, 2H), 4.55 (s, 2H), 4.46-4.53 (m, 1H), 2.36 (s, 3H), 1.36 (d, J = 6.9 Hz, 6H) |
| 6-(2-Amino-4-(2-methylpyridin-4-yl)-1H-imidazol-5-yl)-4-cyclopentyl-2H-benzo[b][1,4]oxazin-3(4H)-one | 69 | 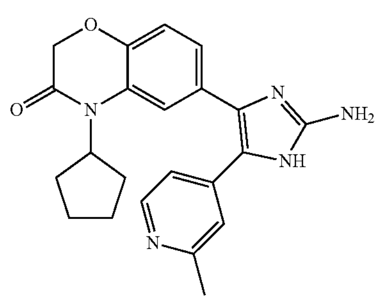 [SMILES: Cc1cc(-c2[nH]c(N)nc2-c2ccc3c(c2)N(C2CCCC2)C(=O)CO3)ccn1] | 39% | Purified by combiflash (4 g column), eluting with 0-10% MeOH in DCM followed by trituration with Et₂O MS (ESI+) for CHNOS m/z 390.27 [M + H]⁺; LC purity 93.6% (Ret. Time- 4.47 min); ¹H NMR (400 MHz, DMSO-d₆): δ 11.12 (bs, 1H), 8.25 (d, J = 5.2 Hz, 1H), 7.23 (s, 1H), 7.07-7.20 (m, 3H), 7.02 (d, J = 8.2 Hz, 1H), 5.51 (bs, 2H), 4.69-4.50 (m, 1H), 4.58 (s, 2H), 2.36 (s, 3H), 1.86-1.93 (m, 2H), 1.70-1.80 (m 2H), 1.59 (bs, , 2H), 1.39-1.50 (m, 2H) |

| Name | Ex | Structure | Yield | Spectral Data 1H NMR & LCMS |
|---|---|---|---|---|
| 6-(2-Amino-4-(2-methylpyridin-4-yl)-1H-imidazol-5-yl)-4-(2-(2-hydroxyethoxy)ethyl)-2H-benzo[b][1,4]oxazin-3(4H)-one | 70 | 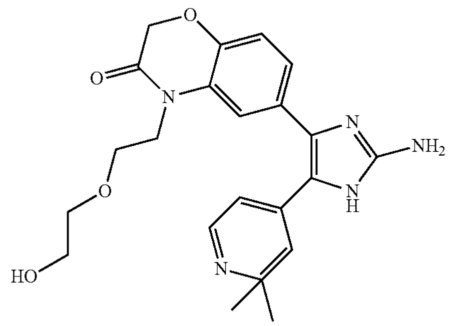 | 16% | Enriched up to 90% by combiflash (12 mg column), eluting with 0-10% MeOH in DCM followed by trituration with Et₂O<br>MS (ESI+) for CHNOS m/z 410.25 [M + H]⁺; LC purity 97.5% (Ret. Time- 4.72 min); ¹H NMR (400 MHz, DMSO-d₆ + d-TFA): δ 8.64 (d, J = 6.4 Hz, 1H), 7.79 (s, 1H), 7.58 (d, J = 5.2 Hz, 1H), 7.47 (s, 1H), 7.11-7.19 (m, 2H), 4.73 (s, 2H), 4.03 (t, J = 5.6 Hz, 2H), 3.57 (t, J = 5.6 Hz, 2H), 3.32-3.85 (m, 4H), 2.63 (s, 3H) |

Synthetic Route 2

4-(2-Amino-5-(2-methylpyridin-4-yl)-1H-imidazol-4-yl)benzene-1,2-diol (Example 71)

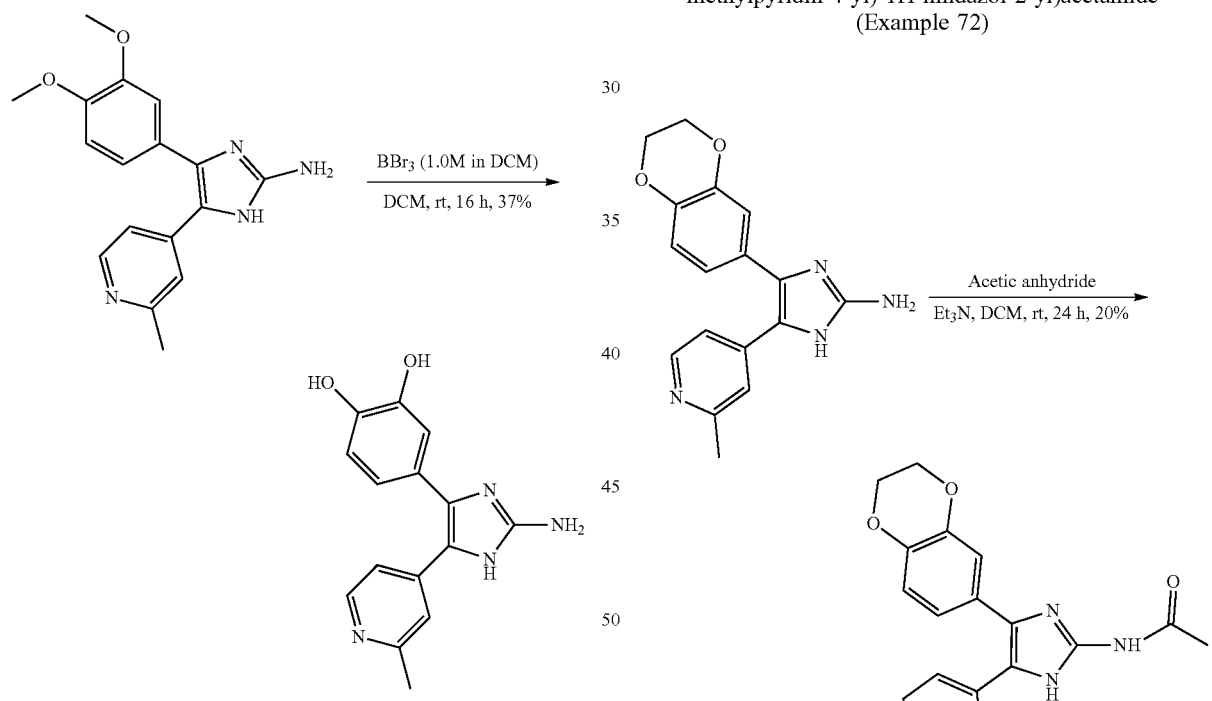

To a solution of 4-(3,4-dimethoxyphenyl)-5-(2-methylpyridin-4-yl)-1H-imidazol-2-amine (300 mg, 0.96 mmol) in DCM (20 mL) was added boron BBr₃ (1M in DCM, 3 mL, 0.29 mmol) slowly at 0° C. The reaction mixture was warmed to rt and further stirred for 16 h. The TLC showed the reaction to be complete. The reaction was quenched with MeOH and concentrated under reduced pressure. The crude residue was enriched by trituration with Et₂O (20 mL). The enriched residue was further purified by prep HPLC to afford 4-(2-Amino-5-(2-methylpyridin-4-yl)-1H-imidazol-4-yl)benzene-1,2-diol as a grey solid. Yield: 100 mg (37%); MS (ESI+) for CHNOS m/z 282.99 [M+H]⁺; LC purity 95.6%; ¹H NMR (400 MHz, DMSO-d₆+d-TFA): δ 8.60 (d, J=6.4 Hz, 1H), 7.77 (d, J=1.2 Hz, 1H), 7.56 (dd J=1.6, 6.4 Hz, 1H), 6.85-6.91 (m, 2H), 6.78 (dd, J=2.0, 8.1 Hz, 1H), 2.49 (s, 3H).

Synthetic Route 3

N-(4-(2,3-Dihydrobenzo[b][1,4]dioxin-6-yl)-5-(2-methylpyridin-4-yl)-1H-imidazol-2-yl)acetamide (Example 72)

To a solution of 4-(2,3-dihydrobenzo[b][1,4]dioxin-6-yl)-5-(2-methylpyridin-4-yl)-1H-imidazol-2-amine (300 mg, 0.97 mmol) in DCM (20 mL) were added triethylamine (197 mg, 1.95 mmol) and acetic anhydride (149 mg, 1.46 mmol) at rt. The reaction mixture was stirred at rt for 24 h. The TLC showed the reaction to be complete. The reaction mixture was diluted with water (25 mL) and extracted with DCM (3×20 mL). The organic layer was washed with brine (50 mL), dried (Na₂SO₄), filtered and concentrated under reduced pressure. The crude residue was purified by column chromatography using silica gel (100-200 mesh), eluting with 0-100% EtOAc in hexane to afford N-(4-(2,3-dihydrobenzo[b][1,4]dioxin-6-yl)-5-(2-methylpyridin-4-yl)-1H-imidazol-2-yl)acetamide as a yellow solid. Yield: 70 mg (20%); MS (ESI+) for CHNOS m/z 351.00 [M+H]$^+$; LC purity 96.2%; $^1$H NMR (400 MHz, DMSO-d$_6$): δ 11.71 (bs, 1H), 11.13 (bs, 1H), 8.22-8.38 (m, 1H), 7.27-7.37 (m, 1H), 7.10-7.20 (m, 1H), 6.77-6.98 (m, 3H), 4.24-4.28 (m, 4H), 2.42 (s, 3H), 2.09 (s, 3H).

Synthetic Route 4

4-(2,3-dihydrobenzo[b][1,4]dioxin-6-yl)-1-methyl-5-(2-methylpyridin-4-yl)-1H-imidazol-2-amine (Example 73)

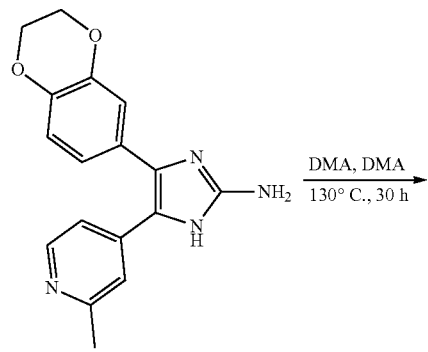

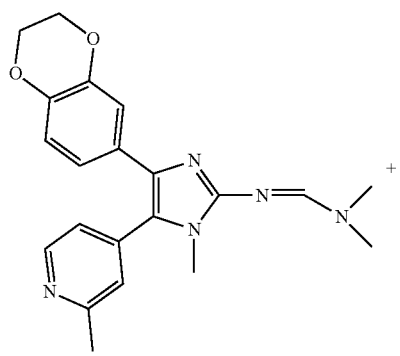

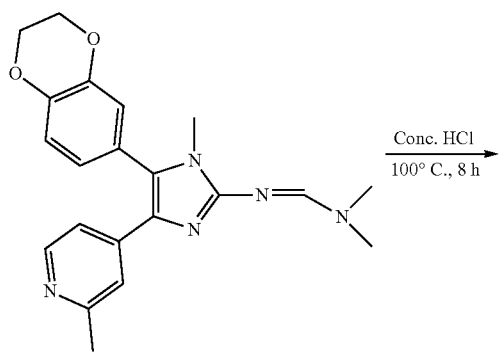

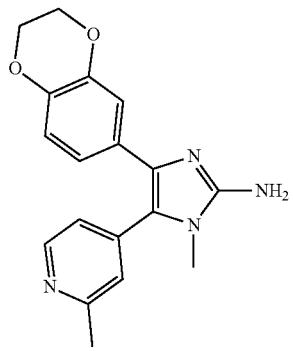

N'-(4-(2,3-dihydrobenzo[b][1,4]dioxin-6-yl)-1-methyl-5-(2-methyl pyridin-4-yl)-1H-imidazol-2-yl)-N,N-dimethylformimidamide and N'-(5-(2,3-dihydrobenzo[b][1,4]dioxin-6-yl)-1-methyl-4-(2-methylpyridin-4-yl)-1H-imidazol-2-yl)-N,N-dimethylformimidamide A solution 4-(2,3-dihydrobenzo[b][1,4]dioxin-6-yl)-5-(2-methylpyridin-4-yl)-1H-imidazol-2-amine (700 mg, 0.22 mmol) in DMF-DMA (3 mL) was stirred at 130° C. for 30 h. The TLC showed the reaction to be complete. The reaction mixture was concentrated under reduced pressure to afford mixture of N'-(4-(2,3-dihydrobenzo[b][1,4]dioxin-6-yl)-1-methyl-5-(2-methylpyridin-4-yl)-1H-imidazol-2-yl)-N,N-dimethylformimidamide and N'-(5-(2,3-dihydrobenzo[b][1,4]dioxin-6-yl)-1-methyl-4-(2-methylpyridin-4-yl)-1H-imidazol-2-yl)-N,N-dimethylformimidamide as a brown solid. Yield: 840 mg (crude). MS (ESI+) for CHNOS m/z 253.17 [M+H]$^+$. The crude product was used in the next step without further purification.

4-(2,3-dihydrobenzo[b][1,4]dioxin-6-yl)-1-methyl-5-(2-methylpyridin-4-yl)-1H-imidazol-2-amine A crude mixture of N'-(4-(2,3-dihydrobenzo[b][1,4]dioxin-6-yl)-1-methyl-5-(2-methylpyridin-4-yl)-1H-imidazol-2-yl)-N,N-dimethylformimidamide and N'-(5-(2,3-dihydrobenzo[b][1,4]dioxin-6-yl)-1-methyl-4-(2-methylpyridin-4-yl)-1H-imidazol-2-yl)-N,N-dimethylformimidamide (68 mg, 0.18 mmol) was added to concentrated hydrochloride solution (2 mL) and stirred at 100° C. for 8 h. The TLC showed the reaction to be complete. The reaction mixture was concentrated under reduced pressure to afford a mixture of two regioisomers. Both regioisomers were isolated by prep HPLC to afford 4-(2,3-dihydrobenzo[b][1,4]dioxin-6-yl)-1-methyl-5-(2-methylpyridin-4-yl)-1H-imidazol-2-amine as a yellow solid, yield=5 mg; MS (ESI+) for CHNOS m/z 323.06 [M+H]$^+$; LC purity 97%; $^1$H NMR (400 MHz, DMSO-d$_6$): δ 8.10 (d, J=5.2 Hz, 1H), 7.21 (s, 1H), 6.98 (d, J=8.2 Hz, 1H), 6.92 (d, J=4.9 Hz, 1H), 6.84 (d, J=1.6 Hz, 1H), 6.78 (dd, J=1.6, 8.2 Hz, 1H), 5.66 (bs, 2H), 4.28-4.31 (m, 4H), 3.10 (s, 3H), 2.31 (s, 3H).

Synthetic Route 5

4-(2,3-Di hydrobenzo[b][1,4]dioxin-6-yl)-N-methyl-5-(2-methylpyridin-4-yl)-1H-imidazol-2-amine (Example 74) & 4-(2,3-Dihydrobenzo[b][1,4]dioxin-6-yl)-N,N-dimethyl-5-(2-methylpyridin-4-yl)-1H-imidazol-2-amine (Example 75)

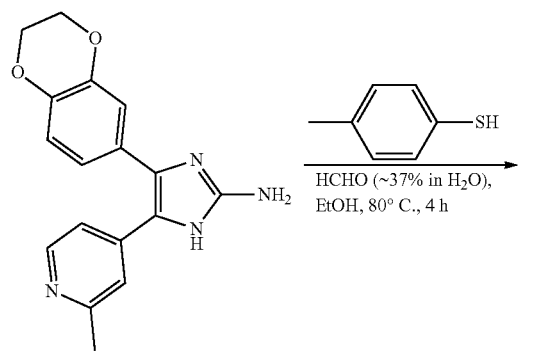

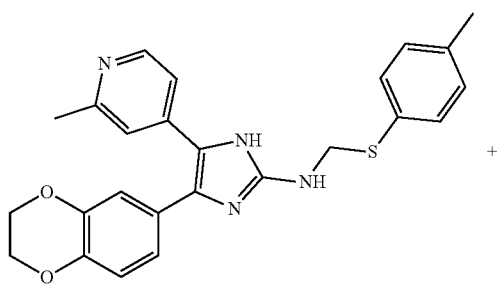

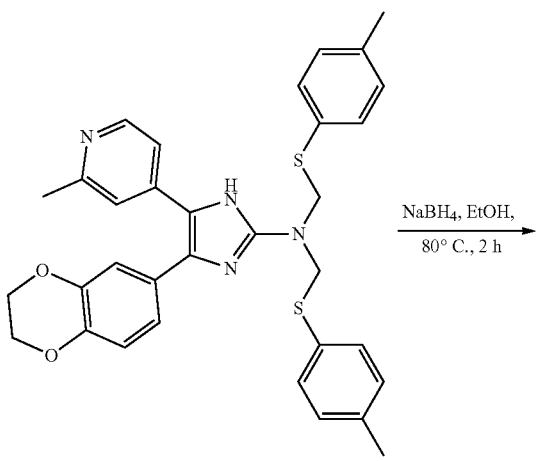

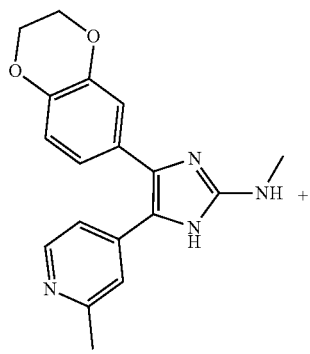

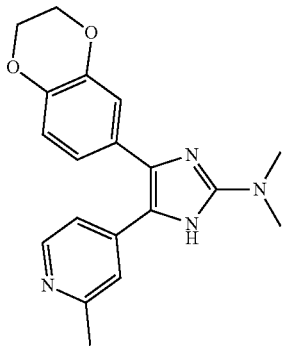

4-(2,3-Dihydrobenzo[b][1,4]dioxin-6-yl)-5-(2-methylpyridin-4-yl)-N-((p-tolylthio)methyl)-1H-imidazol-2-amine & 4-(2,3-Dihydrobenzo[b][1,4]dioxin-6-yl)-5-(2-methylpyridin-4-yl)-N,N-bis(p-tolylthio)methyl-1H-imidazol-2-amine To a solution of 4-(2,3-dihydrobenzo[b][1,4]dioxin-6-yl)-5-(2-methylpyridin-4-yl)-1H-imidazol-2-amine (600 mg, 1.94 mmol), 4-methylbenzenethiol (484 mg, 3.89 mmol) in EtOH (20 mL) was added formaldehyde (37% in H$_2$O, 0.6 mL) at rt. The reaction mixture was stirred at 90° C. for 4 h. The TLC showed reaction to be complete. The solvent was concentrated under reduced pressure. The residue was diluted with H$_2$O (20 mL) and extracted with EtOAc (3×20 mL). The organics were dried (Na$_2$SO$_4$), filtered and concentrated under reduced pressure to give ~1:1 mixture of two compounds as a brown waxy solid which was used in the next step without further purification. Yield: 1.3 g (crude mixture).

4-(2,3-Dihydrobenzo[b][1,4]dioxin-6-yl)-5-(2-methylpyridin-4-yl)-N-((p-tolylthio)methyl)-1H-imidazol-2-amine MS (ESI+) for CHNOS m/z 445.03 [M+H]$^+$ (20% by crude LCMS).

4-(2,3-Di hydrobenzo[b][1,4]dioxin-6-yl)-5-(2-methylpyridin-4-yl)-N,N-bis((p-tolylthio)methyl)-1H-imidazol-2-amine MS (ESI+) for CHNOS m/z 581.04 [M+H]$^+$ (18% by crude LCMS).

4-(2,3-Di hydrobenzo[b][1,4]dioxin-6-yl)-N-methyl-5-(2-methylpyridin-4-yl)-1H-imidazol-2-amine & 4-(2,3-Di hydrobenzo[b][1,4]dioxin-6-yl)-N,N-dimethyl-5-(2-methylpyridin-4-yl)-1H-imidazol-2-amine To a crude mixture of 4-(2,3-dihydrobenzo[b][1,4]dioxin-6-yl)-5-(2-methylpyridin-4-yl)-N-((p-tolylthio)methyl)-1H-imidazol-2-amine & 4-(2,3-dihydrobenzo[b][1,4]dioxin-6-yl)-5-(2-methylpyridin-4-yl)-N,N-bis((p-tolylthio)methyl)-1H-imidazol-2-amine (1.2 g) in EtOH (50 mL) was added NaBH₄ (770 mg, 20.3 mmol) at rt. The reaction mixture was stirred at 80° C. for 2 h. The TLC showed reaction to be complete. The solvent was evaporated under reduced pressure. The residue was diluted with ice-water (30 mL), stirred for 15 min and extracted with EtOAc (3×30 mL). The organics were dried (Na₂SO₄), filtered and concentrated under reduced pressure. The crude residue was purified by prep HPLC.

4-(2,3-dihydrobenzo[b][1,4]dioxin-6-yl)-N-methyl-5-(2-methylpyridin-4-yl)-1H-imidazol-2-amine yellow solid. Yield: 35 mg (4%). MS (ESI+) for CHNOS m/z 323.18 [M+H]⁺; LC purity 99.7% (Ret. Time—4.11 min); 1H NMR (400 MHz, DMSO-d₆+d-TFA): δ 8.60 (d, J=6.5 Hz, 1H), 7.80 (s, 1H), 7.58 (d, J=6.5 Hz, 1H), 7.04 (d, J=1.4 Hz, 1H), 6.90-7.01 (m, 2H), 4.27 (bs, 4H), 2.97 (s, 3H), 2.61 (s, 3H).

4-(2,3-Di hydrobenzo[b][1,4]dioxin-6-yl)-N,N-dimethyl-5-(2-methylpyridin-4-yl)-1H-imidazol-2-amine Yellow solid. Yield: 70 mg (8%). MS (ESI+) for CHNOS m/z 337.22 [M+H]⁺; LC purity 93.7% (Ret. Time—4.22 min); 1H NMR (400 MHz, DMSO-d₆+d-TFA): δ 8.65 (d, J=6.5 Hz, 1H), 7.87 (s, 1H), 7.60 (d, J=5.7 Hz, 1H), 7.05 (d, J=1.5 Hz, 1H), 6.89-7.01 (m, 2H), 4.28 (bs, 4H), 3.18 (s, 6H), 2.62 (s, 3H).

The following intermediates were prepared in a similar manner to 4-(2,3-dihydrobenzo[b][1,4]dioxin-6-yl)-5-(2-methylpyridin-4-yl)-N-((p-tolylthio)methyl)-1H-imidazol-2-amine & 4-(2,3-dihydrobenzo[b][1,4]dioxin-6-yl)-5-(2-methylpyridin-4-yl)-N,N-bis((p-tolylthio)methyl)-1H-imidazol-2-amine.

| Name | Int | Structure | Yield | Spectral Data 1H NMR & LCMS |
|---|---|---|---|---|
| 1-(6-(5-(2-Methylpyridin-4-yl)-2-(((p-tolylthio)methyl)amino)-1H-imidazol-4-yl)-2,3-dihydro-4H-benzo[b][1,4]oxazin-4-yl)ethan-1-one & 1-(6-(2-(bis((p-Tolylthio)methyl)amino)-5-(2-methylpyridin-4-yl)-1H-imidazol-4-yl)-2,3-dihydro-4H-benzo[b][1,4]oxazin-4-yl)ethan-1-one | 133 & 134 | 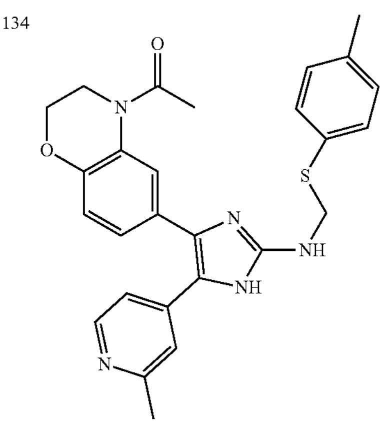 | Crude ~1:1 mixture | MS (ESI+) for CHNOS m/z 486.12[M + H]⁺  +  MS (ESI+) for CHNOS m/z 622.23 [M + H]⁺. |

The following compounds were prepared in a similar manner to 4-(2,3-dihydrobenzo[b][1,4]dioxin-6-yl)-N-methyl-5-(2-methylpyridin-4-yl)-1H-imidazol-2-amine & 4-(2,3-Dihydrobenzo[b][1,4]dioxin-6-yl)-N,N-dimethyl-5-(2-methylpyridin-4-yl)-1H-imidazol-2-amine.

| Name | Ex | Structure | Yield | Spectral Data 1H NMR & LCMS |
|---|---|---|---|---|
| 1-(6-(5-(2-Methylpyridin-4-yl)-2-(((p-tolylthio)methyl)amino)-1H-imidazol-4-yl)-2,3-dihydro-4H-benzo[b][1,4]oxazin-4-yl)ethan-1-one & 1-(6-(2-(bis((p-Tolylthio)methyl)amino)-5-(2-methylpyridin-4-yl)-1H-imidazol-4-yl)-2,3-dihydro-4H-benzo[b][1,4]oxazin-4-yl)ethan-1-one | 76 & 77 | 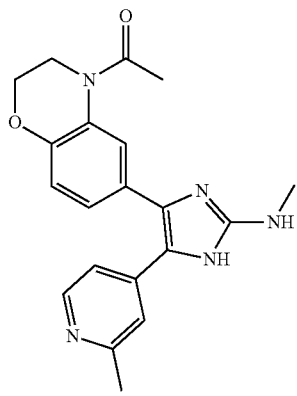 + | Crude ~1:1 mixture | MS (ESI−) for CHNOS m/z 362.17 [M − H]+; |
| | | 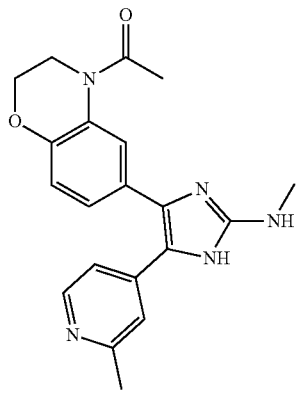 + | | MS (ESI+) for CHNOS m/z 378.20 [M + H]+ |

Synthetic Route 6

4-(3,4-Dihydro-2H-benzo[b][1,4]oxazin-6-yl)-N-methyl-5-(2-methylpyridin-4-yl)-1H-imidazol-2-amine (Example 78) & 4-(3,4-Dihydro-2H-benzo[b][1,4]oxazin-6-yl)-N,N-dimethyl-5-(2-methylpyridin-4-yl)-1H-imidazol-2-amine (Example 79)

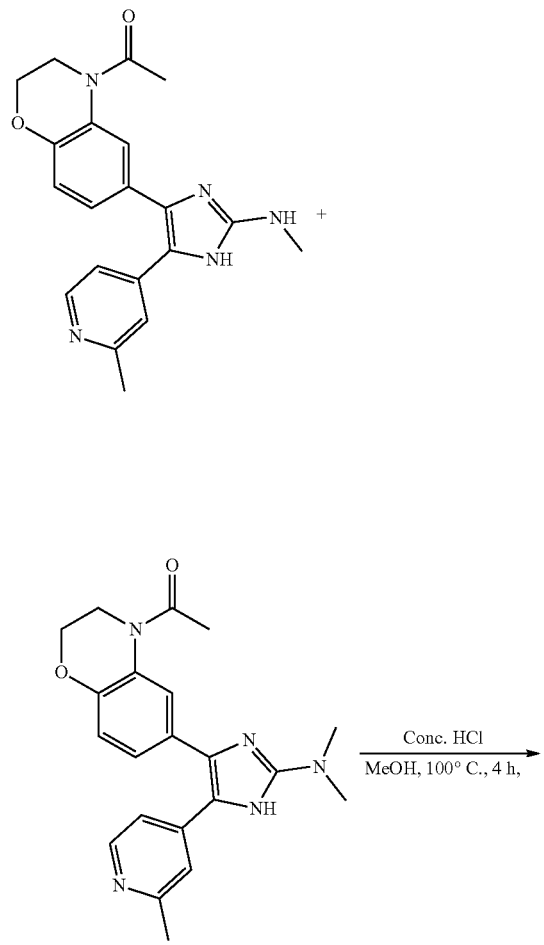

Conc. HCl
MeOH, 100° C., 4 h,

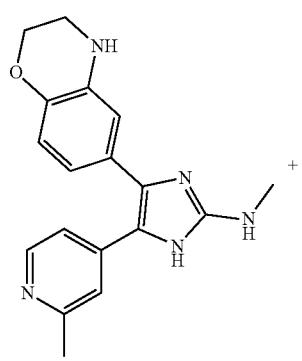

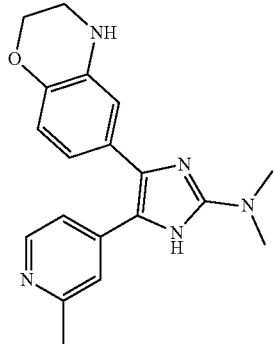

To a solution of 1-(6-(2-(methylamino)-5-(2-methylpyridin-4-yl)-1H-imidazol-4-yl)-2,3-dihydro-4H-benzo[b][1,4]oxazin-4-yl)ethan-1-one and 1-(6-(2-(dimethylamino)-5-(2-methylpyridin-4-yl)-1H-imidazol-4-yl)-2,3-dihydro-4H-benzo[b][1,4]oxazin-4-yl)ethan-1-one (500 mg, 1.34 mmol) in MeOH (15 mL) was added conc. HCl (5.0 mL) at rt. The reaction mixture was stirred at 100° C. for 4 h. The TLC showed reaction to be complete. The reaction mixture was allowed to cool to rt, neutralized with saturated aq NaHCO$_3$ solution and extracted with 10% MeOH in DCM (3×10 mL). The organics were washed with brine (20 mL), dried (Na$_2$SO$_4$), filtered and concentrated under reduced pressure. The crude residue was purified by column chromatography using silica gel (100-200 mesh), eluting with 0-10% MeOH in DCM followed by trituration with Et$_2$O and drying under vacuum to afford 4-(3,4-dihydro-2H-benzo[b][1,4]oxazin-6-yl)-N-methyl-5-(2-methylpyridin-4-yl)-1H-imidazol-2-amine & 4-(3,4-dihydro-2H-benzo[b][1,4]oxazin-6-yl)-N,N-dimethyl-5-(2-methylpyridin-4-yl)-1H-imidazol-2-amine.

4-(3,4-dihydro-2H-benzo[b][1,4]oxazin-6-yl)-N-methyl-5-(2-methylpyridin-4-yl)-1H-imidazol-2-amine Yellow solid. Yield: 40 mg (15%). MS (ESI+) for CHNOS m/z 322.06 [M+H]$^+$; LC purity 92.8% (Ret. Time—3.81 min); 1H NMR (400 MHz, DMSO-d$_6$): δ 11.44 (bs, 1H), 8.20 (d, J=5.3 Hz, 1H), 7.33 (s, 1H), 7.14 (d, J=5.2 Hz, 1H), 6.59-6.72 (m, 2H), 6.51 (d, J=8.1 Hz, 1H), 5.97 (bs, 1H), 5.86 (bs, 1H), 4.14 (bs, 2H), 3.26 (bs, 2H), 2.80 (d, J=4.9 Hz, 3H), 2.37 (s, 3H).

4-(3,4-Dihydro-2H-benzo[b][1,4]oxazin-6-yl)-N,N-dimethyl-5-(2-methylpyridin-4-yl)-1H-imidazol-2-amine Yellow solid. Yield: 30 mg (17%). MS (ESI+) for CHNOS m/z 336.06 [M+H]$^+$; LC purity 96.2% (Ret. Time—4.14 min); 1H NMR (400 MHz, DMSO-d$_6$): δ 11.19 (bs, 1H), 8.18 (d, J=5.1 Hz, 1H), 7.35 (s, 1H), 7.14 (d, J=5.0 Hz, 1H), 6.59-6.74 (m, 2H), 6.50 (d, J=8.1 Hz, 1H), 5.85 (bs, 1H), 4.14 (bs, 2H), 3.26 (bs, 2H), 2.93 (s, 6H), 2.37 (s, 3H).

Synthetic Route 7

4-(2,3-Di hydrobenzo[b][1,4]dioxin-6-yl)-5-(2-methylpyridin-4-yl)thiazol-2-amine (Example 80)

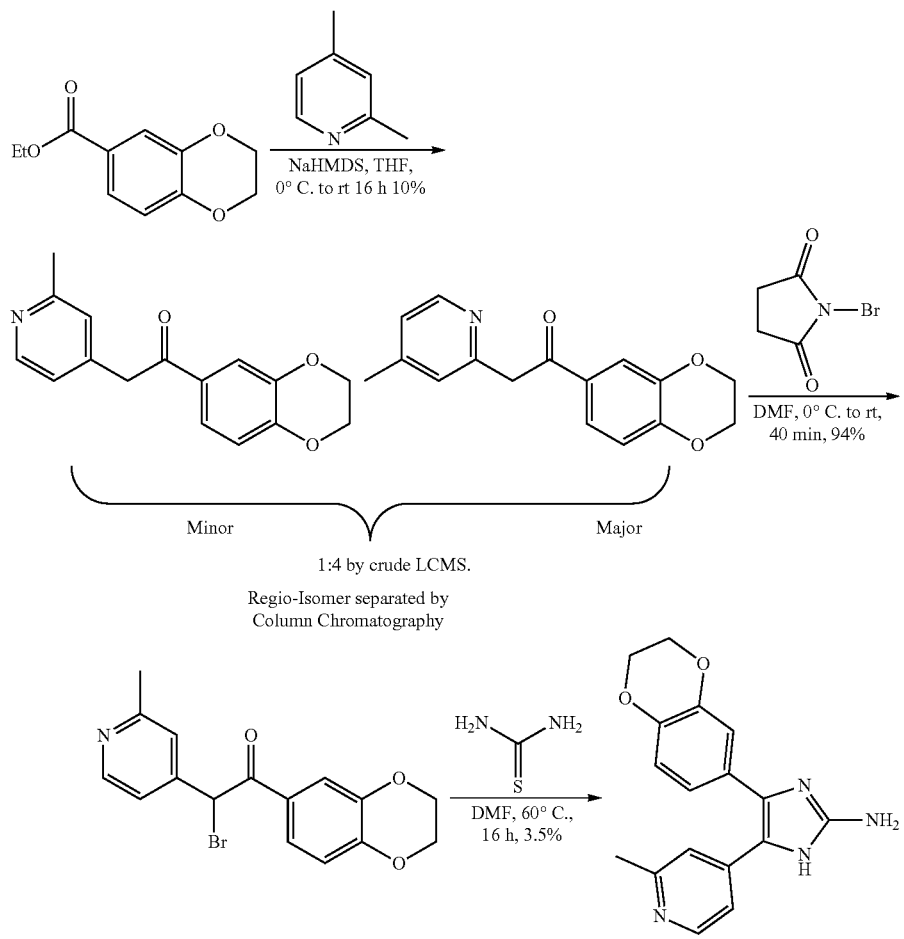

1:4 by crude LCMS.
Regio-Isomer separated by Column Chromatography

1-(2,3-Di hydrobenzo[b][1,4]dioxin-6-yl)-2-(4-methylpyridin-2-yl)ethan-1-one To a solution of 2,4-dimethylpyridine (1.7 g, 15.85 mmol) in THF (10 mL) was added NaHMDS (1M in THF, 36 mL, 36.2 mmol) at rt slowly. The reaction mixture was stirred at rt for 1 h and ethyl 2,3-dihydrobenzo[b][1,4]dioxine-6-carboxylate (3 g, 14.41 mmol) was added to it slowly at rt. The reaction mixture was further stirred at rt for 2 h. The TLC showed the reaction to be complete. The reaction mixture was poured into aq NH$_4$Cl (50 mL) and extracted with EtOAc (3×50 mL). The organics were dried (Na$_2$SO$_4$), filtered and concentrated under reduced pressure. The crude LCMS showed formation of two regioisomers as minor and major in 1:4 ratio. The crude residue was purified by column chromatography using silica gel (100-200 mesh), eluting with 0-50% EtOAc in hexane to isolate the both regioisomers.

1-(2,3-Di hydrobenzo[b][1,4]dioxin-6-yl)-2-(2-methylpyridin-4-yl)ethan-1-one Yellow solid. 400 mg (18%); MS (ESI+) for CHNOS m/z 270.20 [M]$^+$; LC purity 81.6%; $^1$H NMR (400 MHz, DMSO-d$_6$) δ 8.34 (d, J=5.0 Hz, 1H), 7.56 (dd, J=2.0, 8.4 Hz, 1H), 7.52 (d, J=2.0 Hz, 1H), 7.11 (s, 1H), 7.05 (d, J=4.9 Hz, 1H), 6.99 (d, J=8.4 Hz, 1H), 4.27-4.35 (m, 6H), 2.42 (s, 3H). The exact structure was further established by nOe experiment.

1-(2,3-Di hydrobenzo[b][1,4]dioxin-6-yl)-2-(4-methylpyridin-2-yl)ethan-1-one Yellow solid. Yield: 1.4 g (63%). MS (ESI+) for CHNOS m/z 270.20 [M]$^+$

2-Bromo-1-(2,3-dihydrobenzo[b][1,4]dioxin-6-yl)-2-(2-methylpyridin-4-yl)ethan-1-one To a solution of 1-(2,3-dihydrobenzo[b][1,4]dioxin-6-yl)-2-(2-methylpyridin-4-yl)ethan-1-one (400 mg, 51.5 mmol) in DMF (20 mL) was added NBS (278 mg, 1.56 mmol) at rt. The reaction mixture was stirred at rt for 40 min. The TLC showed the reaction to be complete. The reaction mixture was diluted with water (20 mL) and extracted with DCM (3×20 mL). The combined organic layers were dried (Na$_2$SO$_4$), filtered and concentrated under reduced pressure. The crude residue was triturated with diethyl ether to afford 2-Bromo-1-(2,3-dihydrobenzo[b][1,4]dioxin-6-yl)-2-(2-methylpyridin-4-yl)ethan-1-one as a yellow solid. Yield: 605 mg (95%); (MS (ESI+) for CHNOS m/z 347.98 [M+H]$^+$

4-(2,3-Di hydrobenzo[b][1,4]dioxin-6-yl)-5-(2-methylpyridin-4-yl)thiazol-2-amine To a solution of 2-bromo-1-(2,3-dihydrobenzo[b][1,4]dioxin-6-yl)-2-(2-methylpyridin-4-yl)ethan-1-one (500 mg, 1.44 mmol) in DMF (20 mL) was added thiourea (131 mg, 1.72 mmol) at rt. The reaction mixture was stirred at 60° C. for 16 h. The TLC showed the reaction to be complete. The reaction mixture was diluted with water (20 mL) and extracted with DCM (3×20 mL). The organic layer was washed with brine (50 mL), dried (Na$_2$SO$_4$), filtered and concentrated under reduced pressure. The crude residue was purified by column chromatography using silica gel (100-200 mesh), eluting with 0-50% EtOAc in hexane to afford 4-(2,3-dihydrobenzo[b][1,4]dioxin-6-yl)-5-(2-methylpyridin-4-yl)thiazol-2-amine as a yellow solid. Yield: 16 mg (3.5%); CHNOS m/z 325.93 [M+H]$^+$; LC purity 89.8%; $^1$H NMR (400 MHz, DMSO-d$_6$): δ 8.24 (d, J=5.2 Hz, 1H), 7.33 (s, 2H), 7.02 (s, 1H), 6.88 (bs, 2H), 6.76-6.84 (m, 2H), 4.22-4.24 (m, 4H), 2.37 (s, 3H). The exact structure was confirmed by nOe experiment.

Synthetic Route 8

4-(2,3-Di hydrobenzo[b][1,4]dioxin-6-yl)-5-(2-methylpyridin-4-yl)-1,3-dihydro-2H-imidazole-2-thione (Example 81)

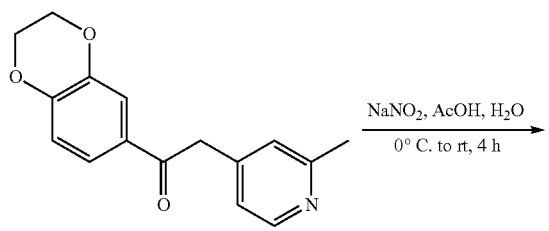

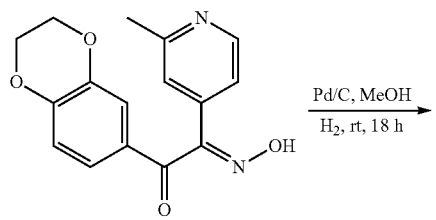

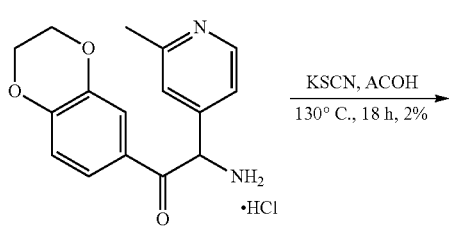

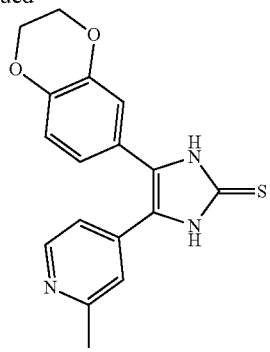

(E)-3-(dimethylamino)-1-(4-(4-fluorophenoxy)phenyl)-2-(pyridin-3-yl)prop-2-en-1-one To a solution of 1-(2,3-dihydrobenzo[b][1,4]dioxin-6-yl)-2-(2-methylpyridin-4-yl)ethan-1-one (2 g, 7.4 mmol) in glacial acetic acid (15 mL) was added a solution of NaNO$_2$ (1.6 g, 22.2 mmol) in H$_2$O (15 mL) drop wise at 0° C. The reaction mixture was stirred at rt for 4 h. The TLC showed the reaction to be complete. The reaction mixture was diluted with water (25 mL), extracted with EtOAc (3×25 mL). The organics were dried (Na$_2$SO$_4$), filtered and concentrated under reduced pressure. The crude residue was purified by column chromatography using silica gel (100-200 mesh), eluting with hexane to 40% EtOAc in hexane to afford (E)-1-(2,3-dihydrobenzo[b][1,4]dioxin-6-yl)-2-(hydroxyimino)-2-(2-methylpyridin-4-yl)ethan-1-one as a yellow solid. Yield: 560 mg (60% by LCMS). MS (ESI+) for CHNOS m/z 299.05 [M+H]$^+$. The compound was used in the next step without purification.

2-Amino-1-(2,3-dihydrobenzo[b][1,4]dioxin-6-yl)-2-(2-methylpyridin-4-yl)ethan-1-one.HCl To a solution of (E)-1-(2,3-dihydrobenzo[b][1,4]dioxin-6-yl)-2-(hydroxyimino)-2-(2-methylpyridin-4-yl)ethan-1-one (225 mg, 0.76 mmol) in IPA (100 mL) were added 6N HCl in IPA (3 mL) Pd/C (200 mg) at rt. The reaction mixture was stirred at rt under H$_2$ balloon pressure for 18 h. The TLC showed the reaction to be complete. The reaction mixture was filtered through celite bed. The celite bed was further washed with IPA (25 mL) and concentrated under reduced pressure to give 2-amino-1-(2,3-dihydrobenzo[b][1,4]dioxin-6-yl)-2-(2-methylpyridin-4-yl)ethan-1-one. HCl as a yellow solid. Yield: 300 mg (crude). MS (ESI+) for CHNOS m/z 285.0 [M+H]$^+$.

4-(2,3-Di hydrobenzo[b][1,4]dioxin-6-yl)-5-(2-methylpyridin-4-yl)-1,3-dihydro-2H-imidazole-2-thione To a solution of 2-amino-1-(2,3-dihydrobenzo[b][1,4]dioxin-6-yl)-2-(2-methylpyridin-4-yl)ethan-1-one HCl (300 mg, 1.06 mmol) in glacial acetic acid (5 mL) was added potassium thiocyanate (308 mg, 3.16 mmol) at rt. The reaction mixture was stirred at 130° C. for 18 h. The TLC showed the reaction to be complete. The reaction mixture was diluted with water (25 mL) and extracted with EtOAC (3×25 mL). The organics were dried (Na$_2$SO$_4$), filtered and concentrated under reduced pressure. The crude residue was purified by prep HPLC to afford 4-(2,3-dihydrobenzo[b][1, 4]dioxin-6-yl)-5-(2-methylpyridin-4-yl)-1,3-dihydro-2H-imidazole-2-thione as an off white solid. Yield: 8 mg (2%). $^1$H NMR (400 MHz, DMSO): δ 12.56 (bs, 2H), 8.33 (d, J=5.2 Hz, 1H), 7.26 (s, 1H), 7.06 (d, J=4.4 Hz, 1H), 6.80-6.92 (m, 3H), 4.27 (bs, 4H), 2.39 (s, 3H); MS (ESI+) for CHNOS m/z 325.93 [M+H]$^+$ Synthetic Route 9

4-(2,3-Di hydrobenzo[b][1,4]dioxin-6-yl)-5-(2-methylpyridin-4-yl)-1,3-dihydro-2H-imidazol-2-one (Example 82)

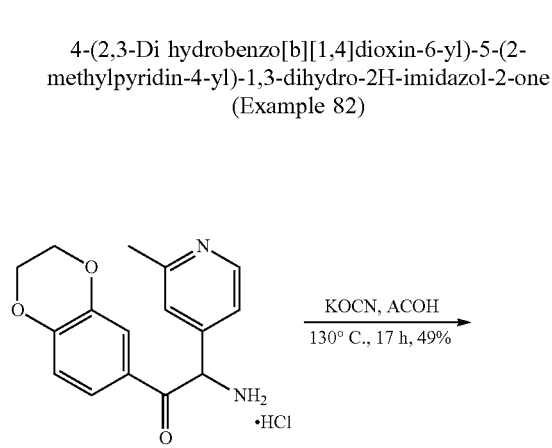

Synthetic Route 10

4-(2-Chloro-4-(2,3-dihydrobenzo[b][1,4]dioxin-6-yl)-1H-imidazol-5-yl)-2-methylpyridine (Example 83)

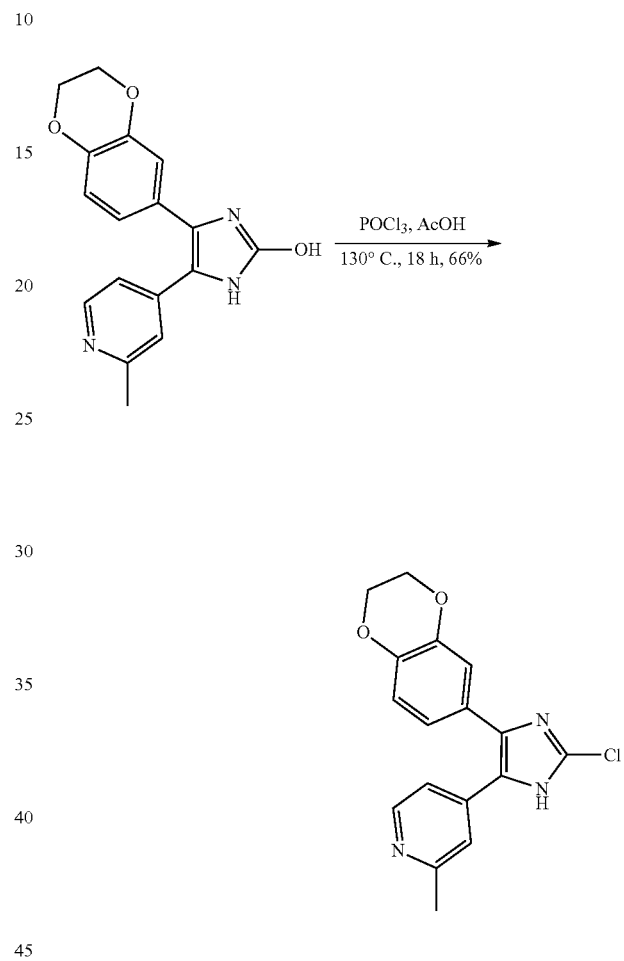

To a solution of 2-amino-1-(2,3-dihydrobenzo[b][1,4]dioxin-6-yl)-2-(2-methylpyridin-4-yl)ethan-1-one.HCl (600 mg, 37% by LCMS, 2.11 mmol) in glacial acetic acid (5 mL) was added potassium cyanate (514 mg, 6.33 mmol) at rt. The reaction mixture was stirred at 130° C. for 17 h. The TLC showed the reaction to be complete. The reaction mixture was diluted with water (25 mL) and extracted with EtOAC (3×25 mL). The organics were dried (Na$_2$SO$_4$), filtered and concentrated under reduced pressure. The crude residue was purified by column chromatography using silica gel (100-200 mesh), eluting with 0-5% MeOH in DCM to afford 4-(2,3-Dihydrobenzo[b][1,4]dioxin-6-yl)-5-(2-methylpyridin-4-yl)-1,3-dihydro-2H-imidazol-2-one as a yellow solid. Yield: 120 mg (49%). MS (ESI+) for CHNOS m/z 309.96 [M+1]$^+$; LC purity 98.9%; $^1$H NMR (400 MHz, DMSO-d$_6$): δ 10.56 (bs, 2H), 8.26 (d, J=5.2 Hz, 1H), 7.16 (s, 1H), 7.01 (d, J=5.0 Hz, 1H), 6.79-7.01 (m, 3H), 4.26 (s, 4H), 2.36 (s, 3H).

A solution of 4-(2,3-dihydrobenzo[b][1,4]dioxin-6-yl)-5-(2-methylpyridin-4-yl)-1H-imidazol-2-ol (300 mg, 0.970 mmol) in POCl$_3$ (5.0 mL) was stirred at 130° C. for 18 h. The TLC showed reaction to be complete. The solvent was evaporated under reduced pressure. The residue was basified to pH 8 using saturated aq NaHCO$_3$ solution (20 mL) and extracted with EtOAC (3×20 mL). The organics were washed with brine (50 mL), dried (Na$_2$SO$_4$), filtered and concentrated under reduced pressure. The crude residue was purified by column chromatography using silica gel (100-200 mesh), eluting with 0-10% MeOH in DCM to give 4-(2-chloro-4-(2,3-dihydrobenzo[b][1,4]dioxin-6-yl)-1H-imidazol-5-yl)-2-methylpyridine as an off white solid. Yield: 210 mg (66%). MS (ESI+) for CHNOS m/z 328.13 [M+H]$^+$; LC purity 99.2% (Ret. Time—4.77 min); 1H NMR (400 MHz, DMSO-d$_6$ at 353.2 K): δ 12.98 (bs, 1H), 8.30 (bs, 1H), 7.34 (s, 1H), 7.15 (d, J=5.1 Hz, 1H), 6.83-6.98 (m, 3H), 4.28 (s, 4H), 2.41 (s, 3H).

Synthetic Route 11

4-(4-(2,3-Dihydrobenzo[b][1,4]dioxin-6-yl)-2-methyl-1H-imidazol-5-yl)-2-methylpyridine (Example 84)

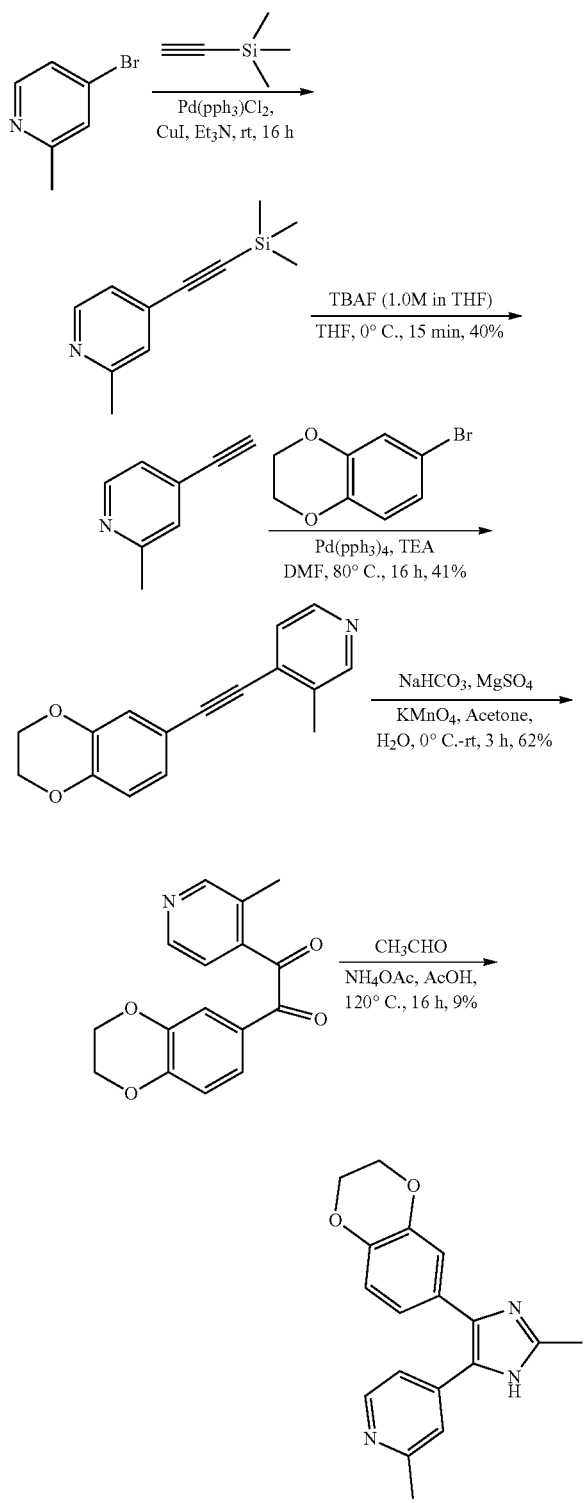

2-Methyl-4-((trimethylsilyl)ethynyl)pyridine

To a solution of 4-bromo-2-methylpyridine (5 g, 29.2 mmol) in trimethylamine (41 mL, 29.2 mmol) were added TMS-acetylene (6.2 mL, 43.8 mmol) and Pd (PPh$_3$)Cl$_2$ under N$_2$ atmosphere at rt. The reaction mixture was stirred at rt for 16 h. The TLC showed the reaction to be complete. The reaction mixture was passed through a celite bed which was washed with EtOAc (150 mL). The filtrate was washed with ice-cold water (2×200 mL). The organic layer was washed with brine (100 mL), dried (Na$_2$SO$_4$), filtered and concentrated under reduced pressure to afford 2-methyl-4-((trimethylsilyl)ethynyl)pyridine as a black liquid. Yield: 6.01 g (crude); MS (ESI+) for CHNOS m/z 190.11 [M+H]$^+$. The crude product was used in the next step without further purification.

4-Ethynyl-2-methylpyridine

To a solution of crude 2-methyl-4-((trimethylsilyl)ethynyl)pyridine (6.0 g, 31.7 mmol) in THF (50 mL) was added TBAF (1M in THF, 35 mL, 34.4 mmol) at 0° C. slowly. The reaction mixture was stirred at 0° C. for 15 min. The TLC showed the reaction to be complete. The reaction mixture was quenched with brine solution (50 mL) and extracted with EtOAc (3×50 mL). The organic layer was dried (Na$_2$SO$_4$), filtered and concentrated under reduced pressure. The crude residue was purified by column chromatography using silica gel (100-200 mesh), eluting with 10% EtOAc in hexane. The solvent was removed at 35° C. under reduced pressure to afford 4-ethynyl-2-methylpyridine as a yellow semi solid. Yield: 1.51 g (40%); MS (ESI+) for CHNOS m/z 117.98 [M+H]$^+$. $^1$H NMR (400 MHz, DMSO-d$_6$): δ 8.45 (d, J=5.0 Hz, 1H), 7.33 (s, 1H), 7.24 (d, J=5.0 Hz, 1H), 4.55 (s, 1H), 2.46 (s, 3H).

4-((2,3-Di hydrobenzo[b][1,4]dioxin-6-yl)ethynyl)-3-methylpyridine

To a solution of 4-ethynyl-2-methylpyridine (1 g, 8.5 mmol) in DMF were added 6-bromo-2,3-dihydrobenzo[b][1,4]dioxine (1.82 g, 8.5 mmol) and triethylamine (7.2 mL, 51.2 mmol) at rt. The reaction mixture was purged with N$_2$ gas for 10 min and Pd(PPh$_3$)$_4$ was added to it. The reaction mixture was again purged with N$_2$ gas for 5 min. The reaction vessel was sealed and stirred at 80° C. for 16 h. The TLC showed the reaction to be complete. The reaction mixture was diluted with ice-cold water (50 mL) and extracted with EtOAc (3×25 mL). The organic layer was dried (Na$_2$SO$_4$), filtered and concentrated under reduced pressure. The crude residue was purified by column chromatography using silica gel (100-200 mesh), eluting with 22% EtOAc in hexane to afford 4-((2,3-dihydrobenzo[b][1,4]dioxin-6-yl)ethynyl)-3-methylpyridine as a yellow solid. Yield: 880 mg (41%); MS (ESI$^+$) for CHNOS m/z 252.09 [M+H]$^+$. $^1$H NMR (400 MHz, DMSO-d$_6$): δ 8.45 (d, J=4.9 Hz, 1H), 7.23-7.53 (m, 2H), 7.05-7.10 (m, 2H), 6.92 d, J=8.2 Hz, 1H), 4.28 (bs, 4H), 2.47 (s, 3H).

1-(2,3-Di hydrobenzo[b][1,4]dioxin-6-yl)-2-(3-methyl pyridin-4-yl)ethane-1,2-dione To a solution of 4-((2,3-dihydrobenzo[b][1,4]dioxin-6-yl) ethynyl)-3-methylpyridine (870 mg, 3.5 mmol) in acetone and water mixture (1:1, 20 mL) were added NaHCO$_3$ (174 mg, 2.07 mmol) and MgSO$_4$.7H$_2$O (1.34 g, 5.19 mmol) at rt. The reaction mixture was cooled to 0° C. and KMnO$_4$ was added portion wise. The reaction mixture was stirred at 0° C. for 3 h. The TLC showed the reaction to be complete. The reaction mixture was quenched with aqueous saturated sodium bisulphite solution (25 mL) and extracted with EtOAc (3×25 mL). The organic layer was dried (Na$_2$SO$_4$), filtered and concentrated under reduced pressure to afford 1-(2,3-dihydrobenzo[b][1,4]dioxin-6-yl)-2-(3-methylpyridin-4-yl)ethane-1,2-dione as a yellow solid. Yield: 610 mg (62%); MS (ESI+) for CHNOS m/z 284.14 [M+H]$^+$. $^1$H NMR (400 MHz, DMSO-d$_6$): δ 8.72-8.79 (m, 1H), 7.54-7.69 (m, 2H), 7.48 (s, 2H), 7.07 (d, J=8.8 Hz, 1H), 4.38 (bs, 2H), 4.27 (bs, 2H), 2.57 (s, 3H).

4-(4-(2,3-Dihydrobenzo[b][1,4]dioxin-6-yl)-2-methyl-1H-imidazol-5-yl)-2-methylpyridine To a solution of 1-(2,3-dihydrobenzo[b][1,4]dioxin-6-yl)-2-(3-methylpyridin-4-yl)ethane-1,2-dione (300 mg, 1.06 mmol) in acetic acid (5 mL) were added ammonium acetate (816 mg, 10.6 mmol) and acetaldehyde (55 mg, 1.27 mmol) at rt. The reaction mixture was stirred at 120° C. for 16 h. The TLC showed the reaction to be complete. The reaction mixture was allowed to cool to rt, diluted with ice-cold water (25 mL), neutralized to pH 5-6 with aqueous ammonia solution and extracted with EtOAc (2×25 mL). The organic layer was dried (Na$_2$SO$_4$), filtered and concentrated under reduced pressure. The crude residue was purified by prep HPLC to afford 4-(4-(2,3-dihydrobenzo[b][1,4]dioxin-6-yl)-2-methyl-1H-imidazol-5-yl)-2-methylpyridine as an off white solid. Yield: 30 mg (9%); MS (ESI+) for CHNOS m/z 308.02 [M+H]$^+$; LC purity 99.8%; $^1$H NMR (400 MHz, DMSO-d$_6$+d-TFA): δ 8.77 (d, J=6.4 Hz, 1H), 7.95 (s, 1H), 7.72 (dd J=1.5, 6.4 Hz, 1H), 7.09 (d, J=1.8 Hz, 1H), 6.96-7.04 (m, 2H), 4.28-4.34 (m, 4H), 2.68 (s, 3H), 2.66 (s, 3H).

The following intermediate was prepared in a similar manner to 4-((2,3-dihydrobenzo[b][1,4]dioxin-6-yl)ethynyl)-3-methylpyridine.

| Name | Int | Structure | Yield | Spectral Data 1H NMR & LCMS |
|---|---|---|---|---|
| 1-(6-((2-Methylpyridin-4-yl)ethynyl)-2,3-dihydro-4H-benzo[b][1,4]oxazin-4-yl)ethan-1-one | 135 | 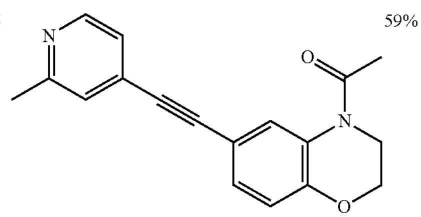 | 59% | MS (ESI+) for CHNOS m/z 293.11 [M + H]$^+$; $^1$H NMR (400 MHz, DMSO-d$_6$): 8.46 (d, J = 5.1 Hz 1H), 7.95 (s, 1H), 7.39 (s, 1H), 7.26-7.31 (m, 2H), 6.94 (d, J = 8.3 Hz 1H), 4.30-4.38 (m, 2H), 3.85-3.90 (m, 2H), 2.90 (s, 3H), 2.72 (s, 3H) |

The following intermediate was prepared in a similar manner 1-(2,3-dihydrobenzo[b][1,4]dioxin-6-yl)-2-(3-methylpyridin-4-yl) ethane-1,2-dione.

| Name | Int | Structure | Yield | Spectral Data 1H NMR & LCMS |
|---|---|---|---|---|
| 1-(4-Acetyl-3,4-dihydro-2H-benzo[b][1,4]oxazin-6-yl)-2-(2-methylpyridin-4-yl)ethane-1,2-dione | 136 | | Crude | MS(ESI+) for CHNOS m/z 325.12 [M + H]$^+$ |

Synthetic Route 12

5-(2,3-Dihydrobenzo[b][1,4]dioxin-6-yl)-N-methyl-4-(2-methylpyridin-4-yl)-1H-imidazole-2-carboxamide (Example 85)

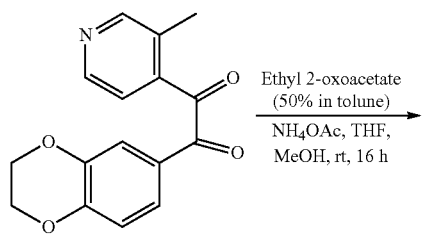

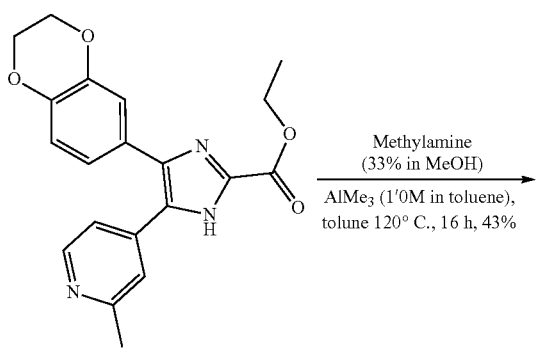

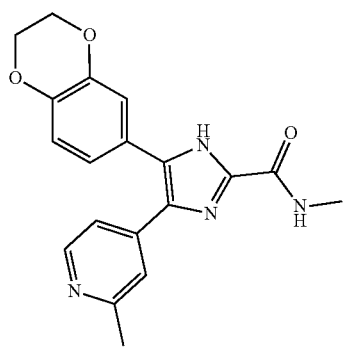

Ethyl 4-(2,3-dihydrobenzo[b][1,4]dioxin-6-yl)-5-(2-methylpyridin-4-yl)-1H-imidazole-2-carboxylate To a solution of 1-(2,3-dihydrobenzo[b][1,4]dioxin-6-yl)-2-(3-methylpyridin-4-yl)ethane-1,2-dione (500 mg, 1.76 mmol) in THF (5 mL) were added NH$_4$OAc (1.36 g, 17.6 mmol), MeOH (2 mL) and ethyl 2-oxoacetate (50% in toluene, 0.54 mL, 2.64 mmol) at rt. The reaction mixture was stirred at rt for 16 h. The TLC showed the reaction to be complete. The reaction mixture was diluted with EtOAc (25 mL) and washed with saturated aqueous NaHCO$_3$ solution (25 mL). The organic layer was dried (Na$_2$SO$_4$), filtered and concentrated under reduced pressure. The crude LCMS showed ~12% conversion to desired compound. The crude residue was purified by prep HPLC to afford ethyl 4-(2,3-dihydrobenzo[b][1,4]dioxin-6-yl)-5-(2-methylpyridin-4-yl)-1H-imidazole-2-carboxylate as an off white solid. MS (ESI+) for CHNOS m/z 366.04 [M+H]$^+$; LC purity 99.7%; $^1$H NMR (400 MHz, DMSO-d$_6$+d-TFA): δ 8.53 (d, J=6.4 Hz, 1H), 8.03 (s, 1H), 7.69 (d, J=5.4 Hz, 1H), 7.06 (s, 1H), 6.95 (s, 2H), 4.34 (q, J=7.0 Hz, 2H), 4.27 (bs, 4H), 2.64 (s, 3H), 1.32 (t, J=7.0 Hz, 3H).

5-(2,3-dihydrobenzo[b][1,4]dioxin-6-yl)-N-methyl-4-(2-methylpyridin-4-yl)-1H-imidazole-2-carboxamide To a solution of ethyl 4-(2,3-dihydrobenzo[b][1,4]dioxin-6-yl)-5-(2-methylpyridin-4-yl)-1H-imidazole-2-carboxylate (180 mg, 60% by LCMS, 0.49 mmol) in toluene (3 mL) were added methylamine (33% in MeOH, 0.1 mL, 0.98 mmol) and trimethylaluminium (2M in toluene, 0.74 mL, 1.47 mmol) at rt. The reaction mixture was stirred at 120° C. for 16 h. The TLC showed the reaction to be complete. The reaction mixture was allowed to cool to rt and evaporated under reduced pressure. The crude residue was purified by column chromatography using silica gel (100-200 mesh), eluting with 3-5% MeOH in DCM to afford a yellow solid. The yellow solid was further triturated with Et$_2$O (5 mL) to afford 5-(2,3-dihydrobenzo[b][1,4]dioxin-6-yl)-N-methyl-4-(2-methylpyridin-4-yl)-1H-imidazole-2-carboxamide as a white solid. Yield: 45 mg (43%); MS (ESI+) for CHNOS m/z 351.00 [M+H]$^+$; LC purity 99.7%; $^1$H NMR (400 MHz, DMSO-d$_6$, +d-TFA): δ 8.57 (d, J=6.4 Hz, 1H), 8.01 (s, 1H), 7.72 (d, J=5.6 Hz, 1H), 6.92-7.09 (m, 3H), 4.28 (bs, 4H), 2.82 (s, 3H), 2.62 (s, 3H).

The following intermediates were prepared in a similar manner to ethyl 4-(2,3-dihydrobenzo[b][1,4]dioxin-6-yl)-5-(2-methylpyridin-4-yl)-1H-imidazole-2-carboxylate.

| Name | Int | Structure | Yield | Spectral Data 1H NMR & LCMS |
|---|---|---|---|---|
| tert-Butyl ((4-(2,3-dihydrobenzo[b][1,4]dioxin-6-yl)-5-(2-methylpyridin-4-yl)-1H-imidazol-2-yl)methyl)carbamate | 137 | 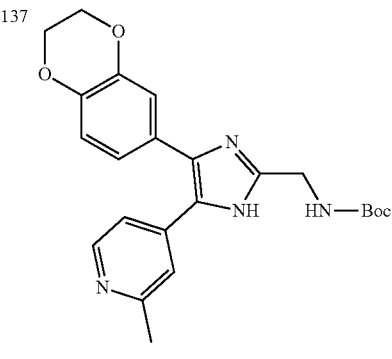 | Crude | MS (ESI+) for CHNOS m/z 423.38 [M + H]+ |
| tert-Butyl ((4-(4-acetyl-3,4-dihydro-2H-benzo[b][1,4]oxazin-6-yl)-5-(2-methylpyridin-4-yl)-1H-imidazol-2-yl)methyl)carbamate | 138 | 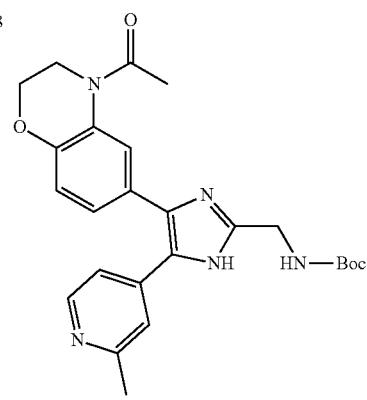 | Crude | MS (ESI−) for CHNOS m/z 462.34 [M + H]+ |

Synthetic Route 13

4-(2,3-dihydrobenzo[b][1,4]dioxin-6-yl)-5-(2-methylpyridin-4-yl)-1H-imidazole-2-carboxylate (Example 86)

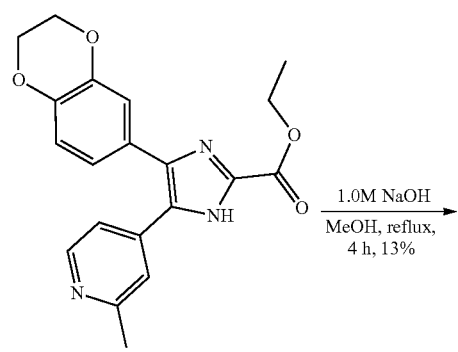

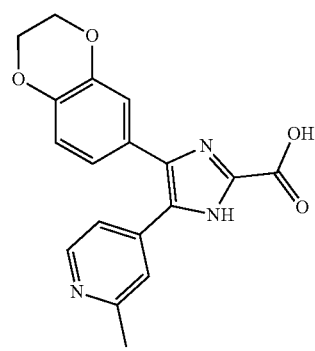

To a solution of ethyl 4-(2,3-dihydrobenzo[b][1,4]dioxin-6-yl)-5-(2-methylpyridin-4-yl)-1H-imidazole-2-carboxylate (160 mg, 0.43 mmol) in MeOH (10 mL) were added 1M NaOH (1.3 mL, 1.31 mmol) at rt. The reaction mixture was stirred at 80° C. for 4 h. The TLC showed the reaction to be complete. The reaction mixture was allowed to cool to rt and evaporated under reduced pressure. The crude residue was enriched by trituration Et$_2$O (5 mL). The product was further purified by prep HPLC purification afford 4-(2,3-dihydrobenzo[b][1,4]dioxin-6-yl)-5-(2-methylpyridin-4-yl)-1H-imidazole-2-carboxylate as an off white solid. Yield: 20 mg (13%); MS (ESI+) for CHNOS m/z 337.99 [M+H]$^+$; LC purity 96.6%; $^1$H NMR (400 MHz, DMSO-d$_6$): δ 8.27 (d, J=5.2 Hz, 1H), 7.39 (s, 1H), 7.14 (d, J=4.7 Hz, 1H), 6.94 (s, 1H), 6.83-6.89 (m, 2H), 4.26 (s, 4H), 2.40 (s, 3H).

Synthetic Route 14

(4-(2,3-Dihydrobenzo[b][1,4]dioxin-6-yl)-5-(2-methylpyridin-4-yl)-1H-imidazol-2-yl)methanamine (Example 87)

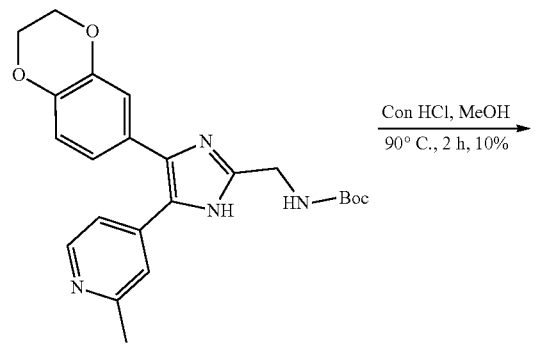

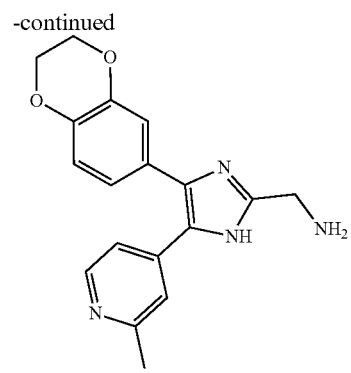

To a solution of tert-butyl ((4-(2,3-dihydrobenzo[b][1,4]dioxin-6-yl)-5-(2-methylpyridin-4-yl)-1H-imidazol-2-yl)methyl)carbamate (370 mg, 0.87 mmol) in MeOH (5.0 mL) was added conc. HCl (2.0 mL) at rt. The resulted mixture was stirred at 90° C. for 2 h. The TLC showed reaction to be complete. The reaction mixture was concentrated under reduced pressure. The residue was neutralised by aq. saturated NaHCO$_3$ solution (20 mL) and extracted with EtOAc (3×20 mL). The organics were dried (Na$_2$SO$_4$), filtered and concentrated under reduced pressure. The crude residue was purified by combiflash, using 12 g silica column, eluting with 0-12% MeOH in DCM followed by trituration of obtained solid with Et$_2$O (5 mL) and drying under reduced pressure to afford 4(4-(2,3-dihydrobenzo[b][1,4]dioxin-6-yl)-5-(2-methylpyridin-4-yl)-1H-imidazol-2-yl)methanamine as a yellow solid. Yield: 30 mg (10%); MS (ESI+) for CHNOS m/z 323.21 [M+H]$^+$; LC purity 95.2% (Ret. Time-3.83 min); $^1$H NMR (400 MHz, DMSO-d$_6$+d-TFA): δ 8.58 (d, J=6.4 Hz, 1H), 7.94 (s, 1H), 7.75 (d, J=6.0 Hz, 1H), 6.93-7.09 (m, 3H), 4.30 (bs, 4H), 4.16 (s, 2H), 2.63 (s, 3H).

The following compound was prepared in a similar manner to (4-(2,3-dihydrobenzo[b][1,4]dioxin-6-yl)-5-(2-methylpyridin-4-yl)-1H-imidazol-2-yl)methanamine.

| Name | Ex | Structure | Yield | Spectral Data 1H NMR & LCMS |
|---|---|---|---|---|
| 4(4-(3,4-Dihydro-2H-benzo[b][1,4]oxazin-6-yl)-5-(2-methylpyridin-4-yl)-1H-imidazol-2-yl)methanamine (methylthio)pyrimidine | 88 | 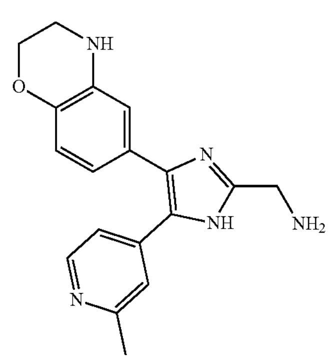 | 32% | MS (ESI+) for CHNOS m/z 322.20 [M + H]$^+$; LC purity 97.0% (Ret. Time- 4.81 min); $^1$H NMR (400 MHz, DMSO-d$_6$ + D$_2$O): δ 8.41 (d, J = 6.3 Hz, 1 H), 7.94 (s, 1H), 7.77 (d, J = 6.1 Hz, 1 H), 6.79 (d, J = 8.0 Hz, 1 H), 6.68 (s, 1H), 6.61 (d, J = 8.0 Hz, 1H), 4.16 (bs, 2H), 4.12 (s, 2H), 3.29 (bs, 2H), 2.59 (s, 3H) |

+

Synthetic Route 15

6-(2-Amino-4-(2-methylpyridin-4-yl)-1H-imidazol-5-yl)-4-(2-aminoethyl)-2H-benzo[b][1,4]oxazin-3(4H)-one (Example 89)

Synthetic Route 16

2-(6-(2-Amino-4-(2-methylpyridin-4-yl)-1H-imidazol-5-yl)-2,3-dihydro-4H-benzo[b][1,4]oxazin-4-yl)ethan-1-ol (Example 90)

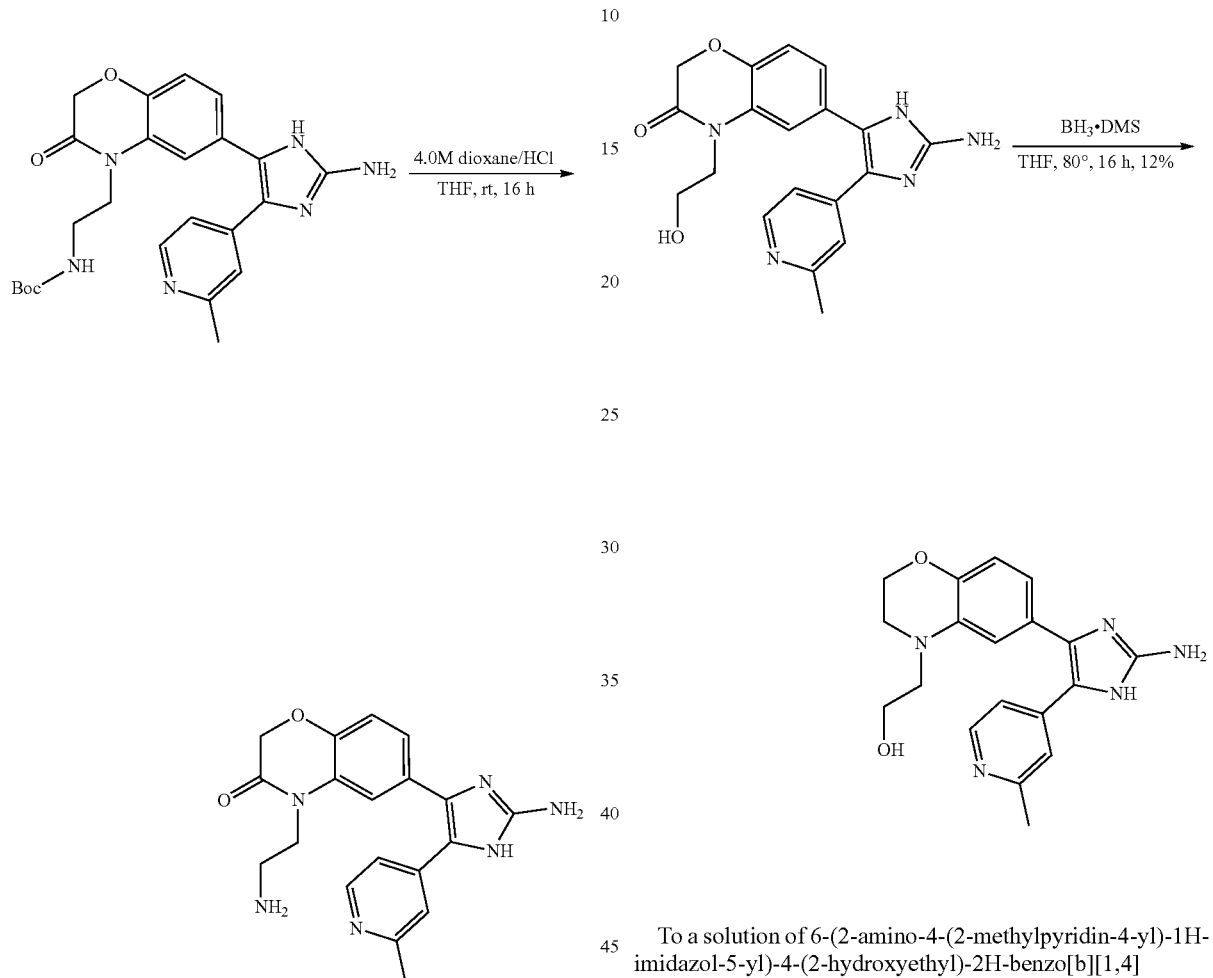

To a solution of tert-butyl (2-(6-(2-amino-4-(2-methylpyridin-4-yl)-1H-imidazol-5-yl)-3-oxo-2,3-dihydro-4H-benzo[b][1,4]oxazin-4-yl)ethyl)carbamate (200 mg, 0.43 mmol) in THF (5.0 mL) was added HCL solution (1.0 mL, 4.0M in dioxane) at rt. The resulted mixture was stirred at rt for 16 h. The TLC showed reaction to be complete. The reaction mixture was concentrated under reduced pressure and triturated with Et$_2$O to afford 6-(2-amino-4-(2-methylpyridin-4-yl)-1H-imidazol-5-yl)-4-(2-aminoethyl)-2H-benzo[b][1,4]oxazin-3(4H)-one as an orange solid. Yield (150 mg, 89% by LCMS and 1H NMR). MS (ESI+) for CHNOS m/z 365.24 [M+H]$^+$; LC purity 98.1% (Ret. Time—4.47 min); 1H NMR (400 MHz, DMSO-d$_6$+d-TFA): δ 8.64 (d, J=6.4 Hz, 1H), 7.77 (s, 1H), 7.60 (d, J=5.4 Hz, 1H), 7.41 (s, 1H), 7.11-7.20 (m, 2H), 4.78 (s, 2H), 4.15 (bs, 2H), 3.02 (bs, 2H), 2.63 (s, 3H), To a solution of 6-(2-amino-4-(2-methylpyridin-4-yl)-1H-imidazol-5-yl)-4-(2-hydroxyethyl)-2H-benzo[b][1,4]oxazin-3(4H)-one (247 mg, 0.676 mmol) in dry THF (5.0 mL) was added BH$_3$.DMS (0.3 mL, 3.38 mmol) at rt. The resulted mixture was stirred at 80° C. for 16 h. The TLC showed reaction to be completed. The reaction was allowed to cool to rt and quenched slowly with MeOH (1.0 mL). The resulted mixture was evaporated under reduced pressure, triturated with Et$_2$O, dried and further purified by Preparative HPLC to afford 2-(6-(2-amino-4-(2-methylpyridin-4-yl)-1H-imidazol-5-yl)-2,3-dihydro-4H-benzo[b][1,4]oxazin-4-yl)ethan-1-ol as a yellow solid. 28 mg (12%). MS (ESI+) for CHNOS m/z 352.22 [M+H]$^+$; LC purity 97.7% (Ret. Time—3.67 min); 1H NMR (400 MHz, DMSO-d$_6$+d-TFA): δ 8.62 (d, J=6.5 Hz, 1H), 7.80 (s, 1H), 7.62 (d, J=6.4 Hz, 1H), 6.78-6.83 (m, 2H), 6.62 (dd, J=1.5, 8.0 Hz, 1H), 4.16-4.21 (m, 2H), 3.48-3.55 (m, 2H), 3.41-3.46 (m, 2H), 3.27-3.32 (m, 2H), 2.61 (s, 3H).

The following compounds were prepared in a similar manner to 2-(6-(2-amino-4-(2-methylpyridin-4-yl)-1H-imidazol-5-yl)-2,3-dihydro-4H-benzo[b][1,4]oxazin-4-yl)ethan-1-ol.

| Name | Ex | Structure | Yield | Spectral Data 1H NMR & LCMS |
|---|---|---|---|---|
| 4-(4-(2-Aminoethyl)-3,4-dihydro-2H-benzo[b][1,4]oxazin-6-yl)-5-(2-methylpyridin-4-yl)-1H-imidazol-2-amine | 91 | 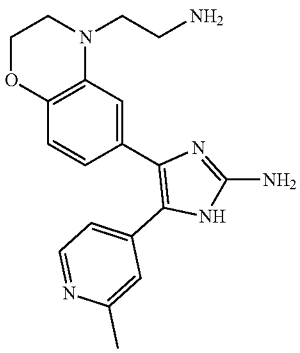 | 8% | Purified by Prep HPLC MS (ESI+) for CHNOS m/z 351.21 [M + H]+; LC purity 99.3% (Ret. Time- 4.65 min); 1H NMR (400 MHz, DMSO-d6 + d-TFA ): δ 8.62 (d, J = 6.5 Hz, 1H), 7.80 (s, 1H), 7.61 (d, J = 6.4 Hz, 1H), 6.92 (s, 1H), 6.84 (d, J = 8.1 Hz, 1H), 6.72 (dd, J = 1.4, 8.1 Hz, 1H), 4.28 (bs, 2H), 3.43-3.51 (m, 2H), 3.39 (bs, 2H), 2.97-3.02 (m, 2H), 2.62 (s, 3H) |
| 4-(4-(Cyclopropylmethyl)-3,4-dihydro-2H-benzo[b][1,4]oxazin-6-yl)-5-(2-methylpyridin-4-yl)-1H-imidazol-2-amine | 92 | | 11% | Purified by Prep HPLC MS (ESI+) for CHNOS m/z 362.25 [M + H]+; LC purity 94.1% (Ret. Time- 5.56 min); 1H NMR (400 MHz, DMSO-d6): δ 11.15 (bs, 1H), 8.27 (d, J = 5.8 Hz, 1H), 7.15-7.69 (m, 2H), 6.58-6.88 (m, 3H), 5.47 (bs, 2H), 4.22 (bs, 2H), 3.40 (bs, 2H), 3.06 (d, J = 6.0 Hz, 2H), 2.46 (s, 3H), 0.94 (bs, 1H), 0.40-0.52 (m, 2H), 0.14-0.22 (m, 2H) |
| 4-(4-isopropyl-3,4-dihydro-2H-benzo[b][1,4]oxazin-6-yl)-5-(2-methylpyridin-4-yl)-1H-imidazol-2-amine | 93 | 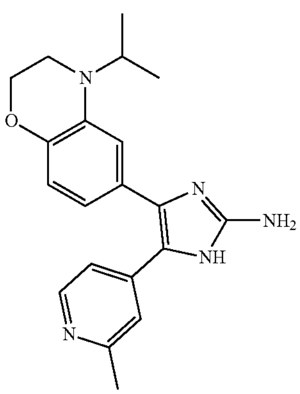 [SMILES: Cc1cc(-c2[nH]c(N)nc2-c2ccc3c(c2)N(C(C)C)CCO3)ccn1] | 8% | Purified by Prep HPLC MS (ESI+) for CHNOS m/z 350.23 [M + H]+; LC purity 95.5% (Ret. Time- 5.52 min); 1H NMR (400 MHz, DMSO-d6 + d-TFA ): δ 8.53 (d, J = 6.4 Hz, 1H), 7.58 (s, 1H), 7.34 (d, J = 5.8 Hz, 1H), 6.84 (s, 1H), 6.78 (d, J = 8.13 Hz 1H), 6.62 (dd, J = 1.4, 8.1 Hz, 1H), 4.19 (bs, 2H), 3.90-4.01 (m, 1H), 3.22 (bs, 2H), 2.61 (s, 3H), 1.05 (d, J = 6.5 Hz, 6H) |
| 4-(4-Cyclopentyl-3,4-dihydro-2H-benzo[b][1,4]oxazin-6-yl)-5-(2-methylpyridin-4-yl)-1H-imidazol-2-amine | 94 | 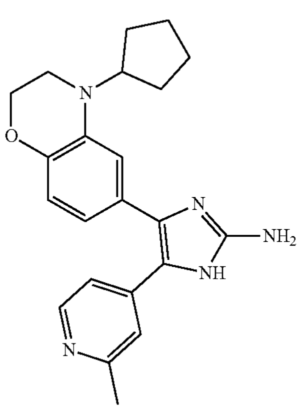 [SMILES: Cc1cc(-c2[nH]c(N)nc2-c2ccc3c(c2)N(C2CCCC2)CCO3)ccn1] | 10% | Purified by Prep HPLC MS (ESI+) for CHNOS m/z 376.27 [M + H]+; LC purity 95.8% (Ret. Time- 5.71 min); 1H NMR (400 MHz, DMSO-d6 + d-TFA): δ 8.55 (d, J = 6.3 Hz, 1H), 7.58 (s, 1H), 7.34 (d, J = 5.2 Hz, 1H), 6.84 (s, 1H), 6.78 (d, J = 8.2 Hz, 1H), 6.61-6.66 (m, 1H), 4.21 (bs, 2H), 3.99-4.05 (m, 1H), 3.24 (bs, 2H), 2.61 (s, 3H), 1.47-1.80 (m, 8H) |

-continued

| Name | Ex | Structure | Yield | Spectral Data 1H NMR & LCMS |
|---|---|---|---|---|
| 2-(2-(6-(2-Amino-5-(2-methylpyridin-4-yl)-1H-imidazol-4-yl)-2,3-dihydro-4H-benzo[b][1,4]oxazin-4-yl)ethoxy)ethan-1-ol | 95 | (structure) | 14% | Purified by Prep HPLC MS (ESI+) for CHNOS m/z 396.32 [M + H]$^+$; LC purity 96.4% (Ret. Time- 4.81 min); 1H NMR (400 MHz, DMSO-$d_6$ + $D_2O$): δ 8.27 (d, J = 6.3 Hz, 1H), 7.49 (bs, 1H), 7.32 (bs, 1H), 6.61-6.79 (m, 2H), 6.56 (d, J = 8.1 Hz, 1H), 4.14 (bs, 2H), 3.31-3.52 (m, 10H), 2.46 (s, 3H) |

Example A: Antibacterial Susceptibility

Minimum Inhibitory Concentrations (MICs) versus planktonic bacteria are determined by the broth microdilution procedure according to the guidelines of the Clinical and Laboratory Standards Institute (Clinical and Laboratory Standards Institute. Methods for Dilution Antimicrobial Susceptibility Tests for Bacteria That Grow Aerobically; Approved Standard-tenth Edition. CLSI document M07-A10, 2015). The broth dilution method involves a two-fold serial dilution of compounds in 96-well microtitre plates, giving a final concentration range of 0.39-200 μM and a maximum final concentration of 2% DMSO. The bacterial strains tested include *Escherichia coli* K12 (EC), *E. coli* NCTC 13441 (UPEC), *Staphylococcus aureus* ATCC 35556 (SA), *Acinetobacter baumannii* ATCC 17978 (AB), *Pseudomonas aeruginosa* ATCC 33359 (PA), *Enterobacter cloacae* DSM 30054 (Ed), *Serratia marcescens* SL1344 (Sm), *Salmonella typhimurium* XNAA5 (St), *Klebsiella pneumoniae* ATCC 10031 (KP2), *K. pneumoniae* NCTC 13438 (KP1), *K. pneumoniae* ATCC 700603 (KP3), *Klebsiella pneumoniae* ATCC 51504 (KP4), *K. pneumoniae* H154680676 (KP5), *K. pneumoniae* H154020667 (KP6), *K. pneumoniae* H154640784 (KP7), *K. pneumoniae* H154600588 (KP8), *K. pneumoniae* H154300688 (KP9), *K. pneumoniae* H151440671 (KP10). Strains are grown in cation-adjusted Müller-Hinton broth or on Luria Bertoni agar at 37° C. in an ambient atmosphere. The MIC is determined as the lowest concentration of compound that inhibits growth following a 20-24 hour incubation period. The results are set out in Table 1. In Table 1 an MIC (μM) of less or equal to 1 is assigned the letter A; a MIC of from 1 to 10 is assigned the letter B; a MIC of from 10 to 100 is assigned the letter C; and a MIC of over 100 is assigned the letter D.

TABLE 1

MIC values against Gram-negative and Gram-positive bacterial strains including Enterobacteriaceae bacteria strains

| Compound | AB | PA | EC | SA | KP1 | KP2 | KP3 | KP4 | KP5 | KP6 | KP7 | KP8 | KP9 | KP10 | UPEC | Ecl | St | Sm |
|---|---|---|---|---|---|---|---|---|---|---|---|---|---|---|---|---|---|---|
| CIP | A | B | A | B | D | A | A |   | D | D | C | D | D | C | D | A | A | A |
| CST | B | B | A | D | B | A | B |   | D | B | A | B | A | A | A | A | A | D |
| DOX | A | C | B | A | C | A | C |   | C | C | C | C | C | B | C | B | B | B |
| IPM | A | B | A | A | C | B | B |   | B | B | C | D | D | C | A | B | B | B |
| TZP | C | B | B | B | D | B | C |   | C | C | C | D | D | D | C | B | C | B |
| TOB | B | B | B | B | C | B | D |   | D | D | B | D | D | B | D | C | B | A |
| 1 | D | D | C | D | D | A |   |   |   |   |   |   |   |   | C |   |   |   |
| 2 | D | D | B | D | C | A |   |   |   |   |   |   |   |   | B |   |   |   |
| 3 | D | D | A | D | B | A | B |   | B | B | B | B | B | B | A | A | A | B |
| 4 | D | D | A | D | C | A |   |   |   |   |   |   |   |   | B | B | B | C |
| 5 | D | D | B | D | C | A |   |   |   |   |   |   |   |   | B |   |   |   |
| 6 | D | D | B | D | C | A |   |   |   |   |   |   |   |   | B |   |   |   |
| 7 | D | D | A | C | B | A | B |   | A | A | B | B | A | A | A | A | A | A |
| 8 | D | D | A | D | C | A |   |   |   |   |   |   |   |   | A |   |   |   |
| 9 | D | D | A | D | B | A | B |   | A | B | A | B | B | A | A | A | A | C |
| 10 | D | D | D | D | D | B |   |   |   |   |   |   |   |   | D |   |   |   |
| 11 | D | D | B | D | C | A |   |   |   |   |   |   |   |   | B |   |   |   |
| 12 | D | D | B | D | C | A | C |   | B | B | C | C | B | B | B |   |   |   |
| 13 | D | D | B | D | C | A |   |   |   |   |   |   |   |   | B |   |   |   |
| 14 | D | D | A | D | B | A |   |   |   |   |   |   |   |   | A |   |   |   |
| 15 | D | D | C | D | C | A |   |   |   |   |   |   |   |   | B |   |   |   |
| 16 | D | D | A | D | A | A | A |   | A | A | A | A | A | A | A | A | A | A |
| 17 | D | D | B | D | C | A |   |   |   |   |   |   |   |   | B |   |   |   |
| 18 | D | D | C | D | D | B |   |   |   |   |   |   |   |   | C |   |   |   |
| 19 | C | D | A | C | A | A | A |   | A | A | B | B | A | A | A | A | A | A |
| 20 | D | D | B | D | C | A |   |   |   |   |   |   |   |   | B |   |   |   |
| 21 | D | D | B | D | C | A |   |   |   |   |   |   |   |   | B | D | D | D |
| 22 | D | D | D | D | D | B |   |   |   |   |   |   |   |   | D |   |   |   |

TABLE 1-continued

MIC values against Gram-negative and Gram-positive bacterial strains including Enterobacteriaceae bacteria strains

| Compound | AB | PA | EC | SA | KP1 | KP2 | KP3 | KP4 | KP5 | KP6 | KP7 | KP8 | KP9 | KP10 | UPEC | Ecl | St | Sm |
|---|---|---|---|---|---|---|---|---|---|---|---|---|---|---|---|---|---|---|
| 23 | D | D | A | D | B | A | B |   | A | A | B | B | A | A | A | A | A | B |
| 24 | D | D | B | D | C | A | C |   | B | B | C | C | C | B | B |   |   |   |
| 25 | D | D | C | D | C | A |   |   |   |   |   |   |   |   | C |   |   |   |
| 26 | D | D | A | D | C | A | C |   | B | B | C | C | B | B | B |   |   |   |
| 27 | D | D | A | D | B | A | B |   | A | A | B | B | B | A | A | A | A | B |
| 28 | D | D | A | D | B | A | B |   | A | A | B | B | A | A | A | A | A | A |
| 29 | D | D | A | D | C | A | C |   | B | B | C | C | B | B | A |   |   |   |
| 30 | D | D | C | D | D | B |   |   |   |   |   |   |   |   | C |   |   |   |
| 31 | D | D | B | D | C | A |   |   |   |   |   |   |   |   | B |   |   |   |
| 32 | D | D | A | D | B | A | B | B | B | B | B | B | B | B | A |   |   |   |
| 33 | D | D | B | D | C | A |   |   |   |   |   |   |   |   | B |   |   |   |
| 34 | D | D | B | D | B | A |   |   |   |   |   |   |   |   | B |   |   |   |
| 35 | D | D | B | D | C | A |   |   |   |   |   |   |   |   | B |   |   |   |
| 36 | D | D | B | D | B | A |   |   |   |   |   |   |   |   | A |   |   |   |
| 37 | D | D | B | D | C | A |   |   |   |   |   |   |   |   | B |   |   |   |
| 38 | D | D | A | D | B | A |   |   |   |   |   |   |   |   | A |   |   |   |
| 39 | D | D | A | D | C | A |   |   |   |   |   |   |   |   | A |   |   |   |
| 40 | D | D | B | D | B | A |   |   |   |   |   |   |   |   | A |   |   |   |
| 41 | D | D | A | D | B | A |   |   |   |   |   |   |   |   | A |   |   |   |
| 42 | D | D | B | D | C | A |   |   |   |   |   |   |   |   | B |   |   |   |
| 43 | D | D | A | D | B | A |   |   |   |   |   |   |   |   | A |   |   |   |
| 44 | D | D | B | D | B | A |   |   |   |   |   |   |   |   | B |   |   |   |
| 45 | D | D | A | D | B | A | B | B | B | B | B | C | B | B | A |   |   |   |
| 46 | D | D | B | D | C | A |   |   |   |   |   |   |   |   | B |   |   |   |
| 47 | D | D | B | D | C | A |   |   |   |   |   |   |   |   | B |   |   |   |
| 48 | D | D | B | D | C | A |   |   |   |   |   |   |   |   | B |   |   |   |
| 49 | D | D | A | D | B | A | B | A | A | A | B | B | B | B | B |   |   |   |
| 50 | D | D | B | D | C | A |   |   |   |   |   |   |   |   | B |   |   |   |
| 51 | D | D | B | D | C | A |   |   |   |   |   |   |   |   | B |   |   |   |
| 52 | D | D | A | D | B | A | B | A | A | A | B | B | B | A | A |   |   |   |
| 53 | D | D | B | D | C | A |   |   |   |   |   |   |   |   | B |   |   |   |
| 54 | D | D | B | D | C | A |   |   |   |   |   |   |   |   | B |   |   |   |
| 55 | D | D | B | D | C | A | B | B | B | B | B | B | B | B | B |   |   |   |
| 56 | D | D | B | D | B | A | B | A | A | A | B | B | B | A | B |   |   |   |
| 57 | D | D | A | D | B | A | B | A | A | A | B | B | B | A | B |   |   |   |
| 58 | D | D | B | D | C | A | C | B | B | B | C | C | B | B | A |   |   |   |
| 59 | D | D | A | D | C | A |   |   |   |   |   |   |   |   | A |   |   |   |
| 60 | D | D | B | D | C | A |   |   |   |   |   |   |   |   | B |   |   |   |
| 61 | D | D | B | D | B | A |   |   |   |   |   |   |   |   | B |   |   |   |
| 62 | D | D | B | D | B | A | B | B | B | B | B | C | B | B | A |   |   |   |
| 63 | D | D | C | D | D | B |   |   |   |   |   |   |   |   | C |   |   |   |
| 64 | D | D | B | D | B | A | B | B | B | B | B | B | B | B | A |   |   |   |
| 65 | D | D | A | D | B | A | B | A | A | A | B | B | A | A | B |   |   |   |
| 66 | D | D | B | D | C | A |   |   |   |   |   |   |   |   | B |   |   |   |
| 67 | D | D | B | D | C | A |   |   |   |   |   |   |   |   | B |   |   |   |
| 68 | D | D | B | D | C | A |   |   |   |   |   |   |   |   | B |   |   |   |
| 69 | D | D | B | D | C | A |   |   |   |   |   |   |   |   | B |   |   |   |
| 70 | D | D | B | D | C | A |   |   |   |   |   |   |   |   | B |   |   |   |
| 71 | D | D | C | D | D | B |   |   |   |   |   |   |   |   | C |   |   |   |
| 72 | D | D | D | D | D | B |   |   |   |   |   |   |   |   | D |   |   |   |
| 73 | D | D | D | D | D | D |   |   |   |   |   |   |   |   | D |   |   |   |
| 74 | D | D | B | D | C | A |   |   |   |   |   |   |   |   | B |   |   |   |
| 75 | D | D | C | D | D | B |   |   |   |   |   |   |   |   | C |   |   |   |
| 78 | D | D | B | D | C | A |   |   |   |   |   |   |   |   | B |   |   |   |
| 79 | D | D | C | D | D | B |   |   |   |   |   |   |   |   | B |   |   |   |
| 80 | D | D | D | D | D | B |   |   |   |   |   |   |   |   | D |   |   |   |
| 81 | D | D | C | D | D | A |   |   |   |   |   |   |   |   | C |   |   |   |
| 82 | D | D | C | D | D | A |   |   |   |   |   |   |   |   | C |   |   |   |
| 83 | D | D | B | D | D | A |   |   |   |   |   |   |   |   | B |   |   |   |
| 84 | D | D | B | D | C | A | C |   | B | B | C | C | C | B | B |   |   |   |
| 85 | D | D | D | D | D | B |   |   |   |   |   |   |   |   | D |   |   |   |
| 86 | D | D | D | D | D | B |   |   |   |   |   |   |   |   | D |   |   |   |
| 87 | D | D | B | D | C | A |   |   |   |   |   |   |   |   | B |   |   |   |
| 88 | D | D | B | D | C | A |   |   |   |   |   |   |   |   | B |   |   |   |
| 89 | D | D | B | D | C | A |   |   |   |   |   |   |   |   | B |   |   |   |
| 90 | D | D | B | D | B | A |   |   |   |   |   |   |   |   | A |   |   |   |
| 91 | D | D | A | D | A | A |   |   |   |   |   |   |   |   | A |   |   |   |

TABLE 1-continued

MIC values against Gram-negative and Gram-positive bacterial strains including Enterobacteriaceae bacteria strains

| Compound | AB | PA | EC | SA | KP1 | KP2 | KP3 | KP4 | KP5 | KP6 | KP7 | KP8 | KP9 | KP10 | UPEC | Ecl | St | Sm |
|---|---|---|---|---|---|---|---|---|---|---|---|---|---|---|---|---|---|---|
| 92 | D | D | A | D | B | A | B | B | A | A | B | B | B | B | B | | | |
| 93 | D | D | A | D | B | A | B | A | A | A | B | B | B | A | A | | | |
| 94 | D | D | A | D | B | A | | | | | | | | | A | | | |
| 95 | D | D | B | D | C | A | | | | | | | | | B | | | |

CIP: ciprofloxacin,
CST: colistin,
DOX: doxycycline,
IPM: imipenem,
TZP: piperacillin/tazobactam,
TOB: tobramycin Thus, the tested compounds show very good potency (A or B) against all strains of Enterobacteriaceae tested, including those which are multidrug-resistant.

Example B: Human Cell Viability

Compounds are assessed for potential non-specific cytotoxic effects against the human hepatocarcinoma cell line ATCC HB-8065 (HepG2). HepG2 cells are seeded at 20,000 cells/well in 96-well microtitre plates in minimal essential medium (MEM) supplemented with a final concentration of 10% FBS. After 24 h, compound dilutions are prepared in MEM supplemented with a final concentration of 1% FBS, and added to the cells. Compounds are tested in two-fold serial dilutions over a final concentration range of 0.2-100 µM in a final DMSO concentration of 1% vol/vol. Thioridazine is used as a positive control. Cells are incubated with compound at 37° C. and 5% CO2 for a further 24 h, after which time the CellTiter-Glo reagent (Promega) is added. Luminescence is measured on a Perkin Elmer Envision plate reader. Data are analysed using a 4 parameter logistic regression to determine the concentration of compound that inhibits cell viability by fifty percent (IC50). The results are provided in Table 2. In Table 2, an IC50 (µM) of less than 25 is assigned the letter C; an IC50 of 25 to 100 is assigned the letter B; and an IC50 of over 100 is assigned the letter A.

TABLE 2

IC50 values against the HepG2 cell line

| Compound | IC50 |
|---|---|
| CST | A |
| 1 | A |
| 2 | A |
| 3 | A |
| 4 | A |
| 5 | A |
| 6 | A |
| 7 | B |
| 8 | A |
| 9 | A |
| 10 | A |
| 11 | A |
| 12 | A |
| 13 | B |
| 14 | A |
| 15 | A |
| 16 | B |
| 17 | A |
| 18 | A |
| 19 | B |
| 20 | B |
| 21 | A |

TABLE 2-continued

IC50 values against the HepG2 cell line

| Compound | IC50 |
|---|---|
| 23 | A |
| 24 | A |
| 25 | A |
| 26 | A |
| 27 | A |
| 28 | B |
| 29 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 71 | A |
| 74 | A |
| 75 | A |
| 80 | A |
| 81 | A |
| 83 | A |
| 84 | A |
| 85 | A |
| 86 | A |
| 87 | A |
| 88 | A |
| 89 | A |
| 90 | A |

TABLE 2-continued

IC50 values against the HepG2 cell line

| Compound | IC50 |
|---|---|
| 91 | A |
| 92 | B |
| 93 | B |
| 94 | B |

CST: colistin

Thus, the majority of tested compounds exhibit no toxicity (A) against human hepatic cell lines as demonstrated against HepG2 cells.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

NUMBERED DISCLOSURES

1. A compound of general formula (I), or a pharmaceutically acceptable salt, hydrate, solvate or ester thereof:

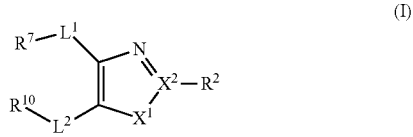
(I)

wherein
$X^1$ is selected from $NR^1$, O or S;
$X^2$ is selected from C or N;
with the proviso that when $X^1$ is S, $X^2$ is C, and when $X^1$ is O, $X^2$ is C;
$L^1$ and $L^2$ are linker groups selected from a direct bond or $C_{1-3}$alkylene;
$R^1$ is selected from hydrogen or $C_{1-4}$alkyl;
$R^2$ is selected from the group consisting of S (sulfinyl), O (oxo), $NR^3R^4$, cyano, methyl (—$CH_3$), ethyl (—$CH_2CH_3$), $C_{3-7}$cycloalkyl, $C_{1-4}$alkoxy, —$SC_{1-4}$alkyl, $C_{1-4}$alkyl-$C_{1-4}$alkoxy, $C_{1-4}$alkyl-$CO_2R^3R^4$, —$CONR^3R^4$, COOH and a 4- to 7-membered heterocyclyl, wherein the 4- to 7-membered heterocyclyl is optionally substituted with one or more $C_{1-6}$alkyl groups;
$R^3$ and $R^4$ are independently selected from the group consisting of hydrogen, $C_{1-6}$alkyl, $COR^5$, $CONR^5R^6$, $CO_2R^5$, $C_{1-4}$alkyl-$NR^5R^6$;
or $R^3$ and $R^4$ together with the nitrogen atom to which they are attached form a 4- to 7-membered cyclic amino group, which group is optionally substituted with one or more substituents selected from the group consisting of $NR^5R^6$, $C_{1-4}$alkoxy and oxo;
$R^5$ and $R^6$ are independently selected from the group consisting of hydrogen and $C_{1-6}$alkyl;
$R^7$ is selected from the group consisting of phenyl, monocyclic 4- to 7-membered heterocyclyl and monocyclic 5- or 6-membered heteroaryl, wherein the phenyl, 4- to 7-membered heterocyclyl and 5- or 6-membered heteroaryl rings are optionally substituted with one or more substituents selected from the group consisting of halogen, $C_{1-4}$alkyl, $C_{1-4}$alkoxy, $CONR^3R^4$, $OR^8$, $OCF_3$, hydroxyl and $R^8$;

or $R^7$ is a fused bicyclic system selected from the group consisting of any one of (Ia) to (Ii):

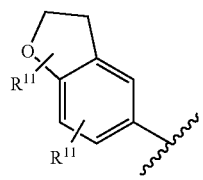
(Ia)

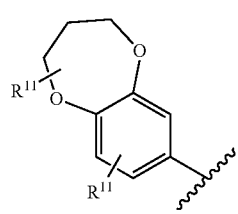
(Ib)

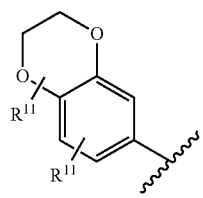
(Ic)

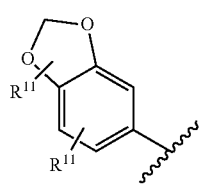
(Id)

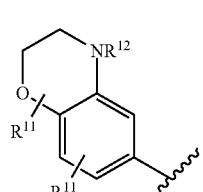
(Ie)

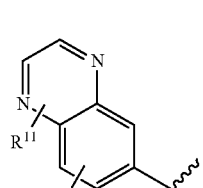
(If)

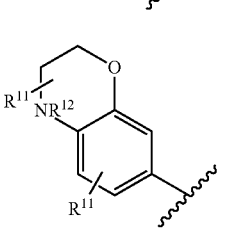
(Ig)

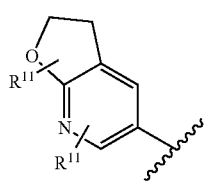
(Ih)

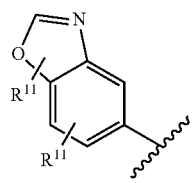
(Ii)

wherein R¹¹ is independently selected from the group consisting of hydrogen, halogen, $C_{1-4}$alkyl, $C_{1-4}$alkoxy, $NR^3R^4$, COOH, hydroxyl and $CONR^3R^4$ and $R^{12}$ is selected from the group consisting of hydrogen, $C_{1-4}$alkyl, $COR^5$, $CONR^5R^6$, $CO_2R^5$ and $C_{1-4}$alkyl-$NR^5R^6$;

R⁸ is selected from the group consisting of a monocyclic 3- to 5-membered cycloalkyl and $CH_2R^9$;

R⁹ is selected from the group consisting of phenyl, monocyclic 5- or 6-membered heteroaryl and monocyclic $C_{3-7}$cycloalkyl, the phenyl or 5- or 6-membered heteroaryl being optionally substituted with one or more substituents selected from the group consisting of halogen, $C_{1-4}$alkyl, O (oxo), S (sulfinyl), $NR^3R^4$, $OR^3$ and $SR^3$;

R¹⁰ is selected from the group consisting of phenyl and monocyclic 5- or 6-membered heteroaryl ring, wherein the phenyl and 5- or 6-membered heteroaryl rings are optionally substituted with one or more substituents selected from the group consisting of halogen, $C_{1-4}$alkyl, O (oxo), S (sulfinyl), $C_{1-4}$alkoxy, $NR^3R^4$, $OR^8$, hydroxyl and R⁸;

or R¹⁰ is a fused bicyclic system selected from the group consisting of any one of (Ia) to (Ii):

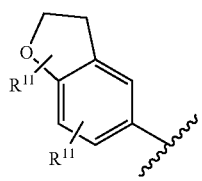
(Ia)

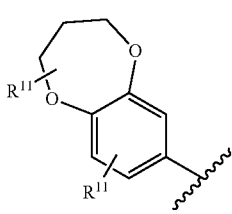
(Ib)

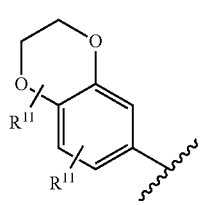
(Ic)

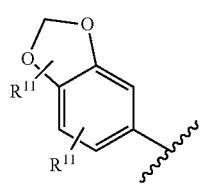
(Id)

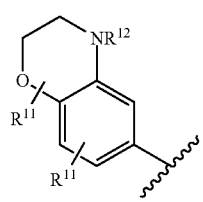
(Ie)

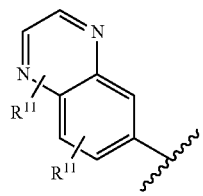
(If)

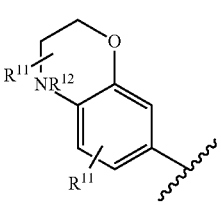
(Ig)

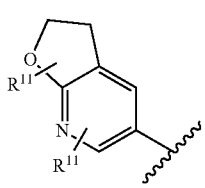
(Ih)

(Ii)

wherein R¹¹ is independently selected from the group consisting of hydrogen, halogen, $C_{1-4}$alkyl, $C_{1-4}$alkoxy, $NR^3R^4$, COOH, hydroxyl and $CONR^3R^4$ and $R^{12}$ is selected from the group consisting of hydrogen, $C_{1-4}$alkyl, $COR^5$, $CONR^5R^6$, $CO_2R^5$ and $C_{1-4}$alkyl-$NR^5R^6$.

2. A compound of general formula (I), or a pharmaceutically acceptable salt, hydrate, solvate or ester thereof, according to numbered disclosure 1, wherein X¹ is NH or NMe, preferably NH.

3. A compound of general formula (I), or a pharmaceutically acceptable salt, hydrate, solvate or ester thereof, according to numbered disclosure 1, wherein X¹ is S.

4. A compound of general formula (I), or a pharmaceutically acceptable salt, hydrate, solvate or ester thereof, according to any one of numbered disclosures 1 to 3, wherein R² is selected from the group consisting of $NR^3R^4$, $CONR^3R^4$, and COOH; wherein R³ and R⁴ are independently selected from the group consisting of hydrogen, $C_{1-6}$alkyl, $COR^5$, $CONR^5R^6$, $CO_2R^5$, $C_{1-4}$alkyl-$NR^5R^6$; wherein $R^5$ and $R^6$ are independently selected from the group consisting of hydrogen and $C_{1-2}$alkyl.

5. A compound of general formula (I), or a pharmaceutically acceptable salt, hydrate, solvate or ester thereof, according to numbered disclosure 4, wherein $R^2$ is $NH_2$.

6. A compound of general formula (I), or a pharmaceutically acceptable salt, hydrate, solvate or ester thereof, according to any preceding numbered disclosure wherein $L^1$ and $L^2$ are preferably a direct bond or methylene, preferably a direct bond.

7. A compound of general formula (I), or a pharmaceutically acceptable salt, hydrate, solvate or ester thereof, according to any preceding numbered disclosure, wherein $R^7$ is selected from the group consisting of phenyl and pyridyl, each of which is optionally substituted with one or more substituents selected from the group consisting of halogen, $C_{1-2}$alkyl, $C_{1-2}$alkoxy, $CONR^3R^4$, $OR^8$, $OCF_3$, and hydroxyl;

or $R^7$ is a fused bicyclic system selected from the group consisting of any one of (Ia) to (Ii):

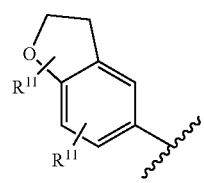
(Ia)

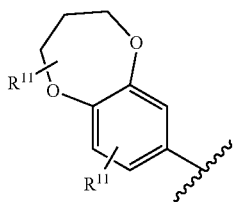
(Ib)

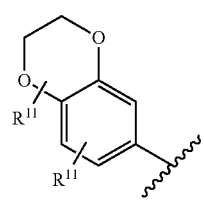
(Ic)

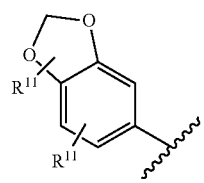
(Id)

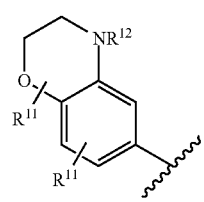
(Ie)

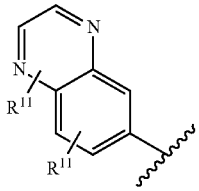
(If)

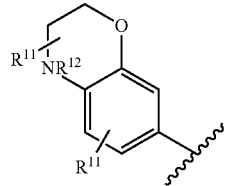
(Ig)

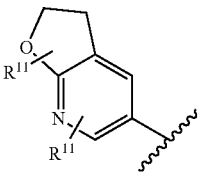
(Ih)

(Ii)

wherein $R^{11}$ is independently selected from hydrogen, halogen, $C_{1-4}$alkyl, $C_{1-4}$alkoxy, $NR^3R^4$, COOH, hydroxyl and $CONR^3R^4$ and $R^{12}$ is selected from the group consisting of hydrogen, $C_{1-4}$alkyl, $COR^5$, $CONR^5R^6$, $CO_2R^5$ and $C_{1-4}$alkyl-$NR^5R^6$;

wherein $R^8$ is $CH_2R^9$, wherein $R^9$ is selected from the group consisting of phenyl, optionally substituted with one or more halogen substituents.

8. A compound of general formula (I), or a pharmaceutically acceptable salt, hydrate, solvate or ester thereof, according to any preceding numbered disclosure, wherein $R^{10}$ is selected from the group consisting of phenyl and pyridyl, each of which are optionally substituted with one or more substituents selected from the group consisting of halogen, $C_{1-4}$alkyl, $C_{1-4}$alkoxy, $NR^3R^4$, $OR^8$, hydroxyl and $R^8$;

or $R^{10}$ is preferably a fused bicyclic system selected from the group consisting of any one of (Ia) to (Ii):

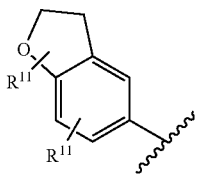
(Ia)

-continued (Ib) 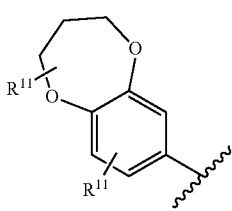

(Ic) 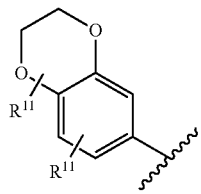

(Id) 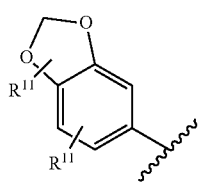

(Ie) 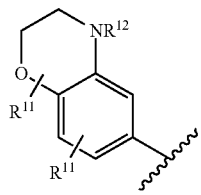

(If) 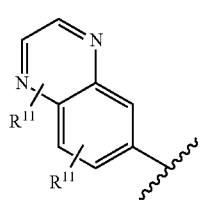

(Ig) 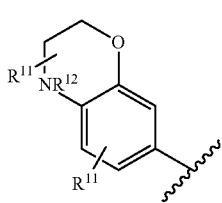

(Ih) 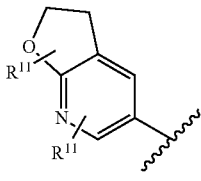

(Ii) 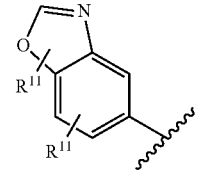

wherein $R^{11}$ is independently selected from hydrogen, halogen, $C_{1-4}$alkyl, $C_{1-4}$alkoxy, $NR^3R^4$, COOH, hydroxyl and $CONR^3R^4$ and $R^{12}$ is selected from the group consisting of hydrogen, $C_{1-4}$alkyl, $COR^5$, $CONR^5R^6$, $CO_2R^5$ and $C_{1-4}$alkyl-$NR^5R^6$.

9. A compound of general formula (I), or a pharmaceutically acceptable salt, hydrate, solvate or ester thereof, according to any preceding numbered disclosure, wherein when $R^7$ is a fused bicyclic system, $R^{10}$ is a monocyclic system, and when $R^7$ is a monocyclic system, $R^{10}$ is a fused bicyclic system.

10. A compound according to any preceding numbered disclosure, or a pharmaceutically acceptable salt, hydrate, solvate or ester thereof, having the general formula (II):

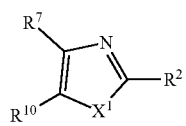

(II)

wherein
$X^1$ is selected from NH or S;
$R^2$ is selected from the group consisting of S (sulfinyl), O (oxo), $NR^3R^4$, cyano, methyl, —$CONR^3R^4$, COOH and monocyclic 4- to 7-membered heterocyclyl, wherein the 4- to 7-membered heterocyclyl is optionally substituted with one or more $C_{1-4}$alkyl groups;
$R^3$ and $R^4$ are independently selected from the group consisting of hydrogen, $C_{1-3}$alkyl, $COR^5$, $CONR^5R^6$, $CO_2R^5$, $C_{1-2}$alkyl-$NR^5R^6$;
or $R^3$ and $R^4$ together with the nitrogen atom to which they are attached form a monocyclic 4- to 7-membered cyclic amine group, which group is optionally substituted with one or more substituents selected from the group consisting of $NR^5R^6$, $C_{1-2}$alkoxy and oxo;
$R^5$ and $R^6$ are independently selected from the group consisting of hydrogen and $C_{1-4}$alkyl;
$R^7$ is selected from the group consisting of phenyl, monocyclic 5- to 7-membered heterocyclyl and monocyclic 5- or 6-membered heteroaryl, wherein the phenyl, 5- to 7-membered heterocyclyl and 5- or 6-membered heteroaryl rings are optionally substituted with one or more substituents selected from the group consisting of halogen, $C_{1-2}$alkyl, $C_{1-2}$alkoxy, $CONR^3R^4$, $OR^8$, $OCF_3$, and hydroxyl;
or $R^7$ is a fused bicyclic system selected from the group consisting of any one of (Ia) to (Ii):

(Ia) 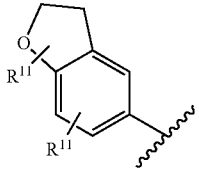

(Ib) 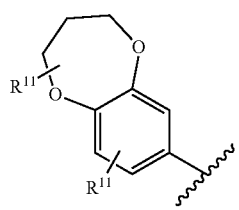

R[10] is selected from the group consisting of phenyl and monocyclic 5- or 6-membered heteroaryl ring, wherein the phenyl and 5- or 6-membered heteroaryl rings are optionally substituted with one or more substituents selected from the group consisting of halogen, $C_{1-4}$alkyl, O (oxo), S (sulfinyl), $C_{1-4}$alkoxy, $NR^3R^4$, $OR^8$, hydroxyl and $R^8$;

or R[10] is a fused bicyclic system selected from the group consisting of any one of (Ia) to (Ii):

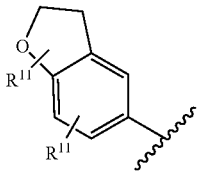
(Ia)

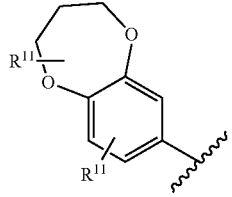
(Ib)

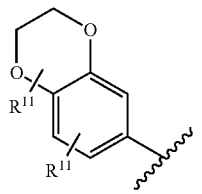
(Ic)

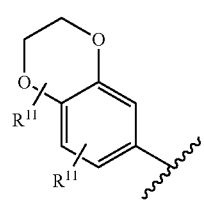
(Ic)

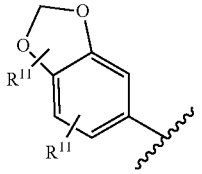
(Id)

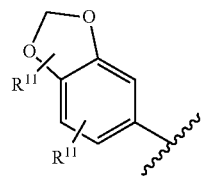
(Id)

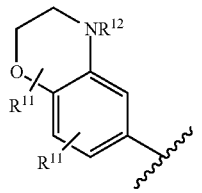
(Ie)

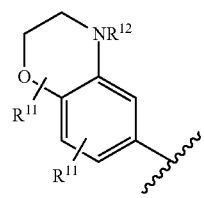
(Ie)

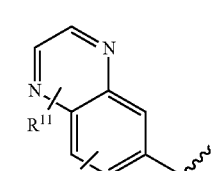
(If)

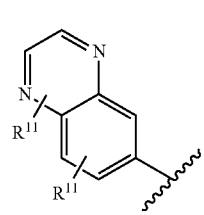
(If)

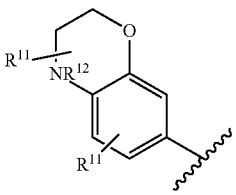
(Ig)

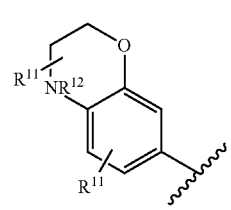
(Ig)

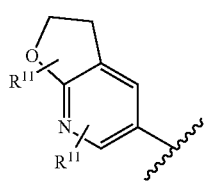
(Ih)

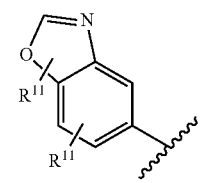
(Ii)

wherein $R^{11}$ and $R^{12}$ are independently selected from hydrogen, methyl and ethyl;

$R^8$ is selected from the group consisting of 4- to 5-membered cycloalkyl and $CH_2R^9$;

$R^9$ is selected from the group consisting of phenyl, monocyclic 5- or 6-membered heteroaryl and monocyclic $C_{3-7}$cycloalkyl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

-continued

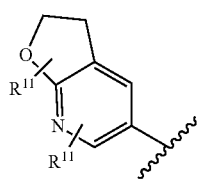
(Ih)

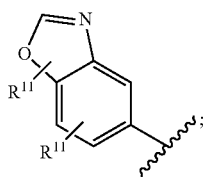
(Ii)

wherein each of $R^{11}$ and $R^{12}$ are hydrogen.

11. A compound according to any preceding numbered disclosure, or a pharmaceutically acceptable salt, hydrate, solvate or ester thereof, having the general formula (III):

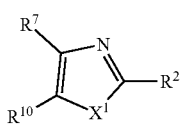
(III)

wherein $X^1$ is selected from NH or S;

$R^2$ is selected from the group consisting of $NHR^3$, COOH and $-CONR^3R^4$;

$R^3$ and $R^4$ are independently selected from the group consisting of hydrogen, $COR^5$, and $CONR^5R^6$;

$R^5$ and $R^6$ are independently selected from the group consisting of hydrogen and $C_{1-2}$alkyl;

$R^7$ is selected from the group consisting of phenyl, monocyclic 6-membered nitrogen containing heterocyclyl and monocyclic 6-membered, nitrogen containing heteroaryl, wherein the phenyl, 6-membered heterocyclyl and 6-membered heteroaryl groups are optionally substituted with one or two substituents selected from the group consisting of Cl, F, $NH_2$, NHMe, $C_{1-2}$alkyl, $C_{1-2}$alkoxy, $CONR^3R^4$, $OCH_2R^9$, $OCF_3$, and hydroxyl;

or $R^7$ is a fused bicyclic system selected from the group consisting of:

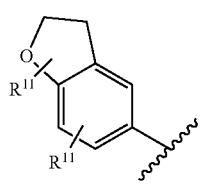
(Ia)

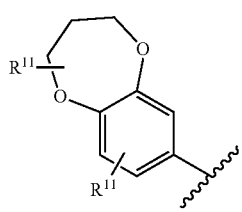
(Ib)

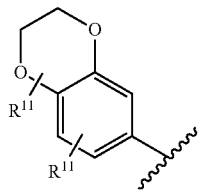
(Ic)

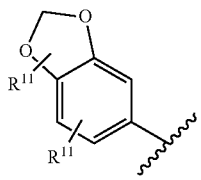
(Id)

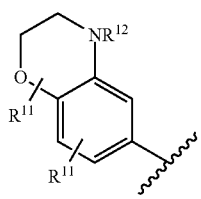
(Ie)

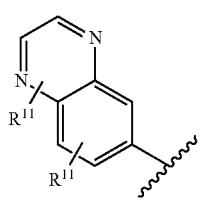
(If)

wherein each of $R^{11}$ and $R^{12}$ are hydrogen;

$R^9$ is selected from the group consisting of phenyl, optionally substituted with one or more substituents selected from the group consisting of Cl, F, methyl, $NH_2$, NHMe, and OH;

$R^{10}$ is selected from the group consisting of phenyl and monocyclic 6-membered, nitrogen containing heteroaryl, monocyclic 6-membered nitrogen containing heterocyclyl, wherein the phenyl, 6-membered heteroaryl and 6-membered heterocyclyl groups are optionally substituted with one or more substituents selected from the group consisting of Cl, F, $NH_2$, NHMe, $C_{1-2}$alkyl, $C_{1-2}$alkoxy, $CONH_2$, CONHMe, $CONMe_2$, $OCH_2C_3$cycloalkyl, $OC_3$cycloalkyl, $OCF_3$ and hydroxyl;

or $R^{10}$ is a fused bicyclic system selected from the group consisting of:

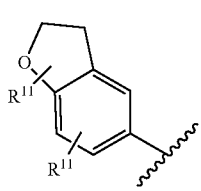
(Ia)

-continued

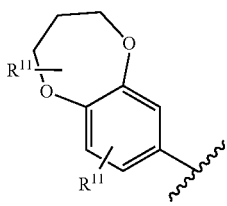
(Ib)

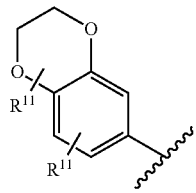
(Ic)

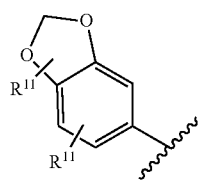
(Id)

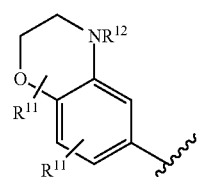
(Ie)

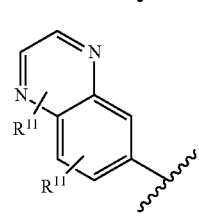
(If)

Wherein each of $R^{11}$ and $R^{12}$ are hydrogen.

12. A compound according to any preceding numbered disclosure, or a pharmaceutically acceptable salt, hydrate, solvate or ester thereof, having the general formula (IV):

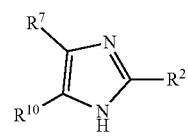
(IV)

wherein
$R^2$ is selected from the group consisting of $NHR^3$;
$R^3$ and $R^4$ are independently selected from the group consisting of hydrogen, $COR^5$, and $CONR^5R^6$;
$R^5$ and $R^6$ are independently selected from the group consisting of hydrogen and $C_{1-2}$alkyl;
$R^7$ is selected from the group consisting of phenyl, pyridyl, and pyrimidine, wherein the phenyl and pyridyl groups are optionally substituted with one or two substituents selected from the group consisting of Cl, F, $NH_2$, Me, NHMe, methoxy, ethoxy, $CONH_2$, CONHMe, $OCH_2R^9$, $OCF_3$, and hydroxyl;

or $R^7$ is a fused bicyclic system selected from the group consisting of:

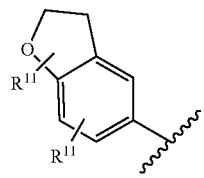
(Ia)

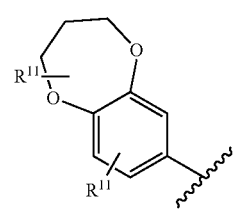
(Ib)

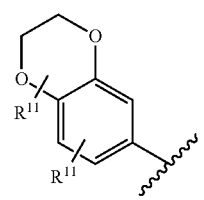
(Ic)

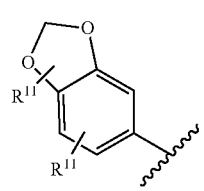
(Id)

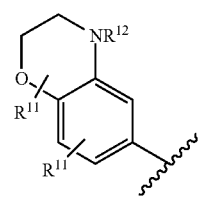
(Ie)

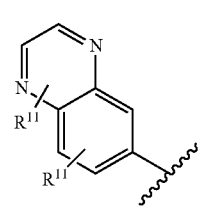
(If)

wherein each of $R^{11}$ and $R^{12}$ are hydrogen;
$R^9$ is selected from the group consisting of phenyl, optionally substituted with F, methyl, $NH_2$ and OH;
$R^{10}$ is selected from the group consisting of phenyl, pyridyl and pyridinone,
wherein the phenyl and pyridyl groups are optionally substituted with one or two substituents selected from the group consisting of Cl, F, $NH_2$, NHMe, $C_{1-2}$alkyl, $C_{1-2}$alkoxy, $CONH_2$, CONHMe, $CONMe_2$, $OCH_2$cyclopropyl and $OC_3$cyclopropyl;

or R¹⁰ is a fused bicyclic system:

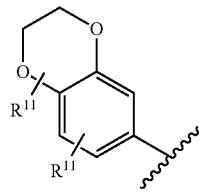
(If)

wherein each of R¹¹ is hydrogen.

13. A compound according to any preceding numbered disclosure, or a pharmaceutically acceptable salt, hydrate, solvate or ester thereof, having the general formula (V):

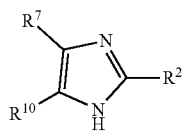
(V)

wherein

R² is selected from the group consisting of NH₂;

R⁷ is selected from the group consisting of phenyl and pyridyl, wherein the phenyl and pyridyl groups are optionally substituted with one or two substituents selected from the group consisting of Cl, F, NH₂, Me, NHMe, methoxy, CONH₂, OCH₂fluorophenyl and hydroxyl;

or R⁷ is a fused bicyclic system selected from the group consisting of:

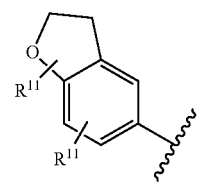
(Ia)

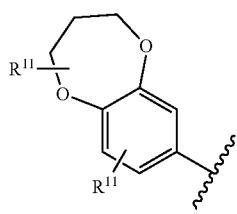
(Ib)

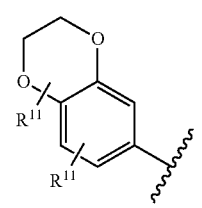
(Ic)

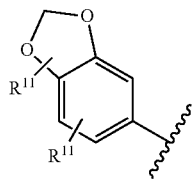
(Id)

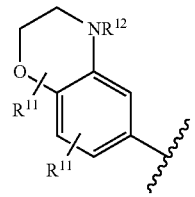
(Ie)

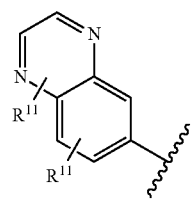
(If)

wherein each of R¹¹ and R¹² are hydrogen;

R¹⁰ is selected from the group consisting of phenyl and pyridyl, wherein the phenyl and pyridyl groups are optionally substituted with one or two substituents selected from the group consisting of Cl, F, NH₂, methyl, methoxy CONH₂, CONHMe, CONMe₂, OCH₂cyclopropyl and OC₃cyclopropyl;

or R¹⁰ is a fused bicyclic system:

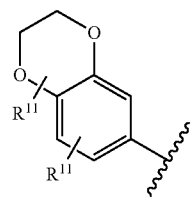
(If)

wherein each of R¹¹ is hydrogen.

14. A pharmaceutical composition comprising a compound according to any preceding numbered disclosure, or a pharmaceutically acceptable salt, hydrate, solvate or ester thereof, and a pharmaceutically acceptable carrier.

15. A compound or pharmaceutical composition according to any preceding numbered disclosure, for use in therapy or prophylaxis.

16. A compound or pharmaceutical composition according to any of numbered disclosures 1 to 14, for use in a method of treatment of an infection with, or a disease caused by, a bacterium.

17. A compound or pharmaceutical composition according to any of numbered disclosures 1 to 14, for the manufacture of a medicament for use in the treatment of an infection with, or a disease caused by, a bacterium.

18. A compound or pharmaceutical composition according to numbered disclosure 16 or 17, wherein the bacterium is Gram-negative or Gram-positive bacterium.

19. A compound or pharmaceutical composition according to numbered disclosure 18, wherein the bacterium is a Gram-negative bacterium, preferably Enterobacteriaceae.

20. A method of treating an infection with, or disease caused by, a bacterium in a subject in need thereof, comprising administering to said subject an effective amount of a compound or composition according to any of numbered disclosures 1 to 14.

21. A method according to numbered disclosure 20, wherein the bacterium is a Gram-negative or Gram-positive bacterium.

22. A method according to numbered disclosure 21, wherein the bacterium is a Gram-negative bacterium, preferably Enterobacteriaceae.

The invention claimed is:

1. A compound, or a pharmaceutically acceptable salt, hydrate, solvate, prodrug, or ester thereof, having the general formula (V):

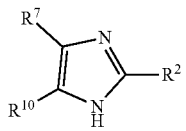

(V)

wherein
R$^2$ is NH$_2$ or methyl (—CH$_3$);
R$_7$ is a fused bicyclic system selected from the group consisting of:

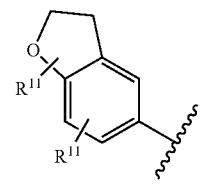

(Ia)

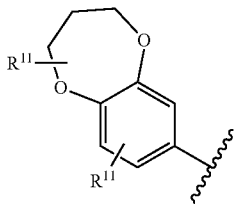

(Ib)

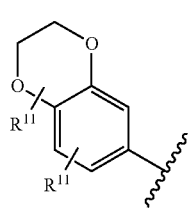

(Ic)

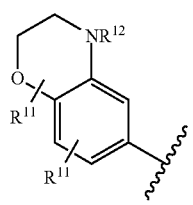

(Ie)

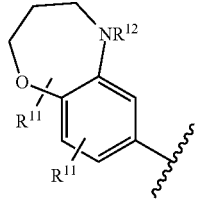

(Ij)

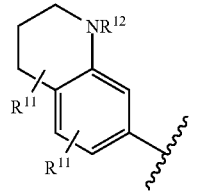

(Ik)

wherein each R$^{11}$ is independently selected from hydrogen and halogen; and
R$^{12}$ is selected from hydrogen, C$_{1-4}$alkyl, C$_{3-7}$cycloalkyl, C$_{4-7}$heterocyclyl, COR$^{13}$, SO$_2$R$^{13}$, C$_{1-4}$alkyl-CO$_2$R$^{14}$, C$_{1-4}$alkyl-OR$^{14}$, C$_{1-4}$alky-NR$^{14}$R$^{15}$, C$_{1-4}$alkyl-C$_{3-7}$cycloalkyl, COC$_{1-4}$alkyl-NR$^{14}$R$^{15}$, an amino acid, and a quaternary ammonium cation (NR$^{16}_4{}^+$);
R$^{13}$ is selected from C$_{1-4}$alkyl, C$_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;
R$^{14}$ and R$^{15}$ are independently selected from hydrogen, C$_{1-4}$alkyl, C$_{1-4}$alkyl-hydroxyl, C$_{3-7}$cycloalkyl, phenyl, monocyclic 5- or 6-membered heteroaryl, and SO$_2$R$^{13}$, the phenyl or 5- or 6-membered heteroaryl being optionally substituted with one or more substituents selected from the group consisting of halogen, C$_{1-2}$alkyl, O (oxo), S (sulfinyl), NR$^3$R$^4$, OR$^3$ and SR$^3$;
R$^{16}$ groups are independently selected from C$_{1-4}$alkyl and phenyl, the phenyl being optionally substituted with one or more substituents selected from the group consisting of halogen, C$_{1-2}$alkyl, O (oxo), S (sulfinyl), NR$^3$R$^4$, OR$^3$ and SR$^3$;
R$^3$ and R$^4$ are independently selected from the group consisting of hydrogen, C$_{1-3}$alkyl, COR$^5$, CONR$^3$R$^6$, CO$_2$R$^5$, C$_{1-2}$alkyl-NR$^5$R$^6$;
or R$^3$ and R$^4$ together with the nitrogen atom to which they are attached form a monocyclic 4- to 7-membered cyclic amine group, which group is optionally substituted with one or more substituents selected from the group consisting of NR$^3$R$^6$, C$_{1-2}$alkoxy and oxo;
R$^5$ and R$^6$ are independently selected from hydrogen and C$_{1-4}$alkyl;
R$^{10}$ is pyridyl, wherein the pyridyl is optionally substituted with one or more substituents selected from the group consisting of halogen, C$_{1-4}$alkyl, O (oxo), S (sulfinyl), C$_{1-4}$alkoxy, CONR$^3$R$^4$, NR$^3$R$^4$, OR$^8$, hydroxyl, OCF$_3$, —CF$_3$, R$^8$, C$_{3-7}$cycloalkyl, C$_{4-7}$heterocyclyl, COR$^{13}$, SO$_2$R$^{13}$, C$_{1-4}$alkyl-CO$_2$R$^{14}$, C$_{1-4}$alkyl-OR$^{14}$, C$_{1-4}$alkyl-NR$^{14}$R$^{15}$, C$_{1-4}$alkyl-C$_{3-7}$cycloalkyl, COC$_{1-4}$alkyl-NR$^{14}$R$^{15}$, an amino acid, and a quaternary ammonium cation (NR$^{16}_4{}^+$), and
R$^8$ is selected from the group consisting of 3- to 5-membered cycloalkyl and CH$_2$R$^9$;

$R^9$ is selected from the group consisting of phenyl, monocyclic 5- or 6-membered heteroaryl and monocyclic $C_{3-7}$cycloalkyl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$.

2. The compound according to claim 1, or a pharmaceutically acceptable salt, hydrate, solvate, prodrug, or ester thereof, wherein $R^2$ is $NH_2$.

3. The compound according to claim 1, or a pharmaceutically acceptable salt, hydrate, solvate, prodrug, or ester thereof, wherein each $R^{11}$ is independently selected from hydrogen and F.

4. The compound according to claim 1, or a pharmaceutically acceptable salt, hydrate, solvate, prodrug, or ester thereof, having the general formula (V):

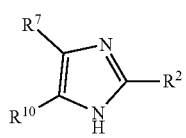

(V)

wherein $R^2$ is $NH_2$, $R^7$ is a fused bicyclic system selected from the group consisting of:

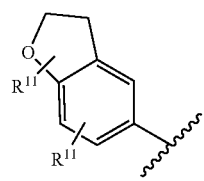

(Ia)

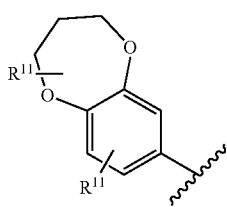

(Ib)

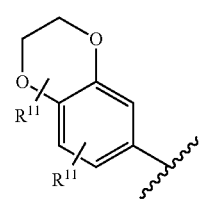

(Ic)

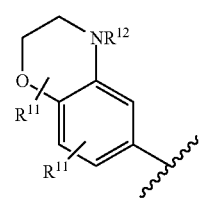

(Ie)

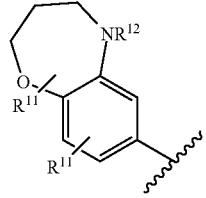

(Ij)

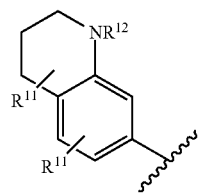

(Ik)

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$ cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$; and $R^{10}$ is pyridyl, wherein the pyridyl is optionally substituted with one or more substituents selected from the group consisting of halogen, $C_{1-4}$alkyl, O (oxo), S (sulfinyl), $C_{1-4}$alkoxy, $CONR^3R^4$, $NR^3R^4$, $OR^8$, hydroxyl, $OCF_3$, —$CF_3$, $R^8$, $C_{3-7}$cycloalkyl, $C_{4-7}$heterocyclyl, $COR^3$, $SO_2R^{13}$, $C_{1-4}$alkyl-$CO_2R^{14}$, $C_{1-4}$alkyl-$OR^{14}$, $C_{1-4}$alkyl-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$).

5. The compound according to claim 1, or a pharmaceutically acceptable salt, hydrate, solvate, prodrug, or ester thereof, wherein $R^2$ is methyl (—$CH_3$);

$R^7$ is a fused bicyclic system selected from the group consisting of:

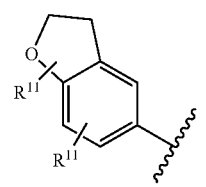

(Ia)

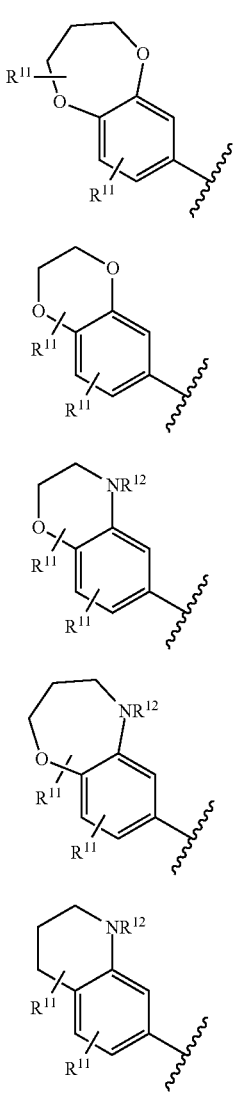

wherein each $R^{11}$ is hydrogen and $R^{12}$ is selected from hydrogen, $C_{1-4}$alkyl, $C_{3-7}$cycloalkyl, $C_{4-7}$heterocyclyl, $COR^{13}$, $SO_2R^{13}$, $C_{1-4}$alkyl-$CO_2R^{14}$, $C_{1-4}$alkyl-$OR^{14}$, $C_{1-4}$alky-$NR^{14}R^{15}$, $C_{1-4}$alkyl-$C_{3-7}$cycloalkyl, $COC_{1-4}$alkyl-$NR^{14}R^{15}$, an amino acid, and a quaternary ammonium cation ($NR^{16}_4{}^+$);

$R^{13}$ is selected from $C_{1-4}$alkyl, $C_{3-7}$cycloalkyl, phenyl, and monocyclic 5- or 6-membered heteroaryl, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{14}$ and $R^{15}$ are independently selected from hydrogen, $C_{1-4}$alkyl, $C_{1-4}$alkyl-hydroxyl, $C_{3-7}$cycloalkyl, phenyl, monocyclic 5- or 6-membered heteroaryl, and $SO_2R^{13}$, the phenyl or 5- or 6-membered heteroaryl being optionally substituted with one or more substituents selected from the group consisting of halogen, $C_{1-2}$alkyl, O (oxo), S (sulfinyl), $NR^3R^4$, $OR^3$ and $SR^3$;

$R^{16}$ groups are independently selected from $C_{1-4}$alkyl and phenyl, the phenyl being optionally substituted with one or more substituents selected from the group consisting of halogen, $C_{1-2}$alkyl, O (oxo), S (sulfinyl), $NR^3R^4$, $OR^3$ and $SR^3$.

6. The compound according to claim 1, or a pharmaceutically acceptable salt, hydrate, solvate, prodrug, or ester thereof, wherein $R^{10}$ is a pyridyl group optionally substituted with one or more substituents selected from the group consisting of Cl, F, $NH_2$, NHMe, $C_{1-2}$alkyl, $C_{1-2}$alkoxy, $CONH_2$, CONHMe, $CONMe_2$, $OCH_2C_3$cycloalkyl, $OC_3$cycloalkyl, $OCF_3$ and hydroxyl.

7. A pharmaceutical composition comprising a compound according to claim 1, or a pharmaceutically acceptable salt, hydrate, solvate, prodrug, or ester thereof, and a pharmaceutically acceptable carrier.

8. The compound or pharmaceutical composition according to claim 1, comprising an effective amount of the compound, wherein said effective amount is an amount effective for use in therapy or prophylaxis of an infection with, or disease caused by, Enterobacteriaceae.

9. The compound or pharmaceutical composition of claim 7, comprising an effective amount of the compound, wherein said effective amount is an amount effective according to claim 1, for use in a method of treatment of an infection with, or a disease caused by, Enterobacteriaceae.

10. The compound according to claim 1 or a pharmaceutically acceptable salt, hydrate, solvate, prodrug, or ester thereof, wherein $R^{11}$ is hydrogen.

\* \* \* \* \*